(12) United States Patent
Belgrader et al.

(10) Patent No.: US 10,954,562 B2
(45) Date of Patent: *Mar. 23, 2021

(54) METHODS AND SYSTEMS FOR PROCESSING POLYNUCLEOTIDES

(71) Applicant: 10X GENOMICS, INC., Pleasanton, CA (US)

(72) Inventors: Phillip Belgrader, Livermore, CA (US); Josephine Harada, San Francisco, CA (US); Tarjei Sigurd Mikkelsen, Dublin, CA (US); Katherine Pfeiffer, Berkeley, CA (US); Serge Saxonov, Oakland, CA (US); John R. Stuelpnagel, Santa Barbara, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,750

(22) Filed: Jan. 27, 2020

(65) Prior Publication Data

US 2020/0216897 A1 Jul. 9, 2020

Related U.S. Application Data

(63) Continuation of application No. 16/692,631, filed on Nov. 22, 2019, now Pat. No. 10,793,905, which is a continuation of application No. 16/426,762, filed on May 30, 2019, now Pat. No. 10,550,429, which is a continuation of application No. 15/939,299, filed on Mar. 22, 2018, now Pat. No. 10,480,029, which is a continuation of application No. 15/720,085, filed on Sep. 29, 2017, now Pat. No. 10,011,872, said application No. 16/426,762 is a continuation of application No. PCT/US2017/068320, filed on Dec. 22, 2017, which is a continuation-in-part of application No. 15/720,085, filed on Sep. 29, 2017.

(60) Provisional application No. 62/438,341, filed on Dec. 22, 2016.

(51) Int. Cl.
| | |
|---|---|
| *C12Q 1/68* | (2018.01) |
| *C12N 15/10* | (2006.01) |
| *C12Q 1/6874* | (2018.01) |
| *C12Q 1/683* | (2018.01) |
| *C12Q 1/6804* | (2018.01) |
| *C12Q 1/6806* | (2018.01) |

(52) U.S. Cl.
CPC ....... *C12Q 1/6874* (2013.01); *C12N 15/1075* (2013.01); *C12Q 1/683* (2013.01); *C12Q 1/6804* (2013.01); *C12Q 1/6806* (2013.01); *C12Q 2525/191* (2013.01); *C12Q 2537/143* (2013.01); *C12Q 2563/179* (2013.01)

(58) Field of Classification Search
CPC .... C12Q 1/6804; C12Q 1/6806; C12Q 1/683; C12Q 1/6874; C12Q 2525/191; C12Q 2537/143; C12Q 2563/179; C12N 15/1075

See application file for complete search history.

(56) References Cited

U.S. PATENT DOCUMENTS

| | | |
|---|---|---|
| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Abate, A.R. et al. "Beating Poisson encapsulation statistics using close-packed ordering" Lab on a Chip (Sep. 21, 2009) 9(18):2628-2631.

(Continued)

*Primary Examiner* — David C Thomas
(74) *Attorney, Agent, or Firm* — Wilson Sonsini Goodrich & Rosati

(57) ABSTRACT

The present disclosure provides compositions, methods, systems, and devices for polynucleotide processing and analyte characterization. Such polynucleotide processing may be useful for a variety of applications, including analyte characterization by polynucleotide sequencing. The compositions, methods, systems, and devices disclosed herein generally describe barcoded oligonucleotides, which can be bound to a bead, such as a gel bead, useful for characterizing one or more analytes including, for example, protein (e.g., cell surface or intracellular proteins), genomic DNA, and RNA (e.g., mRNA or CRISPR guide RNAs). Also described herein, are barcoded labelling agents and oligonucleotide molecules useful for "tagging" analytes for characterization.

29 Claims, 87 Drawing Sheets

Specification includes a Sequence Listing.

(56) References Cited

U.S. PATENT DOCUMENTS

| | | |
|---|---|---|
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,410,246 B1 | 6/2002 | Zhu et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,806,058 B2 | 10/2004 | Jesperson et al. |
| 6,890,741 B2 | 5/2005 | Fan et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,595,060 B2 | 9/2009 | Duke et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,003,312 B2 | 8/2011 | Krutzik et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,394,590 B2 | 3/2013 | Kwong et al. |
| 8,592,150 B2 | 11/2013 | Drmanac et al. |
| 8,658,430 B2 | 2/2014 | Miller et al. |
| 8,691,510 B2 | 4/2014 | Faham et al. |
| 8,822,148 B2 | 9/2014 | Ismagilov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,034,601 B2 | 5/2015 | Hufton et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,217,176 B2 | 12/2015 | Faham et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,365,901 B2 | 6/2016 | Pepin et al. |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,499,865 B2 | 11/2016 | Faham et al. |
| 9,500,664 B2 | 11/2016 | Ness et al. |
| 9,506,119 B2 | 11/2016 | Faham et al. |
| 9,512,487 B2 | 12/2016 | Faham et al. |
| 9,567,631 B2 | 2/2017 | Hindson et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,650,407 B2 | 5/2017 | Gartner et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,708,657 B2 | 7/2017 | Asbury et al. |
| 9,764,322 B2 | 9/2017 | Hiddessen et al. |
| 9,824,068 B2 | 11/2017 | Wong |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,059,989 B2 | 8/2018 | Giresi et al. |
| 10,066,265 B2 | 9/2018 | Klinger et al. |
| 10,077,478 B2 | 9/2018 | Faham et al. |
| 10,144,950 B2 | 12/2018 | Nolan |
| 10,151,003 B2 | 12/2018 | Fan et al. |
| 10,168,328 B2 | 1/2019 | Berka |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,338,066 B2 | 7/2019 | Fan et al. |
| 10,347,365 B2 | 7/2019 | Wong et al. |
| 10,357,771 B2 | 7/2019 | Bharadwaj et al. |
| 10,392,663 B2 | 8/2019 | Emerson et al. |
| 10,395,758 B2 | 8/2019 | Schnall-Levin |
| 10,400,280 B2 | 9/2019 | Hindson et al. |
| 10,428,325 B1 | 10/2019 | Klinger |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,550,429 B2 * | 2/2020 | Harada ............... C12Q 1/6853 |
| 10,590,244 B2 | 3/2020 | Delaney et al. |
| 10,633,691 B2 | 4/2020 | Wu |
| 10,745,742 B2 | 8/2020 | Bent et al. |
| 2002/0005354 A1 | 1/2002 | Spence et al. |
| 2002/0048766 A1 | 4/2002 | Doyle et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0027214 A1 | 2/2003 | Kamb |
| 2003/0036206 A1 | 2/2003 | Chien et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2004/0082059 A1 | 4/2004 | Webb et al. |
| 2005/0019839 A1 | 1/2005 | Jespersen et al. |
| 2005/0037397 A1 | 2/2005 | Mirkin et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |

(56) References Cited

U.S. PATENT DOCUMENTS

| | | |
|---|---|---|
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0263457 A1 | 10/2011 | Krutzik et al. |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2013/0261196 A1 | 10/2013 | Diamond et al. |
| 2014/0065234 A1 | 3/2014 | Shum et al. |
| 2014/0221239 A1 | 8/2014 | Carman et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0315725 A1 | 10/2014 | Faham et al. |
| 2014/0338753 A1 | 11/2014 | Sperling et al. |
| 2015/0005188 A1 | 1/2015 | Levner et al. |
| 2015/0057162 A1 | 2/2015 | Ullman et al. |
| 2015/0066385 A1 | 3/2015 | Schnall-Levin et al. |
| 2015/0148239 A1 | 5/2015 | Peter et al. |
| 2015/0220532 A1 | 8/2015 | Wong |
| 2015/0267191 A1 | 9/2015 | Steelman et al. |
| 2015/0329617 A1 | 11/2015 | Winther et al. |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024493 A1 | 1/2016 | Robins |
| 2016/0024558 A1 | 1/2016 | Hardenbol et al. |
| 2016/0024572 A1 | 1/2016 | Shishkin et al. |
| 2016/0025726 A1 | 1/2016 | Altin et al. |
| 2016/0032282 A1* | 2/2016 | Vigneault ............ C12Q 1/6809 424/135.1 |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0201125 A1 | 7/2016 | Samuels et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0244828 A1 | 8/2016 | Mason |
| 2016/0257993 A1 | 9/2016 | Fu et al. |
| 2016/0281160 A1 | 9/2016 | Jarosz et al. |
| 2016/0289669 A1 | 10/2016 | Fan et al. |
| 2016/0289769 A1 | 10/2016 | Schwartz et al. |
| 2016/0304956 A1 | 10/2016 | Robins |
| 2016/0314242 A1 | 10/2016 | Schnall-Levin et al. |
| 2016/0348093 A1 | 12/2016 | Price et al. |
| 2017/0009274 A1 | 1/2017 | Abate et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2017/0268056 A1 | 9/2017 | Vigneault et al. |
| 2018/0030515 A1 | 2/2018 | Regev et al. |
| 2018/0071695 A1 | 3/2018 | Weitz et al. |
| 2018/0080021 A1 | 3/2018 | Reuter et al. |
| 2018/0080075 A1 | 3/2018 | Brenner et al. |
| 2018/0080078 A1 | 3/2018 | Robins et al. |
| 2018/0105808 A1 | 4/2018 | Mikkelsen et al. |
| 2018/0112212 A1* | 4/2018 | Nicol ................ G01N 33/6845 |
| 2018/0180601 A1 | 6/2018 | Pedersen et al. |
| 2018/0208975 A1 | 7/2018 | Peterson et al. |
| 2018/0216162 A1 | 8/2018 | Belhocine et al. |
| 2018/0251825 A1 | 9/2018 | Stoeckius et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0320224 A1 | 11/2018 | Gaublomme et al. |
| 2018/0334670 A1 | 11/2018 | Bharadwaj et al. |
| 2018/0340169 A1 | 11/2018 | Belhocine et al. |
| 2018/0371538 A1 | 12/2018 | Blauwkamp et al. |
| 2018/0371545 A1 | 12/2018 | Wong et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0145982 A1 | 5/2019 | Chee et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0276818 A1 | 9/2019 | Gehring et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0002764 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0140944 A1 | 5/2020 | Belgrader et al. |

FOREIGN PATENT DOCUMENTS

| | | |
|---|---|---|
| EP | 1923471 A1 | 5/2008 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-9301498 A1 | 1/1993 |
| WO | WO-95/30782 | 11/1995 |
| WO | WO-9942597 A1 | 8/1999 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0189787 A2 | 11/2001 |

(56) References Cited

FOREIGN PATENT DOCUMENTS

| | | |
|---|---|---|
| WO | WO-0190418 A1 | 11/2001 |
| WO | WO-02072631 A2 | 9/2002 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010009735 A2 | 1/2010 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013188872 A1 | 12/2013 |
| WO | WO-2014028378 A2 | 2/2014 |
| WO | WO-2014108810 A2 | 7/2014 |
| WO | WO-2014144495 A1 | 9/2014 |
| WO | WO-2014165559 A2 | 10/2014 |
| WO | WO-2014182835 A1 | 11/2014 |
| WO | WO-2014200767 A1 | 12/2014 |
| WO | WO-2015015199 A2 | 2/2015 |
| WO | WO-2015044428 A1 | 4/2015 |
| WO | WO-2015085275 A2 | 6/2015 |
| WO | WO-2015103339 A1 | 7/2015 |
| WO | WO-2015164212 A1 | 10/2015 |
| WO | WO-2015185067 A1 | 12/2015 |
| WO | WO-2015188839 A2 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016138496 A1 | 9/2016 |
| WO | WO-2016174229 A1 | 11/2016 |
| WO | WO-2016176322 A1 | 11/2016 |
| WO | WO-2017015075 A1 | 1/2017 |
| WO | WO-2017053902 A1 | 3/2017 |
| WO | WO-2017053903 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017117358 A1 | 7/2017 |
| WO | WO-2017184707 A1 | 10/2017 |
| WO | WO-2017197343 A2 | 11/2017 |
| WO | WO-2018039338 A1 | 3/2018 |
| WO | WO-2018057051 A1 | 3/2018 |
| WO | WO-2018058073 A2 | 3/2018 |
| WO | WO-2018064640 A1 | 4/2018 |
| WO | WO-2018075436 A1 | 4/2018 |
| WO | WO-2018119301 A1 | 6/2018 |
| WO | WO-2018119447 A2 | 6/2018 |
| WO | WO-2018125982 A1 | 7/2018 |
| WO | WO-2018132635 A9 | 9/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019173638 A1 | 9/2019 |
| WO | WO-201919321 A1 | 10/2019 |
| WO | WO-2019217758 A1 | 11/2019 |
| WO | WO-2020028882 A1 | 2/2020 |
| WO | WO-2020041148 A2 | 2/2020 |
| WO | WO-2020142779 A1 | 7/2020 |
| WO | WO-2020167862 A1 | 8/2020 |

OTHER PUBLICATIONS

Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Adamson et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Bakker et al. Conditional MHC class I ligands and peptide exchange technology for the human MHC gene products HLA-A1, -A3, -A11, and -B7. Proc Natl Acad Sci U S A. Mar. 11, 2008;105(10):3825-30. doi: 10.1073/pnas.0709717105. Epub Feb. 28, 2008.

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.

(56) References Cited

OTHER PUBLICATIONS

Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Co-pending U.S. Appl. No. 16/530,930, filed Aug. 2, 2019.
Dahotre et al. DNA-Barcoded pMHC Tetramers for Detection of Single Antigen-Specific T Cells by Digital PCR. Anal Chem. Feb. 19, 2019;91(4):2695-2700. doi: 10.1021/acs.analchem.8b04153. Epub Jan. 30, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Datlinger et al. Pooled CRISPR screening with single-cell transcriptome readout. Nature Methods Advance Online Publication (Jan. 18, 2017). DOI: http://www.nature.com/doifinder/10.1038/nmeth.4177. 10 pages.
Delehanty, et al. Peptides for specific intracellular delivery and targeting of nanoparticles: implications for developing nanoparticle-mediated drug delivery. Ther Deliv. Sep. 2010;1(3):411-33.
Dey, et al. Integrated Genome and Transcriptome Sequencing from the Same Cell. Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Effenberger et al. FLEXamers: A Double Tag for Universal Generation of Versatile Peptide-MHC Multimers. J Immunol. Apr. 1, 2019;202(7):2164-2171. doi: 10.4049/jimmunol.1801435. Epub Feb. 13, 2019.
Esser-Kahn, et al. Triggered release from polymer capsules. Macromolecules. 2011; 44:5539-5553.
Gaublomme, et al. Nuclei multiplexing with barcoded antibodies for single-nucleus genomics. Nat Commun. Jul. 2, 2019;10(1):2907. doi: 10.1038/s41467-019-10756-2.
Gee et al. Antigen Identification for Orphan T Cell Receptors Expressed on Tumor-Infiltrating Lymphocytes. Cell. Jan. 25, 2018;172(3):549-563.e16. doi: 10.1016/j.cell.2017.11.043. Epub Dec. 21, 2017.
Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Han et al. Linking T-cell receptor sequence to functional phenotype at the single-cell level. Nat Biotechnol 32(7):684-692 (2014).
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kester, et al. Single-Cell Transcriptomics Meets Lineage Tracing. Cell Stem Cell. Aug. 2, 2018;23(2):166-179. doi: 10.1016/j.stem.2018.04.014. Epub May 10, 2018.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Kondo et al. Yeast cell-surface display—applications of molecular display. Appl Microbiol Biotechnol. Mar. 2004;64(1):28-40. Epub Jan. 10, 2004.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).

(56) References Cited

OTHER PUBLICATIONS

Lagally, et al. Single-Molecular DNA Amplification and Analysis in an Integrated Microfluidic Device. Anal Chem. Feb. 1, 2001;73(3):565-70.

Lennon et al. A scalable, fully automated process for construction of sequence-ready barcoded libraries for 454. Genome Biology 11:R15 (2010).

Love, "A microengraving method for rapid selection of single cells producing antigen-specific antibodies", Nature Biotech, 24:6 703 (Jun. 2006).

Macaulay, et al. G&T-seq: parallel sequencing of single-cell genomes and transcriptomes. Nature Methods, 2015, p. 1-7.

Macaulay, et al. Single-Cell Multiomics: Multiple Measurements from Single Cells. Trends in Genetics 33.2 (2017): 155-168. PMC. Web. Dec. 18, 2017.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Madl, et al. "Bioorthogonal Strategies for Engineering Extracellular matrices", Madal, Chritopher, Adv. Funct. Master. Jan. 19, 2018, vol. 28, 1706046, pp. 1-21.

Mair, et al. Injection molded microfluidic chips featuring integrated interconnects. Lab Chip. Oct. 2006;6(10):1346-54. Epub Jul. 31, 2006.

Mazutis, et al. Single-Cell Analysis and Sorting Using Droplet-Based Microfluidics. Nat Protoc. 8(5): 870-891 (May 2013).

McCoy, R. et al. "Illumina TruSeq Synthetic Long-Reads Empower De Novo Assembly and Resolve Complex, Highly-Repetitive Transposable Elements" PLOS (2014) 9(9):e1016689.

McDaniel, et al. Ultra-high-throughput sequencing of the immune receptor repertoire from millions of lymphocytes.Nature protocols 11.3 (2016): 429-442.

McGinnis et al. MULTI-seq: sample multiplexing for single-cell RNA sequencing using lipid-tagged indices. Nat Methods. Jul. 2019;16(7):619-626. doi: 10.1038/s41592-019-0433-8. Epub Jun. 17, 2019.

McGinnis, et al. MULTI-seq: Scalable sample multiplexing for single-cell RNA sequencing using lipid-tagged indices. bioRxiv (2018) 387241; doi: https://doi.org/10.1101/387241.

McShan et al. Peptide exchange on MHC-I by TAPBPR is driven by a negative allostery release cycle. Nat Chem Biol. Aug. 2018;14(8):811-820. doi: 10.1038/s41589-018-0096-2. Epub Jul. 9, 2018.

Microfluidic ChipShop. Microfluidic product catalogue. Oct. 2009.

Mimitou, et al. Expanding the CITE-seq tool-kit: Detection of proteins, transcriptomes, clonotypes and CRISPR perturbations with multiplexing, in a single assay. bioRxiv preprint first posted online Nov. 8, 2018; doi: http://dx.doi.org/10.1101/466466.

Morozov et al. Interaction of TAPBPR, a tapasin homolog, with MHC-I molecules promotes peptide editing. Proc Natl Acad Sci U S A. Feb. 23, 2016;113(8):E1006-15. doi: 10.1073/pnas.1519894113. Epub Feb. 11, 2016.

Navin. The first five years of single-cell cancer genomics and beyond. Genome Res. Oct. 2015;25(10):1499-507. doi: 10.1101/gr.191098.115.

Neal et al. The Basics of Artificial Antigen Presenting Cells in T Cell-Based Cancer Immunotherapies. J Immunol Res Ther. 2017;2(1):68-79. Epub Jun. 26, 2017.

Nisisako, et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidicallygenerated agarose emulsions" Angew. Chem. Int. Ed. Engl. (2011) 50(2):390-395.

Omidfar et al. Advances in phage display technology for drug discovery. Expert Opin Drug Discov. Jun. 2015;10(6):651-69. doi: 10.1517/17460441.2015.1037738. Epub Apr. 24, 2015.

Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406):190-195 (Jul. 11, 2012).

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Priest, et al. Generation of Monodisperse Gel Emulsions in a Microfluidic Device, Applied Physics Letters, 88:024106 (2006).

Pushkarev et al. "Single-molecule sequencing of an individual human genome," Nature Biotech (2009) 17:847-850.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 UsingMultiplexIdentifierAdaptorsForTheGSFLXTitaniumSeriesChemistry-BasicMIDSet.pdf.

Rosenberg, et al. Single-cell profiling of the developing mouse brain and spinal cord with split-pool barcoding. Science. Apr. 13, 2018;360(6385):176-182. doi: 10.1126/science.aam8999. Epub Mar. 15, 2018.

Rotem, A. et al., "High-throughput single-cell labeling (Hi-SCL) for RNA-Seq using drop-based microfluidics" PLOS One (May 22, 2015) 0116328 (14 pages).

Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.

Schmidt, et al. Quantitative analysis of synthetic cell lineage tracing using nuclease barcoding. ACS synthetic biology 6.6 (2017): 936-942.

Schubert, et al. Microemulsifying fluorinated oils with mixtures of fluorinated and hydrogenated surfactants. Colloids and Surfaces A; Physicochemical and Engineering Aspects, 84(1994) 97-106.

Segaliny et al. Functional TCR T cell screening using single-cell droplet microfluidics. Lab Chip. Dec. 4, 2018;18(24):3733-3749. doi: 10.1039/c8lc00818c.

Seiffert, et al. Microfluidic fabrication of smart microgels from macromolecular precursors. 2010. Polymer.

Seiffert, S. et al., "Smart microgel capsules from macromolecular precursors" J. Am. Chem. Soc. (2010) 132:6606-6609.

Shah, "Fabrication of mono disperse thermosensitive microgels and gel capsules in micro fluidic devices", Soft Matter, 4:2303-2309 (2008).

Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.

Smith, et al. Highly-multiplexed barcode sequencing: an efficient method for parallel analysis of pooled samples. Nucleic Acids Research, 38(13): e142 (2010).

Song, et al. Reactions in droplets in microfluidic channels. Angew Chem Int Ed Engl. Nov. 13, 2006;45(44):7336-56.

Srivatsan, et al. Massively multiplex chemical transcriptomics at single-cell resolution. Science (New York, NY) 367.6473 (2020): 45-51.

(56) References Cited

OTHER PUBLICATIONS

Stahl, et al. Visualization and analysis of gene expression in tissue sections by spatial transcriptomics. Science. Jul. 1, 2016;353(6294):78-82. doi: 10.1126/science.aaf2403.
Stoeckius, et al. Cell Hashing with barcoded antibodies enables multiplexing and doublet detection for single cell genomics. Genome Biol. Dec. 19, 2018;19(1):224. doi: 10.1186/s13059-018-1603-1.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017. Supplemental Materials.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Toebes et al. Design and use of conditional MHC class I ligands. Nat Med. Feb. 2006;12(2):246-51. Epub Feb. 5, 2006.
Toebes et al. Generation of peptide MHC class I monomers and multimers through ligand exchange. Curr Protoc Immunol. Nov. 2009;Chapter 18:Unit 18.16. doi: 10.1002/0471142735.im1816s87.
Tonelli, et al. Perfluoropolyether functional oligomers: unusual reactivity in organic chemistry. Journal of fluorine chemistry. 2002; 118(1) 107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Ullal et al. Cancer Cell Profiling by Barcoding Allows Multiplexed Protein Analysis in Fine-Needle Aspirates. Sci Transl Med. Jan. 15, 2014; 6(219): 219ra9.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Vandormael et al. cDNA phage display for the discovery of theranostic autoantibodies in rheumatoid arthritis. Immunol Res. Feb. 2017;65(1):307-325. doi: 10.1007/s12026-016-8839-1.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Zhang et al. High-throughput determination of the antigen specificities of T cell receptors in single cells. Nat Biotechnol. Nov. 12, 2018. doi: 10.1038/nbt.4282. [Epub ahead of print].
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
Nijman, I.J. et al. "Mutation Discovery by Targeted Genomic Enrichment of Multiplexed Barcoded Samples" Nature Methods (2010) 7:913-915.
Rajan, et al. Recombinant Human B Cell Repertoires Enable Screening for Rare, Specific, and Natively Paired Antibodies. Commun Biol. Jan. 22, 2018;1:5. doi: 10.1038/s42003-017-0006-2.
Reuter, J.A. et al. "Simul-seq: combined DNA and RNA sequencing for whole-genome and transcriptome profiling" Nature Methods (2016) 13(11):953-958.
PCT/US2020/017789 Application filed on Feb. 11, 2020 by Belhocine, Zahara Kamila et al.

* cited by examiner

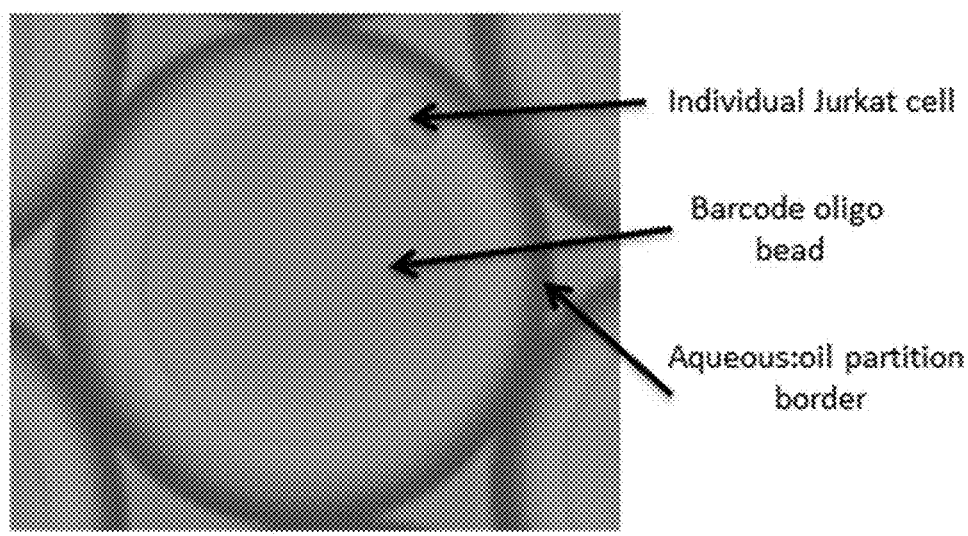
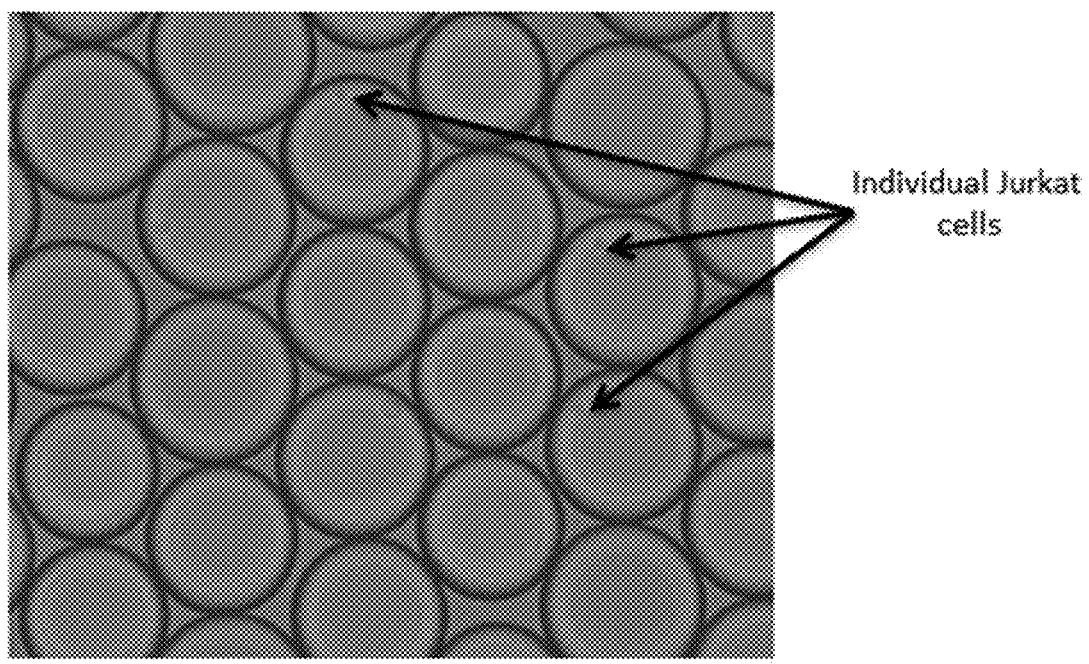
FIG. 8

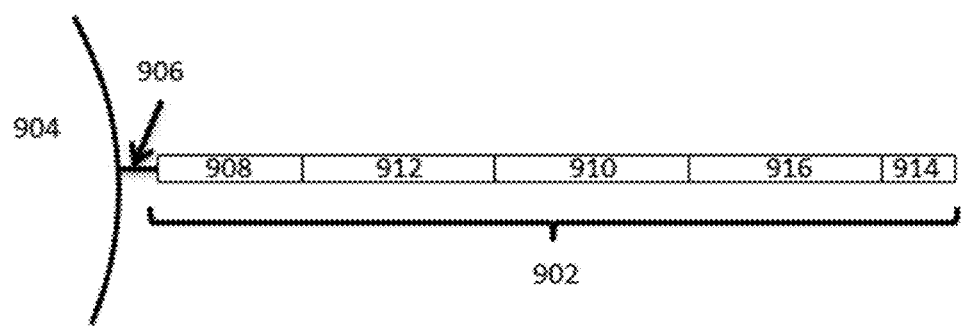
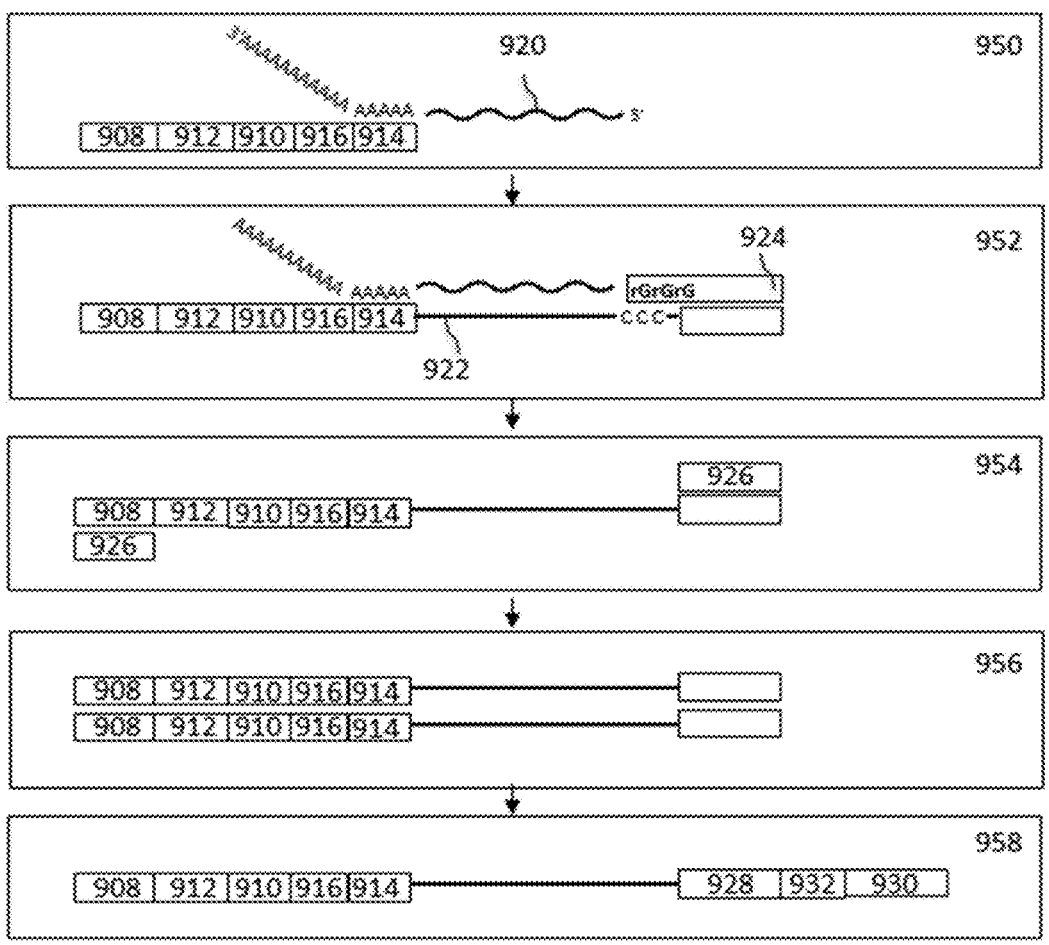
FIG. 9A

2000

Providing a partition comprising a cell and at least one labeling agent, wherein said at least one labeling agent is (i) capable of binding to a cell surface feature of said cell and (ii) is coupled to a reporter oligonucleotide comprising a nucleic acid barcode sequence that permits identification of said at least one labeling agent, wherein said partition comprises an anchor oligonucleotide that is capable of interacting with said reporter oligonucleotide barcode;

2010

In said partition, synthesizing a nucleic acid molecule comprising at least a portion of said nucleic acid barcode sequence or a complement thereof;

2020

Subjecting said nucleic acid molecule to sequencing to identify said labeling agent or said cell.

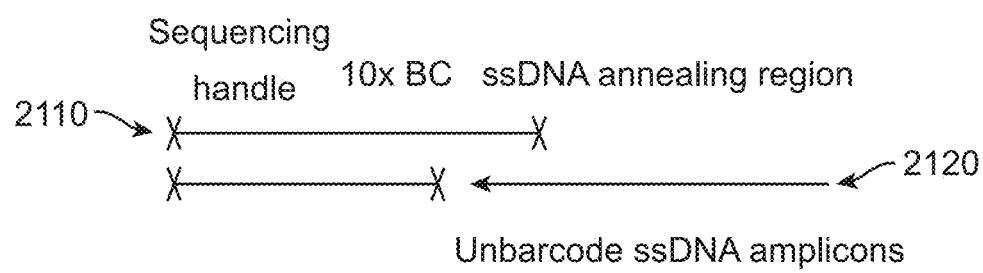
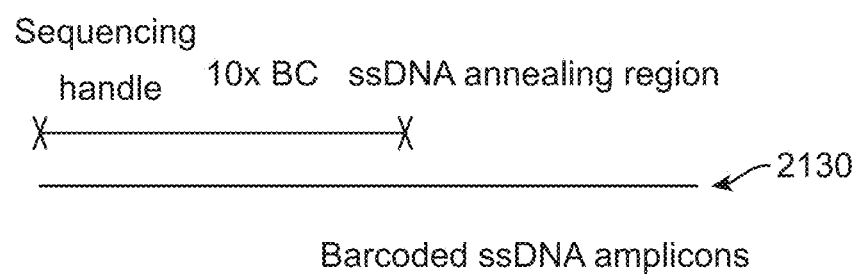
FIG. 21

```
             R1              10X BC      UMI
CTACACGACGCTCTTCCGATCTXXXXXXTCXXXXXXN₁₀T₃₀VN
                                          PolyT
             R1              10X BC      UMI
CTACACGACGCTCTTCCGATCTXXXXXXTCXXXXXXN₁₀(TARGET SEQUENCE)
             R1              10X BC      UMI
CTACACGACGCTCTTCCGATCTXXXXXXTCXXXXXXN₁₀T₃₀VN
                                          PolyT
```

FIG. 23A

```
             R1              10X BC      UMI
CTACACGACGCTCTTCCGATCTXXXXXXTCXXXXXXN₁₀(TARGET SEQUENCE-1)
             R1              10X BC      UMI
CTACACGACGCTCTTCCGATCTXXXXXXTCXXXXXXN₁₀(TARGET SEQUENCE-2)
             R1              10X BC      UMI
CTACACGACGCTCTTCCGATCTXXXXXXTCXXXXXXN₁₀(TARGET SEQUENCE-3)
             R1              10X BC      UMI
CTACACGACGCTCTTCCGATCTXXXXXXTCXXXXXXN₁₀(TARGET SEQUENCE-N)
```

FIG. 23B

```
             R1              10X BC      UMI
CTACACGACGCTCTTCCGATCTXXXXXXTCXXXXXXN₁₀T₃₀VN
                                          PolyT
             R1              10X BC      UMI
CTACACGACGCTCTTCCGATCTXXXXXXTCXXXXXXN₁₀(TARGET SEQUENCE-1)
             R1              10X BC      UMI
CTACACGACGCTCTTCCGATCTXXXXXXTCXXXXXXN₁₀(TARGET SEQUENCE-2)
             R1              10X BC      UMI
CTACACGACGCTCTTCCGATCTXXXXXXTCXXXXXXN₁₀(TARGET SEQUENCE-3)
             R1              10X BC      UMI
CTACACGACGCTCTTCCGATCTXXXXXXTCXXXXXXN₁₀(TARGET SEQUENCE-N)
             R1              10X BC      UMI
CTACACGACGCTCTTCCGATCTXXXXXXTCXXXXXXN₁₀T₃₀VN
                                          PolyT
```

FIG. 23C

```
         R1                UMI        10X BC
CTACACGACGCTCTTCCGATCTNNNNNNNNNXXXXXXTCXXXXXXNNNNNN
                                                Randomer R1                UMI        10X BC
CTACACGACGCTCTTCCGATCTNNNNNNNNNXXXXXXTCXXXXXX(TARGET SEQUENCE-1)

R1                UMI        10X BC
CTACACGACGCTCTTCCGATCTNNNNNNNNNXXXXXXTCXXXXXX(TARGET SEQUENCE-2)

R1                UMI        10X BC
CTACACGACGCTCTTCCGATCTNNNNNNNNNXXXXXXTCXXXXXX(TARGET SEQUENCE-3)

R1                UMI        10X BC
CTACACGACGCTCTTCCGATCTNNNNNNNNNXXXXXXTCXXXXXX(TARGET SEQUENCE-N)

R1                UMI        10X BC
CTACACGACGCTCTTCCGATCTNNNNNNNNNXXXXXXTCXXXXXXNNNNNN
                                                Randomer
```

FIG. 24

| Splint oligo(s): | Assay Primers: |
|---|---|
| polyA-XXX ➡ | X'X'X' Analyte 1 |
| polyA-YYY ➡ | Y'Y'Y' Analyte 2 |
| polyA-ZZZ ➡ | Z'Z'Z' Analyte 3 | pBl -10xBC-(Spacer)-rGrGrG

+

Assay Primers (in solution):

Transcript Counting

[PCR primer site]-T$_{30}$VN

Antigen Counting (DNA conjugated antibodies)

[PCR primer site]-N$_{10}$X$_{10}$

CRISPR (gRNA BC)

[PCR primer site]-N$_{10}$S$_{10}$

Other

[PCR primer site]-N$_{10}$o$_{10}$

Alpha
CTACACGACGCTCTTCCGATCTXXXXXXGTXXXXXXN$_{10}$T$_{30}$VN
GCGAGAAGGCTAGAXXXXXXCAXXXXXX

Beta
CTACACGACGCTCTTCCGATCTXXXXXXCAXXXXXXN$_{10}$T$_{30}$VN
GCGAGAAGGCTAGAXXXXXXGTXXXXXX

Gamma
CTACACGACGCTCTTCCGATCTXXXXXXAGXXXXXXN$_{10}$T$_{30}$VN
GCGAGAAGGCTAGAXXXXXXTCXXXXXX

Delta
CTACACGACGCTCTTCCGATCTXXXXXXTCXXXXXXN$_{10}$T$_{30}$VN
GCGAGAAGGCTAGAXXXXXXAGXXXXXX R1      10X BC   UMI
CTACACGACGCTCTTCCGATCTXXXXXXTCXXXXXXN$_{10}$T$_{30}$VN
PolyT

FIG. 27B

P5 Scheme
AATGATACGGCGACCACCGAGATCTACACXXXXXXXGTXXXXXXACACTCTTTCCCTACACGACGCTCTTCCGATCTN₁₀T₃₀VN
GTGGCTCTAGATGTGXXXXXXCAXXXXXXTGTGAGAAAGGGATGTGCTGCGAGAAGGCTAGA P5　　　　　　10X BC　　　　　　R1　　　UMI
AATGATACGGCGACCACCGAGATCTACACXXXXXXXGTXXXXXXACACTCTTTCCCTACACGACGCTCTTCCGATCTN₁₀T₃₀VN
　　　　　　　　　　　　　　　　　　　　　　　　　　　　　　　　　　　　　　PolyT

R2 inline
CAGACGTGTGCTCTTCCGATCTXXXXXXGTXXXXXXN₁₀T₃₀VN
CGAGAAGGCTAGAXXXXXXCAXXXXXX R2　　　　　10X BC　　UMI
CAGACGTGTGCTCTTCCGATCTXXXXXXGTXXXXXXN₁₀T₃₀VN
　　　　　　　　　　　　　　　PolyT

FIG. 27C

R1 Early UMI Scheme

Alpha
CTACACGACGCTCTTCCGATCTNNNNNNNNNNXXXXXXGT XXXXXXXX
GCGAGAAGGCTAGA              CXXXXXXX

Beta
CTACACGACGCTCTTCCGATCTNNNNNNNNNNXXXXXXCA XXXXXXXX
GCGAGAAGGCTAGA              GTXXXXXX

Gamma
CTACACGACGCTCTTCCGATCTNNNNNNNNNNXXXXXXAG XXXXXXXX
GCGAGAAGGCTAGA              TXXXXXXX

Delta
CTACACGACGCTCTTCCGATCTNNNNNNNNNNXXXXXXTC XXXXXXXX
GCGAGAAGGCTAGA              AXXXXXXX R1  UMI  10X BC
CTACACGACGCTCTTCCGATCTNNNNNNNNNNXXXXXXTCXXXXXXNNNNNN
                                              Randomer

FIG. 27D

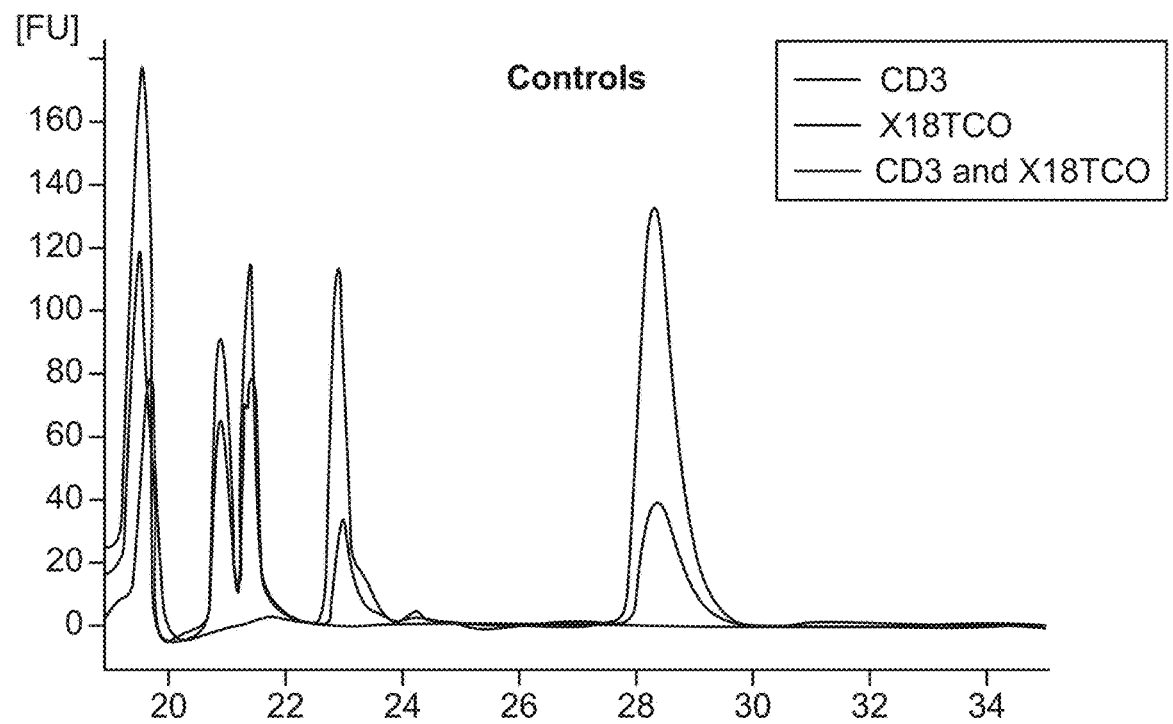
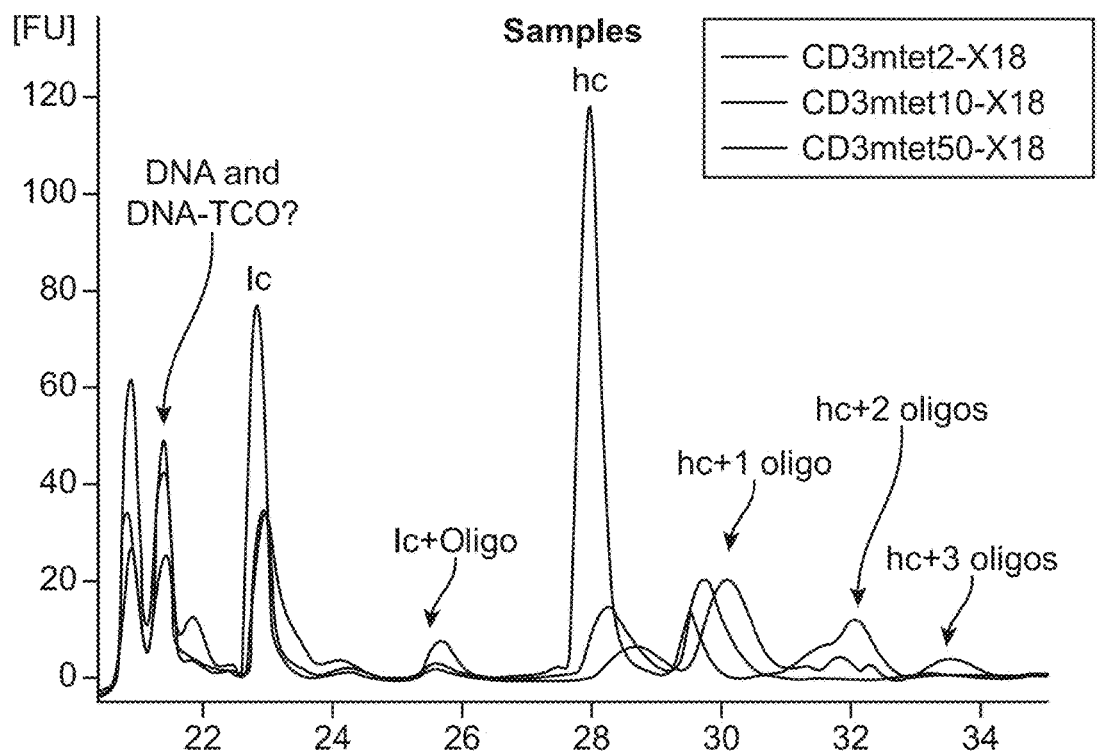
FIG. 37

| MW (kDa) | Relative Band % (Coomassie gel) | | | | | | |
|---|---|---|---|---|---|---|---|
| | Protein G | 1x DBCO 1.5x oligo | 2X DBCO | | | 4x DBCO 1.5x oligo | 6x DBCO 1.5x oligo |
| | | | 1x oligo | 1.5x oligo | 2x oligo | | |
| 155.6 | | | | | | | 7.0 |
| 117.6 | | | | | | 4.6 | 20.1 |
| 85.0 | | | 2.8 | 4.6 | 6.9 | 20.3 | 21.2 |
| 70.0 | | | 1.6 | 2.9 | 4.0 | 7.7 | 5.4 |
| 58.2 | | 32.9 | 46.6 | 45.8 | 44.4 | 44.4 | 37.2 |
| 39.6 | 100 | 67.1 | 49.0 | 46.7 | 44.7 | 23.0 | 9.1 |

FIG. 47B

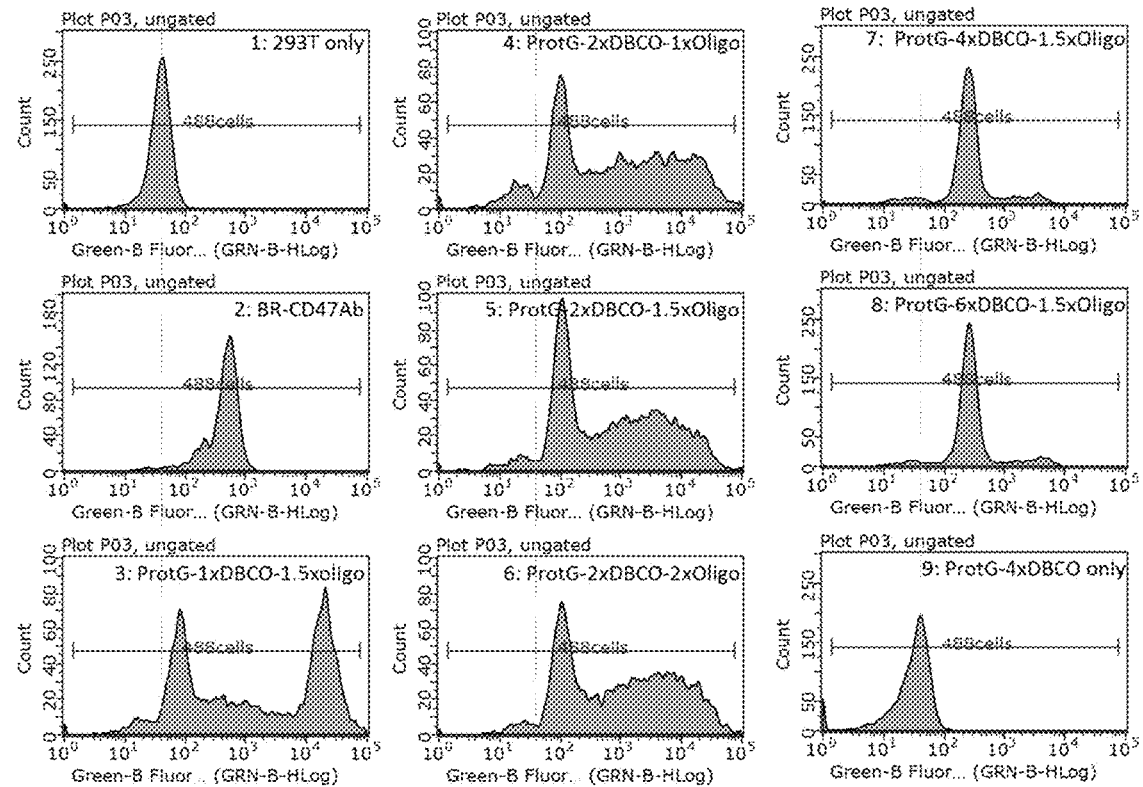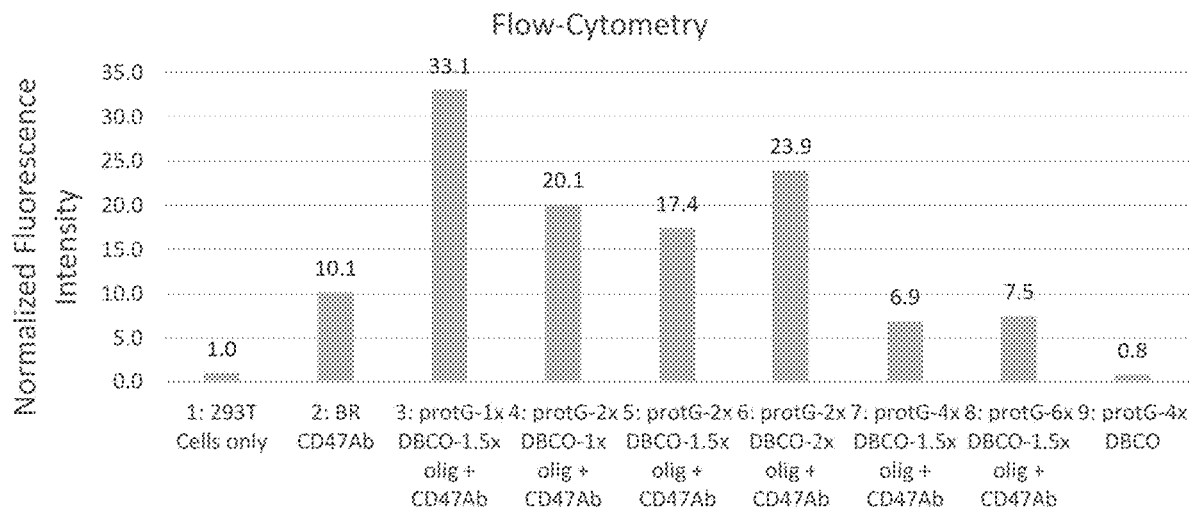
FIG. 48

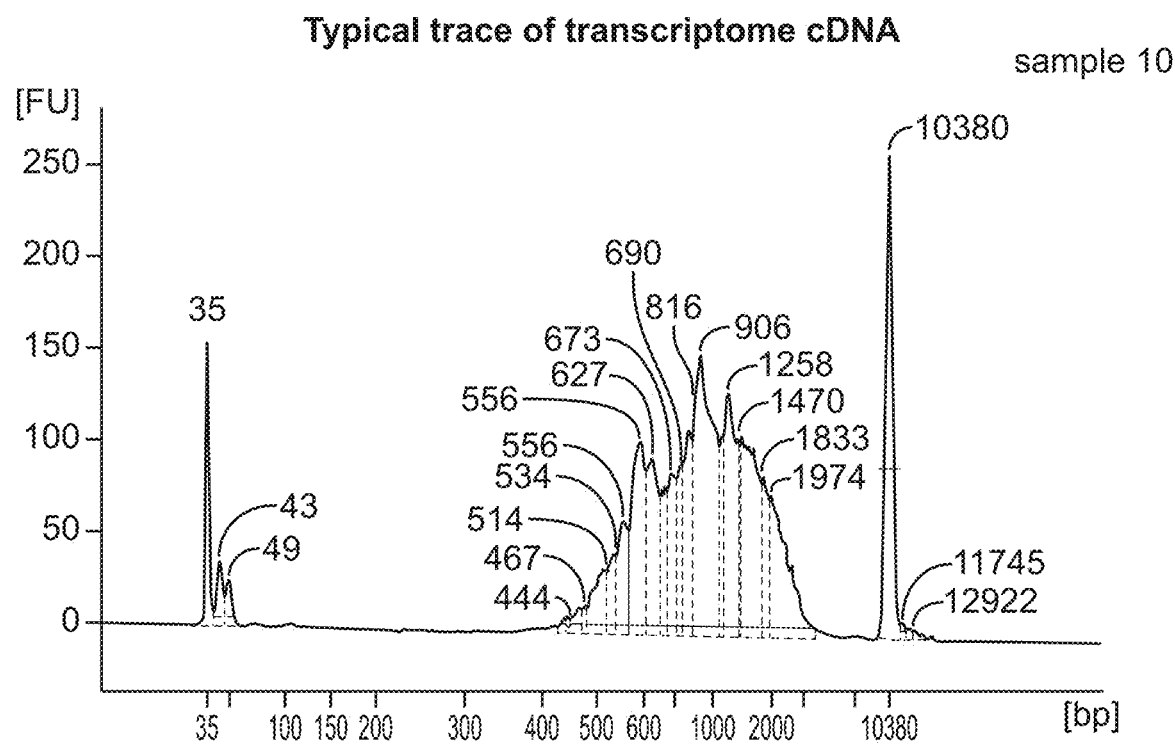
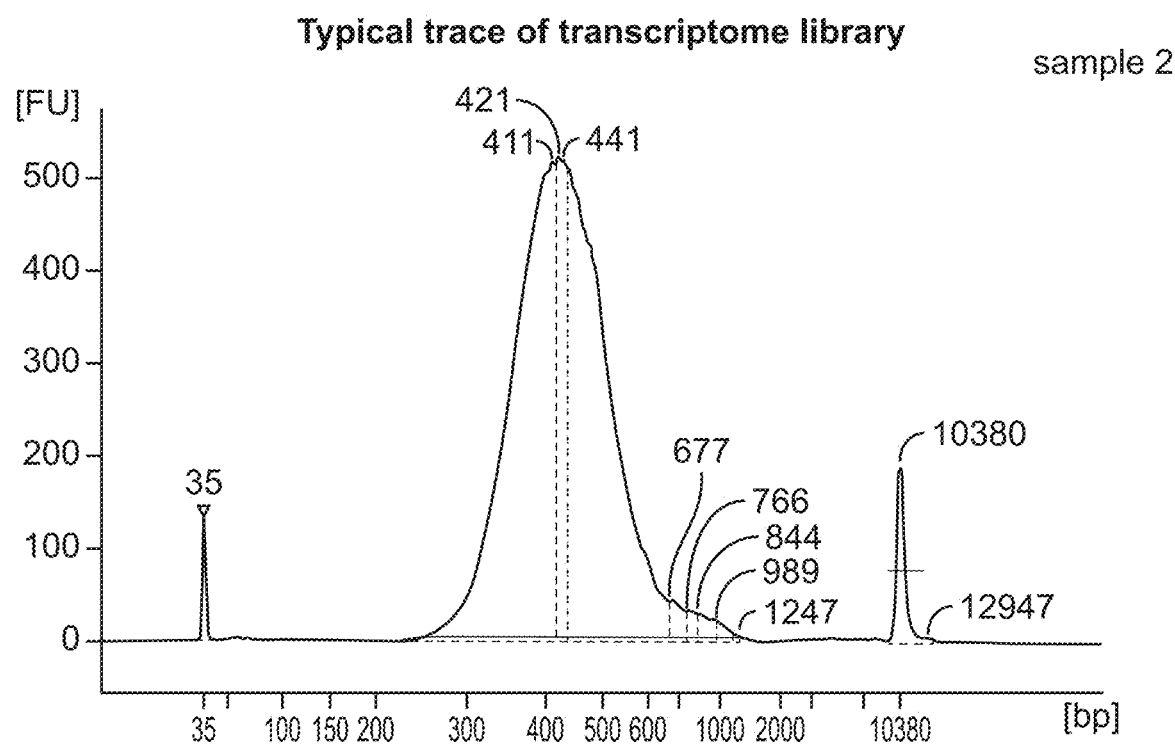
FIG. 49A

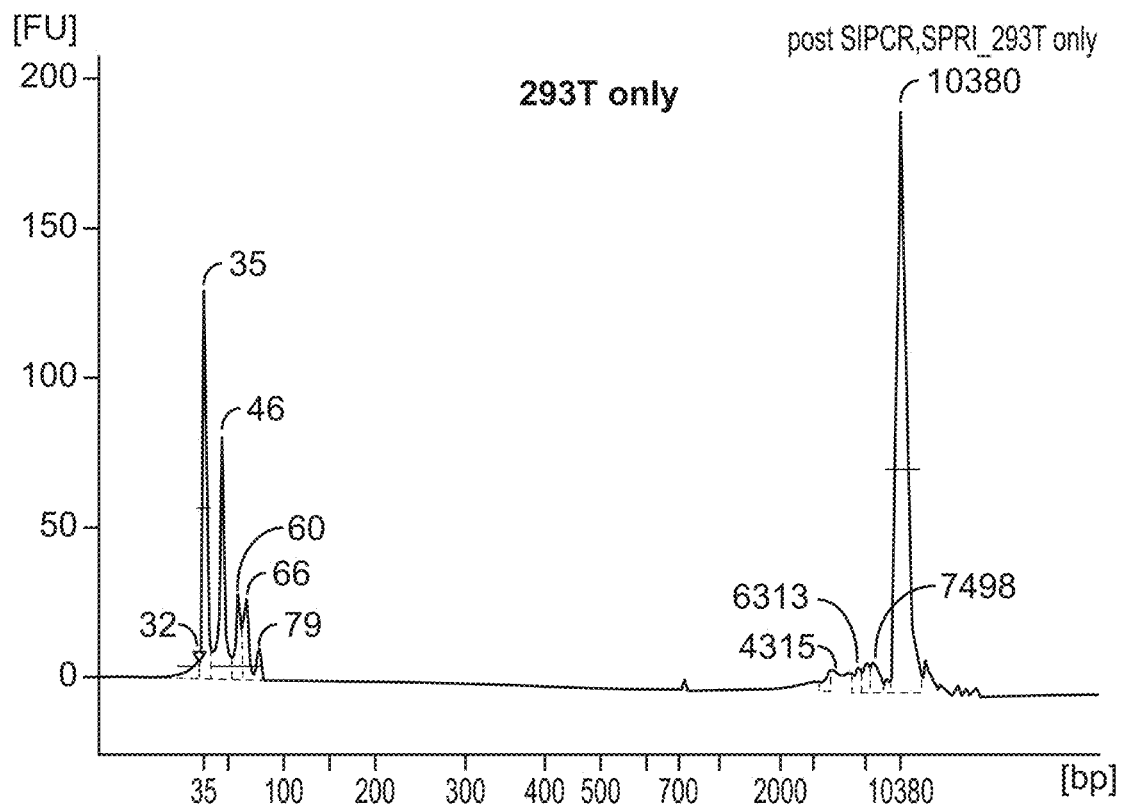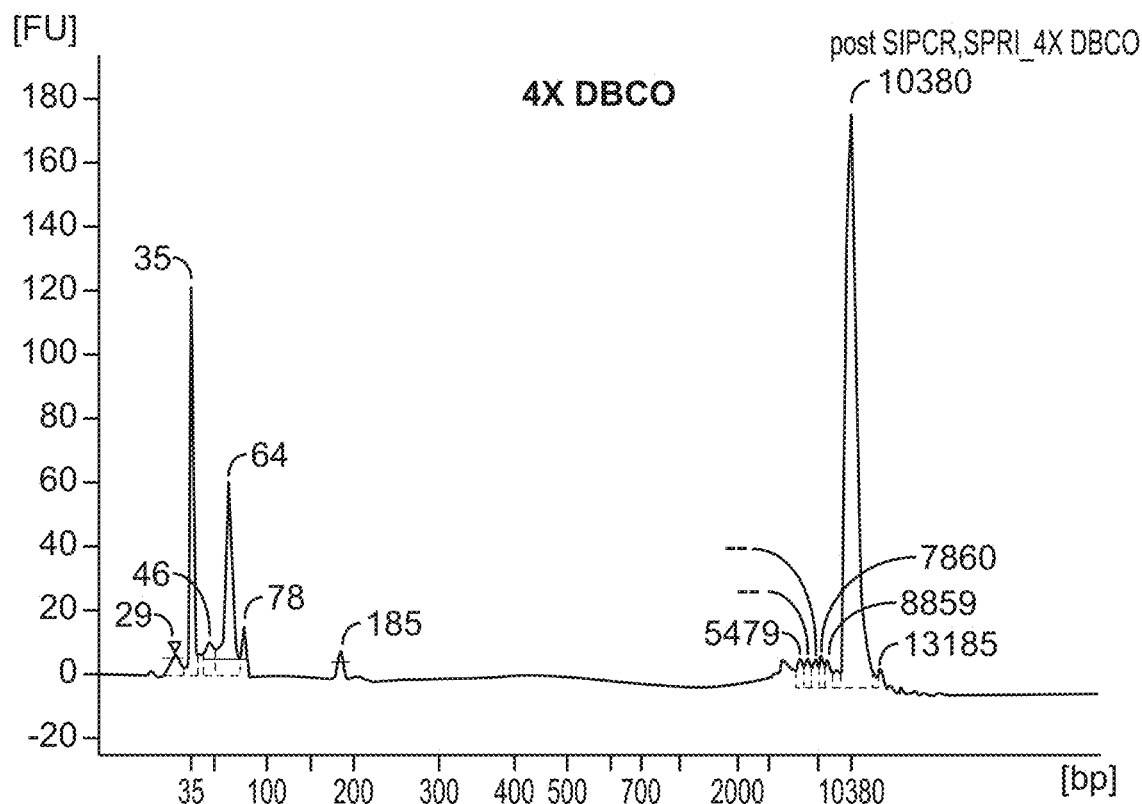
FIG. 49B

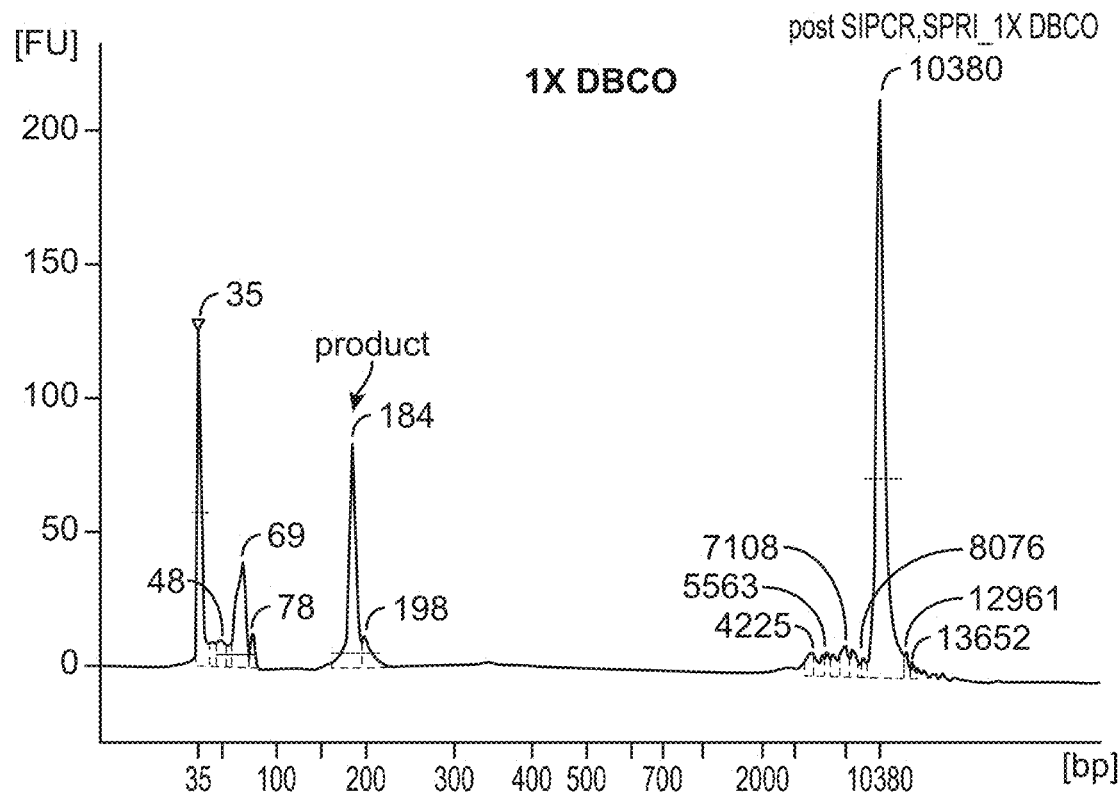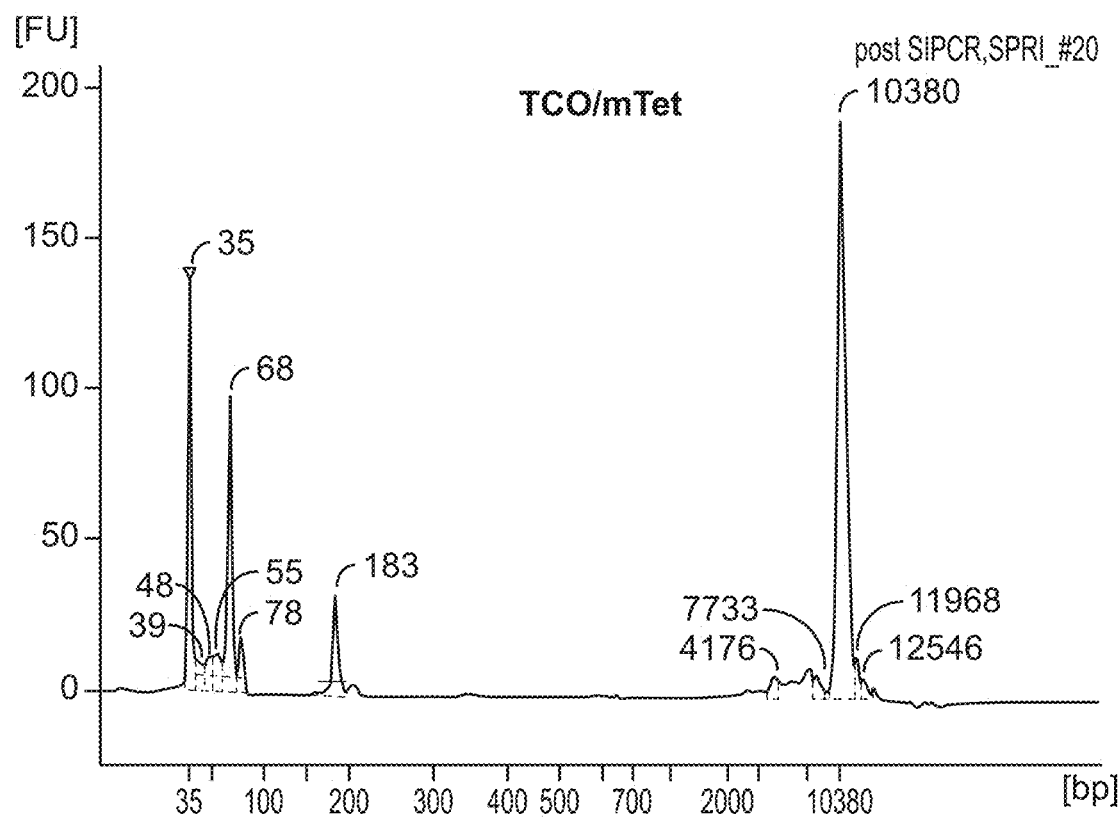
FIG. 49C

| Description | Corrected Area | Product Peak Size (bp) |
|---|---|---|
| 293T Cells only | 11.0 | - |
| protG-1x DBCO-1.5x oligo + CD47Ab | 178.4 | 184 |
| protG-2x DBCO-2x oligo + CD47Ab | 120.5 | 184 |
| protG-4x DBCO-1.5x oligo + CD47Ab | 17.6 | 185 |
| protG-6x DBCO-1.5x oligo + CD47Ab | 32.4 | 184 |
| protG-TCO/mtet-10x oligo + CD47Ab | 45.6 | 183 |
| protG-oligo | 5.0 | - |

FIG. 49D

Alpha
CTACACGACGCTCTTCCGATCTXXXXXXXGTXXXXXXXN$_{10}$T$_{30}$VN
GCGAGAAGGCTAGAXXXXXXXCAXXXXXXX

Beta
CTACACGACGCTCTTCCGATCTXXXXXXXCAXXXXXXXN$_{10}$T$_{30}$VN
GCGAGAAGGCTAGAXXXXXXXGTXXXXXXX

Gamma
CTACACGACGCTCTTCCGATCTXXXXXXXAGXXXXXXXN$_{10}$T$_{30}$VN
GCGAGAAGGCTAGAXXXXXXXTCXXXXXXX

Delta
CTACACGACGCTCTTCCGATCTXXXXXXXTCXXXXXXXN$_{10}$T$_{30}$VN
GCGAGAAGGCTAGAXXXXXXXAGXXXXXXX

FIG. 50B

Alpha
GTCAGATGTGTATAAGAGACAGXXXXXXXGTXXXXXXXN$_{10}$GCTTCGTACGCGAAACTAGCGT
CACATATTCTCTGTCXXXXXXXCAXXXXXXX
Beta
GTCAGATGTGTATAAGAGACAGXXXXXXXGTXXXXXXXN$_{10}$GCTTCGTACGCGAAACTAGCGT
CACATATTCTCTGTCXXXXXXXCAXXXXXXX
Gamma
GTCAGATGTGTATAAGAGACAGXXXXXXXGTXXXXXXXN$_{10}$GCTTCGTACGCGAAACTAGCGT
CACATATTCTCTGTCXXXXXXXCAXXXXXXX
Delta
GTCAGATGTGTATAAGAGACAGXXXXXXXGTXXXXXXXN$_{10}$GCTTCGTACGCGAAACTAGCGT
CACATATTCTCTGTCXXXXXXXCAXXXXXXX

FIG. 50C

5' CTACACGACGCTCTTCCGATCTNNNNNNNNNNNNNNNNNNNNNTTTCTTATATrGrGrG
3' AAAGAATATA C C CTAGACTGACGTGGAACCTGGCGATTTCAAC-FAM

I
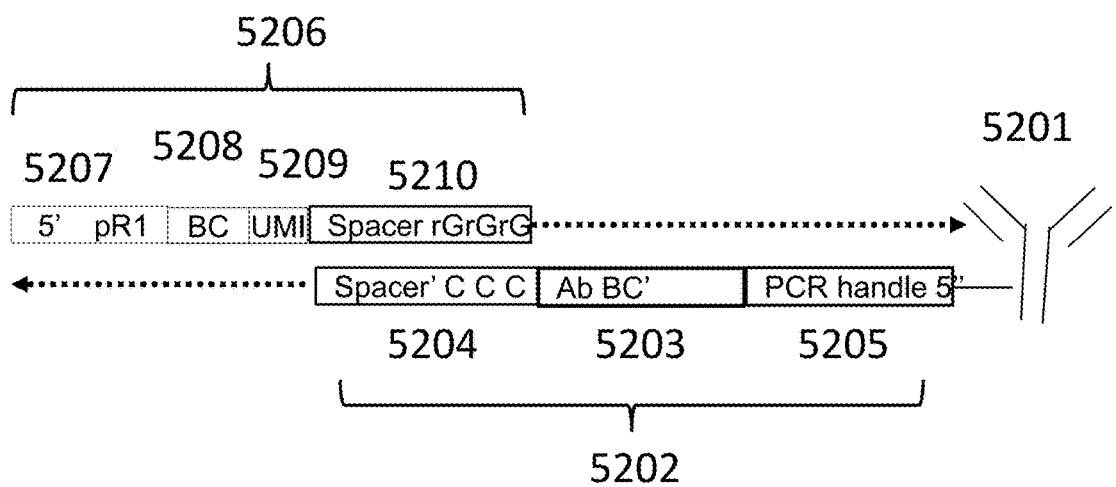
II
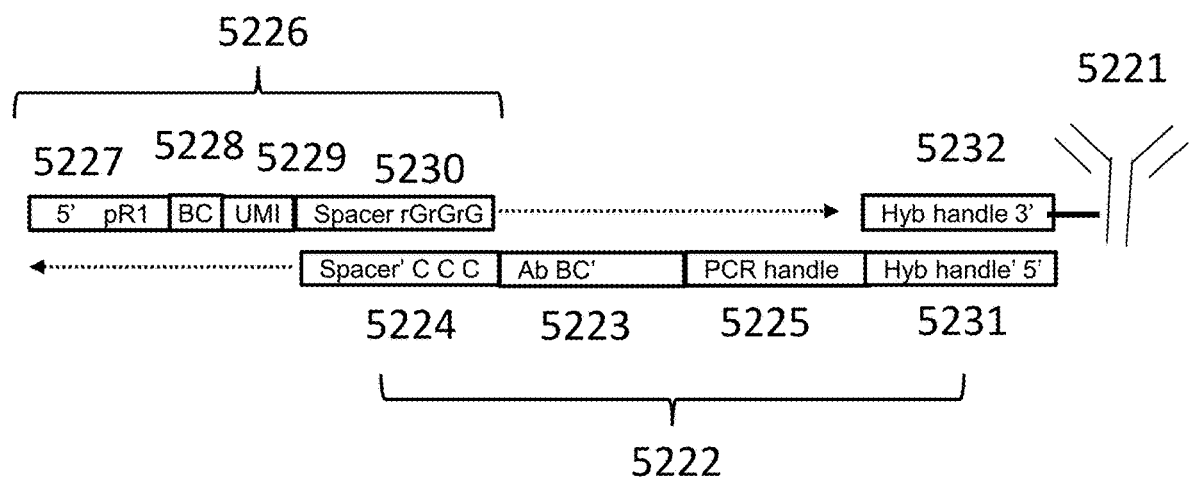
FIG. 52B

I  Jurkat + CD47/CD99
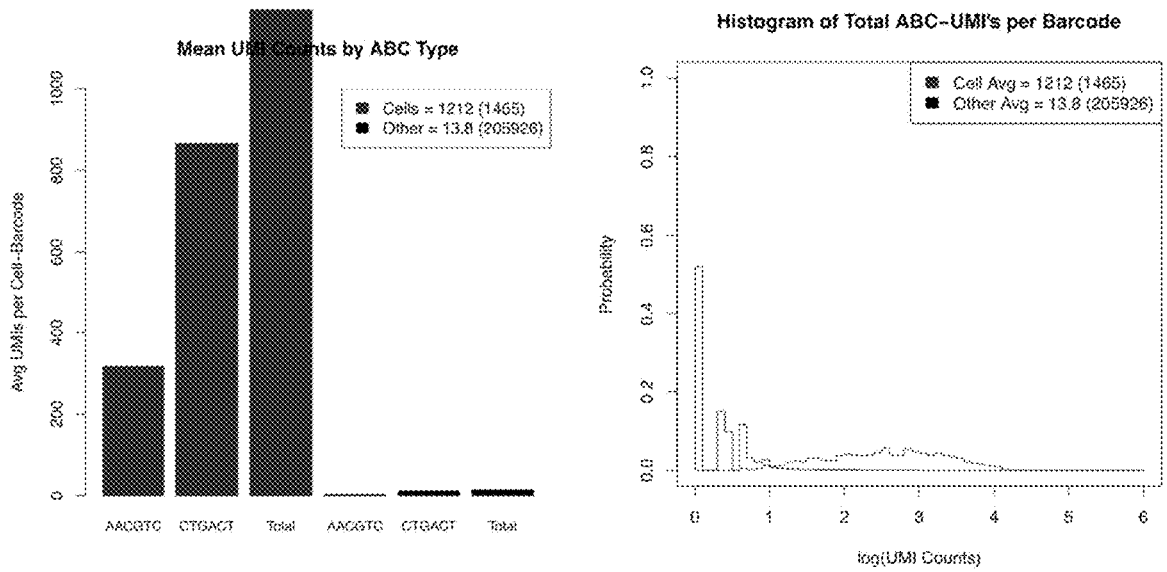
II  Jurkat + CD47
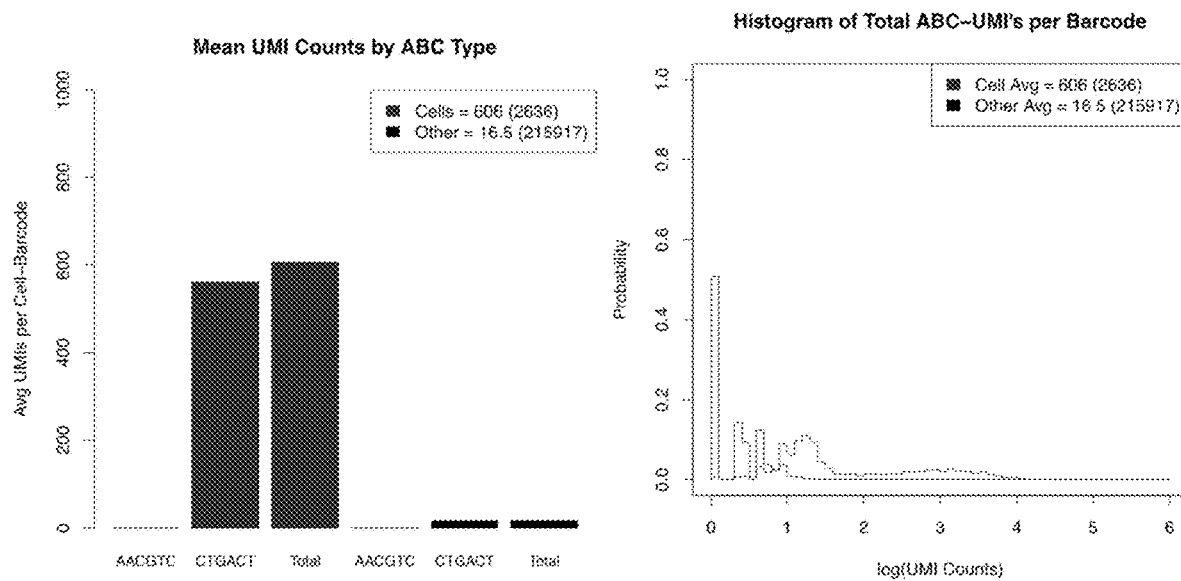
FIG. 53A

| Sample | Sample ID | Avg UMIs per Cell | Avg UMIs per Other | BC3 per Cell | BC4 per Cell | Total # of Cell BCs detected in AbBC expt | # cells, SC5 | # cells, AbBC topN (~#cells, SC5) | AbBC topN cells ∩ SC5 cells | AbBC called cells | AbBC cells ∩ SC5 cells | SC5 cells ∩ AbBC topN /SC5 cells | BCAb cells ∩ SC5' cells /AbBC cells |
|---|---|---|---|---|---|---|---|---|---|---|---|---|---|
| Unbiased Jurkat + BC4 | 33600 | 498 | 13.9 | 64647 | 635932 | 128481 | 1419 | 1418 | 378 | 1362 | 370 | 0.27 | 0.27 |
| Unbiased Jurkat + BC3/4 | 33601 | 577 | 17.1 | 247587 | 404815 | 126514 | 1141 | 1141 | 368 | 992 | 316 | 0.32 | 0.32 |
| Unbiased Jurkat + BC4 | 33602 | 996 | 9.14 | 1474578 | 6119 | 144263 | 1505 | 1504 | 862 | 1193 | 762 | 0.57 | 0.64 |
| Unbiased Jurkat spike BC3/4 | 33603 | 38.8 | 14.1 | 1163 | 71316 | 206337 | 1898 | 1980 | 103 | 62631 | 1570 | 0.05 | 0.03 |

FIG. 53B

| Sample | Description | Mean Reads per Cell | Valid Barcodes | Reads Mapped Confidently to Transcriptome | Fraction Reads in Cells |
|---|---|---|---|---|---|
| 37358 | cDNA control | 217,543 | 83.60% | 56.00% | 95.70% |
| 37772 | Unbiased-5: CG-CD3 GEM 53/85C Dy | 31,899 | 70.20% | 32.90% | 95.10% |
| 37773 | Unbiased-6: CG-CD3 GEM 53/85C Dy | 29,602 | 69.20% | 29.90% | 94.40% |
| 37776 | Unbiased-21: SC-CD3 GEM 53/85C D | 36,549 | 76.00% | 37.10% | 95.40% |
| 37777 | Unbiased-22: SC-CD3 GEM 53/85C D | 44,884 | 76.40% | 39.20% | 96.10% |
| 37780 | Unbiased-7: CG-CD3 GEM 53/85C St | 33,828 | 76.20% | 38.30% | 94.40% |
| 37781 | Unbiased-8: CG-CD3 GEM 53/85C St | 33,085 | 71.90% | 33.90% | 94.60% |
| 37784 | Unbiased-23: SC-CD3 GEM 53/85C S | 40,137 | 77.70% | 40.20% | 95.30% |
| 37785 | Unbiased-24: SC-CD3 GEM 53/85C S | 40,931 | 80.30% | 39.10% | 95.00% |
| 37770 | Unbiased-1: CG-CD3 GEM 53C Dyna | 29,136 | 91.40% | 64.50% | 94.90% |
| 37771 | Unbiased-2: CG-CD3 GEM 53C Dyna | 28,533 | 91.30% | 65.40% | 95.30% |
| 37774 | Unbiased-17: SC-CD3 GEM 53C Dyn | 42,069 | 91.30% | 62.40% | 95.10% |
| 37775 | Unbiased-18: SC-CD3 GEM 53C Dyn | 38,234 | 91.90% | 63.00% | 95.30% |
| 37778 | Unbiased-3: CG-CD3 GEM 53C Strep | 32,773 | 92.60% | 67.70% | 94.90% |
| 37779 | Unbiased-4: CG-CD3 GEM 53C Strep | 30,309 | 92.80% | 67.40% | 94.40% |
| 37782 | Unbiased-19: SC-CD3 GEM 53C Stre | 45,118 | 92.00% | 61.40% | 95.20% |
| 37783 | Unbiased-20: SC-CD3 GEM 53C Stre | 37,621 | 92.00% | 61.60% | 94.50% |

Heat kill (top section) / No Heat kill (bottom section)

| A | B |

FIG. 54A

| Fraction Reads Usable | Reads Mapped Confidently to Exonic Regions | Reads Mapped Confidently to Intronic Regions | Reads Mapped Confidently to Intergenic Regions | Reads Mapped Antisense to Gene | Fraction reads unmapped | cDna PCR Duplication (20k raw reads per cell) | Median Genes per Cell (20k raw reads per cell) | Median UMI Counts per Cell (20k raw reads per cell) |
|---|---|---|---|---|---|---|---|---|
| 26.20% | 64.50% | 12.70% | 8.90% | 9.00% | 3.30% | 46.90% | 1,103 | 2,764 |
| 15.20% | 41.60% | 9.00% | 16.60% | 12.80% | 4.70% | 43.30% | 730 | 1,690 |
| 13.70% | 38.90% | 9.30% | 16.80% | 14.00% | 4.70% | 42.80% | 684 | 1,562 |
| 17.20% | 47.40% | 13.20% | 13.50% | 13.90% | 5.10% | 44.60% | 812 | 1,935 |
| 18.30% | 48.90% | 12.60% | 13.10% | 13.00% | 5.10% | 43.20% | 855 | 2,077 |
| 17.60% | 47.80% | 12.00% | 14.50% | 12.80% | 4.50% | 48.30% | 781 | 1,796 |
| 15.60% | 43.90% | 11.20% | 15.30% | 14.30% | 4.60% | 46.00% | 750 | 1,666 |
| 18.60% | 50.40% | 14.90% | 12.90% | 12.90% | 4.60% | 49.60% | 803 | 1,880 |
| 18.10% | 50.30% | 16.20% | 13.40% | 14.00% | 4.90% | 52.20% | 747 | 1,714 |
| 29.80% | 71.10% | 12.00% | 7.90% | 6.20% | 6.50% | 68.70% | 673 | 1,824 |
| 30.30% | 71.60% | 11.90% | 7.40% | 5.80% | 6.40% | 64.80% | 751 | 2,057 |
| 28.80% | 69.40% | 15.30% | 7.30% | 6.70% | 6.70% | 64.70% | 752 | 2,009 |
| 29.10% | 69.90% | 15.30% | 7.10% | 6.60% | 6.60% | 65.30% | 751 | 2,000 |
| 31.30% | 73.60% | 11.70% | 6.90% | 5.70% | 5.90% | 64.60% | 848 | 2,133 |
| 30.90% | 73.40% | 12.30% | 6.70% | 5.90% | 6.10% | 63.90% | 855 | 2,147 |
| 28.30% | 68.40% | 18.60% | 6.70% | 6.70% | 6.30% | 68.00% | 757 | 1,744 |
| 28.20% | 68.60% | 18.20% | 6.50% | 6.80% | 6.80% | 67.90% | 741 | 1,702 |

| A | B |

FIG. 54B

METHODS AND SYSTEMS FOR PROCESSING POLYNUCLEOTIDES

CROSS-REFERENCE

This application is a continuation of U.S. patent application Ser. No. 16/692,631, filed on Nov. 22, 2019, which is a continuation of Ser. No. 16/426,762, filed on May 30, 2019, now U.S. Pat. No. 10,480,029, which is a continuation-in-part of U.S. patent application Ser. No. 15/933,299, filed Mar. 22, 2018, now U.S. Pat. No. 10,480,029, which is a continuation of U.S. patent application Ser. No. 15/720,085, filed on Sep. 29, 2017, now U.S. Pat. No. 10,011,872, which claims priority to U.S. Provisional Patent Application No. 62/438,341, filed on Dec. 22, 2016; U.S. patent application Ser. No. 16/426,762 is also a continuation of U.S. Patent Application No. PCT/US2017/068320, filed Dec. 22, 2017, which claims priority to U.S. Provisional Patent Application No. 62/438,341, filed on Dec. 22, 2016, and is also a continuation-in-part of U.S. patent application Ser. No. 15/720,085, filed on Sep. 29, 2017, now U.S. Pat. No. 10,011,872, which claims priority to U.S. Provisional Patent Application No. 62/438,341, filed on Dec. 22, 2016. Each of the above-referenced applications is herein incorporated by reference in its entirety for all purposes.

SEQUENCE LISTING

The instant application contains a Sequence Listing which has been submitted electronically in ASCII format and is hereby incorporated by reference in its entirety. Said ASCII copy, created on May 23, 2019, is named 43487742601SL.txt and is 24,672 bytes in size.

BACKGROUND

Significant advances in analyzing and characterizing biological and biochemical materials and systems have led to unprecedented advances in understanding the mechanisms of life, health, disease and treatment. Among these advances, technologies that target and characterize the genomic make up of biological systems have yielded some of the most groundbreaking results, including advances in the use and exploitation of genetic amplification technologies, and nucleic acid sequencing technologies.

Nucleic acid sequencing can be used to obtain information in a wide variety of biomedical contexts, including diagnostics, prognostics, biotechnology, and forensic biology. Sequencing may involve basic methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others. Nucleic acid sequencing technologies, including next-generation DNA sequencing, have been useful for genomic and proteomic analysis of cell populations.

SUMMARY

Recognized herein is the need for methods, compositions and systems for analyzing genomic and proteomic information from individual cells or a small population of cells. Such cells include, but are not limited to, cancer cells, fetal cells, and immune cells involved in immune responses. Provided herein are methods, compositions and systems for analyzing individual cells or a small population of cells, including the analysis and attribution of nucleic acids and proteins from and to these individual cells or cell populations.

In an aspect, the present disclosure provides a method of characterizing a cell. The method comprises (a) providing a partition comprising a cell and at least one labelling agent, wherein the at least one labelling agent is (i) capable of binding to a cell surface feature of the cell and (ii) is coupled to a reporter oligonucleotide comprising a nucleic acid barcode sequence that permits identification of the at least one labelling agent, wherein the partition comprises an anchor oligonucleotide that is capable of interacting with the reporter oligonucleotide barcode; (b) in the partition, synthesizing a nucleic acid molecule comprising at least a portion of the nucleic acid barcode sequence or a complement thereof; and (c) subjecting the nucleic acid molecule to sequencing to identify the labelling agent or the cell.

In some embodiments, in (a), the at least one labelling agent is bound to the cell surface feature. In some embodiments, prior to (a), the at least one labelling agent is subjected to conditions suitable for binding the at least one labelling agent to the cell surface feature. In some embodiments, subjecting the at least one labelling agent to the conditions suitable for binding the at least one labelling agent to the cell surface feature is performed when the cell and the at least one labelling agent are free from the partition. In some embodiments, prior to (a), the at least one labelling agent is coupled to the reporter oligonucleotide.

In some embodiments, in (b), the reporter oligonucleotide is subjected to a primer extension reaction that generates the nucleic acid molecule. In some embodiments, the primer extension reaction comprises subjecting the reporter oligonucleotide to conditions suitable to hybridize the anchor oligonucleotide to the reporter oligonucleotide and extend the anchor oligonucleotide using the reporter oligonucleotide as a template.

In some embodiments, in (b), the anchor oligonucleotide is coupled to a bead. In some embodiments, in (b), the anchor oligonucleotide is coupled to a bead and the method further comprises releasing the anchor oligonucleotide from the bead prior to the synthesizing. In some embodiments, the bead is a gel bead. In some embodiments, the releasing comprises subjecting the bead to a stimulus that degrades the bead. In some embodiments, the stimulus is a chemical stimulus. In some embodiments, the bead comprises at least about 1,000 copies of the anchor oligonucleotide. In some embodiments, the bead comprises at least about 10,000 copies of the anchor oligonucleotide. In some embodiments, the bead comprises at least about 100,000 copies of the anchor oligonucleotide.

In some embodiments, prior to (c), the nucleic acid molecule is released from the partition. In some embodiments, (c) comprises identifying the at least one labelling agent. In some embodiments, (c) comprises identifying the cell surface feature from identifying the at least one labelling agent. In some embodiments, (c) comprises determining an abundance of the given cell surface feature on the cell. In some embodiments, (c) comprises identifying the cell. In some embodiments, (c) comprises identifying the at least one labelling agent and the cell.

In some embodiments, the reporter oligonucleotide comprises a unique molecular identification (UMI) sequence. In some embodiments, the UMI sequence permits identification of the cell. In some embodiments, (c) comprises determining a sequence of the UMI sequence and identifying the cell.

In some embodiments, the partition is a droplet in an emulsion. In some embodiments, the at least one labelling agent is selected from the group comprising of an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a probody, an aptamer, a monobody, an affimer, a darpin, a protein scaffold, an antigen, an antigen presenting particle and a major histocompatibility complex (MHC). In some embodiments, the cell surface feature is selected from the group comprising of a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, and an adherens junction. In some embodiments, the partition comprises only one cell.

In some embodiments, the cell is bound to at least one of the at least one labelling agent. In some embodiments, the at least one of the at least one labelling agent comprises at least two of the same labelling agent. In some embodiments, the at least one of the at least one labelling agent comprises at least two different labelling agents. In some embodiments, the cell is bound to at least about 5 different labelling agents. In some embodiments, the cell is bound to at least about 10 different labelling agents. In some embodiments, the cell is bound to at least about 50 different labelling agents. In some embodiments, the cell is bound to at least about 100 different labelling agents. In some embodiments, the (c) comprises determining an identity of at least a subset of the different labelling agents.

In some embodiments, the method further comprises (i) liberating nucleic acid from the cell and (ii) subjecting the nucleic acid or a derivative thereof to sequencing. In some embodiments, the nucleic acid is liberated from the cell into the partition.

In an aspect, the present disclosure provides a system for characterizing a cell. The system comprises an electronic display screen comprising a user interface that displays a graphical element that is accessible by a user to execute a protocol to characterize the cell; and a computer processor coupled to the electronic display screen and programmed to execute the protocol upon selection of the graphical element by the user, which protocol comprises: (a) providing a partition comprising a cell and at least one labelling agent, wherein the at least one labelling agent is (i) capable of binding to a cell surface feature of the cell and (ii) is coupled to a reporter oligonucleotide comprising a nucleic acid barcode sequence that permits identification of the at least one labelling agent, wherein the partition comprises an anchor oligonucleotide that is capable of interacting with the reporter oligonucleotide barcode; (b) in the partition, synthesizing a nucleic acid molecule comprising at least a portion of the nucleic acid barcode sequence or a complement thereof; and (c) subjecting the nucleic acid molecule to sequencing to identify the labelling agent or the cell.

In some embodiments, in protocol (a), the at least one labelling agent is bound to the cell surface feature. In some embodiments, prior to protocol (a), the at least one labelling agent is subjected to conditions suitable for binding the at least one labelling agent to the cell surface feature. In some embodiments, subjecting the at least one labelling agent to the conditions suitable for binding the at least one labelling agent to the cell surface feature is performed when the cell and the at least one labelling agent are free from the partition. In some embodiments, prior to protocol (a), the at least one labelling agent is coupled to the reporter oligonucleotide.

In some embodiments, in protocol (b), the reporter oligonucleotide is subjected to a primer extension reaction that generates the nucleic acid molecule. In some embodiments, the primer extension reaction comprises subjecting the reporter oligonucleotide to conditions suitable to hybridize the anchor oligonucleotide to the reporter oligonucleotide and extend the anchor oligonucleotide using the reporter oligonucleotide as a template.

In some embodiments, in protocol (b), the anchor oligonucleotide is coupled to a bead. In some embodiments, in (b), the anchor oligonucleotide is coupled to a bead and the method further comprises releasing the anchor oligonucleotide from the bead prior to the synthesizing. In some embodiments, the bead is a gel bead. In some embodiments, the releasing comprises subjecting the bead to a stimulus that degrades the bead. In some embodiments, the stimulus is a chemical stimulus. In some embodiments, the bead comprises at least about 1,000 copies of the anchor oligonucleotide. In some embodiments, the bead comprises at least about 10,000 copies of the anchor oligonucleotide. In some embodiments, the bead comprises at least about 100,000 copies of the anchor oligonucleotide.

In some embodiments, prior to protocol (c), the nucleic acid molecule is released from the partition. In some embodiments, protocol (c) comprises identifying the at least one labelling agent. In some embodiments, protocol (c) comprises identifying the cell surface feature from identifying the at least one labelling agent. In some embodiments, protocol (c) comprises determining an abundance of the given cell surface feature on the cell. In some embodiments, protocol (c) comprises identifying the cell. In some embodiments, protocol (c) comprises identifying the at least one labelling agent and the cell.

In some embodiments, the reporter oligonucleotide comprises a unique molecular identification (UMI) sequence. In some embodiments, the UMI sequence permits identification of the cell. In some embodiments, protocol (c) comprises determining a sequence of the UMI sequence and identifying the cell.

In some embodiments, the partition is a droplet in an emulsion. In some embodiments, the at least one labelling agent is selected from the group comprising of an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a probody, an aptamer, a monobody, an affimer, a darpin, a protein scaffold, an antigen, an antigen presenting particle and a major histocompatibility complex (MHC). In some embodiments, the cell surface feature is selected from the group comprising of a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, and an adherens junction. In some embodiments, the partition comprises only one cell.

In some embodiments, the cell is bound to at least one of the at least one labelling agent. In some embodiments, the at least one of the at least one labelling agent comprises at least two of the same labelling agent. In some embodiments, the at least one of the at least one labelling agent comprises at least two different labelling agents. In some embodiments, the cell is bound to at least about 5 different labelling agents. In some embodiments, the cell is bound to at least about 10 different labelling agents. In some embodiments, the cell is bound to at least about 50 different labelling agents. In some embodiments, the cell is bound to at least about 100 different labelling agents. In some embodiments, protocol (c) comprises determining an identity of at least a subset of the different labelling agents.

In some embodiments, protocol comprises (i) liberating nucleic acid from the cell and (ii) subjecting the nucleic acid or a derivative thereof to sequencing. In some embodiments, the nucleic acid is liberated from the cell into the partition.

An additional aspect of the disclosure provides a method for analyte characterization. The method includes: (a) providing a plurality of partitions, where a given partition of the plurality of partitions comprises a plurality of barcode molecules and a plurality of analytes. In some cases, the plurality of barcode molecules comprises at least 1,000 barcode molecules. In addition, (i) a first individual barcode molecule of the plurality of barcode molecules can comprise a first nucleic acid barcode sequence that is capable of coupling to a first analyte of the plurality of analytes, and (ii) a second individual barcode molecule of the plurality of barcoded molecules can comprise a second nucleic acid barcode sequence that is capable of coupling to a second analyte of the plurality of analytes where the first analyte and the second analyte are different types of analytes. The method also includes (b) in the given partition, (i) synthesizing a first nucleic acid molecule comprising at least a portion of the first nucleic acid barcode sequence or complement thereof, and (ii) synthesizing a second nucleic acid molecule comprising at least a portion of the second nucleic acid barcode sequence or complement thereof; and (c) removing the first nucleic acid molecule and the second nucleic acid molecule from the given partition.

In some embodiments, the method further comprises subjecting the first nucleic acid molecule and the second nucleic acid molecule, or a derivative of the first nucleic acid molecule and/or the second nucleic acid molecule, to sequencing to characterize the first analyte and/or the second analyte. In some embodiments, the method further comprises repeating (a)-(c) based on a characterization of the first analyte or the second analyte from the sequencing. In some embodiments, the method further comprises selecting the first analyte or the second analyte based on a characterization of the first analyte or the second analyte obtained from the sequencing or a subsequent sequencing upon repeating (a)-(c).

In some embodiments, (b) further comprises: (1) synthesizing the first nucleic acid molecule comprising at least a portion of the first nucleic acid barcode sequence or complement thereof, and (2) synthesizing the second nucleic acid molecule comprising at least a portion of the second nucleic acid barcode sequence or complement thereof.

In some embodiments, the first analyte is a nucleic acid molecule, such as genomic deoxyribonucleic acid (gDNA) or messenger RNA (mRNA).

In some embodiments, the first analyte is a labelling agent capable of coupling to a cell surface feature of a cell. In some embodiments, the first individual barcode molecule or the second individual barcode molecule is capable of coupling to the labelling agent via a third nucleic acid molecule coupled to the labelling agent. In some embodiments, the cell surface feature is a receptor, an antigen, or a protein. In some embodiments, the labelling agent is an antibody, an antibody fragment or a major histocompatibility complex (MEW). In some embodiments, the given partition comprises the cell or one or more components of the cell. In some embodiments, the given partition comprises a single cell. In some embodiments, the first nucleic acid molecule or the second nucleic molecule comprises a third barcode sequence. In some embodiments, the third barcode sequence is derived from a third nucleic acid molecule. In some embodiments, the third nucleic acid molecule is coupled to a labelling agent capable of binding to a cell surface feature of a cell.

In some embodiments, the first analyte and second analyte are different types of nucleic acid molecules. In some embodiments, the first analyte is a ribonucleic acid molecule and the second analyte is a deoxyribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to the second analyte. In some embodiments, the first barcode molecule or the second barcode molecule comprises a unique molecular identification (UMI) sequence.

In some embodiments, the first analyte is a nucleic acid molecule and the second analyte is a labelling agent capable of coupling to a cell surface feature. In some embodiments, the first analyte is a messenger ribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to the labelling agent. In some embodiments, the labelling agent is an antibody, or an epitope binding fragment thereof, or a major histocompatibility complex (WIC). In some embodiments, the cell surface feature is selected from the group consisting of a receptor, an antigen, or a protein.

In some embodiments, the first analyte comprises a nucleic acid molecule with a nucleic acid sequence or complement thereof that encodes at least a portion of a V(D)J sequence of an immune cell receptor. In some embodiments, the nucleic acid molecule is a messenger ribonucleic acid. In some embodiments, the nucleic acid molecule is complementary DNA (cDNA) derived from reverse transcription of an mRNA encoding the at least a portion of the V(D)J sequence.

In some embodiments, the first analyte comprises a nucleic acid molecule with a nucleic acid sequence that is capable of functioning as a component of a gene editing reaction. In some embodiments, the gene editing reaction comprises clustered regularly interspaced short palindromic repeats (CRISPR)-based gene editing.

In some embodiments, at least one of the first individual barcode molecule and the second individual barcode molecule is coupled to a bead, such as a gel bead. The bead can be degradable. In some embodiments, the method further comprises, after (a), releasing the first individual barcode molecule or the second individual barcode from the bead. In some embodiments, the given partition further comprises an agent capable of releasing the first individual barcode molecule or the second individual barcode from the bead.

In some embodiments, the given partition selected is a droplet among a plurality of droplets or a well among a plurality of wells. In some embodiments, the first nucleic acid barcode sequence and the second nucleic barcode sequence are identical. In some embodiments, the method further comprises performing one or more reactions subsequent to removing the first nucleic acid molecule and the second nucleic acid molecule from the given partition.

Another aspect of the disclosure provides a composition for characterizing a plurality of analytes. The composition comprises a partition comprising a plurality of barcode molecules and the plurality of analytes. The plurality of barcode molecules can comprise at least 1,000 barcode molecules. In addition, (i) a first individual barcode molecule of the plurality of barcode molecules can comprise a first nucleic acid barcode sequence that is capable of coupling to a first analyte of the plurality of analytes; and (ii) a second individual barcode molecule of the plurality of barcoded molecules can comprise a second nucleic acid barcode sequence that is capable of coupling to a second analyte of the plurality of analytes, where the first analyte and the second analyte are different types of analytes.

In some embodiments, the first analyte is a nucleic acid molecule, such as genomic deoxyribonucleic acid (gDNA) or is messenger RNA (mRNA).

In some embodiments, the first analyte is a labelling agent capable of coupling to a cell surface feature of a cell. In some embodiments, the first individual barcode molecule or the second individual barcode molecule is capable of coupling to the labelling agent via a third nucleic acid molecule coupled to the labelling agent. In some embodiments, the cell surface feature is a receptor, an antigen, or a protein. In some embodiments, the labelling agent is an antibody, or an epitope binding fragment thereof, or a major histocompatibility complex (MHC). In some embodiments, the partition comprises the cell or one or more components of the cell. In some embodiments, the partition comprises a single cell. In some embodiments, the first nucleic acid molecule or the second nucleic molecule comprises a third barcode sequence. In some embodiments, the third barcode sequence is derived from a third nucleic acid molecule. In some embodiments, the third nucleic acid molecule is coupled to a labelling agent capable of binding to a cell surface feature of a cell.

In some embodiments, the first analyte and second analyte are different types nucleic acid molecules. In some embodiments, the first analyte is a ribonucleic acid molecule and the second analyte is a deoxyribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to the second analyte. In some embodiments, the first barcode molecule or the second barcode molecule comprises a unique molecular identification (UMI) sequence.

In some embodiments, the first analyte is a nucleic acid molecule and the second analyte is a labelling agent capable of coupling to a cell surface feature. In some embodiments, the first analyte is a ribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to a third nucleic acid molecule coupled to the labelling agent. In some embodiments, the labelling agent is an antibody, or an epitope binding fragment thereof, or a major histocompatibility complex (MHC). In some embodiments, the cell surface feature is a receptor, an antigen, or a protein.

In some embodiments, the first analyte comprises a nucleic acid molecule with a nucleic acid sequence or complement thereof that encodes at least a portion of a V(D)J sequence of an immune cell receptor. In some embodiments, the nucleic acid sequence is a ribonucleic acid molecule. In some embodiments, the nucleic acid molecule comprises a nucleic acid sequence that is complementary DNA (cDNA) derived from reverse transcription of an mRNA encoding the at least a portion of the V(D)J sequence.

In some embodiments, the first analyte comprises a nucleic acid molecule with a nucleic acid sequence that is capable of functioning as a component of a gene editing reaction. In some embodiments, the gene editing reaction comprises clustered regularly interspaced short palindromic repeats (CRISPR)-based gene editing. In some embodiments, at least one of the first individual barcode molecule and the second individual barcode molecule is coupled to a bead, such as a gel bead. The bead may be degradable. In some embodiments, the given partition further comprises an agent capable of releasing the first individual barcode molecule or the second individual barcode from the bead. In some embodiments, the given partition is a droplet among a plurality of droplets or a well among a plurality of wells. In some embodiments, the first nucleic acid barcode sequence and the second nucleic barcode sequence are identical.

An additional aspect of the disclosure provides a system for characterizing a plurality of analytes. The system comprises a partitioning unit for providing a partition comprising a plurality of barcode molecules and the plurality of analytes, where: (i) a first individual barcode molecule of the plurality of barcode molecules comprises a first nucleic acid barcode sequence and is capable of coupling to a first analyte of the plurality of analytes; and (ii) a second individual barcode molecule of the plurality of barcode molecules comprises a second nucleic acid barcode sequence and is capable of coupling to a second analyte of the plurality of analytes, where the first analyte and the second analyte are different types of analytes. The system also includes a controller coupled to the partitioning unit, where the controller is programmed to (i) direct the partitioning unit to provide the partition; (ii) subject the partition to conditions that are sufficient to: (1) synthesize a first nucleic acid molecule comprising at least a portion of the first nucleic acid barcode sequence or complement thereof; and (2) synthesize a second nucleic acid molecule comprising at least a portion of the second nucleic acid barcode sequence or complement thereof, where sequencing of the first nucleic acid molecule and the second nucleic acid molecule, or derivatives thereof, characterizes the first analyte or the second analyte.

In some embodiments, the partitioning unit comprises a plurality of channels. In some embodiments, the partitioning unit further comprises at least one channel junction, where the at least one channel junction is configured to provide the partition. In some embodiments, the system also includes (i) a first channel fluidically connected to the at least one channel junction and configured to provide a first fluid to the at least one channel junction; (ii) and a second channel fluidically connected to the at least one channel junction and configured to provide a second fluid, immiscible with the first fluid, to the at least one channel junction.

In some embodiments, the first analyte is a nucleic acid molecule, such as genomic deoxyribonucleic acid (gDNA) or messenger RNA (mRNA).

In some embodiments, the first analyte is a labelling agent capable of coupling to a cell surface feature of a cell. In some embodiments, the first individual barcode molecule or the second individual barcode molecule is capable of coupling to the labelling agent via a third nucleic acid molecule coupled to the labelling agent. In some embodiments, the cell surface feature is a receptor, an antigen, or a protein. In some embodiments, the labelling agent is an antibody, or an epitope binding fragment thereof, or a major histocompatibility complex (MHC). In some embodiments, the partition comprises the cell or one or more components of the cell. In some embodiments, the partition comprises a single cell. In some embodiments, the first nucleic acid molecule or the second nucleic molecule comprises a third barcode sequence. In some embodiments, the third barcode sequence is derived from a third nucleic acid molecule. In some embodiments, the third nucleic acid molecule is coupled to a labelling agent capable of binding to a cell surface feature of a cell.

In some embodiments, the first analyte and second analyte are different types nucleic acid molecules. In some embodiments, the first analyte is a ribonucleic acid molecule and the second analyte is a deoxyribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to the second analyte. In some embodiments, the first barcode molecule or the second barcode molecule comprises a unique molecular identification (UMI) sequence.

In some embodiments, the first analyte is a nucleic acid molecule and the second analyte is a labelling agent capable of coupling to a cell surface feature. In some embodiments, the first analyte is a ribonucleic acid molecule. In some embodiments, (i) the first individual barcode molecule comprises a first priming sequence capable of hybridizing to the first analyte; or (ii) the second individual barcode molecule comprises a second priming sequence capable of hybridizing to a third nucleic acid molecule coupled to the labelling agent. In some embodiments, the labelling agent is an antibody, or an epitope binding fragment thereof, or a major histocompatibility complex (MHC). In some embodiments, the cell surface feature is a receptor, an antigen, or a protein.

In some embodiments, the first analyte comprises a nucleic acid molecule with a nucleic acid sequence or complement thereof that encodes at least a portion of a V(D)J sequence of an immune cell receptor. In some embodiments, the nucleic acid sequence is a messenger ribonucleic acid molecule. In some embodiments, the nucleic acid molecule is complementary DNA (cDNA) derived from reverse transcription of an mRNA encoding the at least a portion of the V(D)J sequence.

In some embodiments, the first analyte comprises a nucleic acid molecule with a nucleic acid sequence that is capable of functioning as a component of a gene editing reaction. In some embodiments, the gene editing reaction comprises clustered regularly interspaced short palindromic repeats (CRISPR)-based gene editing.

In some embodiments, at least one of the first individual barcode molecule and the second individual barcode molecule is coupled to a bead, such as a gel bead. The bead may be degradable. In some embodiments, the partition further comprises an agent capable of releasing the first individual barcode molecule or the second individual barcode molecule from the bead. In some embodiments, the partition is a droplet among a plurality of droplets or a well among a plurality of wells. In some embodiments, the nucleic acid barcode sequence and the second nucleic barcode sequence are identical. In some embodiments, the partition comprises at least 1,000 barcode molecules.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 8 provides an image of individual cells co-partitioned along with individual barcode bearing beads;

FIGS. 9A-9E provide schematic illustrations of example barcoded oligonucleotide structures for use in analysis of RNA and example operations for performing RNA analysis ("AAAAAAAAAAAAAAAA" disclosed as SEQ ID NO: 1);

FIG. 20 shows a method for characterizing a cell, according to embodiments;

FIG. 21 shows an oligonucleotide with modifications that may prevent extension by a polymerase;

FIG. 23A shows a bead coupled with an oligonucleotide comprising a target-specific primer and oligonucleotides with poly-T primers (SEQ ID NOS 4-5, and 4, respectively, in order of appearance); FIG. 23B shows a bead coupled with a plurality of oligonucleotides, each of which comprises a target-specific primer (SEQ ID NOS 5, 5, 5, and 5, respectively, in order of appearance); FIG. 23C shows a bead coupled with a plurality of oligonucleotides, each of which comprises a target-specific primer and a plurality of oligonucleotides, each of which comprises a poly-T primer (SEQ ID NOS 4-5, 5, 5, 5, and 4, respectively, in order of appearance);

FIG. 24 shows a bead coupled with a plurality of oligonucleotides, each of which comprises a target-specific primer and a plurality of oligonucleotides, each of which comprises a random N-mer primer for total RNA (SEQ ID NOS 6-7, 7, 7, 7, and 6, respectively, in order of appearance);

FIG. 27B shows y oligonucleotides with backbones comprising R1 sequences and poly-T primers (SEQ ID NOS 15, 45, 16, 46, 17, 47, 4, 48, and 4, respectively, in order of appearance). FIG. 27C shows oligonucleotides with P5, R1, and R2 sequences and poly-T primers (SEQ ID NOS 18, 49, 18-19, 50, and 19, respectively, in order of appearance). FIG. 27D shows oligonucleotides with R1 sequences and random N-mer primers (SEQ ID NOS 20, 51, 21, 51, 22, 51, 6, 51, and 6, respectively, in order of appearance).

FIG. 37 shows analysis results of the CD3 protein-single-stranded DNA (ssDNA) conjugate;

FIGS. 47A-B depicts data obtained from an example experiment described in Example XI;

FIG. 48 depicts data obtained from an example experiment described in Example XI;

FIGS. 49A-D depict data obtained from an example experiment described in Example XI;

FIGS. 50B and 50C schematically depict example sequences that can be coupled to a bead (SEQ ID NOS 33, 52, 34, 53, 35, 54, 36, 55, 37, 56, 37, 56, 37, 56, 37, and 56, respectively, in order of appearance);

FIG. 51A depicts sequences (SEQ ID NOS 38 and 39, respectively, in order of appearance) used in an example experiment described in Example XII.

FIG. 52B schematically depicts example extension schemes to link barcodes;

FIGS. 53A and 53B provide data obtained from an example experiment described in Example XIII;

FIGS. 54A, 54B and 55 provide data obtained from example experiments described in Example XIV.

FIG. 58A shows a representative denaturing agarose gel while FIG. 58B shows a representative SDS-PAGE gel.

DETAILED DESCRIPTION

Figure 1:
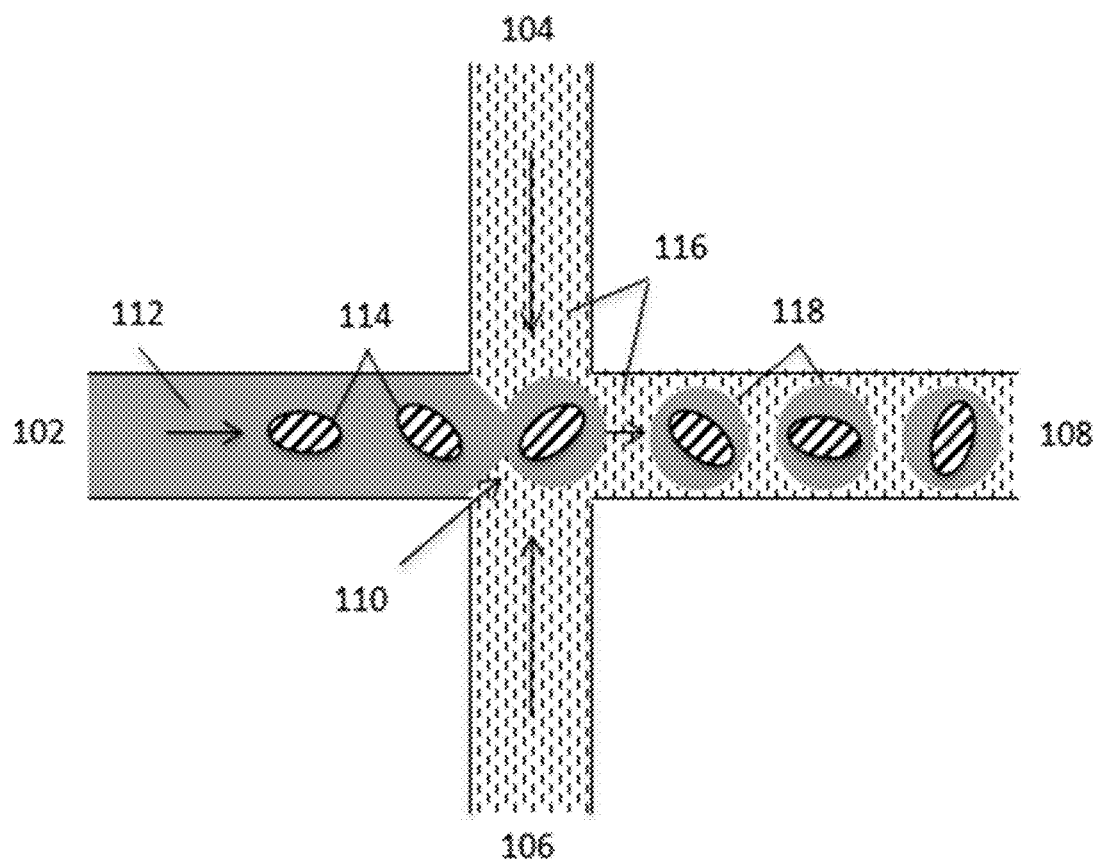
FIG. 1 schematically illustrates a microfluidic channel structure for partitioning individual or small groups of cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that can be part of an analyte to convey information about the analyte. A barcode can be a tag attached to an analyte (e.g., nucleic acid molecule) or a combination of the tag in addition to an endogenous characteristic of the analyte (e.g., size of the analyte or end sequence(s)). The barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "subject," as used herein, generally refers to an animal, such as a mammalian species (e.g., human) or avian (e.g., bird) species, or other organism, such as a plant. The subject can be a vertebrate, a mammal, a mouse, a primate, a simian or a human. Animals may include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome," as used herein, generally refers to an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). Such devices may provide a plurality of raw genetic data corresponding to the genetic information of a subject (e.g., human), as generated by the device from a sample provided by the subject. In some situations, systems and methods provided herein may be used with proteomic information.

The term "variant," as used herein, generally refers to a genetic variant, such as a nucleic acid molecule comprising a polymorphism. A variant can be a structural variant or copy number variant, which can be genomic variants that are larger than single nucleotide variants or short indels. A variant can be an alteration or polymorphism in a nucleic acid sample or genome of a subject. Single nucleotide polymorphisms (SNPs) are a form of polymorphisms. Polymorphisms can include single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alteration may be a base change, insertion, deletion, repeat, copy number variation, or transversion.

The term "bead," as used herein, generally refers to a particle. The bead may be a solid or semi-solid particle. The bead may be a gel. The bead may be formed of a polymeric material. The bead may be magnetic or non-magnetic.

The term "sample," as used herein, generally refers to a biological sample of a subject. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free (or cell free) sample. A cell-free sample may include extracellular polynucleotides. Extracellular polynucleotides may be isolated from a bodily sample that may be selected from a group consisting of blood, plasma, serum, urine, saliva, mucosal excretions, sputum, stool and tears.

The term "nucleic acid," as used herein, generally refers to a monomeric or polymeric form of nucleotides of any length, either deoxyribonucleotides or ribonucleotides, or analogs or variants thereof. A nucleic acid molecule may include one or more unmodified or modified nucleotides. Nucleic acid may have any three dimensional structure, and may perform any function. The following are non-limiting examples of nucleic acids: ribonucleic acid (RNA), deoxyribonucleic acid (DNA), coding or non-coding regions of a gene or gene fragment, loci (locus) defined from linkage analysis, exons, introns, messenger RNA (mRNA), transfer ribonucleic acid (RNA), ribosomal RNA, short interfering RNA (siRNA), short-hairpin RNA (shRNA), micro-RNA (miRNA), ribozymes, complementary deoxyribonucleic acid (cDNA), recombinant polynucleotides, branched polynucleotides, plasmids, vectors, isolated DNA of any sequence, isolated RNA of any sequence, nucleic acid probes, and primers. Nucleic acid may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. A nucleic acid may include one or more subunits selected from adenosine (A), cytosine (C), guanine (G), thymine (T) and uracil (U), or variants thereof. In some examples, a nucleic acid is DNA or RNA, or derivatives thereof. A nucleic acid may be single-stranded or double stranded. A nucleic acid may be circular.

The term "nucleotide," as used herein, generally refers to a nucleic acid subunit, which may include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

The term "analyte," as used herein, generally refers to a substance or one or more constituents thereof that is for identification, such as detection (e.g., detection via sequencing). Examples of analytes include, without limitation, DNA, RNA, a labelling agent, antibody, and protein. An analyte may be a cell or one or more constituents of a cell.

Analytes may be of different types. In some examples, in a plurality of analytes, a given analyte is of a different structural or functional class from other analytes of the plurality. Examples of different types of analytes include DNA and RNA; a nucleic acid molecule and a labelling agent; a transcript and genomic nucleic acid; a plurality of nucleic acid molecules, where each nucleic acid molecule has a different function, such as a different cellular function. A sample may have a plurality of analytes of different types, such as a mixture of DNA and RNA molecules, or a mixture of nucleic acid molecules and labelling agents. In some cases, different types of analytes do not include labelling agents directed to separate cell surface features of a cell.

The term "epitope binding fragment," as used herein generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an $F(ab')_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

Nucleic acid sequencing technologies have yielded substantial results in sequencing biological materials, including providing substantial sequence information on individual organisms, and relatively pure biological samples. However, these systems have traditionally not been effective at being able to identify and characterize cells at the single cell level.

Nucleic acid sequencing technologies may derive the nucleic acids that they sequence from collections of cells obtained from tissue or other samples, such as biological fluids (e.g., blood, plasma, etc). The cells can be processed (e.g., all together in an ensemble approach) to extract the genetic material that represents an average of the population of cells, which can then be processed into sequencing ready DNA libraries that are configured for a given sequencing technology. Although often discussed in terms of DNA or nucleic acids, the nucleic acids derived from the cells may include DNA, or RNA, including, e.g., mRNA, total RNA, or the like, that may be processed to produce cDNA for sequencing.

In addition to the inability to attribute characteristics to particular subsets of cells or individual cells, such ensemble sample preparation methods can be, from the outset, predisposed to primarily identifying and characterizing the majority constituents in the sample of cells, and may not be designed to pick out the minority constituents, e.g., genetic or proteomic material contributed by one cell, a few cells, or a small percentage of total cells in the sample. Likewise, where analyzing expression levels, e.g., of mRNA or cell surface proteins, an ensemble approach can be predisposed to presenting potentially inaccurate data from cell populations that are non-homogeneous in terms of expression levels. In some cases, where expression is high in a small minority of the cells in an analyzed population, and absent in the majority of the cells of the population, an ensemble method may indicate low level expression for the entire population.

These inaccuracies can be further magnified through processing operations used in generating the sequencing libraries from these samples. Some next generation sequencing technologies (e.g., massively parallel sequencing) may rely upon the geometric amplification of nucleic acid fragments, such as via polymerase chain reaction, in order to produce sufficient DNA for the sequencing library. However, such amplification can be biased toward amplification of majority constituents in a sample, and may not preserve the starting ratios of such minority and majority components. While some of these difficulties may be addressed by utilizing different sequencing systems, such as single molecule systems that do not require amplification, the single molecule systems, as well as the ensemble sequencing methods of other next generation sequencing (NGS) systems, can also have large input DNA requirements. Some single molecule sequencing systems, for example, can have sample input DNA requirements of from 500 nanograms (ng) to upwards of 10 micrograms (μg), which may not be obtainable from individual cells or small subpopulations of cells. Likewise, other NGS systems can be optimized for starting amounts of sample DNA in the sample of from approximately 50 nanograms (ng) to about 1 microgram (μg). Starting amounts of DNA may be at least about 1 ng, 10 ng, 20 ng, 30 ng, 40 ng, 50 ng, 100 ng, 500 ng, 1 μg, 10 μg, or 100 μg.

Disclosed herein are methods and systems for characterizing surface features, proteins, and nucleic acids of small populations of cells, and in some cases, for characterizing surface features, proteins, and nucleic acids of individual cells. The methods described herein may compartmentalize the analysis of individual cells or small populations of cells, including e.g., cell surface features, proteins, and nucleic acids of individual cells or small groups of cells, and then allow that analysis to be attributed back to the individual cell or small group of cells from which the cell surface features, proteins, and nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells from different tissue types of an individual or the same tissue type from different individuals, or biological organisms such as microorganisms from differing genera, species, strains, variants, or any combination of any or all of the foregoing. For example, differing cell types may include normal and tumor tissue from an individual, various cell types obtained from a human subject such as a variety of immune cells (e.g., B cells, T cells, and the like), multiple different bacterial species, strains and/or variants from environmental, forensic, microbiome or other samples, or any of a variety of other mixtures of cell types.

In one aspect, the methods and systems described herein provide for the compartmentalization, depositing or partitioning of the nucleic acid contents of individual cells from a sample material containing cells, into discrete compartments or partitions (referred to interchangeably herein as partitions), where each partition maintains separation of its own contents from the contents of other partitions. In another aspect, the methods and system described herein provide for the compartmentalization, depositing or partitioning of individual cells from a sample material containing cells, into discrete partitions, where each partition maintains separation of its own contents from the contents of other partitions. In another aspect, the methods and system described herein provide for the compartmentalization, depositing or partitioning of individual cells from a sample material containing cells after at least one labelling agent has been bound to a cell surface feature of the cell, into discrete partitions, where each partition maintains separation of its own contents from the contents of other partitions. Unique identifiers, e.g., barcodes, may be previously, subsequently or concurrently delivered to the partitions that hold the compartmentalized or partitioned cells, in order to allow for the later attribution of the characteristics of the individual cells to the particular compartment. Further, unique identifiers, e.g., barcodes, may be coupled to labelling agents and previously, subsequently or concurrently delivered to the partitions that hold the compartmentalized or partitioned cells, in order to allow for the later attribution of the characteristics of the individual cells to the particular compartment. Barcodes may be delivered, for example on an oligonucleotide, to a partition via any suitable mechanism.

In some embodiments, barcoded oligonucleotides are delivered to a partition via a microcapsule. In some cases, barcoded oligonucleotides are initially associated with the microcapsule and then released from the microcapsule upon application of a stimulus which allows the oligonucleotides to dissociate or to be released from the microcapsule. In some embodiments, anchor oligonucleotides are delivered to a partition via a microcapsule. In some cases, anchor oligonucleotides are initially associated with the microcapsule and then released from the microcapsule upon application of a stimulus which allows the anchor oligonucleotides to dissociate or to be released from the microcapsule.

A microcapsule may be or may include a solid support or solid particle such as a bead. A solid support or a solid particle may be a bead. A microcapsule may be a droplet. A microcapsule, in some embodiments, may be or may comprise a bead. In some embodiments, a bead may be porous, non-porous, solid, semi-solid, semi-fluidic, or fluidic. In some embodiments, a bead may be dissolvable, disruptable, or degradable. In some cases, a bead may not be degradable. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the beads may be silica beads. In some cases, the beads may be rigid. In some cases, the beads may be flexible and/or compressible.

In some embodiments, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor comprises one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials. For example, a polymer can be a natural polymer or a synthetic polymer. In some cases, a bead may comprise both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly (ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads may also be formed from materials other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to attach oligonucleotides (e.g., barcoded oligonucleotides) to the bead. In some cases, polymers may be further polymerized with a cross-linker species or other type of monomer to generate a further polymeric network. Non-limiting examples of chemical cross-linkers (also referred to as a "crosslinker" or a "crosslinker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilane, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some embodiments, disulfide linkages can be formed between molecular precursor units (e.g., monomers, oligomers, or linear polymers) or precursors incorporated into a bead and oligonucleotides. Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some embodiments, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g., monomers, oligomers, linear polymers), oligonucleotides, primers, and other entities. In some cases, the covalent bonds comprise carbon-carbon bonds or thioether bonds.

In some cases, a bead may comprise an acrydite moiety, which in certain aspects may be used to attach one or more oligonucleotides (e.g., barcode sequence, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as an oligonucleotide (e.g., barcode sequence, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment is reversible, such that when the disulfide bond is broken (e.g., in the presence of a reducing agent), the attached species is released from the bead. In other cases, an acrydite moiety comprises a reactive hydroxyl group that may be used for attachment.

Functionalization of beads for attachment of oligonucleotides may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to an oligonucleotide, such as a primer (e.g., a primer for amplifying target nucleic acids, barcoded oligonucleotide, etc) to be incorporated into the bead. In some cases, the primer comprises a P5 sequence for attachment to a sequencing flow cell for Illumina sequencing. In some cases, the primer comprises a P7 sequence for attachment to a sequencing flow cell for Illumina sequencing. In some cases, the primer comprises a barcode sequence. In some cases, the primer further comprises a unique molecular identifier (UMI). In some cases, the primer comprises an R1 primer sequence for Illumina sequencing. In some cases, the primer comprises an R2 primer sequence for Illumina sequencing.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal about 10000, 100000, 1000000, 10000000, 100000000, 1000000000, 10000000000, or 100000000000) of reducing agent may be used for reduction. Controlling the number of disulfide linkages that are reduced to free thiols may be useful in ensuring bead structural integrity during functionalization. In some cases, optically-active agents, such as fluorescent dyes may be may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

In some cases, an acrydite moiety linked to precursor, another species linked to a precursor, or a precursor itself comprises a labile bond, such as chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

Species (e.g., oligonucleotides comprising barcodes) attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides (e.g. barcoded oligonucleotides and/or anchor oligonucleotides), reagents for a nucleic acid amplification reaction (e.g., primers, polymerases, dNTPs, cofactors (e.g., ionic co-factors)) including those described herein, reagents for enzymatic reactions (e.g., enzymes, co-factors, substrates), or reagents for a nucleic acid modification reactions such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some cases, the diameter of a bead may be about 1 micrometer ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, or 1 mm. In some cases, a bead may have a diameter of at least about 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or more. In some cases, a bead may have a diameter of less than or equal to about 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, or 1 mm. In some cases, a bead may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$.

In certain aspects, beads are provided as a population or plurality of beads having a relatively monodisperse size distribution. Such monodispersity can provide relatively consistent amounts of reagents within partitions and maintain relatively consistent bead characteristics. In particular, the beads described herein may have size distributions that have a coefficient of variation in their cross-sectional dimensions of less than or equal to about 50%, less than or equal to about 40%, less than or equal to about 30%, less than or equal to about 20%, less than or equal to about 15%, less than or equal to about 10%, or less than or equal to about 5%.

Beads may be of any suitable shape. Examples of bead shapes include, but are not limited to, spherical, non-spherical, oval, oblong, amorphous, circular, cylindrical, and variations thereof.

In addition to, or as an alternative to the cleavable linkages between the beads and the associated molecules, e.g., barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead is degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., an oligonucleotide, e.g., barcoded oligonucleotide) may result in release of the species from the bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., an oligonucleotide, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent may break the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it can be useful to avoid exposing such beads to the stimulus or stimuli that cause such degradation prior to a given time, in order to avoid premature bead degradation and issues that arise from such degradation, including, for example poor flow characteristics and aggregation. By way of example, where beads comprise reducible cross-linking groups, such as disulfide groups, it can be useful to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, reducing agent free (or DTT free) enzyme preparations may be provided in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than or equal to about $1/10$th, less than or equal to about $1/50$th, or less than or equal to about $1/100$th of the lower ranges for such materials used in degrading the beads. For example, for DTT, the reducing agent free preparation will typically have less than or equal to about 0.01 mM, 0.005 mM, 0.001 mM DTT, 0.0005 mM DTT, or 0.0001 mM DTT. In some cases, the amount of DTT will be undetectable.

In some cases, a stimulus may be used to trigger degradation of the bead, which may result in the release of contents from the bead. Generally, a stimulus may cause degradation of the bead structure, such as degradation of the covalent bonds or other types of physical interaction. These stimuli may be useful in inducing a bead to degrade and/or to release its contents. Examples of stimuli that may be used include chemical stimuli, thermal stimuli, optical stimuli (e.g., light) and any combination thereof, as described more fully below.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, or 10 mM. The reducing agent may be present at a concentration of at least about 0.1 mM, 0.5 mM, 1 mM, 5 mM, 10 mM, or greater. The reducing agent may be present at concentration of at most about 0.1 mM, 0.5 mM, 1 mM, 5 mM, or 10 mM.

Any suitable number of nucleic acid molecules (e.g., primer, barcoded oligonucleotide, anchor oligonucleotide) can be associated with a bead such that, upon release from the bead, the nucleic acid molecules (e.g., primer, barcoded oligonucleotide, anchor oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer is limited by the process of producing oligonucleotide bearing beads.

In some aspects, the partitions refer to containers or vessels (such as wells, microwells, tubes, vials, through ports in nanoarray substrates, e.g., BioTrove nanoarrays, or other containers). In some aspects, the compartments or partitions comprise partitions that are flowable within fluid streams. These partitions may comprise, e.g., micro-vesicles that have an outer barrier surrounding an inner fluid center or core, or, in some cases, they may comprise a porous matrix that is capable of entraining and/or retaining materials within its matrix. In some aspects, partitions comprise droplets of aqueous fluid within a non-aqueous continuous phase, e.g., an oil phase. Examples of different vessels are described in U.S. Patent Application Publication No. 2014/0155295, which is entirely incorporated herein by reference for all purposes. Examples of emulsion systems for creating stable droplets in non-aqueous or oil continuous phases are described in detail in U.S. Patent Application Publication No. 2010/0105112, which is entirely incorporated herein by reference for all purposes.

In the case of droplets in an emulsion, allocating individual cells to discrete partitions may generally be accomplished by introducing a flowing stream of cells in an aqueous fluid into a flowing stream of a non-aqueous fluid, such that droplets are generated at the junction of the two streams. By providing the aqueous cell-containing stream at a certain concentration of cells, the occupancy of the resulting partitions (e.g., number of cells per partition) can be controlled. Where single cell partitions are implemented, the relative flow rates of the fluids can be selected such that, on average, the partitions contain less than one cell per partition, in order to ensure that those partitions that are occupied, are primarily singly occupied. In some embodiments, the relative flow rates of the fluids can be selected such that a majority of partitions are occupied, e.g., allowing for only a small percentage of unoccupied partitions. In some aspects, the flows and channel architectures are controlled as to ensure a number of singly occupied partitions, less than a certain level of unoccupied partitions and less than a certain level of multiply occupied partitions.

The systems and methods described herein can be operated such that a majority of occupied partitions include no more than one cell per occupied partition. In some cases, the partitioning process is conducted such that fewer than 25% of the occupied partitions contain more than one cell, and in some cases, fewer than 20% of the occupied partitions have more than one cell. In some cases, fewer than 10% or fewer than 5% of the occupied partitions include more than one cell per partition.

In some cases, it can be useful to avoid the creation of excessive numbers of empty partitions. For example, from a cost perspective and/or efficiency perspective, it may helpful to minimize the number of empty partitions. While this may be accomplished by providing sufficient numbers of cells into the partitioning zone, the Poissonian distribution may expectedly increase the number of partitions that may include multiple cells. As such, in accordance with aspects described herein, the flow of one or more of the cells, or other fluids directed into the partitioning zone are conducted such that, in some cases, no more than 50% of the generated partitions, no more than 25% of the generated partitions, or no more than 10% of the generated partitions are unoccupied. Further, in some aspects, these flows are controlled so as to present non-Poissonian distribution of single occupied partitions while providing lower levels of unoccupied partitions. The above ranges of unoccupied partitions can be achieved while still providing any of the single occupancy rates described above. For example, the use of the systems and methods described herein creates resulting partitions that have multiple occupancy rates of less than or equal to about 25%, 20%, 15%, 10%, or 5%, while having unoccupied partitions of less than or equal to about 50%, 40%, 30%, 20%, 10%, or 5%.

As will be appreciated, the above-described occupancy rates are also applicable to partitions that include both cells and additional reagents and agents, including, but not limited to, microcapsules carrying barcoded oligonucleotides, microcapsules carrying anchoring oligonucleotides, labelling agents, labelling agents comprising reporter oligonucleotides, labelling agents comprising reporter oligonucleotides comprising a nucleic barcode sequence, and cells with one or more labelling agents bound to one or more cell surface features. In some aspects, a substantial percentage of the overall occupied partitions can include a microcapsule (e.g., bead) comprising barcodes or anchoring oligonucleotides and a cell with or without bound labelling agents.

Although described in terms of providing substantially singly occupied partitions, above, in certain cases, it can be useful to provide multiply occupied partitions, e.g., containing two, three, four or more cells and/or microcapsules (e.g., beads) comprising barcoded oligonucleotides or anchor oligonucleotides within a single partition. Accordingly, the flow characteristics of the cell and/or bead containing fluids and partitioning fluids may be controlled to provide for such multiply occupied partitions. In particular, the flow parameters may be controlled to provide an occupancy rate at greater than or equal to about 50% of the partitions, greater than or equal to about 75%, or greater than or equal to about 80%, 90%, 95%, or higher.

In some cases, additional microcapsules are used to deliver additional reagents to a partition. In such cases, it may be advantageous to introduce different beads into a common channel or droplet generation junction, from different bead sources, i.e., containing different associated reagents, through different channel inlets into such common channel or droplet generation junction. In such cases, the flow and frequency of the different beads into the channel or junction may be controlled to provide for a suitable ratio of microcapsules from each source, while ensuring the pairing or combination of such beads into a partition with the number of cells.

The partitions described herein may comprise small volumes, e.g., less than or equal to 10 □L, 5 □L, 1 □L, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than or equal to 1000 pL, 900 pL, 800 pL, 700 pL, 600 pL, 500 pL, 400 pL, 300 pL, 200 pL, 100 pL, 50 pL, 20 pL, 10 pL, or 1 pL. Where co-partitioned with microcapsules, it will be appreciated that the sample fluid volume, e.g., including co-partitioned cells, within the partitions may be less than or equal to 90%, 80%, 70%, 60%, 50%, 40%, 30%, 20%, 10%, or less than the above described volumes.

As is described elsewhere herein, partitioning species may generate a population or plurality of partitions. In such cases, any suitable number of partitions can be generated to generate the plurality of partitions. For example, in a method described herein, a plurality of partitions may be generated that comprises at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions or at least about 1,000,000,000 partitions. Moreover, the plurality of partitions may comprise both unoccupied partitions (e.g., empty partitions) and occupied partitions Microfluidic channel networks can be utilized to generate partitions as described herein. Alternative mechanisms may also be employed in the partitioning of individual cells, including porous membranes through which aqueous mixtures of cells are extruded into non-aqueous fluids.

An example of a simplified microfluidic channel structure for partitioning individual cells is illustrated in FIG. 1. Cells may be partitioned with or without labelling agents bound to cell surface features, as described herein. As described herein, in some cases, the majority of occupied partitions include no more than one cell per occupied partition and, in some cases, some of the generated partitions are unoccupied. In some cases, though, some of the occupied partitions may include more than one cell. In some cases, the partitioning process may be controlled such that fewer than 25% of the occupied partitions contain more than one cell, and in some cases, fewer than 20% of the occupied partitions have more than one cell, while in some cases, fewer than 10% or fewer than 5% of the occupied partitions include more than one cell per partition. As shown, the channel structure can include channel segments 102, 104, 106 and 108 communicating at a channel junction 110. In operation, a first aqueous fluid 112 that includes suspended cells 114, may be transported along channel segment 102 into junction 110, while a second fluid 116 that is immiscible with the aqueous fluid 112 is delivered to the junction 110 from channel segments 104 and 106 to create discrete droplets 118 of the aqueous fluid including individual cells 114, flowing into channel segment 108.

In some aspects, this second fluid 116 comprises an oil, such as a fluorinated oil, that includes a fluorosurfactant for stabilizing the resulting droplets, e.g., inhibiting subsequent coalescence of the resulting droplets. Examples of partitioning fluids and fluorosurfactants are described in U.S. Patent Application Publication No. 2010/0105112, which is entirely incorporated herein by reference for all purposes.

In other aspects, in addition to or as an alternative to droplet based partitioning, cells (with or without labelling agents bound to cell surface features, as described herein) may be encapsulated within a microcapsule that comprises an outer shell or layer or porous matrix in which is entrained one or more individual cells or small groups of cells, and may include other reagents. Encapsulation of cells may be carried out by a variety of processes. Such processes combine an aqueous fluid containing the cells to be analyzed with a polymeric precursor material that may be capable of being formed into a gel or other solid or semi-solid matrix upon application of a particular stimulus to the polymer precursor. Such stimuli include, e.g., thermal stimuli (either heating or cooling), photo-stimuli (e.g., through photo-curing), chemical stimuli (e.g., through crosslinking, polymerization initiation of the precursor (e.g., through added initiators), or the like.

Preparation of microcapsules comprising cells may be carried out by a variety of methods. For example, air knife droplet or aerosol generators may be used to dispense droplets of precursor fluids into gelling solutions in order to form microcapsules that include individual cells or small groups of cells. Likewise, membrane based encapsulation systems may be used to generate microcapsules comprising encapsulated cells as described herein. In some aspects, microfluidic systems like that shown in FIG. 1 may be readily used in encapsulating cells as described herein. In particular, and with reference to FIG. 1, the aqueous fluid comprising the cells and the polymer precursor material is flowed into channel junction 110, where it is partitioned into droplets 118 comprising the individual cells 114, through the flow of non-aqueous fluid 116. In the case of encapsulation methods, non-aqueous fluid 116 may also include an initiator to cause polymerization and/or crosslinking of the polymer precursor to form the microcapsule that includes the entrained cells. Examples of polymer precursor/initiator pairs are described in U.S. Patent Application Publication No. 2014/0378345, which is entirely incorporated herein by reference for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) co-monomer, an agent such as tetraethylmethylenediamine (TEMED) may be provided within the second fluid streams in channel segments 104 and 106, which initiates the copolymerization of the acrylamide and BAC into a cross-linked polymer network or, hydrogel.

Upon contact of the second fluid stream 116 with the first fluid stream 112 at junction 110 in the formation of droplets, the TEMED may diffuse from the second fluid 116 into the aqueous first fluid 112 comprising the linear polyacrylamide, which will activate the crosslinking of the polyacrylamide within the droplets, resulting in the formation of the gel, e.g., hydrogel, microcapsules 118, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions, e.g., $Ca^{2+}$, can be used as an encapsulation process using the described processes. Likewise, agarose droplets may also be transformed into capsules through temperature based gelling, e.g., upon cooling, or the like. In some cases, encapsulated cells can be selectively releasable from the microcapsule, e.g., through passage of time, or upon application of a particular stimulus, that degrades the microcapsule sufficiently to allow the cell, or its contents to be released from the microcapsule, e.g., into a partition, such as a droplet. For example, in the case of the polyacrylamide polymer described above, degradation of the microcapsule may be accomplished through the introduction of an appropriate reducing agent, such as DTT or the like, to cleave disulfide bonds that cross link the polymer matrix. See, e.g., U.S. Patent Application Publication No. 2014/0378345, which is entirely incorporated herein by reference for all purposes.

Encapsulated cells or cell populations provide certain potential advantages of being storable, and more portable than droplet based partitioned cells. Furthermore, in some cases, it may cells to be analyzed can be incubated for a select period of time, in order to characterize changes in such cells over time, either in the presence or absence of different stimuli. In such cases, encapsulation of individual cells may allow for longer incubation than partitioning in emulsion droplets, although in some cases, droplet partitioned cells may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of cells may constitute the partitioning of the cells into which other reagents are co-partitioned. Alternatively, encapsulated cells may be readily deposited into other partitions, e.g., droplets, as described above.

In accordance with certain aspects, the cells may be partitioned along with lysis reagents in order to release the contents of the cells within the partition. In such cases, the lysis agents can be contacted with the cell suspension concurrently with, or immediately prior to the introduction of the cells into the partitioning junction/droplet generation zone, e.g., through an additional channel or channels upstream of channel junction 110. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the cells to cause the release of the cell's contents into the partitions. For example, in some cases, surfactant based lysis solutions may be used to lyse cells. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of cells that may be in addition to or in place of droplet partitioning, where any pore size of the encapsulate is sufficiently small to retain nucleic acid fragments of a suitable size, following cellular disruption.

In addition to the lysis agents co-partitioned with the cells described above, other reagents can also be co-partitioned with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cells, the cells may be exposed to an appropriate stimulus to release the cells or their contents from a co-partitioned microcapsule. For example, in some cases, a chemical stimulus may be co-partitioned along with an encapsulated cell to allow for the degradation of the microcapsule and release of the cell or its contents into the larger partition. In some cases, this stimulus may be the same as the stimulus described elsewhere herein for release of oligonucleotides from their respective microcapsule (e.g., bead). In alternative aspects, this may be a different and non-overlapping stimulus, in order to allow an encapsulated cell to be released into a partition at a different time from the release of oligonucleotides into the same partition.

Additional reagents may also be co-partitioned with the cells, such as endonucleases to fragment the cell's DNA, DNA polymerase enzymes and dNTPs used to amplify the cell's nucleic acid fragments and to attach the barcode oligonucleotides to the amplified fragments. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In one example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Di-aminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Additional agents may also be co-partitioned with the cells, such as one or more labelling agents capable of binding to one or more cell surface features of the cell(s). Cell surface features may comprise a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, and an adherens junction. The labelling agents may comprise an antibody, and antibody fragment, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold. The labelling agents may be coupled, through the coupling approaches as described herein, to a reporter oligonucleotide comprising a nucleic acid barcode sequence that permits identification of the labelling agent, as described herein. In some embodiments, the nucleic acid barcode sequence coupled to the labelling agent may comprise a unique molecular identifier (UMI) sequence segment, as described herein.

A labelling agent may comprise an antigen presenting particle. In some cases, an antigen presenting particle may comprise an antigen on or adjacent to its surface. The antigen presenting particle may bind to one or more molecules on the surface of a cell in a sample, e.g., through the antigen on the antigen presenting particle. In some cases, an antigen presenting particle may be used as a labelling agent for an immune cell, e.g., a T cell or a B cell. Such antigen presenting particle may bind to a T cell receptor and/or B cell receptor. In some cases, the antigen presenting particle comprise an antigen that is recognized (e.g., bound) by an immune cell. The antigen presenting particle may be a cell, e.g., a cancer cell or other antigen presenting cell. The antigen presenting particle may be a pathogen, e.g., a bacterium, a fungus, a microbe or a virus. In certain cases, the antigen presenting particle (e.g., a cell or a virus) may comprise an antigen expression vector that expresses the antigen on the surface of the particle. The antigen expression vector may comprise a barcode for identifying the nucleic acid or amino acid sequence of the antigen.

An example method for using an antigen presenting particle to analyze a cell may comprise one or more of the following operations. A sample comprising immune cells (e.g., blood or a fraction thereof) are mixed with a population of antigen presenting particles, and incubated to allow for the immune cells and antigen presenting particles to interact. The immune cells and antigen presenting particles bound to the immune cells are purified using an antibody that selectively binds to the immune cells. The bound immune cells and antigen presenting particles are partitioned into droplets with beads (e.g., gel beads). Each of the beads comprises anchor oligonucleotide comprising a primer for mRNA molecules, a barcode and a UMI. At least one of the droplets contains an immune cell, an antigen presenting particle, and a gel bead. The immune cell and the antigen presenting particle in the droplet are lysed. The mRNA molecules from the immune cell and the antigen presenting particle are released. Reverse transcription is performed with the mRNA molecules and the anchor oligonucleotide from the bead. Thus, the resulting cDNA are tagged with the barcode and UMI from the anchor oligonucleotide. The resulting cDNA are then sequenced, e.g., to a high depth per cell on a sequencer (e.g., an Illumina sequencer). With the sequence reads, V(D)J regions of the immune cell are assembled and characteristics of the antigen presenting particle are also determined. When the antigen presenting particles are cancer cells, mutations and/or single-nucleotide polymorphisms (SNPs) may be determined with the sequence reads to identify a sub-populations of tumor cells that are targeted by an immune cell with the corresponding V(D)J sequences. When the antigen presenting particles are viruses, viral genome may be assembled to identify the sub-clone of viruses that are targeted by the immune cells with the corresponding V(D)J sequences. The method may yield pairs of V(D)J sequences and antigen-identifying sequences (e.g., mRNA of tumor cells or the genome of viruses) that are useful in developing personalized immunotherapies or vaccines against specific viral strains.

A protein labeled by a labelling agent (e.g., an antibody labeled by a barcode) may be used as a probe in a binding assay. The protein may be an antibody or a cell surface protein, e.g., a cell receptor such as a T-cell receptor and B-cell receptor. The labelling agent may comprise a barcode and/or a UMI. In some cases, another labelling agent comprising the same barcode and/or UMI may be used to analyze nucleic acids from the same cell as the protein. The nucleic acids and the protein from the same cell may be identified by the barcode and/or UMI. In some cases, the nucleic acid sequence of the cell surface protein may be determined using the labelling agent for analyzing nucleic acids, so that the amino acid sequence of the cell surface protein may also be determined. The labeled protein from the cell may then be used as a probe in a binding assay against a target molecule (e.g., a protein). For example, in the binding assay, whether the labeled cell surface protein can bind to the target protein may be determined. The label of the cell surface protein may be separated from the cell surface protein, e.g., by denaturation. Then the barcode and/or UMI on the label may be sequenced. The sequences of the barcode and/or UMI may be used to correlate the binding assay result with the sequence of the cell surface protein. Thus, the interaction of the protein with the target molecule may be correlated with the sequence of the protein. In some cases, the interaction between the protein and the target molecule may be quantified using the UMI.

Once the contents of the cells are released into their respective partitions, the nucleic acids contained therein may be further processed within the partitions. In accordance with the methods and systems described herein, the nucleic acid contents of individual cells can be provided with unique identifiers such that, upon characterization of those nucleic acids they may be attributed as having been derived from the same cell or cells. The ability to attribute characteristics to individual cells or groups of cells is provided by the assignment of unique identifiers specifically to an individual cell or groups of cells. Unique identifiers, e.g., in the form of nucleic acid barcodes can be assigned or associated with individual cells or populations of cells, in order to tag or label the cell's components (and as a result, its characteristics) with the unique identifiers. These unique identifiers can then be used to attribute the cell's components and characteristics to an individual cell or group of cells. In some aspects, this is carried out by co-partitioning the individual cells or groups of cells with the unique identifiers. In some aspects, the unique identifiers are provided in the form of oligonucleotides (also referred to herein as anchor oligonucleotides) that comprise nucleic acid barcode sequences that may be attached to or otherwise associated with the nucleic acid contents of individual cells, or to other components of the cells, and particularly to fragments of those nucleic acids. The oligonucleotides may be partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned cells. These sequences include, e.g., targeted or random/universal amplification primer sequences for amplifying the genomic DNA from the individual cells within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems. Co-partitioning of oligonucleotides and associated barcodes and other functional sequences or labels, along with sample materials as describe herein, may be performed, for example, as described in U.S. Patent Application Publication No. 2014/0227684, which is entirely incorporated herein by reference for all purposes.

Briefly, in one example, microcapsules, such as beads, are provided that each include large numbers of the above described barcoded oligonucleotides (also referred to herein as anchor oligonucleotides) releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the oligonucleotides into the partitions, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each bead can be provided with large numbers of oligonucleotide molecules attached. In particular, the number of molecules of oligonucleotides including the barcode sequence on an individual bead can be at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

Moreover, when the population of beads is partitioned, the resulting population of partitions can also include a diverse barcode library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each partition of the population can include at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

In some cases, multiple different barcodes can be incorporated within a given partition, either attached to a single or multiple beads within the partition. For example, in some cases, a mixed, but known barcode sequences set may provide greater assurance of identification in the subsequent processing, e.g., by providing a stronger address or attribution of the barcodes to a given partition, as a duplicate or independent confirmation of the output from a given partition.

The oligonucleotides may be releasable from the beads upon the application of a particular stimulus to the beads. In some cases, the stimulus may be a photo-stimulus, e.g., through cleavage of a photo-labile linkage that releases the oligonucleotides. In other cases, a thermal stimulus may be used, where elevation of the temperature of the beads environment will result in cleavage of a linkage or other release of the oligonucleotides form the beads. In still other cases, a chemical stimulus is used that cleaves a linkage of the oligonucleotides to the beads, or otherwise results in release of the oligonucleotides from the beads. In one case, such compositions include the polyacrylamide matrices described above for encapsulation of cells, and may be degraded for release of the attached oligonucleotides through exposure to a reducing agent, such as DTT. Examples of other systems and methods are described in U.S. Patent Application Publication No. 2014/0155295 and US. Patent Application Publication No. 2014/0378345, each of which is entirely incorporated herein by reference for all purposes.

Figure 2:
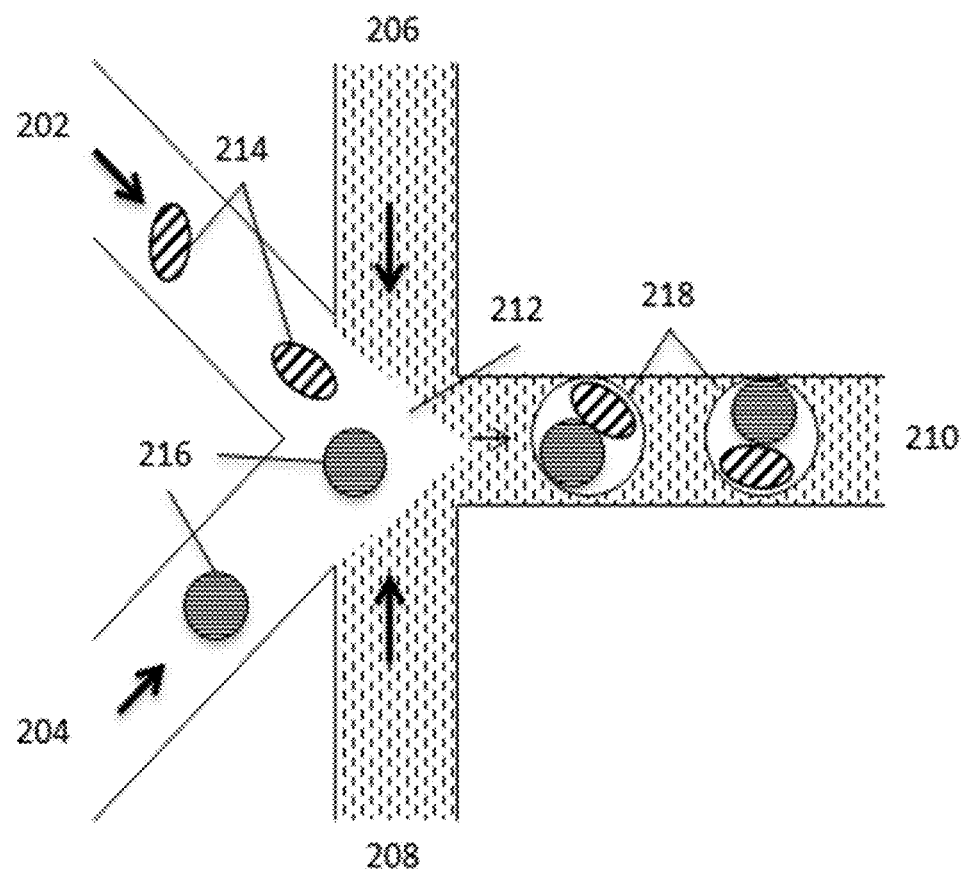
FIG. 2 schematically illustrates a microfluidic channel structure for co-partitioning cells and microcapsules (e.g., beads) comprising additional reagents.
Figure 3A:
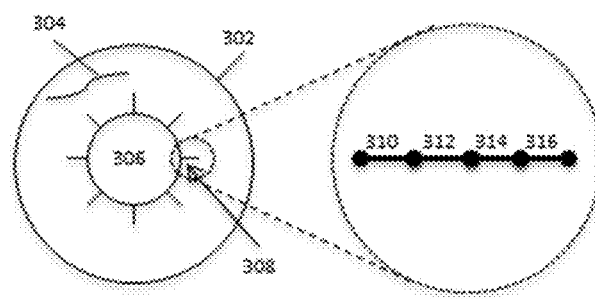
FIGS. 3A-3F schematically illustrate an example process for amplification and barcoding of cell's nucleic acids.
Figure 3B:
Figure 3C:
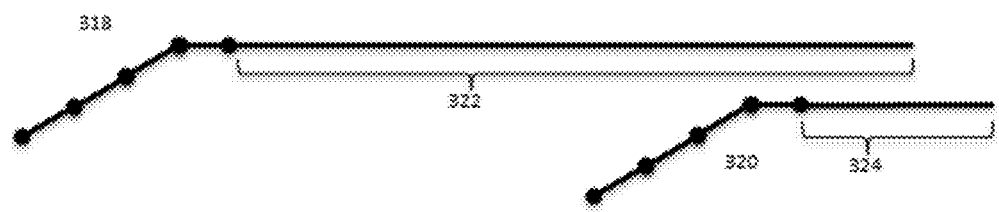
Figure 3D:
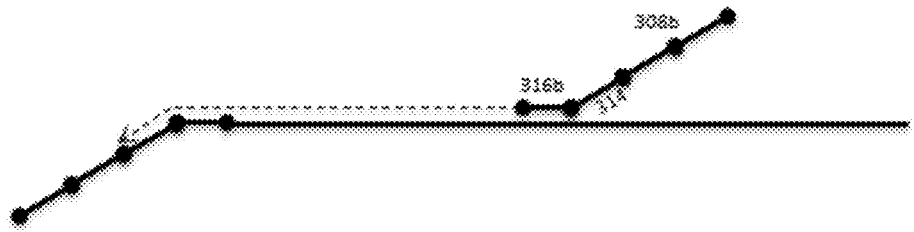
Figure 3E:
Figure 3F:
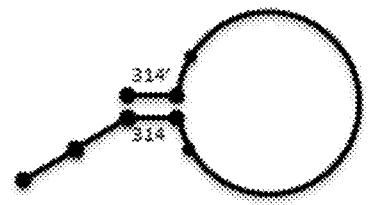

In accordance with the methods and systems described herein, the beads including the attached oligonucleotides may be co-partitioned with the individual cells, such that a single bead and a single cell are contained within an individual partition. While single cell/single bead occupancy is one possible state, it will be appreciated that multiply occupied partitions (either in terms of cells, beads or both), or unoccupied partitions (either in terms of cells, beads or both) may often be present. An example of a microfluidic channel structure for co-partitioning cells and beads comprising barcode oligonucleotides is schematically illustrated in FIG. 2. As described elsewhere herein, in some aspects, a substantial percentage of the overall occupied partitions may include both a bead and a cell and, in some cases, some of the partitions that are generated may be unoccupied. In some cases, some of the partitions may have beads and cells that are not partitioned 1:1. In some cases, multiply occupied partitions may be provided, e.g., containing two, three, four or more cells and/or beads within a single partition. As shown, channel segments 202, 204, 206, 208 and 210 are provided in fluid communication at channel junction 212. An aqueous stream comprising the individual cells 214, is flowed through channel segment 202 toward channel junction 212. As described above, these cells may be suspended within an aqueous fluid, or may have been pre-encapsulated, prior to the partitioning process.

Concurrently, an aqueous stream comprising the barcode carrying beads 216, is flowed through channel segment 204 toward channel junction 212. A non-aqueous partitioning fluid 216 is introduced into channel junction 212 from each of side channels 206 and 208, and the combined streams are flowed into outlet channel 210. Within channel junction 212, the two combined aqueous streams from channel segments 202 and 204 are combined, and partitioned into droplets 218, that include co-partitioned cells 214 and beads 216. By controlling the flow characteristics of each of the fluids combining at channel junction 212, as well as controlling the geometry of the channel junction, partitioning can be optimized to achieve a suitable occupancy level of beads, cells or both, within the partitions 218 that are generated.

In some cases, lysis agents, e.g., cell lysis enzymes, may be introduced into the partition with the bead stream, e.g., flowing through channel segment 204, such that the cell may be lysed at or after the time of partitioning. In some cases, cell membranes are maintained intact, such as to allow for the characterization of cell surface markers, as described later herein. Additional reagents may also be added to the partition in this configuration, such as endonucleases to fragment the cell's DNA, DNA polymerase enzyme and dNTPs used to amplify the cell's nucleic acid fragments and to attach the barcode oligonucleotides to the amplified fragments. A chemical stimulus, such as DTT, may be used to release the barcodes from their respective beads into the partition. In such cases, the chemical stimulus can be provided along with the cell-containing stream in channel segment 202, such that release of the barcodes only occurs after the two streams have been combined, e.g., within the partitions 218. Where the cells are encapsulated, however, introduction of a common chemical stimulus, e.g., that both releases the oligonucleotides form their beads, and releases cells from their microcapsules may generally be provided from a separate additional side channel (not shown) upstream of or connected to channel junction 212.

A number of other reagents may be co-partitioned along with the cells, beads, lysis agents and chemical stimuli, including, for example, protective reagents, like proteinase K, chelators, nucleic acid extension, replication, transcription or amplification reagents such as polymerases, reverse transcriptases, transposases which can be used for transposon based methods (e.g., Nextera), nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

The channel networks, e.g., as described herein, can be fluidly coupled to appropriate fluidic components. For example, the inlet channel segments, e.g., channel segments 202, 204, 206 and 208 are fluidly coupled to appropriate sources of the materials they are to deliver to channel junction 212. For example, channel segment 202 may be fluidly coupled to a source of an aqueous suspension of cells 214 to be analyzed, while channel segment 204 may be fluidly coupled to a source of an aqueous suspension of beads 216. Channel segments 206 and 208 may then be fluidly connected to one or more sources of the non-aqueous fluid. These sources may include any of a variety of different fluidic components, from simple reservoirs defined in or connected to a body structure of a microfluidic device, to fluid conduits that deliver fluids from off-device sources, manifolds, or the like. Likewise, the outlet channel segment 210 may be fluidly coupled to a receiving vessel or conduit for the partitioned cells. Again, this may be a reservoir defined in the body of a microfluidic device, or it may be a fluidic conduit for delivering the partitioned cells to a subsequent process operation, instrument or component.

FIG. 8 shows images of individual Jurkat cells co-partitioned along with barcode oligonucleotide containing beads in aqueous droplets in an aqueous in oil emulsion. As illustrated, individual cells may be readily co-partitioned with individual beads. As will be appreciated, optimization of individual cell loading may be carried out by a number of methods, including by providing dilutions of cell populations into the microfluidic system in order to achieve suitable cell loading per partition as described elsewhere herein.

In operation, once lysed, the nucleic acid contents of the individual cells are then available for further processing within the partitions, including, e.g., fragmentation, amplification and barcoding, as well as attachment of other functional sequences. Fragmentation may be accomplished through the co-partitioning of shearing enzymes, such as endonucleases, in order to fragment the nucleic acids into smaller fragments. These endonucleases may include restriction endonucleases, including type II and type IIs restriction endonucleases as well as other nucleic acid cleaving enzymes, such as nicking endonucleases, and the like. In some cases, fragmentation may not be implemented, and full length nucleic acids may be retained within the partitions, or in the case of encapsulated cells or cell contents, fragmentation may be carried out prior to partitioning, e.g., through enzymatic methods, e.g., those described herein, or through mechanical methods, e.g., mechanical, acoustic or other shearing.

Once co-partitioned, and the cells are lysed to release their nucleic acids, the oligonucleotides disposed upon the bead may be used to barcode and amplify fragments of those nucleic acids. Briefly, in one aspect, the oligonucleotides present on the beads that are co-partitioned with the cells, are released from their beads into the partition with the cell's nucleic acids. The oligonucleotides can include, along with the barcode sequence, a primer sequence at its 5' end. This primer sequence may be a random oligonucleotide sequence intended to randomly prime numerous different regions on the cell's nucleic acids, or it may be a specific primer sequence targeted to prime upstream of a specific targeted region of the cell's genome.

Once released, the primer portion of the oligonucleotide can anneal to a complementary region of the cell's nucleic acid. Extension reaction reagents, e.g., DNA polymerase, nucleoside triphosphates, co-factors (e.g., Mg2+ or Mn2+), that may also be co-partitioned with the cells and beads, then extend the primer sequence using the cell's nucleic acid as a template, to produce a complementary fragment to the strand of the cell's nucleic acid to which the primer annealed, which complementary fragment includes the oligonucleotide and its associated barcode sequence. Annealing and extension of multiple primers to different portions of the cell's nucleic acids will result in a large pool of overlapping complementary fragments of the nucleic acid, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow formation of a hairpin structure or partial hairpin structure that may reduce the ability of the molecule to be the basis for producing further iterative copies. As described herein, the cell's nucleic acids may include any nucleic acids within the cell including, for example, the cell's DNA, e.g., genomic DNA, RNA, e.g., messenger RNA, and the like. For example, in some cases, the methods and systems described herein are used in characterizing expressed mRNA, including, e.g., the presence and quantification of such mRNA, and may include RNA sequencing processes as the characterization process. Alternatively or additionally, the reagents partitioned along with the cells may include reagents for the conversion of mRNA into cDNA, e.g., reverse transcriptase enzymes and reagents, to facilitate sequencing processes where DNA sequencing is employed. In some cases, where the nucleic acids to be characterized comprise RNA, e.g., mRNA, schematic illustration of one example of this is shown in FIG. 3.

As shown, oligonucleotides that include a barcode sequence are co-partitioned in, e.g., a droplet 302 in an emulsion, along with a sample nucleic acid 304. The oligonucleotides 308 may be provided on a bead 306 that is co-partitioned with the sample nucleic acid 304, which oligonucleotides are releasable from the bead 306, as shown in panel A. The oligonucleotides 308 may include a barcode sequence 312, in addition to one or more functional sequences, e.g., sequences 310, 314 and 316. For example, oligonucleotide 308 is shown as comprising barcode sequence 312, as well as sequence 310 that may function as an attachment or immobilization sequence for a given sequencing system, e.g., a P5 sequence used for attachment in flow cells of an Illumina Hiseq® or Miseq® system. As shown, the oligonucleotides also include a primer sequence 316, which may include a random or targeted N-mer for priming replication of portions of the sample nucleic acid 304. Also included within oligonucleotide 308 is a sequence 314 which may provide a sequencing priming region, such as a "read1" or R1 priming region, that is used to prime polymerase mediated, template directed sequencing by synthesis reactions in sequencing systems. As will be appreciated, the functional sequences may be selected to be compatible with a variety of different sequencing systems, e.g., 454 Sequencing, Ion Torrent Proton or PGM, Illumina X10, etc., and the requirements thereof. In some cases, the barcode sequence 312, immobilization sequence 310 and R1 sequence 314 may be common to all of the oligonucleotides attached to a given bead. The primer sequence 316 may vary for random N-mer primers, or may be common to the oligonucleotides on a given bead for certain targeted applications. Moreover, in some cases, barcoded oligonucleotides may be generated as described in U.S. Patent Publication No. 20160257984, which is herein incorporated by reference in its entirety.

An oligonucleotide of an anchor agent or a labelling agent may comprise modifications that render it non-extendable by a polymerase. When binding to a nucleic acid in a sample for a primer extension reaction, the oligonucleotide may serve as a template, not a primer. When the oligonucleotide also comprises a barcode (e.g., the oligonucleotide is a reporter oligonucleotide), such design may increase the efficiency of molecular barcoding by increasing the affinity between the oligonucleotide and the unbarcoded sample nucleic acids, and eliminate the potential formation of adaptor artifacts. In some cases, the oligonucleotide may comprise a random N-mer sequence that is capped with modifications that render it non-extendable by a polymerase. In some cases, the composition of the random N-mer sequence may be designed to maximize the binding efficiency to free, unbarcoded ssDNA molecules. The design may include a random sequence composition with a higher GC content, a partial random sequence with fixed G or C at specific positions, the use of guanosines, the use of locked nucleic acids, or any combination thereof.

A modification for blocking primer extension by a polymerase may be a carbon spacer group of different lengths or a dideoxynucleotide. In some cases, the modification may be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification may also be a uracil base, 2'OMe modified RNA, C3-18 spacers (e.g., structures with 3-18 consecutive carbon atoms, such as C3 spacer), ethylene eglycol multimer spacers (e.g., spacer 18 (hexa-ethyleneglycol spacer), biotin, di-deoxynucleotide triphosphate, ethylene glycol, amine, or phosphate.

FIG. 21 shows an oligonucleotide with such modification. The double-stranded oligonucleotide 2110 comprises a single-stranded DNA (ssDNA) annealing region with a random N-mer sequence at its 3' end. The unbarcoded ssDNA 2120 from a sample binds to oligonucleotide 2110. The random N-mer sequence of the oligonucleotide 2110 has modifications (shown as "X") on the 3' end. When oligonucleotide 2110 and unbarcoded ssDNA 2120 bind to each other in a primer extension reaction, only unbarcoded ssDNA 2120 can be extended using oligonucleotide 3310 as a template.

Figure 22:
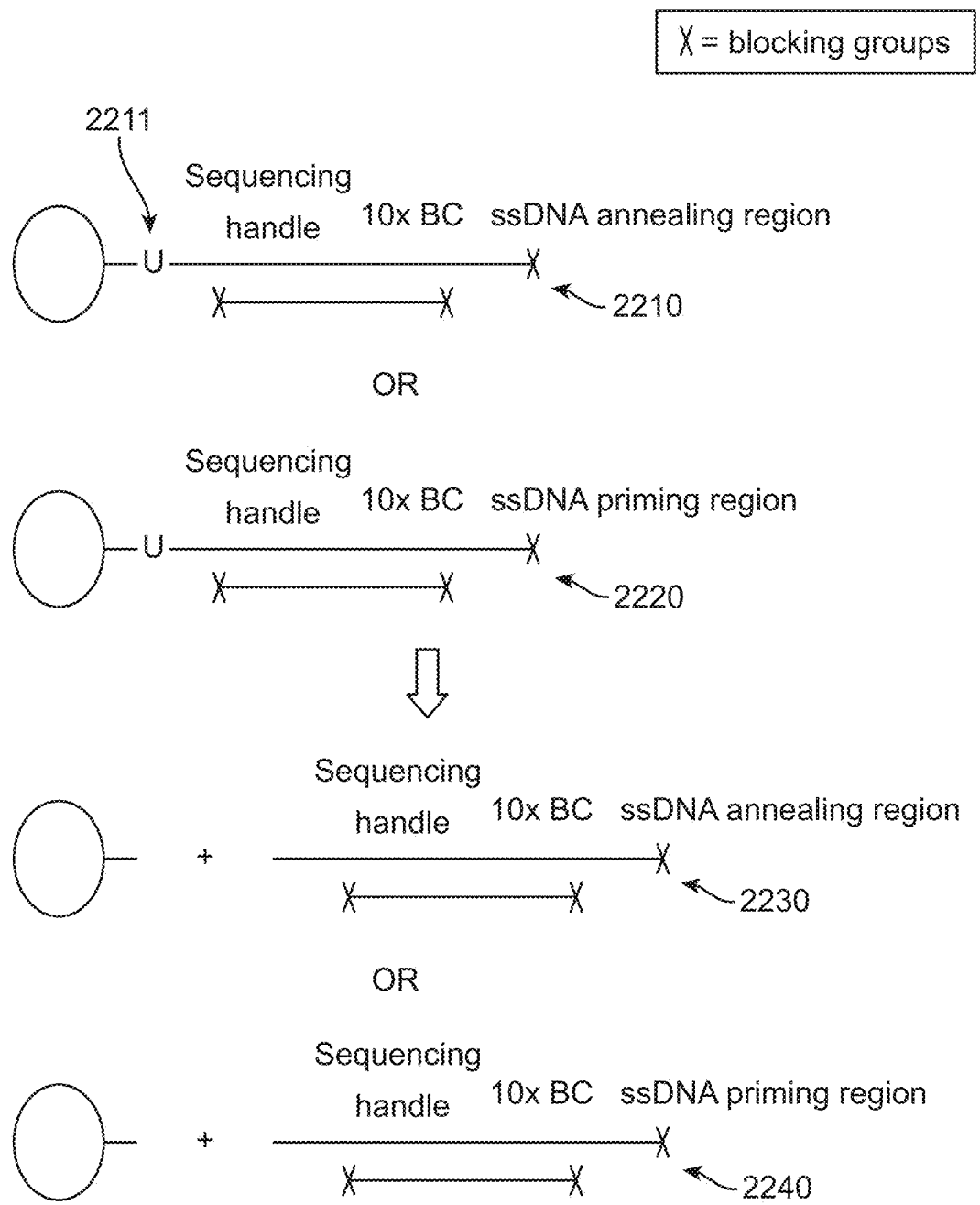
FIG. 22 shows oligonucleotides comprising a U-excising element.

In some cases, the oligonucleotide with a random N-mer sequence may be coupled to a solid support (e.g., a bead) via a U-excising element, e.g., an ssDNA sequence with uracil. FIG. 22 shows an example of such oligonucleotide. Double-stranded oligonucleotide 2210 comprises an ssDNA annealing region that contains a random N-mer sequence at its 3' end. Oligonucleotide 2210 is coupled to a bead via an ssDNA 2211 that has a uracil. Oligonucleotide 2210 also comprises modifications preventing extension by a polymerase. Oligonucleotide 2210 may be released from the bead by uracil-DNA glycosylase (to remove the uracil) and an endonuclease (to induce the ssDNA break), resulting the released oligonucleotide 2230. Oligonucleotide 2220 comprises an ssDNA priming region has similar design as Oligonucleotide 2210. In some cases, the difference between an ssDNA annealing region and an ssDNA priming region is the presence or absence of a blocking group (e.g., "X"), respectively. Unblocked ssDNA can be extended and function as a primer, while blocked ssDNA can function as a passive annealing sequence.

As will be appreciated, in some cases, the functional sequences may include primer sequences useful for RNA-seq applications. For example, in some cases, the oligonucleotides may include poly-T primers for priming reverse transcription of RNA for RNA-seq. In still other cases, oligonucleotides in a given partition, e.g., included on an individual bead, may include multiple types of primer sequences in addition to the common barcode sequences, such as both DNA-sequencing and RNA sequencing primers, e.g., poly-T primer sequences included within the oligonucleotides coupled to the bead. In such cases, a single partitioned cell may be both subjected to DNA and RNA sequencing processes.

A primer on a labelling agent or an anchor agent (e.g., a primer for RNA-seq applications) may be a target-specific primer. A target-specific primer may bind to a specific sequence in a RNA molecule or a DNA molecule (e.g., complementary DNA (cDNA) from RNA, or endogenous DNA from a cell). For example, the specific sequence may be a sequence that is not in the poly-A tail of an RNA molecule or its cDNA. In some cases, the target-specific primer may bind to RNA molecules such as mRNA molecules or non-coding RNA molecules, e.g., rRNA, tRNA, mRNA, or miRNA molecules. In some cases, the target-specific primer may bind to RNA molecules introduced to a cell. In some cases, the RNA molecules introduced to a cell may be RNA molecules used in gene editing methods (e.g., Clustered regularly interspaced short palindromic repeats (CRISPR) RNA (crRNA) or guide RNA for CRISPR gene editing). For example, the target-specific primer may bind to crRNA for identifying the crRNA introduced to a cell and/or determining the effect of the crRNA on the transcriptome of the cell. In some cases, the target-specific primer may be used to determine copy numbers of disease (e.g., cancer)-related genes while simultaneously analyzing the rest of the transcriptome. In other cases, the target-specific primer may be used to analyze RNA molecules from pathogens infecting the cell, e.g., for distinguishing pathogen infected cells from non-pathogen infected cells and/or determining how the pathogen alters the cells transcriptome. In some cases, a target-specific primer may bind to DNA molecules, e.g., endogenous DNA molecules from a cell, or synthetic DNA molecules. For example, a target-specific primer may bind to a barcode, e.g., a barcode of a cell (e.g., inside a cell or on the surface of a cell), a barcode of a protein (e.g., an antibody barcode), or a barcode of a nucleic acid (e.g., a CRISPR barcode).

A target-specific primer may be combined with one or more barcodes, one or more UMIs, one or more poly-T primers for mRNA, and/or one or more random N-mer primers (randomers) for total RNA in the same or different oligonucleotides. In some cases, a bead disclosed herein may comprise an oligonucleotide with a target-specific primer and one or more oligonucleotides with a poly-T primer, e.g., as shown in FIG. 23A. In some cases, a bead may have a plurality of oligonucleotides, each of which comprises a target-specific primer, e.g., as shown in FIG. 23B. In some cases, a bead may have a plurality of oligonucleotides, each of which comprises a target-specific primer and a plurality of oligonucleotides, each of which comprises a poly-T primer, e.g., as shown in FIG. 23C. In some cases, a bead may have a plurality of oligonucleotides, each of which comprises a target-specific primer and a plurality of oligonucleotides, each of which comprises a random N-mer primer for total RNA, e.g., as shown in FIG. 24.

On a bead, the ratio of oligonucleotides with target-specific primers to oligonucleotides with non-specific (poly-T or random N-mer) primers may be adjusted to match the needs of a specific application. In some cases, at least 0.1%, 1%, 5%, 10%, 20%, 30%, 40%, 50%, 60%, 70%, 80%, 90%, 95%, 99%, or 100% of the oligonucleotides on a bead may comprise target-specific primers. In some cases, at least 0.1%, 1%, 5%, 10%, 20%, 30%, 40%, 50%, 60%, 70%, 80%, 90%, 95%, 99%, or 100% of the oligonucleotides on a bead may comprise non-specific (poly-T or random N-mer) primers. The oligonucleotide may be made by attaching (e.g., by ligation) one or more oligonucleotide backbones on a bead and then attaching (e.g., by ligation) one or more primer sequences to the backbones.

An oligonucleotide of an anchor agent or a labelling agent may be a splint oligonucleotide. A splint oligonucleotide may comprise two or more different primers. The primers may have different functions. For example, a splint oligonucleotide may comprise two or more of the following: a poly-T primer, a random N-mer primer, and a target-specific primer.

Figure 25A:
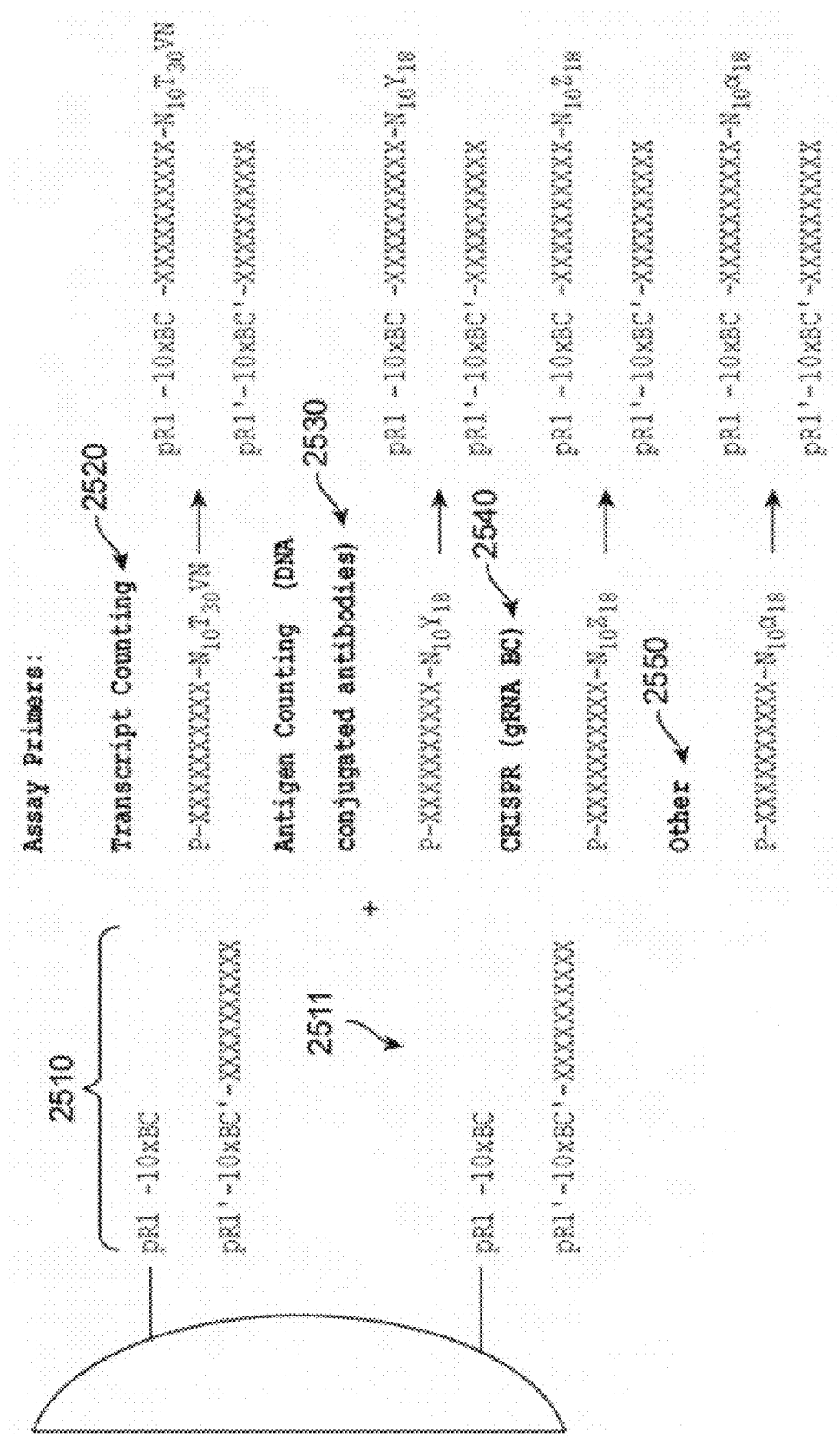
FIGS. 25A-C show exemplary oligonucleotides comprising adapters and assay primers (SEQ ID NOS 8-9, respectively, in order of appearance)
Figures 25B, 25C:
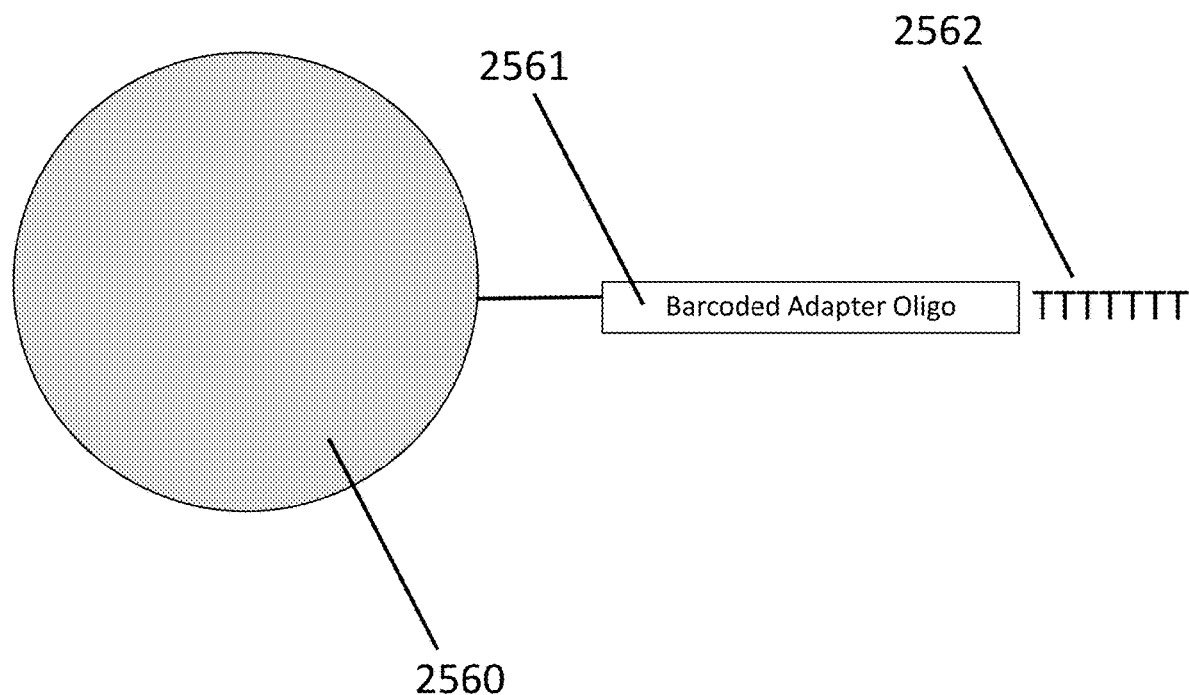

An oligonucleotide of an anchor agent or a labelling agent may comprise an adapter that is capable of binding or ligating to an assay primer. The adapter may allow the anchor agent or the labelling agent to be attached to any suitable assay primers and used in any suitable assays. The assay primer may comprise a priming region and a sequence that is capable of binding or ligating to the adapter. In some cases, the adapter may be a non-specific primer (e.g., a 5' overhang) and the assay primer may comprise a 3' overhang that can be ligated to the 5' overhang. The priming region on the assay primer may be any primer described herein, e.g., a poly-T primer, a random N-mer primer, a target-specific primer, or a labelling agent capture sequence. FIG. 25A shows exemplary adapters and assay primers. Oligonucleotide 2510 comprises an adapter 2511, which is a 5' overhang comprising 10 nucleotides. The adapter 2511 can be ligated to the assay primers, each of which comprises a 3' overhang comprising 10 nucleotides that complementary to the 5' overhang of adapter 2511. The anchor oligonucleotide may be used in any assay by attaching to the assay primer designed for that assay. FIG. 26B shows exemplary adapters and assay primers that allows the anchor agent or the labelling agent to be attached to any suitable assay primers and used in any suitable assays. Barcoded adapter oligonucleotide 2561 is attached to a bead 2560, such as a gel bead, and comprises a poly(dT) sequence 2562. FIG. 26C shows exemplary splint oligos comprising a poly-A sequence that facilitates coupling to the barcoded adapter oligonucleotide 2561 and a second sequence (shown as "XXX", "YYY", and "ZZZ") that facilitates coupling with an assay primer. Assay primers comprise a sequence complementary to the splint oligo second sequence (shown as "X'X'X'", "Y'Y'Y'", and "Z'Z'Z'") and an assay-specific sequence that determines assay primer functionality (e.g., a poly-T primer, a random N-mer primer, a target-specific primer, or a labelling agent capture sequence as described herein).

Figure 26:
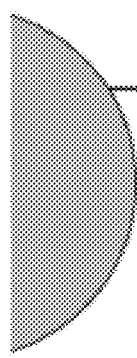
FIG. 26 shows an oligonucleotide with an adapter comprising a switch oligo (SEQ ID NO: 10)
Figure 27A:
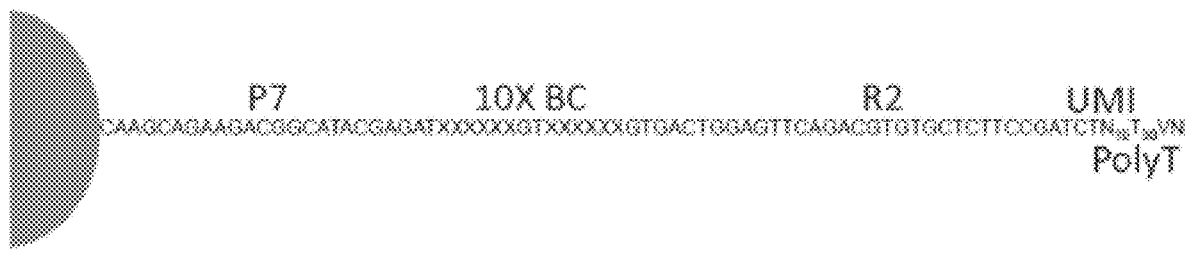
FIG. 27A shows oligonucleotides with backbones comprising P7 and R2 sequences and poly-T primers (SEQ ID NOS 11, 41, 12, 42, 13, 43, 14, 44, and 11, respectively, in order of appearance).

In some cases, the barcoded adapter comprises a switch oligo, e.g., with a 3' end 3rG. FIG. 26 shows a bead (such as a gel bead) comprising a barcoded adapter oligonucleotide functionalized with a 3rG sequence that enables template switching (e.g., reverse transcriptase template switching), but is not specific for any particular assay. Assay primers added to the reaction determine the particular assay by binding to targeted molecules and are extended by a reverse transcriptase enzyme/polymerase followed by template switching onto the barcoded adapter oligonucleotide to incorporate the barcode and other functional sequences. The priming region determines the assay and, in some embodiments, comprises a poly-T sequence for mRNA analysis, random primers for gDNA analysis, or a capture sequence that can bind a nucleic acid molecule coupled to a labelling agent (e.g., an antibody) or a nucleic acid molecule that can function in a CRISPR assay (e.g., CRISPR/Cas9) via a targeted priming sequence.

Based upon the presence of primer sequence 316, the oligonucleotides can prime the sample nucleic acid as shown in panel B, which allows for extension of the oligonucleotides 308 and 308a using polymerase enzymes and other extension reagents also co-partitioned with the bead 306 and sample nucleic acid 304. As shown in panel C, following extension of the oligonucleotides that, for random N-mer primers, may anneal to multiple different regions of the sample nucleic acid 304; multiple overlapping complements or fragments of the nucleic acid are created, e.g., fragments 318 and 320. Although including sequence portions that are complementary to portions of sample nucleic acid, e.g., sequences 322 and 324, these constructs are generally referred to herein as comprising fragments of the sample nucleic acid 304, having the attached barcode sequences.

The barcoded nucleic acid fragments may then be subjected to characterization, e.g., through sequence analysis, or they may be further amplified in the process, as shown in panel D. For example, additional oligonucleotides, e.g., oligonucleotide 308b, also released from bead 306, may prime the fragments 318 and 320. This shown for fragment 318. In particular, again, based upon the presence of the random N-mer primer 316b in oligonucleotide 308b (which in some cases can be different from other random N-mers in a given partition, e.g., primer sequence 316), the oligonucleotide anneals with the fragment 318, and is extended to create a complement 326 to at least a portion of fragment 318 which includes sequence 328, that comprises a duplicate of a portion of the sample nucleic acid sequence. Extension of the oligonucleotide 308b continues until it has replicated through the oligonucleotide portion 308 of fragment 318. As illustrated in panel D, the oligonucleotides may be configured to prompt a stop in the replication by the polymerase at a given point, e.g., after replicating through sequences 316 and 314 of oligonucleotide 308 that is included within fragment 318. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 312 to prevent a non-uracil tolerant polymerase to cease replication of that region. As a result a fragment 326 is created that includes the full-length oligonucleotide 308b at one end, including the barcode sequence 312, the attachment sequence 310, the R1 primer region 314, and the random N-mer sequence 316b. At the other end of the sequence may be included the complement 316' to the random N-mer of the first oligonucleotide 308, as well as a complement to all or a portion of the R1 sequence, shown as sequence 314'. The R1 sequence 314 and its complement 314' are then able to hybridize together to form a partial hairpin structure 328. As will be appreciated because the random N-mers differ among different oligonucleotides, these sequences and their complements may not be expected to participate in hairpin formation, e.g., sequence 316', which is the complement to random N-mer 316, may not be expected to be complementary to random N-mer sequence 316b. This may not be the case for other applications, e.g., targeted primers, where the N-mers may be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 326.

In general, the amplification of the cell's nucleic acids is carried out until the barcoded overlapping fragments within the partition constitute at least 1× coverage of the particular portion or all of the cell's genome, at least 2×, at least 3×, at least 4×, at least 5×, at least 10×, at least 20×, at least 40× or more coverage of the genome or its relevant portion of interest. Once the barcoded fragments are produced, they may be directly sequenced on an appropriate sequencing system, e.g., an Illumina Hiseq®, Miseq® or X10 system, or they may be subjected to additional processing, such as further amplification, attachment of other functional sequences, e.g., second sequencing primers, for reverse reads, sample index sequences, and the like.

Figure 4:
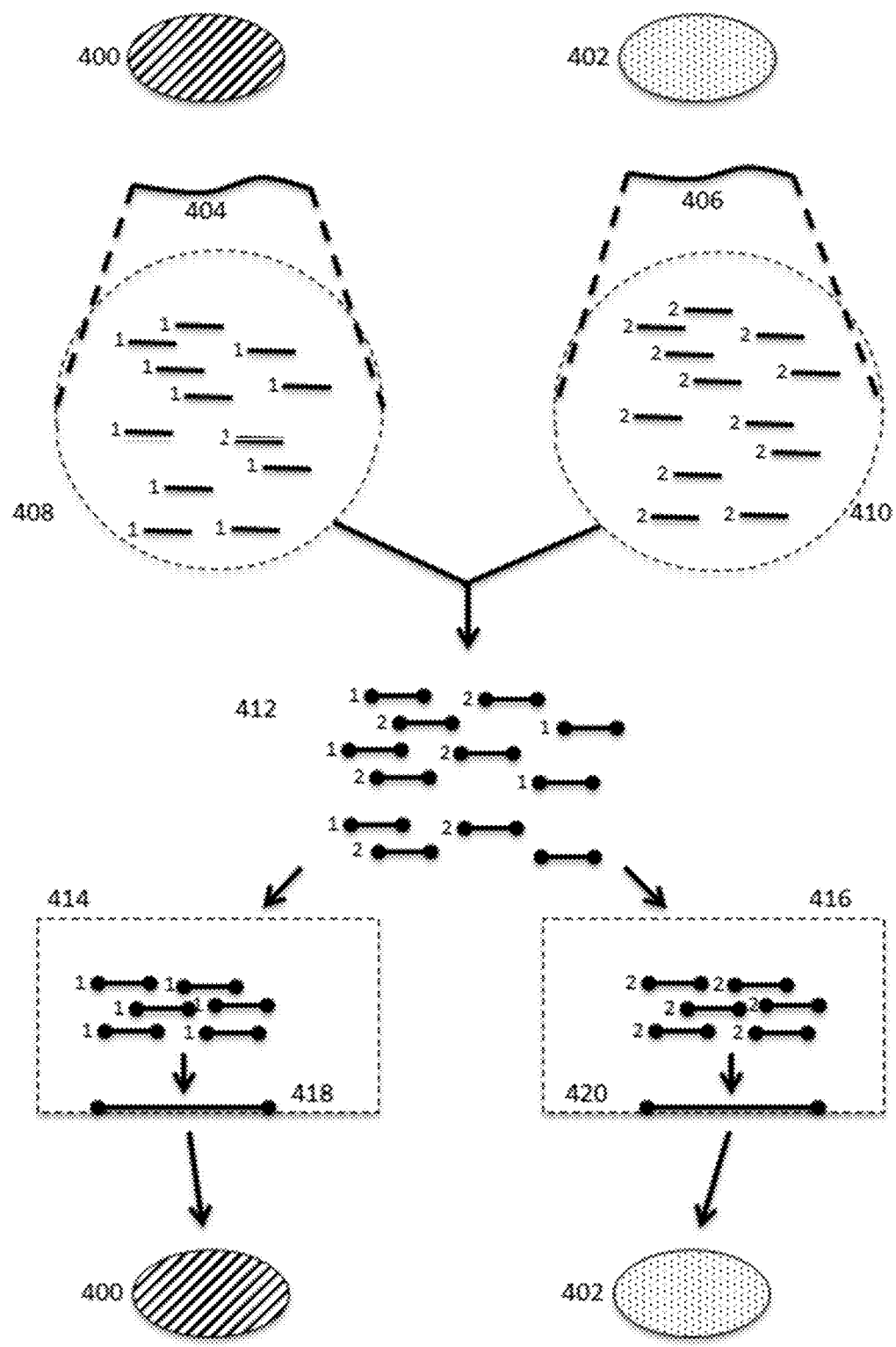
FIG. 4 provides a schematic illustration of use of barcoding of cell's nucleic acids in attributing sequence data to individual cells or groups of cells for use in their characterization.

All of the fragments from multiple different partitions may then be pooled for sequencing on high throughput sequencers as described herein, where the pooled fragments comprise a large number of fragments derived from the nucleic acids of different cells or small cell populations, but where the fragments from the nucleic acids of a given cell will share the same barcode sequence. In particular, because each fragment is coded as to its partition of origin, and consequently its single cell or small population of cells, the sequence of that fragment may be attributed back to that cell or those cells based upon the presence of the barcode, which will also aid in applying the various sequence fragments from multiple partitions to assembly of individual genomes for different cells. This is schematically illustrated in FIG. 4. As shown in one example, a first nucleic acid 404 from a first cell 400, and a second nucleic acid 406 from a second cell 402 are each partitioned along with their own sets of barcode oligonucleotides as described above. The nucleic acids may comprise a chromosome, entire genome or other large nucleic acid from the cells.

Within each partition, each cell's nucleic acids 404 and 406 is then processed to separately provide overlapping set of second fragments of the first fragment(s), e.g., second fragment sets 408 and 410. This processing also provides the second fragments with a barcode sequence that is the same for each of the second fragments derived from a particular first fragment. As shown, the barcode sequence for second fragment set 408 is denoted by "1" while the barcode sequence for fragment set 410 is denoted by "2". A diverse library of barcodes may be used to differentially barcode large numbers of different fragment sets. However, it is not necessary for every second fragment set from a different first fragment to be barcoded with different barcode sequences. In some cases, multiple different first fragments may be processed concurrently to include the same barcode sequence. Diverse barcode libraries are described in detail elsewhere herein.

The barcoded fragments, e.g., from fragment sets 408 and 410, may then be pooled for sequencing using, for example, sequence by synthesis technologies available from Illumina or Ion Torrent division of Thermo-Fisher, Inc. Once sequenced, the sequence reads 412 can be attributed to their respective fragment set, e.g., as shown in aggregated reads 414 and 416, at least in part based upon the included barcodes, and in some cases, in part based upon the sequence of the fragment itself. The attributed sequence reads for each fragment set are then assembled to provide the assembled sequence for each cell's nucleic acids, e.g., sequences 418 and 420, which in turn, may be attributed to individual cells, e.g., cells 400 and 402.

While described in terms of analyzing the genetic material present within cells, the methods and systems described herein may have much broader applicability, including the ability to characterize other aspects of individual cells or cell populations, by allowing for the allocation of reagents and/or agents to individual cells, and providing for the attributable analysis or characterization of those cells in response to those reagents and/or agents. These methods and systems may be valuable in being able to characterize cells for, e.g., research, diagnostic, or pathogen identification. By way of example, a wide range of different cell surface features, e.g., cell surface proteins like cluster of differentiation or CD proteins, have significant diagnostic relevance in characterization of diseases like cancer.

In one particularly useful application, the methods and systems described herein may be used to characterize cell features, such as cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, and an adherens junction. In particular, the methods described herein may be used to attach one or more labelling agents to these cell features, that when partitioned as described above, may be barcoded and analyzed, e.g., using DNA sequencing technologies, to ascertain the presence, and in some cases, relative abundance or quantity of such cell features of an individual cell or population of cells.

In a particular example, a library of potential cell surface feature labelling agents may be provided associated with a first set of nucleic acid reporter molecules, e.g., where a different reporter oligonucleotide sequence is associated with a specific labelling agent, and therefore capable of binding to a specific cell surface feature. Cell surface feature labelling agents may include, but are not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold. In some aspects, different members of the library may be characterized by the presence of a different oligonucleotide sequence label, e.g., an antibody to a first type of cell surface protein or receptor may have associated with it a first known reporter oligonucleotide sequence, while an antibody to a second receptor protein may have a different known reporter oligonucleotide sequence associated with it. Prior to co-partitioning, the cells may be incubated with the library of labelling agents, that may represent antibodies to a broad panel of different cell surface features, e.g., receptors, proteins, etc., and which include their associated reporter oligonucleotides. Unbound labelling agents may be washed from the cells, and the cells may then be co-partitioned along with the barcode oligonucleotides described above. As a result, the partitions may include the cell or cells, as well as the bound labelling agents and their known, associated reporter oligonucleotides.

Without the need for lysing the cells within the partitions, one may then subject the reporter oligonucleotides to the barcoding operations described above for cellular nucleic acids, to produce barcoded, reporter oligonucleotides, where the presence of the reporter oligonucleotides can be indicative of the presence of the particular cell surface feature, and the barcode sequence will allow the attribution of the range of different cell surface features to a given individual cell or population of cells based upon the barcode sequence that was co-partitioned with that cell or population of cells. As a result, one may generate a cell-by-cell profile of the cell surface features within a broader population of cells. This aspect of the methods and systems described herein, is described in greater detail below.

Figure 5:
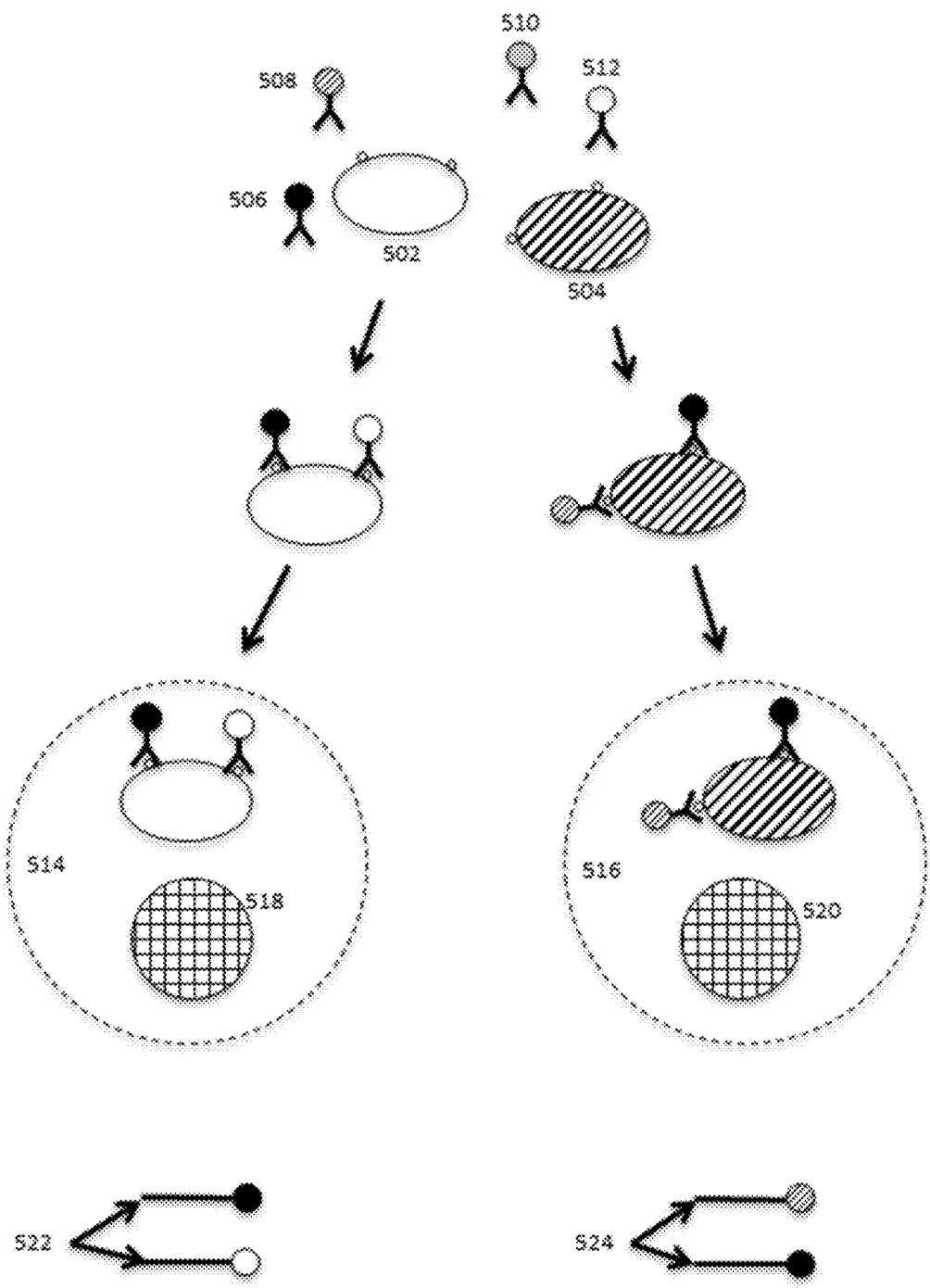
FIG. 5 provides a schematic illustration of cells associated with labeled cell-binding ligands.

This example is schematically illustrated in FIG. 5. As shown, a population of cells, represented by cells 502 and 504 are incubated with a library of cell surface associated labelling agents, e.g., antibodies, antibody fragments, cell surface receptor binding molecules, receptor ligands, small molecules, bi-specific antibodies, bi-specific T-cell engagers, T-cell receptor engagers, B-cell receptor engagers, pro-bodies, aptamers, monobodies, affimers, darpins, protein scaffolds, or the like, where each different type of binding group includes an associated nucleic acid reporter molecule associated with it, shown as labelling agents and associated reporter oligonucleotide 506, 508, 510 and 512 (with the reporter oligonucleotides being indicated by the differently shaded circles). Where the cell expresses the surface features that are bound by the library of labelling agents, the labelling agents and their associated reporter oligonucleotides can become associated or coupled with the cell surface feature. Individual cells may then be partitioned into separate partitions, e.g., droplets 514 and 516, as described herein, along with their associated labelling agents/reporter oligonucleotides, as well as a bead containing individual barcode oligonucleotides (e.g., anchor oligonucleotides) as described elsewhere herein, e.g., beads 518 and 520, respectively. As with other examples described herein, the barcoded oligonucleotides may be released from the beads and used to attach the barcode sequence the reporter oligonucleotides present within each partition with a barcode that is common to a given partition, but which varies widely among different partitions. For example, as shown in FIG. 5, the reporter oligonucleotides that associate with cell 502 in partition 514 are barcoded with barcode sequence 522, while the reporter oligonucleotides associated with cell 504 in partition 516 are barcoded with barcode sequence 524. As a result, one is provided with a library of oligonucleotides that reflects the surface features of the cell, as reflected by the reporter molecule, but which is substantially attributable to an individual cell by virtue of a common barcode sequence, allowing a single cell level profiling of the surface characteristics of the cell. As will be appreciated, this process is not limited to cell surface receptors but may be used to identify the presence of a wide variety of specific cell structures, chemistries or other characteristics.

Single cell processing and analysis methods and systems described herein can be utilized for a wide variety of applications, including analysis of specific individual cells, analysis of different cell types within populations of differing cell types, analysis and characterization of large populations of cells for environmental, human health, epidemiological forensic, or any of a wide variety of different applications.

A particularly valuable application of the single cell analysis processes described herein is in the sequencing and characterization of a diseased cell. A diseased cell can have altered metabolic properties, gene expression, protein expression, and/or morphologic features. Examples of diseases include inflammatory disorders, metabolic disorders, nervous system disorders, and cancer.

Of particular interest are cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences.

Non-limiting examples of cancer cells include cells of cancers such as Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

Where cancer cells are to be analyzed, primer sequences useful in any of the various operations for attaching barcode sequences and/or amplification reactions may comprise gene specific sequences which target genes or regions of genes associated with or suspected of being associated with cancer. For example, this can include genes or regions of genes where the presence of mutations (e.g., insertions, deletions, polymorphisms, copy number variations, and gene fusions) associated with a cancerous condition are suspected to be present in a cell population.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. As will be appreciated, such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome. Further, the cell surface features of fetal cells may be used to identify any of a number of disorders or diseases.

Also of interest are immune cells. The methods, compositions, and systems disclosed herein can be utilized for sequence analysis of the immune repertoire, including genomic, proteomic, and cell surface features. Analysis of information underlying the immune repertoire can provide a significant improvement in understanding the status and function of the immune system.

Non-limiting examples of immune cells which can be analyzed utilizing the methods described herein include B cells, T cells (e.g., cytotoxic T cells, natural killer T cells, regulatory T cells, and T helper cells), natural killer cells, cytokine induced killer (CIK) cells; myeloid cells, such as granulocytes (basophil granulocytes, eosinophil granulocytes, neutrophil granulocytes/hypersegmented neutrophils), monocytes/macrophages, mast cell, thrombocytes/megakaryocytes, and dendritic cells. In some embodiments, individual T cells are analyzed using the methods disclosed herein. In some embodiments, individual B cells are analyzed using the methods disclosed herein.

Immune cells express various adaptive immunological receptors relating to immune function, such as T cell receptors and B cell receptors. T cell receptors and B cells receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (WIC) molecules. The TCR is generally a heterodimer of two chains, each of which is a member of the immunoglobulin superfamily, possessing an N-terminal variable (V) domain, and a C terminal constant domain. In humans, in 95% of T cells the TCR consists of an alpha ($\alpha$) and beta ($\beta$) chain, whereas in 5% of T cells the TCR consists of gamma and delta ($\gamma/\delta$) chains. This ratio can change during ontogeny and in diseased states as well as in different species. When the TCR engages with antigenic peptide and MHC (peptide/MHC), the T lymphocyte is activated through signal transduction.

Each of the two chains of a TCR contains multiple copies of gene segments—a variable 'V' gene segment, a diversity 'D' gene segment, and a joining 'l' gene segment. The TCR alpha chain is generated by recombination of V and J segments, while the beta chain is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 1' gene segment. Each light chain gene contains multiple copies of two different gene segments for the variable region of the protein—a variable 'V' gene segment and a joining 1' gene segment. The recombination can generate a molecule with one of each of the V, D, and J segments. Furthermore, several bases may be deleted and others added (called N and P nucleotides) at each of the two junctions, thereby generating further diversity. After B cell activation, a process of affinity maturation through somatic hypermutation occurs. In this process progeny cells of the activated B cells accumulate distinct somatic mutations throughout the gene with higher mutation concentration in the CDR regions leading to the generation of antibodies with higher affinity to the antigens. In addition to somatic hypermutation activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

In some embodiments, the methods, compositions and systems disclosed herein are utilized to analyze the various sequences of TCRs and BCRs from immune cells, for example various clonotypes. In some embodiments, methods, compositions and systems disclosed herein are used to analyze the sequence of a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In some embodiments, methods, compositions and systems disclosed herein are used to analyze the sequence of a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions may comprise gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

MHCs, including full or partial MHC-peptides, may be used as labelling agents that are coupled to oligonucleotides that comprise a barcode sequence that identifies its associated MHC (and, thus, for example, the MHC's TCR binding partner). In some cases, MHCs are used to analyze one or more cell-surface features of a T-cell, such as a TCR. In some cases, multiple MHCs are associated together in a larger complex to improve binding affinity of MHCs to TCRs via multiple ligand binding synergies.

Figure 56A:
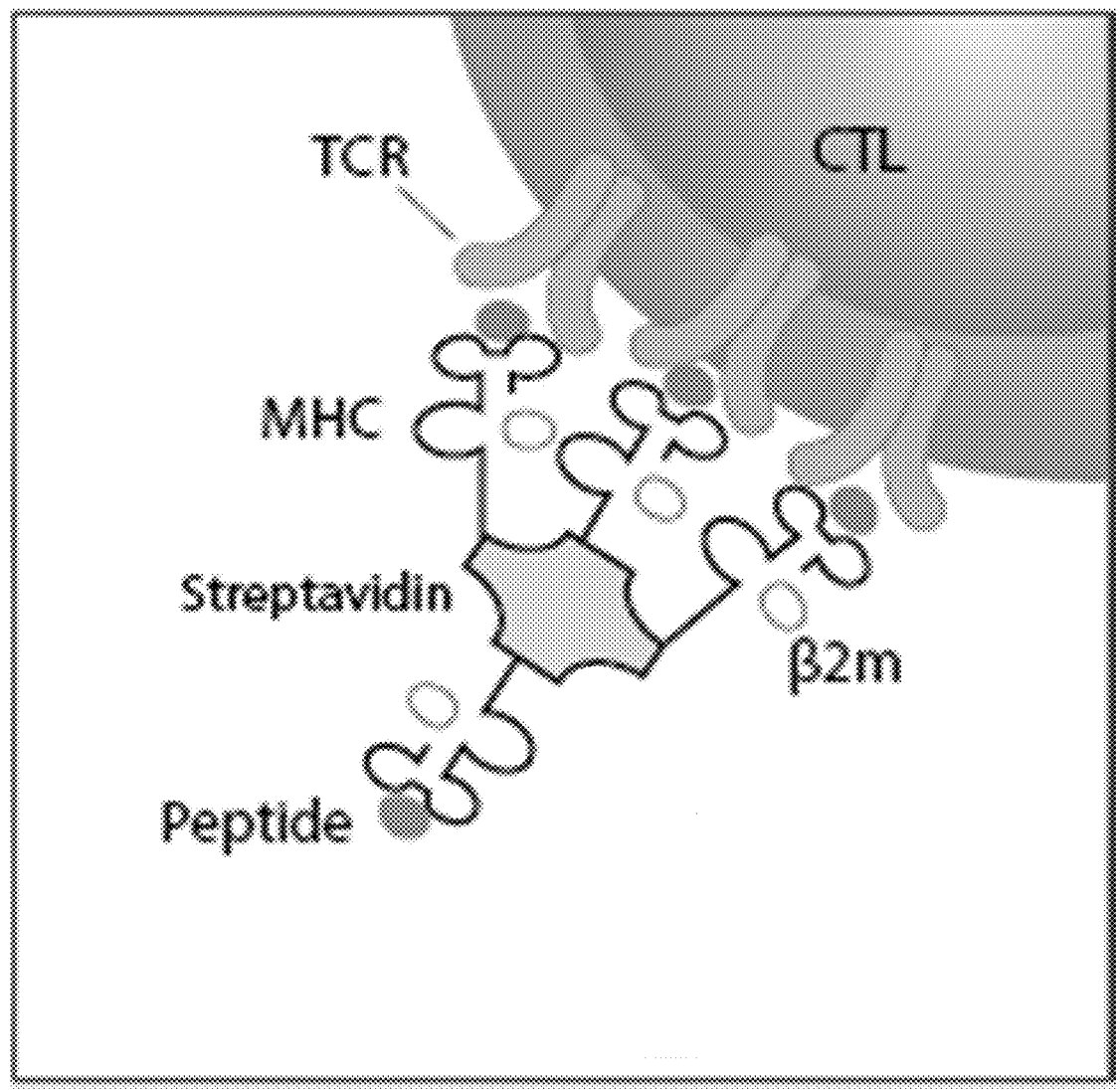
FIGS. 56A-C schematically depict an example barcoding scheme that includes major histocompatibility complexes.

For example, as shown in FIG. 56A, the MHC peptides can individually be associated with biotin and bound to a streptavidin moiety such that the streptavidin moiety comprises multiple MHC moieties. Each of these moieties can bind to a TCR such that the streptavidin binds to the target T-cell via multiple MCH/TCR binding interactions. These multiple interactions synergize and can substantially improve binding affinity. Such improved affinity can improve labelling of T-cells and also reduce the likelihood that labels will dissociate from T-cell surfaces.

Figure 56B:
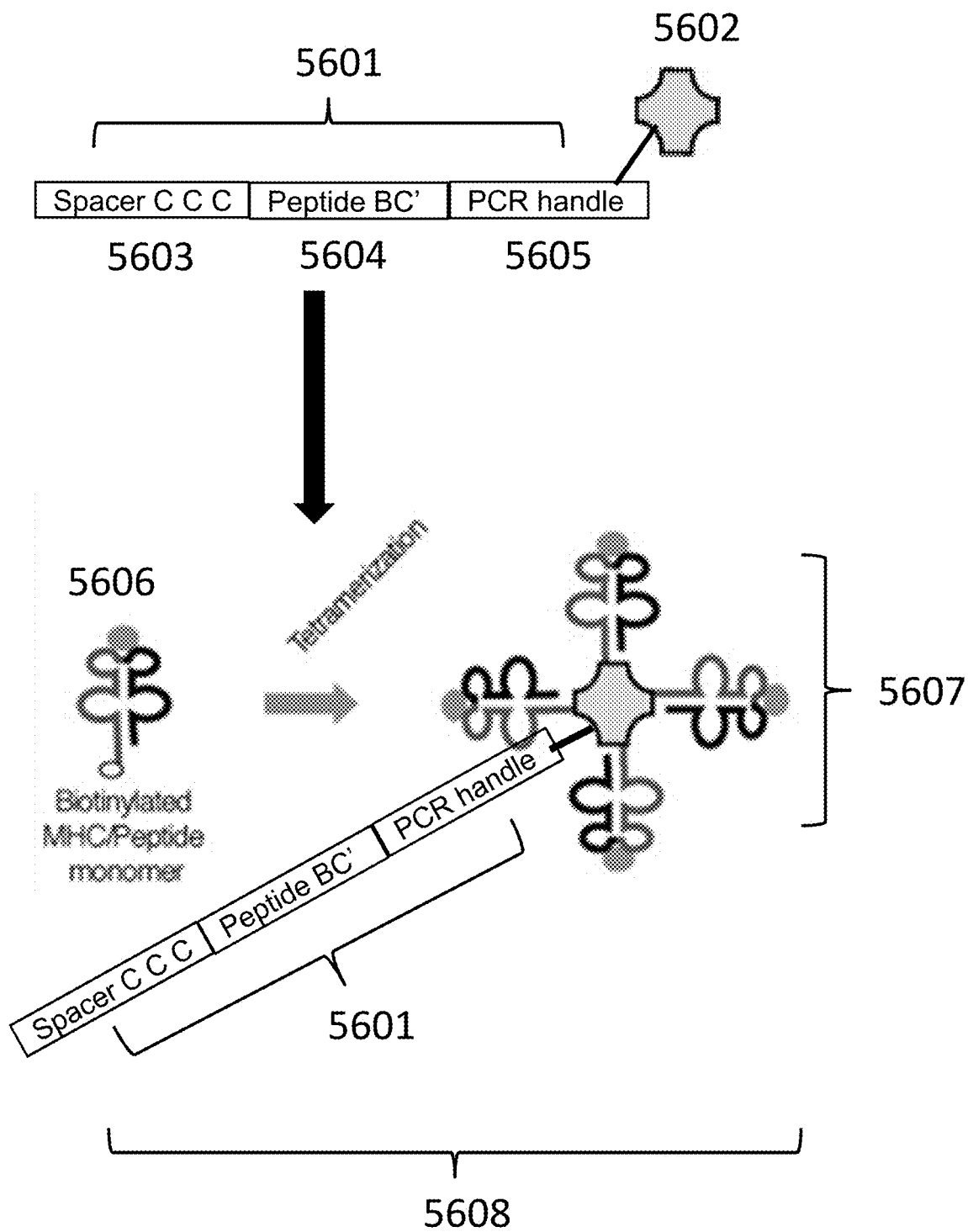
Figure 56C:
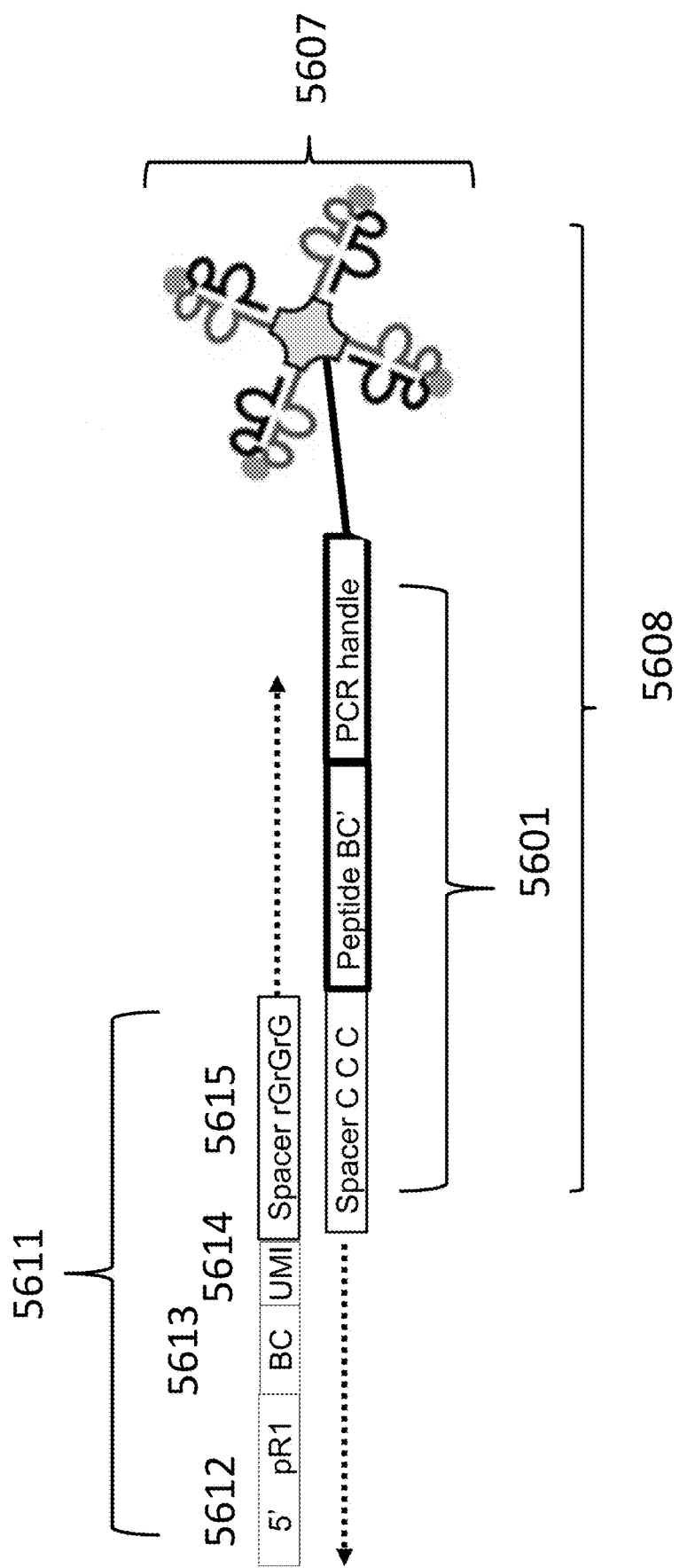

As shown in FIG. 56B and continuing with this example, a barcoded oligonucleotide 5601 can be modified with streptavidin 5602 and contacted with multiple molecules of biotinylated MHC 5606 such that the biotinylated MHC 5606 molecules are coupled with the streptavidin conjugated barcoded oligonucleotide 5601. The result is a barcoded MHC multimer complex 5608. As shown in FIG. 56B, the oligonucleotide 5601 barcode sequence 5602 can identify the MHC 5604 as its associated label and also includes sequences for hybridization with other oligonucleotides (e.g., sequence 5603 comprising a 'Spacer C C C' and sequence 5605 comprising a 'Spacer PCR handle'). One such other oligonucleotide is oligonucleotide 5611 that comprises a complementary sequence 5615 (e.g., rGrGrG corresponding to C C C), a barcode sequence 5613 and, such as, for example, a UMI 5614 as shown in FIG. 56C. In some cases, oligonucleotide 5611 may at first be associated with a bead and released from the bead. In any case, though, oligonucleotide 5611 can hybridize with oligonucleotide 5601 of the MHC-oligonucleotide complex 5608. The hybridized oligonucleotides 5611 and 5601 can then be extended in primer extension reactions such that constructs comprising sequences that correspond to each of the two barcode sequences 5613 and 5604 are generated. In some cases, one or both of these corresponding sequences may be a complement of the original sequence in oligonucleotide 5611 or 5601. One or both of the resulting constructs can be optionally further processed (e.g., to add any additional sequences and/or for clean-up) and subjected to sequencing. As described elsewhere herein, the sequence in such a construct derived from barcode sequence 5613 may be used to identify a partition or a cell within a partition and the sequence derived from barcode sequence 5604 may be used to identify the particular TCR on the surface of the cell, permitting a multi-assay analysis.

Furthermore, while the example shown in FIG. 56B and FIG. 56C shows streptavidin directly coupled to its oligonucleotide, the streptavidin may also be coupled to a hybridization oligonucleotide which then hybridizes with the identifying barcoded oligonucleotide, similar to the example scheme shown in FIG. 52B (panel II) and described elsewhere herein.

The ability to characterize individual cells from larger diverse populations of cells is also of significant value in both environmental testing as well as in forensic analysis, where samples may, by their nature, be made up of diverse populations of cells and other material that "contaminate" the sample, relative to the cells for which the sample is being tested, e.g., environmental indicator organisms, toxic organisms, and the like for, e.g., environmental and food safety testing, victim and/or perpetrator cells in forensic analysis for sexual assault, and other violent crimes, and the like.

Additional useful applications of the above described single cell sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. Nature 460, 1127-1131 (2009)). These differences have been postulated as being related to a person's susceptibility to neuro-logical disorders (see, e.g., Muotri, A. R. et al. Nature 468, 443-446 (2010)), or provide the brain with a diversity with which to respond to challenges. As such, the methods described herein may be used in the sequencing and characterization of individual neural cells.

The single cell analysis methods described herein may also be useful in the analysis of gene expression, both in terms of identification of RNA transcripts and their quantitation. In particular, using the single cell level analysis methods described herein, one can isolate and analyze the RNA transcripts present in individual cells, populations of cells, or subsets of populations of cells. In particular, in some cases, the barcode oligonucleotides may be configured to prime, replicate and consequently yield barcoded fragments of RNA from individual cells. For example, in some cases, the barcode oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcode oligonucleotides.

Figure 6:
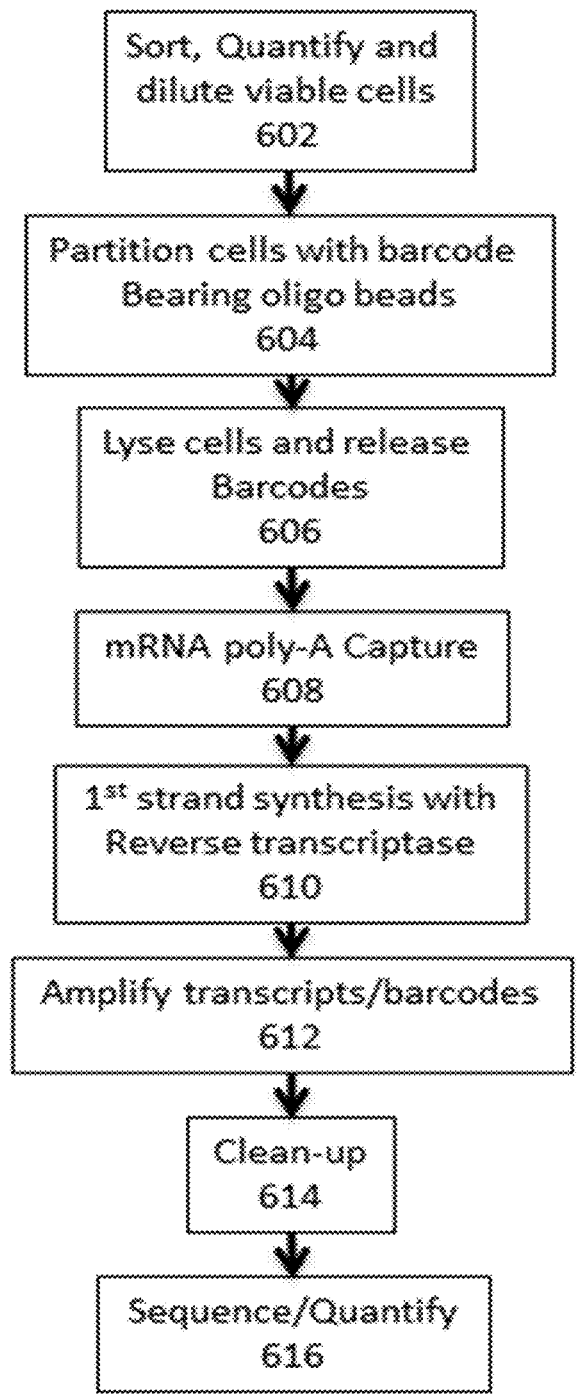
FIG. 6 provides a schematic illustration of an example workflow for performing RNA analysis using the methods described herein.

FIG. 6 provides a schematic of one example method for RNA expression analysis in individual cells using the methods described herein. As shown, at operation 602 a cell containing sample is sorted for viable cells, which are quantified and diluted for subsequent partitioning. At operation 604, the individual cells separately co-partitioned with gel beads bearing the barcoding oligonucleotides as described herein. The cells are lysed and the barcoded oligonucleotides released into the partitions at operation 606, where they interact with and hybridize to the mRNA at operation 608, e.g., by virtue of a poly-T primer sequence, which is complementary to the poly-A tail of the mRNA. Using the poly-T barcode oligonucleotide as a priming sequence, a reverse transcription reaction is carried out at operation 610 to synthesize a cDNA of the mRNA that includes the barcode sequence. The barcoded cDNAs are then subjected to additional amplification at operation 612, e.g., using a PCR process, purification at operation 614, before they are placed on a nucleic acid sequencing system for determination of the cDNA sequence and its associated barcode sequence(s). In some cases, as shown, operations 602 through 608 can occur while the reagents remain in their original droplet or partition, while operations 612 through 616 can occur in bulk (e.g., outside of the partition). In the case where a partition is a droplet in an emulsion, the emulsion can be broken and the contents of the droplet pooled in order to complete operations 612 through 616. In some cases, barcode oligonucleotides may be digested with exonucleases after the emulsion is broken. Exonuclease activity can be inhibited by ethylenediaminetetraacetic acid (EDTA) following primer digestion. In some cases, operation 610 may be performed either within the partitions based upon co-partitioning of the reverse transcription mixture, e.g., reverse transcriptase and associated reagents, or it may be performed in bulk.

The structure of the barcode oligonucleotides may include a number of sequence elements in addition to the oligonucleotide barcode sequence. One example of a barcode oligonucleotide for use in RNA analysis as described above is shown in FIG. 7. As shown, the overall oligonucleotide 702 is coupled to a bead 704 by a releasable linkage 706, such as a disulfide linker. The oligonucleotide may include functional sequences that are used in subsequent processing, such as functional sequence 708, which may include one or more of a sequencer specific flow cell attachment sequence, e.g., a P5 sequence for Illumina sequencing systems, as well as sequencing primer sequences, e.g., a R1 primer for Illumina sequencing systems. A barcode sequence 710 is included within the structure for use in barcoding the sample RNA. An mRNA specific priming sequence, such as poly-T sequence 712 is also included in the oligonucleotide structure. An anchoring sequence segment 714 may be included to ensure that the poly-T sequence hybridizes at the sequence end of the mRNA. This anchoring sequence can include a random short sequence of nucleotides, e.g., 1-mer, 2-mer, 3-mer or longer sequence, which will ensure that the poly-T segment is more likely to hybridize at the sequence end of the poly-A tail of the mRNA. An additional sequence segment 716 may be provided within the oligonucleotide sequence. In some cases, this additional sequence provides a unique molecular identifier (UMI) sequence segment, e.g., as a random sequence (e.g., such as a random N-mer sequence) that varies across individual oligonucleotides coupled to a single bead, whereas barcode sequence 710 can be constant among oligonucleotides tethered to an individual bead. This unique sequence serves to provide a unique identifier of the starting mRNA molecule that was captured, in order to allow quantitation of the number of original expressed RNA. As will be appreciated, although shown as a single oligonucleotide tethered to the surface of a bead, individual bead can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead. This unique molecular identifier (UMI) sequence segment may include from 5 to about 8 or more nucleotides within the sequence of the oligonucleotides. In some cases, the unique molecular identifier (UMI) sequence segment can be 2, 3, 4, 5, 6, 7, 8, 9, 10, 11, 12, 13, 14, 15, 16, 17, 18, 19 or 20 nucleotides in length or longer. In some cases, the unique molecular identifier (UMI) sequence segment can be at least 2, 3, 4, 5, 6, 7, 8, 9, 10, 11, 12, 13, 14, 15, 16, 17, 18, 19 or 20 nucleotides in length or longer. In some cases, the unique molecular identifier (UMI) sequence segment can be at most 2, 3, 4, 5, 6, 7, 8, 9, 10, 11, 12, 13, 14, 15, 16, 17, 18, 19 or 20 nucleotides in length or shorter. In some cases, the oligonucleotide may comprise a target-specific primer. The target-specific primer may bind to specific sequence in a RNA molecule or a DNA molecule derived therefrom. For example, the specific sequence may be a sequence that is not in the poly-A tail.

Figure 7:
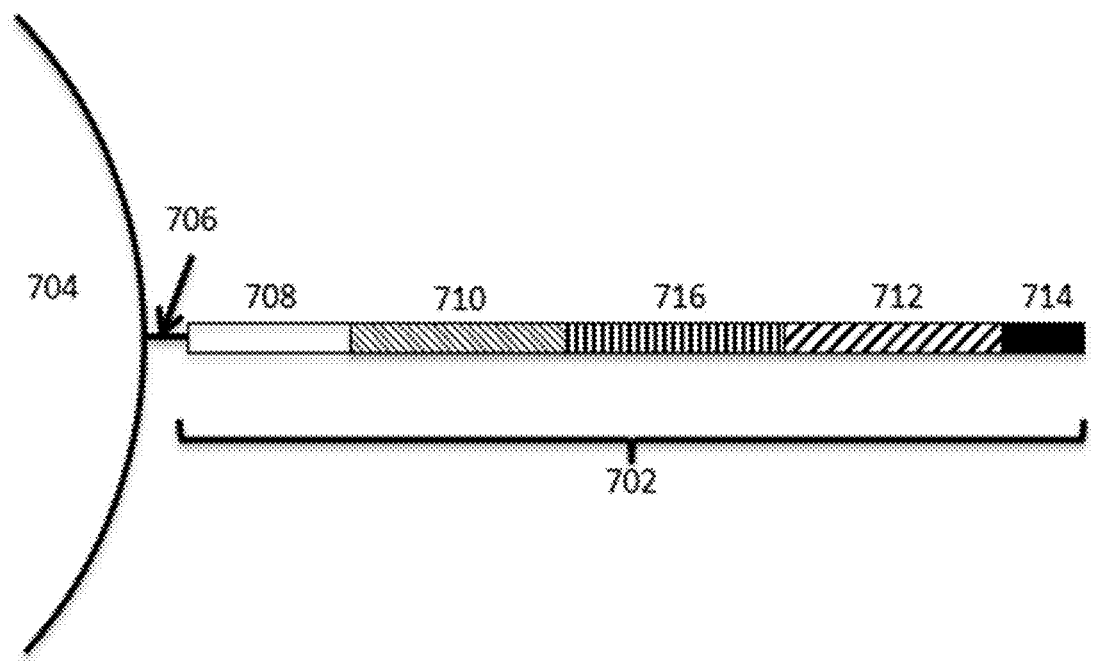
FIG. 7 provides a schematic illustration of an example barcoded oligonucleotide structure for use in analysis of ribonucleic (RNA) using the methods described herein.

In operation, and with reference to FIGS. 6 and 7, a cell is co-partitioned along with a barcode bearing bead and lysed while the barcoded oligonucleotides are released from the bead. The poly-T portion of the released barcode oligonucleotide then hybridizes to the poly-A tail of the mRNA. The poly-T segment then primes the reverse transcription of the mRNA to produce a cDNA of the mRNA, but which includes each of the sequence segments 708-716 of the barcode oligonucleotide. Again, because the oligonucleotide 702 includes an anchoring sequence 714, it will more likely hybridize to and prime reverse transcription at the sequence end of the poly-A tail of the mRNA. Within any given partition, all of the cDNA of the individual mRNA molecules will include a common barcode sequence segment 710. However, by including the unique random N-mer sequence, the transcripts made from different mRNA molecules within a given partition will vary at this unique sequence. This provides a quantitation feature that can be identifiable even following any subsequent amplification of the contents of a given partition, e.g., the number of unique segments associated with a common barcode can be indicative of the quantity of mRNA originating from a single partition, and thus, a single cell. The transcripts may then be amplified, cleaned up and sequenced to identify the sequence of the cDNA of the mRNA, as well as to sequence the barcode segment and the unique sequence segment.

While a poly-T primer sequence is described, other targeted or random priming sequences may also be used in priming the reverse transcription reaction. Likewise, although described as releasing the barcoded oligonucleotides into the partition along with the contents of the lysed cells, it will be appreciated that in some cases, the gel bead bound oligonucleotides may be used to hybridize and capture the mRNA on the solid phase of the gel beads, in order to facilitate the separation of the RNA from other cell contents.

An additional example of a barcode oligonucleotide for use in RNA analysis, including messenger RNA (mRNA, including mRNA obtained from a cell) analysis, is shown in FIG. 9A. As shown, the overall oligonucleotide 902 can be coupled to a bead 904 by a releasable linkage 906, such as a disulfide linker. The oligonucleotide may include functional sequences that are used in subsequent processing, such as functional sequence 908, which may include a sequencer specific flow cell attachment sequence, e.g., a P5 sequence for Illumina sequencing systems, as well as functional sequence 910, which may include sequencing primer sequences, e.g., a R1 primer binding site for Illumina sequencing systems. A barcode sequence 912 is included within the structure for use in barcoding the sample RNA. An RNA specific (e.g., mRNA specific) priming sequence, such as poly-T sequence 914 is also included in the oligonucleotide structure. An anchoring sequence segment (not shown) may be included to ensure that the poly-T sequence hybridizes at the sequence end of the mRNA. An additional sequence segment 916 may be provided within the oligonucleotide sequence. This additional sequence can provide a unique molecular identifier (UMI) sequence segment, e.g., as a random N-mer sequence that varies across individual oligonucleotides coupled to a single bead, whereas barcode sequence 912 can be constant among oligonucleotides tethered to an individual bead. As described elsewhere herein, this unique sequence can serve to provide a unique identifier of the starting mRNA molecule that was captured, in order to allow quantitation of the number of original expressed RNA, e.g., mRNA counting. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular RNA (e.g., mRNA) analysis and in reference to FIG. 9A, a cell is co-partitioned along with a barcode bearing bead, switch oligo 924, and other reagents such as reverse transcriptase, a reducing agent and dNTPs into a partition (e.g., a droplet in an emulsion). In operation 950, the cell is lysed while the barcoded oligonucleotides 902 are released from the bead (e.g., via the action of the reducing agent) and the poly-T segment 914 of the released barcode oligonucleotide then hybridizes to the poly-A tail of mRNA 920 that is released from the cell. Next, in operation 952 the poly-T segment 914 is extended in a reverse transcription reaction using the mRNA as a template to produce a cDNA 922 complementary to the mRNA and also includes each of the sequence segments 908, 912, 910, 916 and 914 of the barcode oligonucleotide. Terminal transferase activity of the reverse transcriptase can add additional bases to the cDNA (e.g., polyC). The switch oligo 924 may then hybridize with the additional bases added to the cDNA and facilitate template switching. A sequence complementary to the switch oligo sequence can then be incorporated into the cDNA 922 via extension of the cDNA 922 using the switch oligo 924 as a template. Within any given partition, all of the cDNAs of the individual mRNA molecules will include a common barcode sequence segment 912. However, by including the unique random N-mer sequence 916, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. Following operation 952, the cDNA 922 is then amplified with primers 926 (e.g., PCR primers) in operation 954. Next, the amplified product is then purified (e.g., via solid phase reversible immobilization (SPRI)) in operation 956. At operation 958, the amplified product is then sheared, ligated to additional functional sequences, and further amplified (e.g., via PCR). The functional sequences may include a sequencer specific flow cell attachment sequence 930, e.g., a P7 sequence for Illumina sequencing systems, as well as functional sequence 928, which may include a sequencing primer binding site, e.g., for a R2 primer for Illumina sequencing systems, as well as functional sequence 932, which may include a sample index, e.g., an i7 sample index sequence for Illumina sequencing systems. In some cases, operations 950 and 952 can occur in the partition, while operations 954, 956 and 958 can occur in bulk solution (e.g., in a pooled mixture outside of the partition). In the case where a partition is a droplet in an emulsion, the emulsion can be broken and the contents of the droplet pooled in order to complete operations 954, 956 and 958. In some cases, operation 954 may be completed in the partition. In some cases, barcode oligonucleotides may be digested with exonucleases after the emulsion is broken. Exonuclease activity can be inhibited by ethylenediaminetetraacetic acid (EDTA) following primer digestion. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

In an alternative example of a barcode oligonucleotide for use in RNA (e.g., cellular RNA) analysis as shown in FIG. 9A, functional sequence 908 may be a P7 sequence and functional sequence 910 may be a R2 primer binding site. Moreover, the functional sequence 930 may be a P5 sequence, functional sequence 928 may be a R1 primer binding site, and functional sequence 932 may be an i5 sample index sequence for Illumina sequencing systems. The configuration of the constructs generated by such a barcode oligonucleotide can help minimize (or avoid) sequencing of the poly-T sequence during sequencing.

Figure 9B:
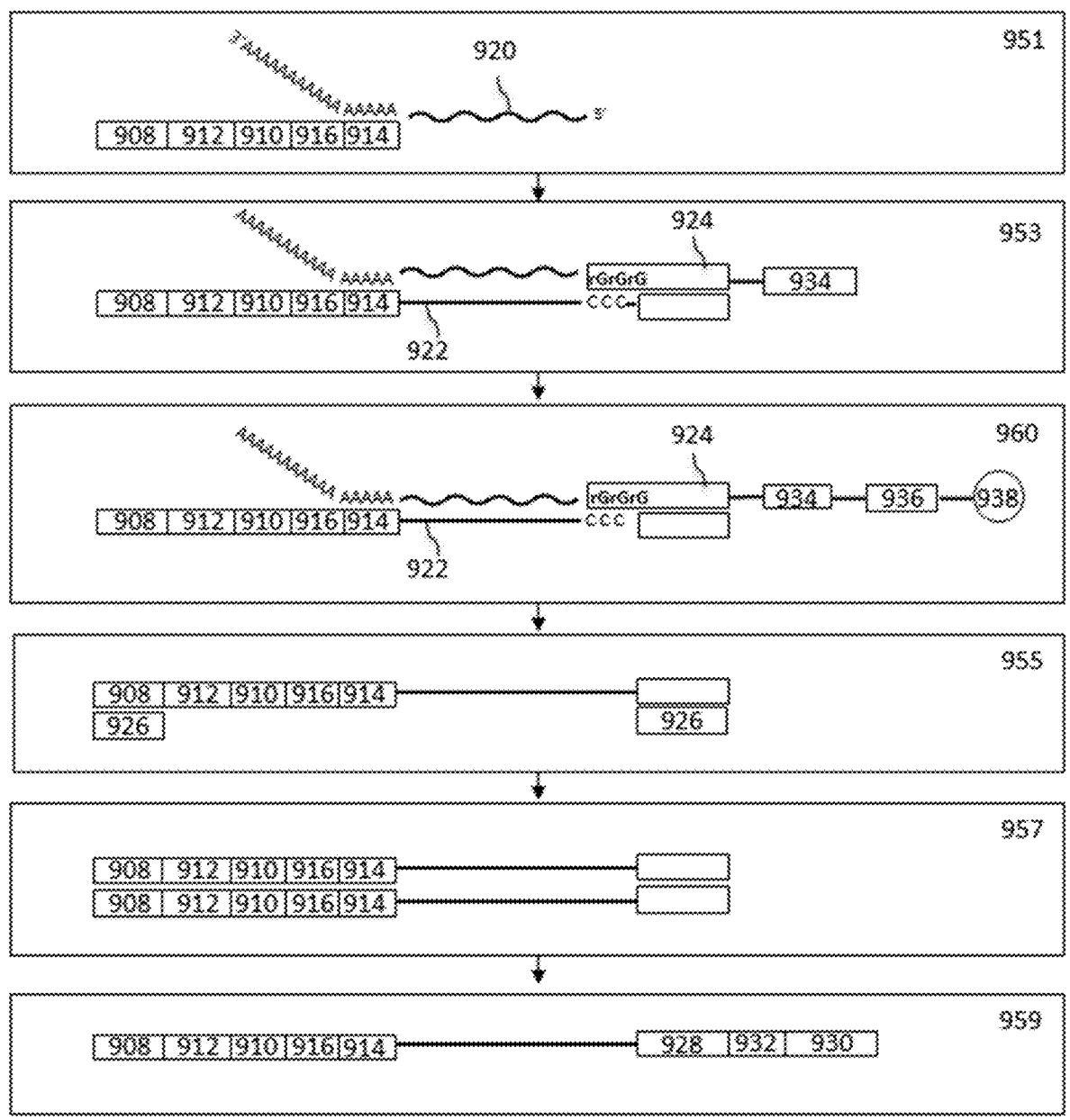

Shown in FIG. 9B is another example method for RNA analysis, including cellular mRNA analysis. In this method, the switch oligo 924 is co-partitioned with the individual cell and barcoded bead along with reagents such as reverse transcriptase, a reducing agent and dNTPs into a partition (e.g., a droplet in an emulsion). The switch oligo 924 may be labeled with an additional tag 934, e.g., biotin. In operation 951, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide hybridizes to the poly-A tail of mRNA 920 that is released from the cell. In operation 953, the poly-T segment 914 is then extended in a reverse transcription reaction using the mRNA as a template to produce a cDNA 922 complementary to the mRNA and also includes each of the sequence segments 908, 912, 910, 916 and 914 of the barcode oligonucleotide. Terminal transferase activity of the reverse transcriptase can add additional bases to the cDNA (e.g., polyC). The switch oligo 924 may then hybridize with the cDNA and facilitate template switching. A sequence complementary to the switch oligo sequence can then be incorporated into the cDNA 922 via extension of the cDNA 922 using the switch oligo 924 as a template. Next, an isolation operation 960 can be used to isolate the cDNA 922 from the reagents and oligonucleotides in the partition. The additional tag 934, e.g., biotin, can be contacted with an interacting tag 936, e.g., streptavidin, which may be attached to a magnetic bead 938. At operation 960 the cDNA can be isolated with a pull-down operation (e.g., via magnetic separation, centrifugation) before amplification (e.g., via PCR) in operation 955, followed by purification (e.g., via solid phase reversible immobilization (SPRI)) in operation 957 and further processing (shearing, ligation of sequences 928, 932 and 930 and subsequent amplification (e.g., via PCR)) in operation 959. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, as shown, operations 951 and 953 can occur in the partition, while operations 960, 955, 957 and 959 can occur in bulk solution (e.g., in a pooled mixture outside of the partition). In the case where a partition is a droplet in an emulsion, the emulsion can be broken and the contents of the droplet pooled in order to complete operation 960. The operations 955, 957, and 959 can then be carried out following operation 960 after the transcripts are pooled for processing.

Figure 9C:
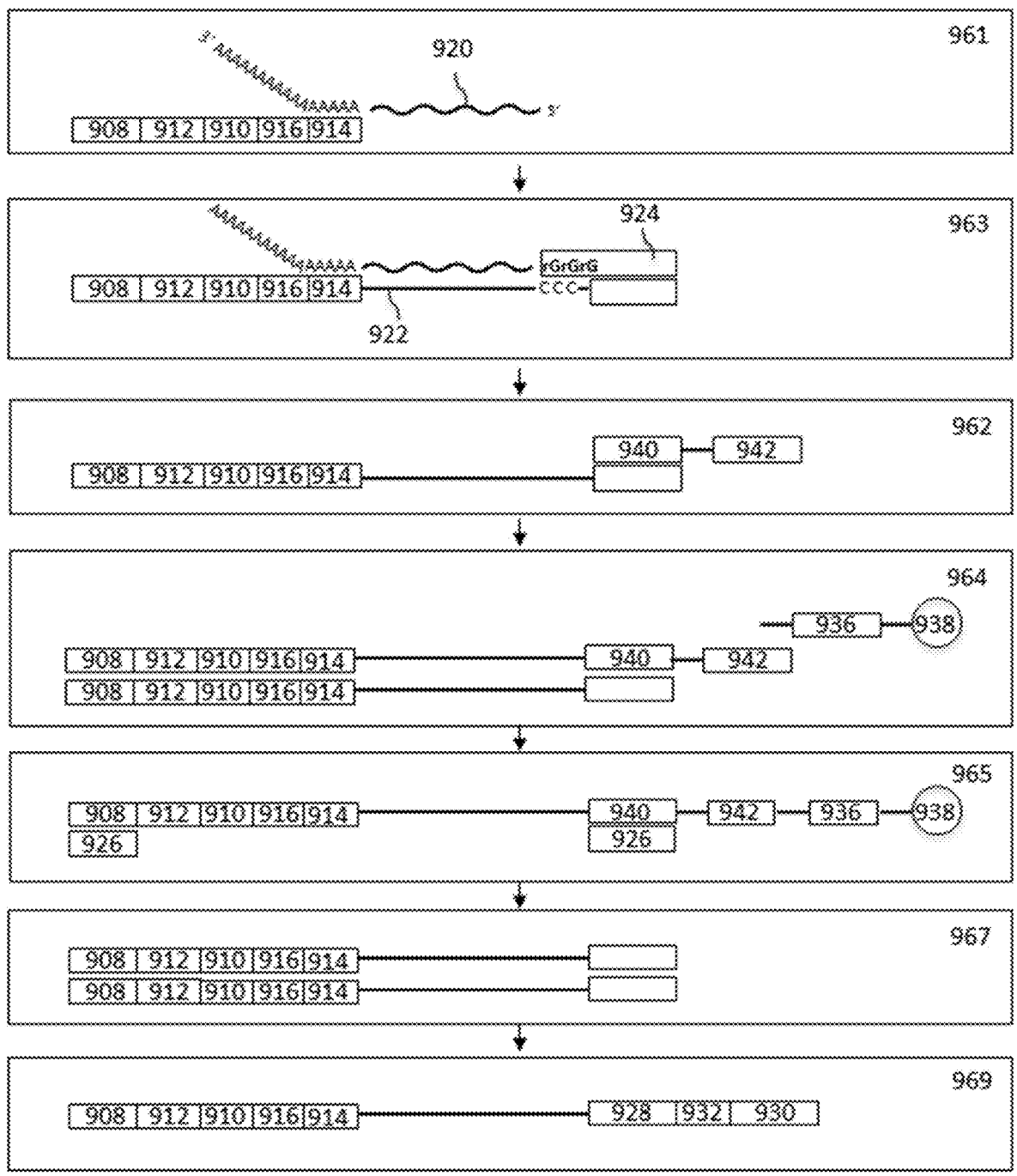

Shown in FIG. 9C is another example method for RNA analysis, including cellular mRNA analysis. In this method, the switch oligo 924 is co-partitioned with the individual cell and barcoded bead along with reagents such as reverse transcriptase, a reducing agent and dNTPs in a partition (e.g., a droplet in an emulsion). In operation 961, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide then hybridizes to the poly-A tail of mRNA 920 that is released from the cell. Next, in operation 963 the poly-T segment 914 is then extended in a reverse transcription reaction using the mRNA as a template to produce a cDNA 922 complementary to the mRNA and also includes each of the sequence segments 908, 912, 910, 916 and 914 of the barcode oligonucleotide. Terminal transferase activity of the reverse transcriptase can add additional bases to the cDNA (e.g., polyC). The switch oligo 924 may then hybridize with the cDNA and facilitate template switching. A sequence complementary to the switch oligo sequence can then be incorporated into the cDNA 922 via extension of the cDNA 922 using the switch oligo 924 as a template. Following operation 961 and operation 963, mRNA 920 and cDNA 922 are denatured in operation 962. At operation 964, a second strand is extended from a primer 940 having an additional tag 942, e.g., biotin, and hybridized to the cDNA 922. Also in operation 964, the biotin labeled second strand can be contacted with an interacting tag 936, e.g., streptavidin, which may be attached to a magnetic bead 938. The cDNA can be isolated with a pull-down operation (e.g., via magnetic separation, centrifugation) before amplification (e.g., via polymerase chain reaction (PCR)) in operation 965, followed by purification (e.g., via solid phase reversible immobilization (SPRI)) in operation 967 and further processing (shearing, ligation of sequences 928, 932 and 930 and subsequent amplification (e.g., via PCR)) in operation 969. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 961 and 963 can occur in the partition, while operations 962, 964, 965, 967, and 969 can occur in bulk (e.g., outside the partition). In the case where a partition is a droplet in an emulsion, the emulsion can be broken and the contents of the droplet pooled in order to complete operations 962, 964, 965, 967 and 969.

Figure 9D:
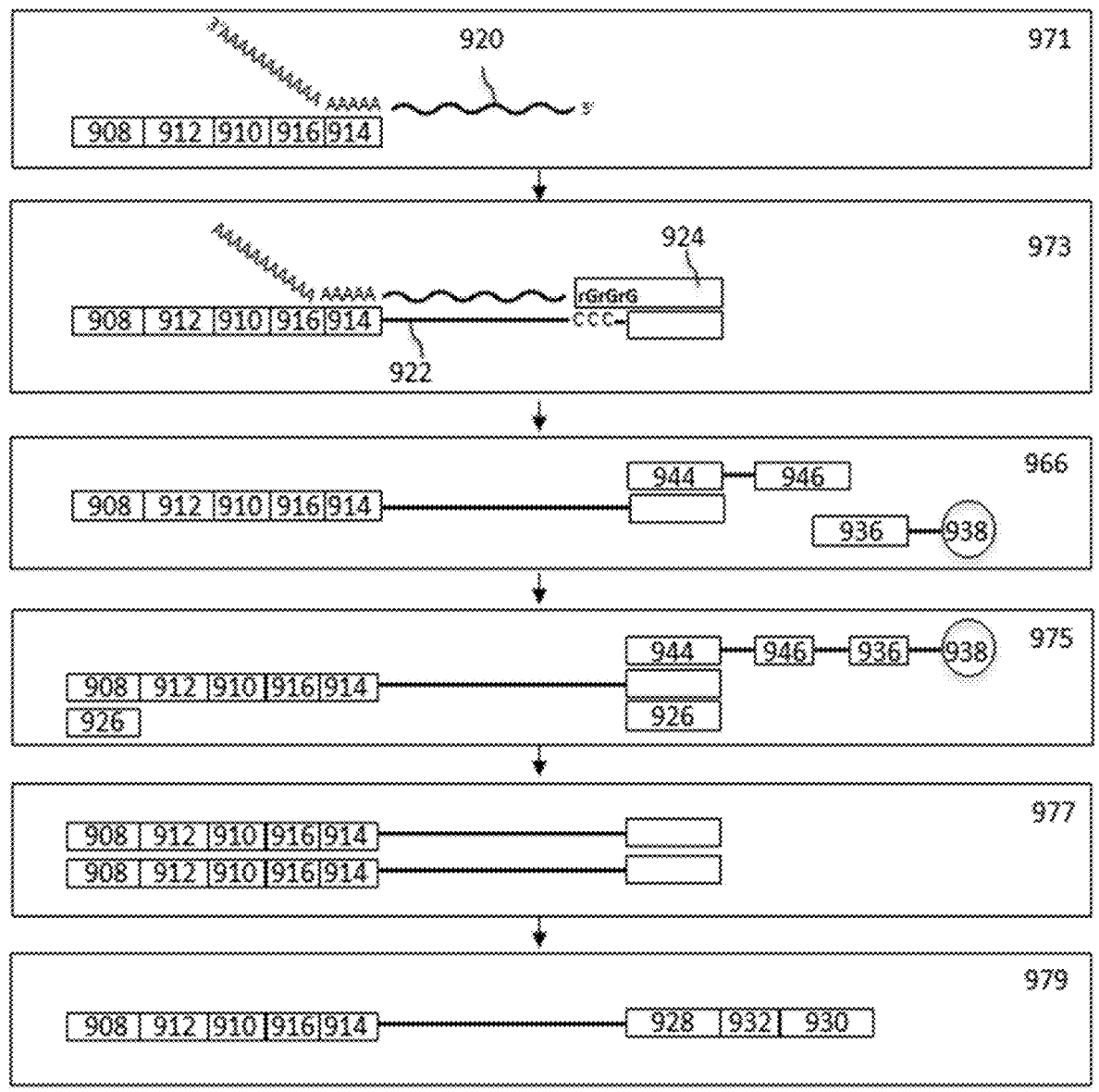

Shown in FIG. 9D is another example method for RNA analysis, including cellular mRNA analysis. In this method, the switch oligo 924 is co-partitioned with the individual cell and barcoded bead along with reagents such as reverse transcriptase, a reducing agent and dNTPs. In operation 971, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next the poly-T segment 914 of the released barcode oligonucleotide then hybridizes to the poly-A tail of mRNA 920 that is released from the cell. Next in operation 973, the poly-T segment 914 is then extended in a reverse transcription reaction using the mRNA as a template to produce a cDNA 922 complementary to the mRNA and also includes each of the sequence segments 908, 912, 910, 916 and 914 of the barcode oligonucleotide. Terminal transferase activity of the reverse transcriptase can add additional bases to the cDNA (e.g., polyC). The switch oligo 924 may then hybridize with the cDNA and facilitate template switching. A sequence complementary to the switch oligo sequence can then be incorporated into the cDNA 922 via extension of the cDNA 922 using the switch oligo 924 as a template. In operation 966, the mRNA 920, cDNA 922 and switch oligo 924 can be denatured, and the cDNA 922 can be hybridized with a capture oligonucleotide 944 labeled with an additional tag 946, e.g., biotin. In this operation, the biotin-labeled capture oligonucleotide 944, which is hybridized to the cDNA, can be contacted with an interacting tag 936, e.g., streptavidin, which may be attached to a magnetic bead 938. Following separation from other species (e.g., excess barcoded oligonucleotides) using a pull-down operation (e.g., via magnetic separation, centrifugation), the cDNA can be amplified (e.g., via PCR) with primers 926 at operation 975, followed by purification (e.g., via solid phase reversible immobilization (SPRI)) in operation 977 and further processing (shearing, ligation of sequences 928, 932 and 930 and subsequent amplification (e.g., via PCR)) in operation 979. In some cases where sequence 908 is a P7 sequence and sequence 910 is a R2 primer binding site, sequence 930 is a P5 sequence and sequence 928 is a R1 primer binding site and sequence 932 is an i5 sample index sequence. In other cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 971 and 973 can occur in the partition, while operations 966, 975, 977 (purification), and 979 can occur in bulk (e.g., outside the partition). In the case where a partition is a droplet in an emulsion, the emulsion can be broken and the contents of the droplet pooled in order to complete operations 966, 975, 977 and 979.

Figure 9E:
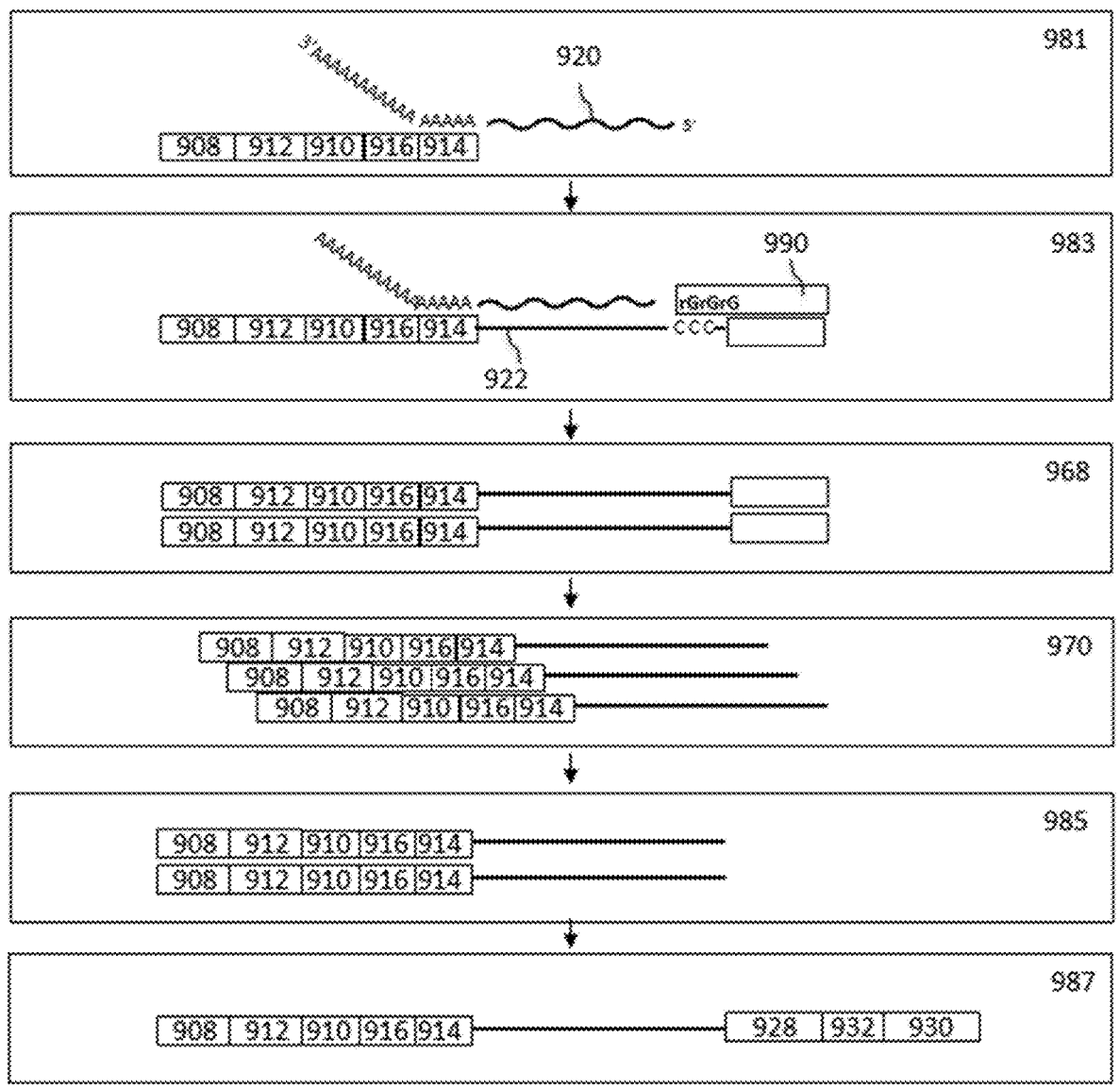

Shown in FIG. 9E is another example method for RNA analysis, including cellular RNA analysis. In this method, an individual cell is co-partitioned along with a barcode bearing bead, a switch oligo 990, and other reagents such as reverse transcriptase, a reducing agent and dNTPs into a partition (e.g., a droplet in an emulsion). In operation 981, the cell is lysed while the barcoded oligonucleotides (e.g., 902 as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment of the released barcode oligonucleotide then hybridizes to the poly-A tail of mRNA 920 released from the cell. Next at operation 983, the poly-T segment is then extended in a reverse transcription reaction to produce a cDNA 922 complementary to the mRNA and also includes each of the sequence segments 908, 912, 910, 916 and 914 of the barcode oligonucleotide. Terminal transferase activity of the reverse transcriptase can add additional bases to the cDNA (e.g., polyC). The switch oligo 990 may then hybridize with the cDNA and facilitate template switching. A sequence complementary to the switch oligo sequence and including a T7 promoter sequence, can be incorporated into the cDNA 922. At operation 968, a second strand is synthesized and at operation 970 the T7 promoter sequence can be used by T7 polymerase to produce RNA transcripts in in vitro transcription. At operation 985 the RNA transcripts can be purified (e.g., via solid phase reversible immobilization (SPRI)), reverse transcribed to form DNA transcripts, and a second strand can be synthesized for each of the DNA transcripts. In some cases, prior to purification, the RNA transcripts can be contacted with a DNase (e.g., DNAase I) to break down residual DNA. At operation 987 the DNA transcripts are then fragmented and ligated to additional functional sequences, such as sequences 928, 932 and 930 and, in some cases, further amplified (e.g., via PCR). In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, prior to removing a portion of the DNA transcripts, the DNA transcripts can be contacted with an RNase to break down residual RNA. In some cases, operations 981 and 983 can occur in the partition, while operations 968, 970, 985 and 987 can occur in bulk (e.g., outside the partition). In the case where a partition is a droplet in an emulsion, the emulsion can be broken and the contents of the droplet pooled in order to complete operations 968, 970, 985 and 987.

Figure 10:
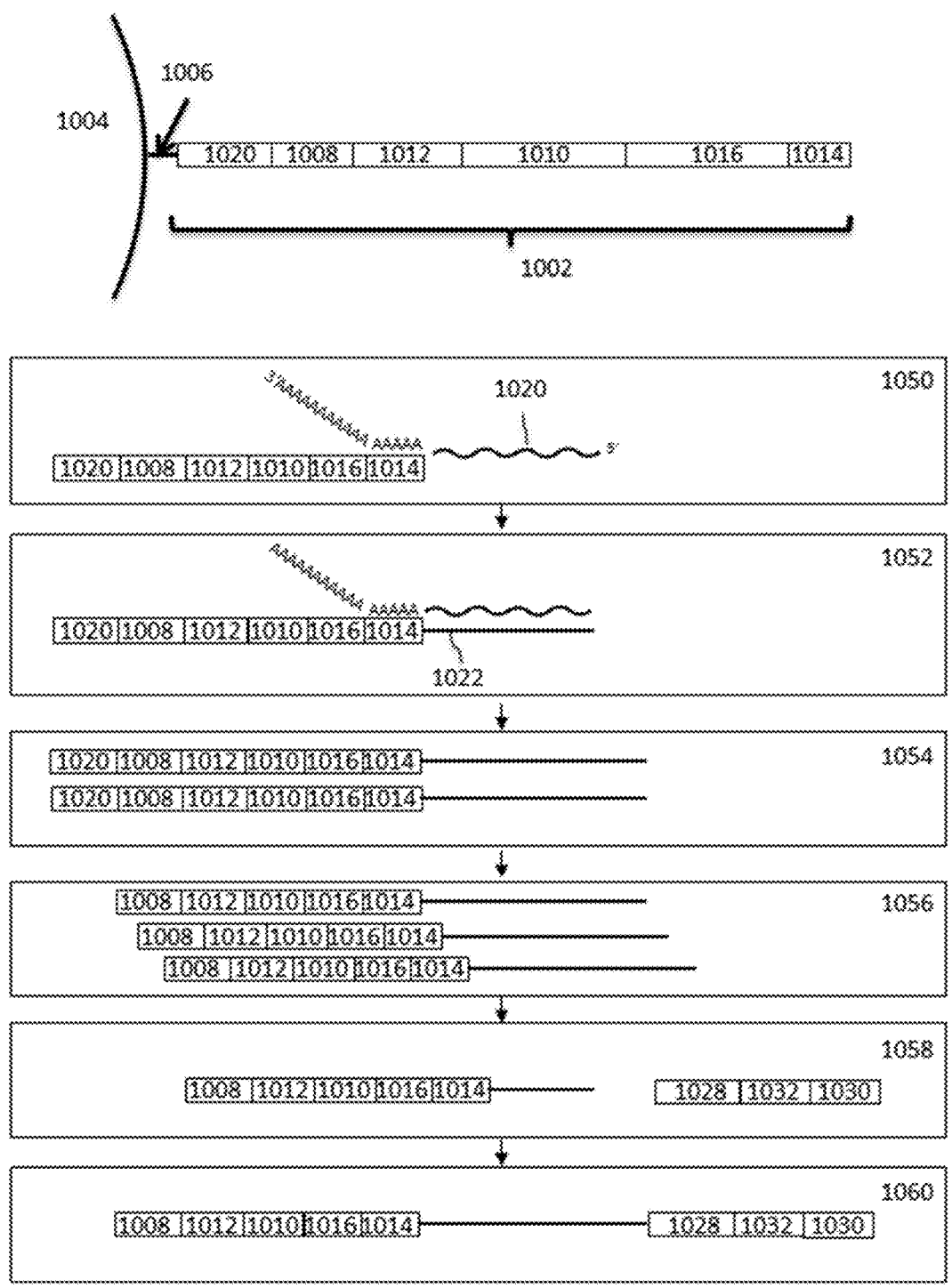
FIG. 10 provides a schematic illustration of example barcoded oligonucleotide structure for use in example analysis of RNA and use of a sequence for in vitro transcription ("AAAAAAAAAAAAAAAA" disclosed as SEQ ID NO: 1)

Another example of a barcode oligonucleotide for use in RNA analysis, including messenger RNA (mRNA, including mRNA obtained from a cell) analysis is shown in FIG. 10. As shown, the overall oligonucleotide 1002 is coupled to a bead 1004 by a releasable linkage 1006, such as a disulfide linker. The oligonucleotide may include functional sequences that are used in subsequent processing, such as functional sequence 1008, which may include a sequencer specific flow cell attachment sequence, e.g., a P7 sequence, as well as functional sequence 1010, which may include sequencing primer sequences, e.g., a R2 primer binding site. A barcode sequence 1012 is included within the structure for use in barcoding the sample RNA. An RNA specific (e.g., mRNA specific) priming sequence, such as poly-T sequence 1014 may be included in the oligonucleotide structure. An anchoring sequence segment (not shown) may be included to ensure that the poly-T sequence hybridizes at the sequence end of the mRNA. An additional sequence segment 1016 may be provided within the oligonucleotide sequence. This additional sequence can provide a unique molecular identifier (UMI) sequence segment, as described elsewhere herein. An additional functional sequence 1020 may be included for in vitro transcription, e.g., a T7 RNA polymerase promoter sequence. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular RNA analysis and in reference to FIG. 10, a cell is co-partitioned along with a barcode bearing bead, and other reagents such as reverse transcriptase, reducing agent and dNTPs into a partition (e.g., a droplet in an emulsion). In operation 1050, the cell is lysed while the barcoded oligonucleotides 1002 are released (e.g., via the action of the reducing agent) from the bead, and the poly-T segment 1014 of the released barcode oligonucleotide then hybridizes to the poly-A tail of mRNA 1020. Next at operation 1052, the poly-T segment is then extended in a reverse transcription reaction using the mRNA as template to produce a cDNA 1022 of the mRNA and also includes each of the sequence segments 1020, 1008, 1012, 1010, 1016, and 1014 of the barcode oligonucleotide. Within any given partition, all of the cDNAs of the individual mRNA molecules will include a common barcode sequence segment 1012. However, by including the unique random N-mer sequence, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. At operation 1054 a second strand is synthesized and at operation 1056 the T7 promoter sequence can be used by T7 polymerase to produce RNA transcripts in in vitro transcription. At operation 1058 the transcripts are fragmented (e.g., sheared), ligated to additional functional sequences, and reverse transcribed. The functional sequences may include a sequencer specific flow cell attachment sequence 1030, e.g., a P5 sequence, as well as functional sequence 1028, which may include sequencing primers, e.g., a R1 primer binding sequence, as well as functional sequence 1032, which may include a sample index, e.g., an i5 sample index sequence. At operation 1060 the RNA transcripts can be reverse transcribed to DNA, the DNA amplified (e.g., via PCR), and sequenced to identify the sequence of the cDNA of the mRNA, as well as to sequence the barcode segment and the unique sequence segment. In some cases, operations 1050 and 1052 can occur in the partition, while operations 1054, 1056, 1058 and 1060 can occur in bulk (e.g., outside the partition). In the case where a partition is a droplet in an emulsion, the emulsion can be broken and the contents of the droplet pooled in order to complete operations 1054, 1056, 1058 and 1060.

In an alternative example of a barcode oligonucleotide for use in RNA (e.g., cellular RNA) analysis as shown in FIG. 10, functional sequence 1008 may be a P5 sequence and functional sequence 1010 may be a R1 primer binding site. Moreover, the functional sequence 1030 may be a P7 sequence, functional sequence 1028 may be a R2 primer binding site, and functional sequence 1032 may be an i7 sample index sequence.

Figure 11:
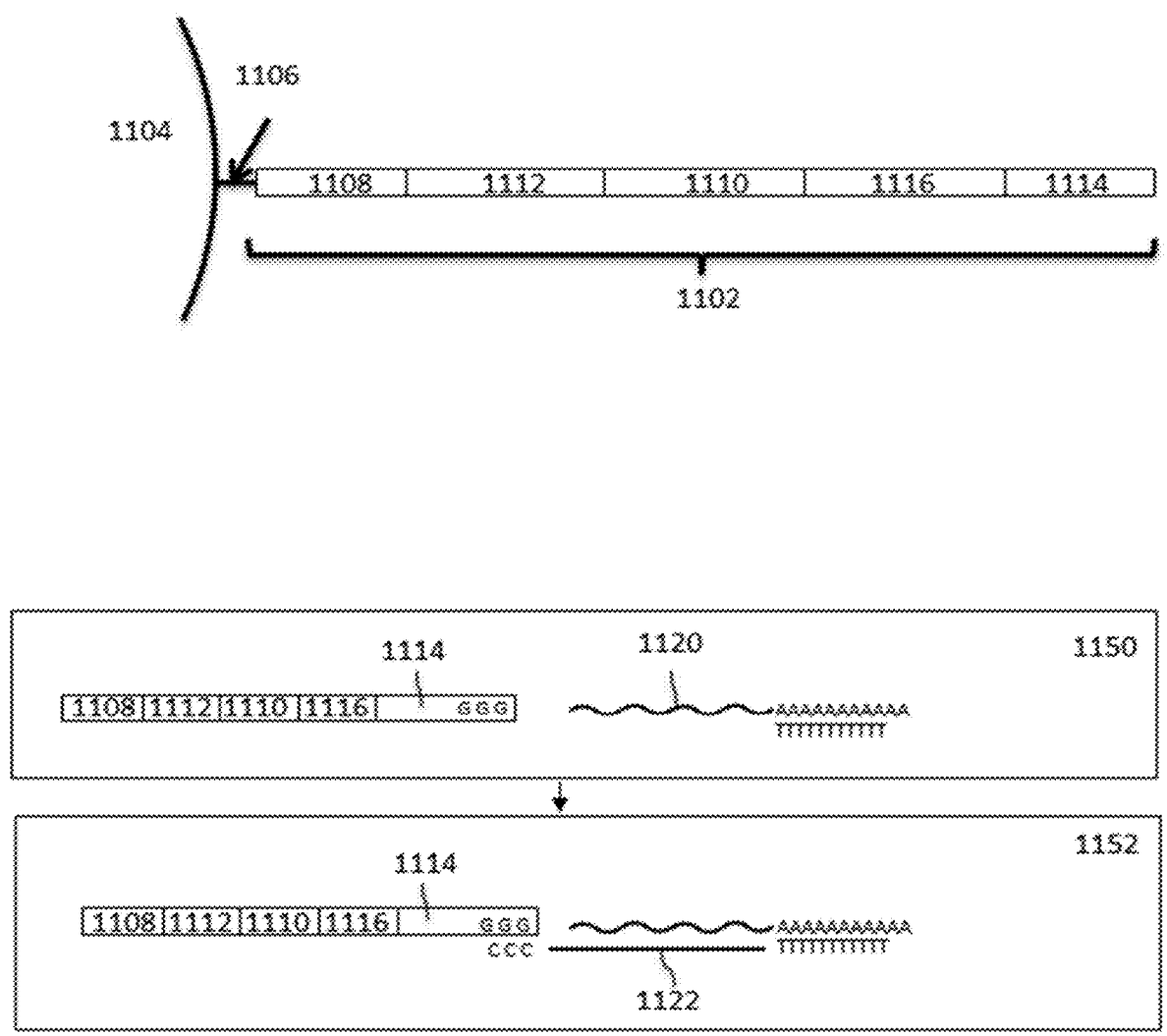
FIG. 11 provides a schematic illustration of an example barcoded oligonucleotide structure for use in analysis of RNA and example operations for performing RNA analysis (SEQ ID NOS 2-3 and 2-3, respectively, in order of appearance)

An additional example of a barcode oligonucleotide for use in RNA analysis, including messenger RNA (mRNA, including mRNA obtained from a cell) analysis is shown in FIG. 11. As shown, the overall oligonucleotide 1102 is coupled to a bead 1104 by a releasable linkage 1106, such as a disulfide linker. The oligonucleotide may include functional sequences that are used in subsequent processing, such as functional sequence 1108, which may include a sequencer specific flow cell attachment sequence, e.g., a P5 sequence, as well as functional sequence 1110, which may include sequencing primer sequences, e.g., a R1 primer binding site. In some cases, sequence 1108 is a P7 sequence and sequence 1110 is a R2 primer binding site. A barcode sequence 1112 is included within the structure for use in barcoding the sample RNA. An additional sequence segment 1116 may be provided within the oligonucleotide sequence. In some cases, this additional sequence can provide a unique molecular identifier (UMI) sequence segment, as described elsewhere herein. An additional sequence 1114 may be included to facilitate template switching, e.g., polyG. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular mRNA analysis and in reference to FIG. 11, a cell is co-partitioned along with a microcapsule (e.g., bead bearing a barcoded oligonucleotide), polyT sequence, and other reagents such as a DNA polymerase, a reverse transcriptase, oligonucleotide primers, dNTPs, and reducing agent into a partition (e.g., a droplet in an emulsion). The partition can serve as a reaction volume. As described elsewhere herein, the partition serving as the reaction volume can comprise a container or vessel such as a well, a microwell, vial, a tube, through ports in nanoarray substrates, or micro-vesicles having an outer barrier surrounding an inner fluid center or core, emulsion, or a droplet. In some embodiments, the partition comprises a droplet of aqueous fluid within a non-aqueous continuous phase, e.g., an oil phase. Within the partition, the cell can be lysed and the barcoded oligonucleotides can be released from the bead (e.g., via the action of the reducing agent or other stimulus). Cell lysis and release of the barcoded oligonucleotides from the microcapsule may occur simultaneously in the partition (e.g., a droplet in an emulsion) or the reaction volume. In some embodiments, cell lysis precedes release of the barcoded oligonucleotides from the microcapsule. In some embodiments, release of the barcoded oligonucleotides from the microcapsule precedes cell lysis.

Subsequent to cell lysis and the release of barcoded oligonucleotides from the microcapsule, the reaction volume can be subjected to an amplification reaction to generate an amplification product. In an example amplification reaction, the polyT sequence hybridizes to the polyA tail of mRNA 1120 released from the cell as illustrated in operation 1150. Next, in operation 1152, the polyT sequence is then extended in a reverse transcription reaction using the mRNA as a template to produce a cDNA 1122 complementary to the mRNA. Terminal transferase activity of the reverse transcriptase can add additional bases to the cDNA (e.g., polyC) in a template independent manner. The additional bases added to the cDNA, e.g., polyC, can then hybridize with 1114 of the barcoded oligonucleotide. This can facilitate template switching and a sequence complementary to the barcoded oligonucleotide can be incorporated into the cDNA. In various embodiments, the barcoded oligonucleotide does not hybridize to the template polynucleotide.

The barcoded oligonucleotide, upon release from the microcapsule, can be present in the reaction volume at any suitable concentration. In some embodiments, the barcoded oligonucleotide is present in the reaction volume at a concentration of about 0.2 µM, 0.3 µM, 0.4 µM, 0.5 µM, 1 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM or 500 µM. In some embodiments, the barcoded oligonucleotide is present in the reaction volume at a concentration of at least about 0.2 µM, 0.3 µM, 0.4 µM, 0.5 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM, 500 µM or greater. In some embodiments, the barcoded oligonucleotide is present in the reaction volume at a concentration of at most about 0.2 µM, 0.3 µM, 0.4 µM, 0.5 µM, 1 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM or 500 µM.

The transcripts can be further processed (e.g., amplified, portions removed, additional sequences added, etc.) and characterized as described elsewhere herein. In some embodiments, the transcripts are sequenced directly. In some embodiments, the transcripts are further processed (e.g., portions removed, additional sequences added, etc) and then sequenced. In some embodiments, the reaction volume is subjected to a second amplification reaction to generate an additional amplification product. The transcripts or first amplification products can be used as the template for the second amplification reaction. In some embodiments, primers for the second amplification reaction comprise the barcoded oligonucleotide and polyT sequence. In some embodiments, primers for the second amplification reaction comprise additional primers co-partitioned with the cell. In some embodiments, these additional amplification products are sequenced directly. In some embodiments, these additional amplification products are further processed (e.g., portions removed, additional sequences added, etc) and then sequenced. The configuration of the amplification products (e.g., first amplification products and second amplification products) generated by such a method can help minimize (or avoid) sequencing of the poly-T sequence during sequencing.

Figure 12A:
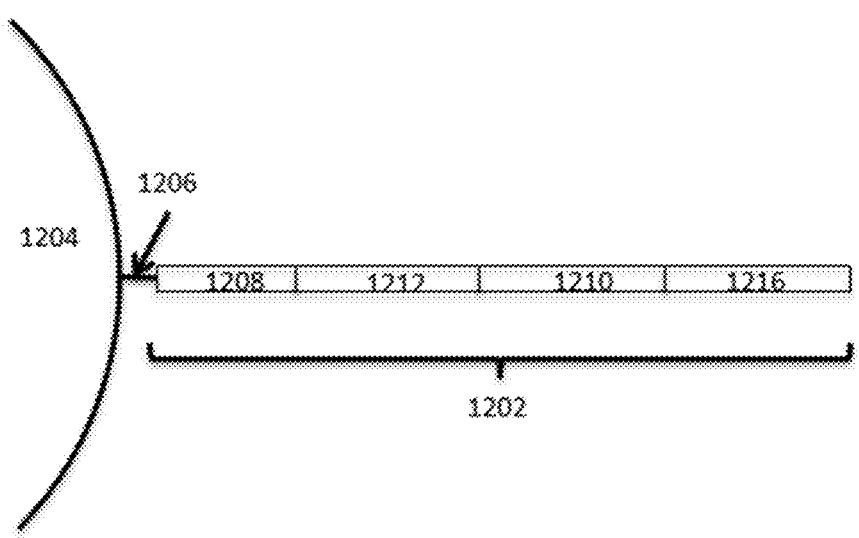
FIGS. 12A-12B provide schematic illustrations of example barcoded oligonucleotide structure for use in analysis of RNA.

An additional example of a barcode oligonucleotide for use in RNA analysis, including cellular RNA analysis is shown in FIG. 12A. As shown, the overall oligonucleotide 1202 is coupled to a bead 1204 by a releasable linkage 1206, such as a disulfide linker. The oligonucleotide may include functional sequences that are used in subsequent processing, such as functional sequence 1208, which may include a sequencer specific flow cell attachment sequence, e.g., a P5 sequence, as well as functional sequence 1210, which may include sequencing primer sequences, e.g., a R1 primer binding site. In some cases, sequence 1208 is a P7 sequence and sequence 1210 is a R2 primer binding site. A barcode sequence 1212 is included within the structure for use in barcoding the sample RNA. An additional sequence segment 1216 may be provided within the oligonucleotide sequence. In some cases, this additional sequence can provide a unique molecular identifier (UMI) sequence segment, as described elsewhere herein. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead. In an example method of cellular RNA analysis using this barcode, a cell is co-partitioned along with a barcode bearing bead and other reagents such as RNA ligase and a reducing agent into a partition (e.g., a droplet in an emulsion). The cell is lysed while the barcoded oligonucleotides are released (e.g., via the action of the reducing agent) from the bead. The barcoded oligonucleotides can then be ligated to the 5' end of mRNA transcripts while in the partitions by RNA ligase. Subsequent operations may include purification (e.g., via solid phase reversible immobilization (SPRI)) and further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for the additional operations.

Figure 12B:
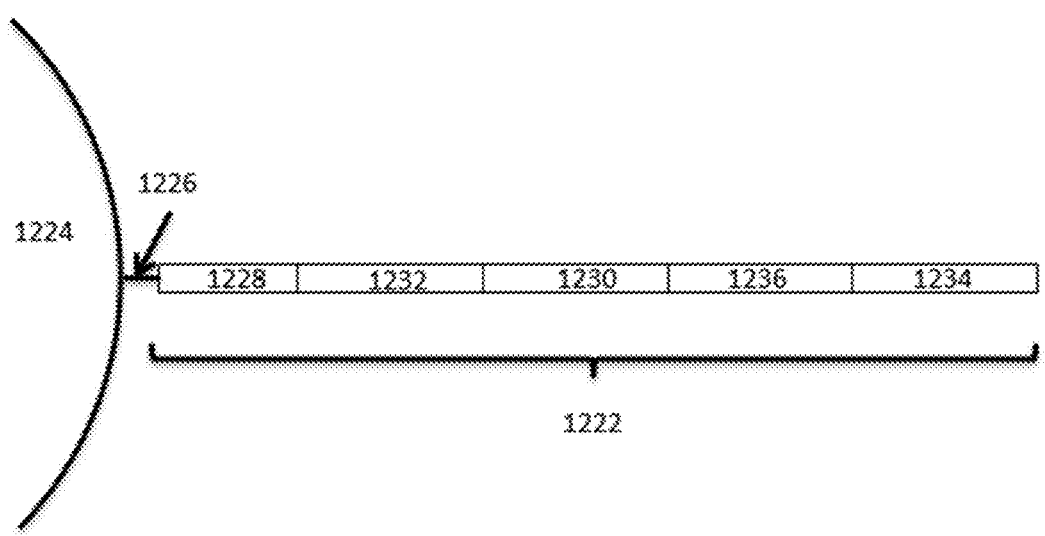

An additional example of a barcode oligonucleotide for use in RNA analysis, including cellular RNA analysis is shown in FIG. 12B. As shown, the overall oligonucleotide 1222 is coupled to a bead 1224 by a releasable linkage 1226, such as a disulfide linker. The oligonucleotide may include functional sequences that are used in subsequent processing, such as functional sequence 1228, which may include a sequencer specific flow cell attachment sequence, e.g., a P5 sequence, as well as functional sequence 1230, which may include sequencing primer sequences, e.g., a R1 primer binding site. In some cases, sequence 1228 is a P7 sequence and sequence 1230 is a R2 primer binding site. A barcode sequence 1232 is included within the structure for use in barcoding the sample RNA. A priming sequence 1234 (e.g., a random priming sequence) can also be included in the oligonucleotide structure, e.g., a random hexamer. An additional sequence segment 1236 may be provided within the oligonucleotide sequence. In some cases, this additional sequence provides a unique molecular identifier (UMI) sequence segment, as described elsewhere herein. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead. In an example method of cellular mRNA analysis using the barcode oligonucleotide of FIG. 12B, a cell is co-partitioned along with a barcode bearing bead and additional reagents such as reverse transcriptase, a reducing agent and dNTPs into a partition (e.g., a droplet in an emulsion). The cell is lysed while the barcoded oligonucleotides are released from the bead (e.g., via the action of the reducing agent). In some cases, sequence 1228 is a P7 sequence and sequence 1230 is a R2 primer binding site. In other cases, sequence 1228 is a P5 sequence and sequence 1230 is a R1 primer binding site. The priming sequence 1234 of random hexamers can randomly hybridize cellular mRNA. The random hexamer sequence can then be extended in a reverse transcription reaction using mRNA from the cell as a template to produce a cDNA complementary to the mRNA and also includes each of the sequence segments 1228, 1232, 1230, 1236, and 1234 of the barcode oligonucleotide. Subsequent operations may include purification (e.g., via solid phase reversible immobilization (SPRI)), further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA and cDNA from cells. Alternatively, rRNA removal agents may be applied during additional processing operations. The configuration of the constructs generated by such a method can help minimize (or avoid) sequencing of the poly-T sequence during sequencing.

The single cell analysis methods described herein may also be useful in the analysis of the whole transcriptome. Referring back to the barcode of FIG. 12B, the priming sequence 1234 may be a random N-mer. In some cases, sequence 1228 is a P7 sequence and sequence 1230 is a R2 primer binding site. In other cases, sequence 1228 is a P5 sequence and sequence 1230 is a R1 primer binding site. In an example method of whole transcriptome analysis using this barcode, the individual cell is co-partitioned along with a barcode bearing bead, poly-T sequence, and other reagents such as reverse transcriptase, polymerase, a reducing agent and dNTPs into a partition (e.g., droplet in an emulsion). In an operation of this method, the cell is lysed while the barcoded oligonucleotides are released from the bead (e.g., via the action of the reducing agent) and the poly-T sequence hybridizes to the poly-A tail of cellular mRNA. In a reverse transcription reaction using the mRNA as template, cDNAs of cellular mRNA can be produced. The RNA can then be degraded with an RNase. The priming sequence 1234 in the barcoded oligonucleotide can then randomly hybridize to the cDNAs. The oligonucleotides can be extended using polymerase enzymes and other extension reagents co-partitioned with the bead and cell similar to as shown in FIG. 3 to generate amplification products (e.g., barcoded fragments), similar to the example amplification product shown in FIG. 3 (panel F). The barcoded nucleic acid fragments may, in some cases subjected to further processing (e.g., amplification, addition of additional sequences, clean up processes, etc. as described elsewhere herein) characterized, e.g., through sequence analysis. In this operation, sequencing signals can come from full length RNA.

In an example method, the barcode sequence can be appended to the 3' end of the template polynucleotide sequence (e.g., mRNA). Such configuration may be useful, for example, if the sequence the 3' end of the template polynucleotide is to be analyzed. In some embodiments, the barcode sequence can be appended to the 5' end of a template polynucleotide sequence (e.g., mRNA). Such configuration may be useful, for example, if the sequence at the 5' end of the template polynucleotide is to be analyzed.

In another aspect, a partition comprises a cell co-partitioned with a primer having a sequence towards a 3' end that hybridizes to the template polynucleotide, a template switching oligonucleotide having a first predefined sequence towards a 5' end, and a microcapsule, such as a bead, having barcoded oligonucleotides releasably coupled thereto. In some embodiments, the oligonucleotides coupled to the bead include barcode sequences that are identical (e.g., all oligonucleotides sharing the same barcode sequence). In some aspects, the oligonucleotides coupled to the beads additionally include unique molecular identifier (UMI) sequence segments (e.g., all oligonucleotides having different unique molecular identifier sequences).

Figure 18:
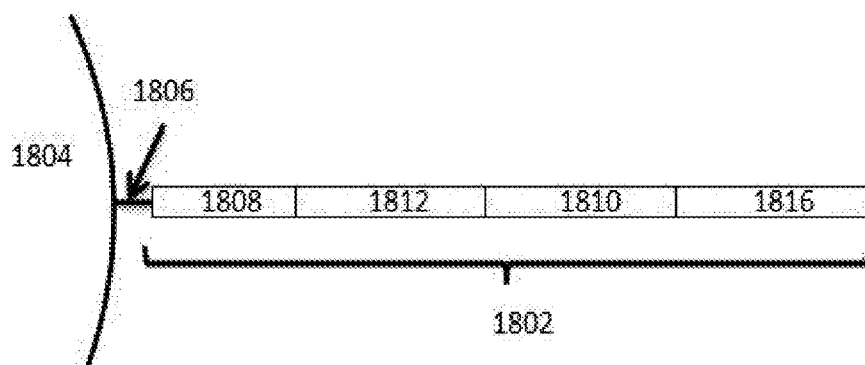
FIG. 18 provides a schematic illustration of an example barcoded oligonucleotide structure.

FIG. 18 shows a barcoded oligonucleotide coupled to a bead. As shown, the overall oligonucleotide 1802 is coupled to a bead 1804 by a releasable linkage 1806, such as a disulfide linker. The oligonucleotide may include functional sequences that are useful for subsequent processing, such as functional sequence 1808, which may include a sequencer specific flow cell attachment sequence, e.g., a P5 sequence, as well as functional sequence 1810, which may include sequencing primer sequences, e.g., a R1 primer binding site. In some cases, sequence 1808 is a P7 sequence and sequence 1810 is a R2 primer binding site. A barcode sequence 1812 can be included within the structure for use in barcoding the template polynucleotide. The functional sequences may be selected for compatibility with a variety of different sequencing systems, e.g., 454 Sequencing, Ion Torrent Proton or PGM, Illumina X10, etc., and the requirements thereof. In some cases, the barcode sequence 1812, functional sequences 1808 (e.g., flow cell attachment sequence) and 1810 (e.g., sequencing primer sequences) may be common to all of the oligonucleotides attached to a given bead. The barcoded oligonucleotide can also comprise a sequence 1816 to facilitate template switching (e.g., a polyG sequence). In some cases, the additional sequence provides a unique molecular identifier (UMI) sequence segment, as described elsewhere herein.

Although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode sequence can be constant or relatively constant for a given bead.

In an example method of cellular polynucleotide analysis using the barcode oligonucleotide of FIG. 18, a cell is co-partitioned along with a bead bearing a barcoded oligonucleotide and additional reagents such as reverse transcriptase, primers, oligonucleotides (e.g., template switching oligonucleotides), dNTPs, and reducing agent into a partition (e.g., a droplet in an emulsion). Within the partition, the cell can be lysed to yield a plurality of template polynucleotides (e.g., DNA such as genomic DNA, RNA such as mRNA, etc). In some cases, the cell is lysed using lysis reagents that are co-partitioned with the cell.

Where the bead is a degradable or disruptable bead, the barcoded oligonucleotide can be released from the bead following the application of stimulus as previously described. Following release from the bead, the barcoded oligonucleotide can be present in the partition at any suitable concentration. In some embodiments, the barcoded oligonucleotide is present in the partition at a concentration that is suitable for generating a sufficient yield of amplification products for downstream processing and analysis, including, but not limited to, sequencing adaptor attachment and sequencing analysis. In some embodiments, the concentration of the barcoded oligonucleotide is limited by the loading capacity of the barcode bearing bead, or the amount of oligonucleotides deliverable by the bead.

The template switching oligonucleotide, which can be co-partitioned with the cell, bead bearing barcoded oligonucleotides, etc, can be present in the partition at any suitable concentration. In some embodiments, the template switching oligonucleotide is present in the partition at a concentration that is suitable for efficient template switching during an amplification reaction. The concentration of the template switching oligonucleotide can be dependent on the reagents used for droplet generation. In some embodiments, the template switching oligonucleotide is among a plurality of template switching oligonucleotides.

In some embodiments, the barcoded oligonucleotide and template switching oligonucleotide are present in the partition at similar concentrations. In some embodiments, the barcoded oligonucleotide and template switching oligonucleotides may be present in proportions reflective of the amount of amplification products to be generated using each oligonucleotide. In some embodiments, the template switching oligonucleotide is present in the partition at a greater concentration than the barcoded oligonucleotide. This difference in concentration can be due to limitations on the capacity of the barcode bearing bead. In some embodiments, the concentration of the template switching oligonucleotide in the reaction volume is at least 2, 5, 10, 20, 50, 100, or 200 times that of the concentration of the barcoded oligonucleotide in the same reaction volume when the barcoded oligonucleotide is free in the partition (e.g., not attached to the bead).

Figure 19:
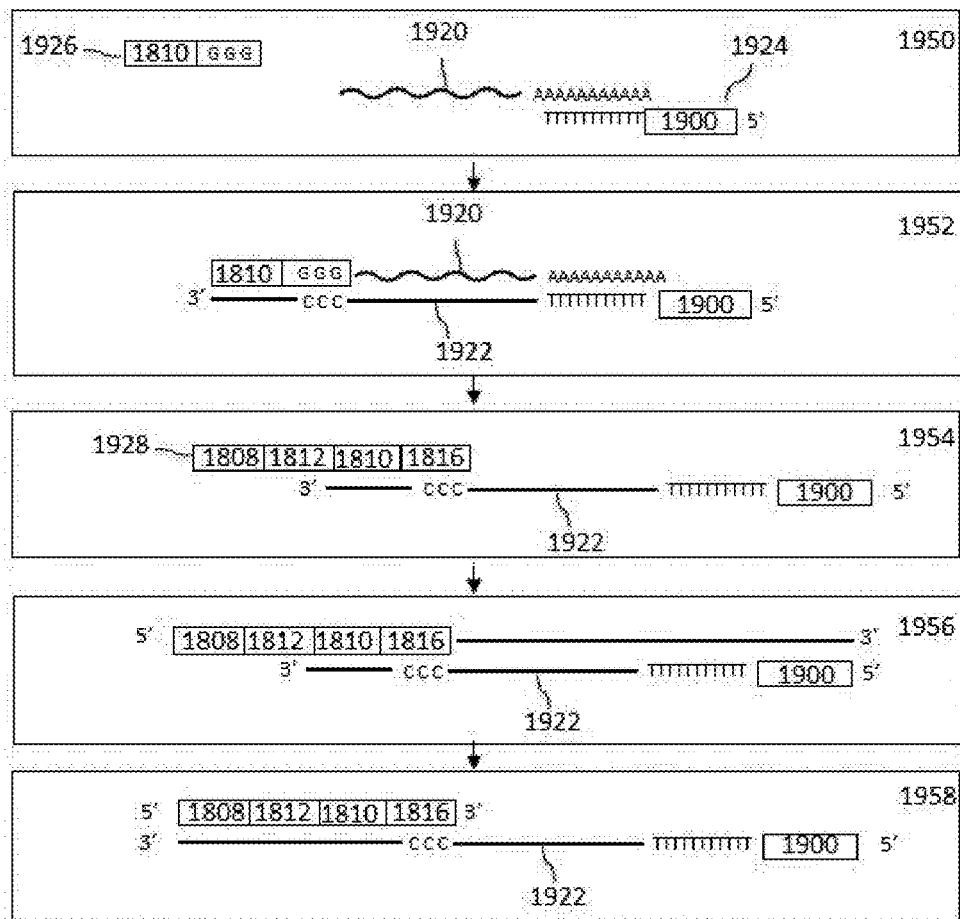
FIG. 19 shows example operations for performing RNA analysis (SEQ ID NOS 2-3, 2-3, 3, 3, and 3, respectively, in order of appearance)

As illustrated in FIG. 19, a reaction mixture comprising a template polynucleotide from a cell 1920 and (i) the primer 1924 having a sequence towards a 3' end that hybridizes to the template polynucleotide (e.g., polyT) and (ii) a template switching oligonucleotide 1926 that comprises a first predefined sequence 1810 towards a 5' end can be subjected to an amplification reaction to yield a first amplification product. In some cases, the template polynucleotide is an mRNA with a polyA tail and the primer that hybridizes to the template polynucleotide comprises a polyT sequence towards a 3' end, which is complementary to the polyA segment. The first predefined sequence can comprise at least one of an adaptor sequence, a barcode sequence, a unique molecular identifier (UMI) sequence, a primer binding site, and a sequencing primer binding site or any combination thereof. In some cases, the first predefined sequence 1810 is a sequence that can be common to all partitions of a plurality of partitions. For example, the first predefined sequence may comprise a flow cell attachment sequence, an amplification primer binding site, or a sequencing primer binding site and the first amplification reaction facilitates the attachment the predefined sequence to the template polynucleotide from the cell. In some embodiments, the first predefined sequence comprises a primer binding site. In some embodiments, the first predefined sequence comprises a sequencing primer binding site. As illustrated in operation 1950, the sequence towards a 3' end (e.g., polyT) of the primer 1924 hybridizes to the template polynucleotide 1920. In a first amplification reaction, extension reaction reagents, e.g., reverse transcriptase, nucleoside triphosphates, co-factors (e.g., Mg2+ or Mn2+), that are also co-partitioned, can extend the primer 1924 sequence using the cell's nucleic acid as a template, to produce a transcript, e.g., cDNA, 1922 having a fragment complementary to the strand of the cell's nucleic acid to which the primer annealed. In some cases, the reverse transcriptase has terminal transferase activity and the reverse transcriptase adds additional nucleotides, e.g., polyC, to the cDNA in a template independent manner. As illustrated in operation 1952, the template switching oligonucleotide 1926, for example a template switching oligonucleotide which includes a polyG sequence, can hybridize to the cDNA 1922 and facilitate template switching in the first amplification reaction. The transcript, therefore, may comprise the sequence of the primer 1924, a sequence complementary to the template polynucleotide from the cell, and a sequence complementary to the template switching oligonucleotide.

Among a plurality of partitions, each partition containing one or more cells or no cells, the primer and template switching oligonucleotide may be universal to all partitions. Where analysis of mRNA is conducted, for example, the primer may comprise at least a polyT segment capable of hybridizing and priming an extension reaction from the polyA segment of an mRNA. Where analysis of a variety of polynucleotides is conducted, the primer may comprise a random sequence capable of hybridizing to and priming extension reactions randomly on various polynucleotide templates. As template switching can occur with the use of an enzyme having terminal transferase activity, a template switching oligonucleotide having a sequence capable of hybridizing to the appended bases can be used for template switching in manner that is independent of the sequence of the polynucleotide templates to be analyzed. In some embodiments, the template switching oligonucleotide can comprise a first predefined sequence towards a 5' end that does not specifically hybridize to the template. In some embodiments, analysis of particular genes is conducted. In such cases, the primer may comprise a gene specific sequence capable of hybridizing to and priming extension reactions from templates comprising specific genes. In some embodiments, multiple genes are analyzed and a primer is among a plurality of primers. Each of the plurality of primers may have a sequence for a particular gene of interest.

Subsequent to the first amplification reaction, the first amplification product or transcript can be subjected to a second amplification reaction to generate a second amplification product. In some cases, additional sequences (e.g., functional sequences such as flow cell attachment sequence, sequencing primer binding sequences, barcode sequences, etc) are to be attached. The first and second amplification reactions can be performed in the same volume, such as for example in a droplet. In some cases, the first amplification product is subjected to a second amplification reaction in the presence of a barcoded oligonucleotide to generate a second amplification product having a barcode sequence. The barcode sequence can be unique to a partition, that is, each partition has a unique barcode sequence. The barcoded oligonucleotide may comprise a sequence of at least a segment of the template switching oligonucleotide and at least a second predefined sequence. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide may comprise a second defined sequence such as at least one of an adaptor sequence, a unique molecular identifier (UMI) sequence, a primer binding site, and a sequencing primer binding site or any combination thereof.

In some embodiments, the second amplification reaction uses the first amplification product as a template and the barcoded oligonucleotide as a primer. As illustrated in operation 1954, the segment of the template switching oligonucleotide on the barcoded oligonucleotide 1928 can hybridize to the portion of the cDNA or complementary fragment 1922 having a sequence complementary to the template switching oligonucleotide or that which was copied from the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence using the first amplification product as template as illustrated in operation 1956. The second amplification product can comprise a second predefined sequence (e.g., 1808, 1812, and 1810), a sequence of a segment of the template polynucleotide (e.g., mRNA), and a sequence complementary to the primer (e.g., 1924).

In some embodiments, the second amplification product uses the barcoded oligonucleotide as a template and at least a portion of the first amplification product as a primer. As illustrated in operation 1954, the segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence (e.g., first amplification product) using the barcoded oligonucleotide as template as illustrated in operation 1958. The second amplification product may comprise the sequence of the primer (e.g., 1924), a sequence which is complementary to the sequence of the template polynucleotide (e.g., mRNA), and a sequence complementary to the second predefined sequence (e.g., 1808, 1812, and 1810).

In some embodiments, the second amplification reaction is performed subsequent to the first amplification reaction in the presence of an intervening purification operation. An intervening purification operation can be used, for example, to purify the template (e.g., first amplification product) from excess reagents, including excess primers such as template switching oligonucleotides. In some embodiments, the amplification reaction is performed in the absence of an intervening purification operation. In certain embodiments, an intervening purification operation is not performed so that all sample preparation is performed in a same reaction volume. In the absence of an intervening purification operation, the template switching oligonucleotide may compete with barcoded oligonucleotide in the second amplification reaction as the barcoded oligonucleotide comprises at least a segment of the template switching oligonucleotide. Competition between the template switching oligonucleotide and barcoded oligonucleotide in the second amplification reaction to generate additional amplification product may result in a second amplification product lacking a barcode sequence. In some embodiments, the template switching oligonucleotide may out-compete the barcoded oligonucleotide in the second amplification reaction if the template switching oligonucleotide is present at a higher concentration in the reaction volume than the barcoded oligonucleotide. Various approaches can be utilized to favor the use of the barcoded oligonucleotide in the second amplification reaction to generate amplification products having a barcode sequence in situations where the barcoded oligonucleotide is present at a lower concentration than the template switching oligonucleotide in the reaction volume.

In some embodiments, the template switching oligonucleotide is not available for primer extension during the second amplification reaction. In some embodiments, the template switching oligonucleotide is degraded prior to the second amplification reaction. In some embodiments, the template switching oligonucleotide is degraded during the second amplification reaction. The template switching oligonucleotide may comprise ribonucleic acids (RNA). A template switching oligonucleotide comprising RNA can be degraded, for example, by elevated temperatures or alkaline conditions. In some embodiments, the template switching oligonucleotide comprises at least 10%, 15%, 20%, 25%, 30%, 35%, 40%, 45%, 50%, 55%, 60%, 65%, 70%, 75%, 80%, 85%, 90%, or 95% RNA. In some embodiments, the template switching oligonucleotide comprises 100% RNA. In some embodiments, a first reaction rate of the second amplification reaction using the barcoded oligonucleotide is greater than a second reaction rate of the second amplification using the template switching oligonucleotide.

In some embodiments, the barcoded oligonucleotide can hybridize to the first amplification product at a higher annealing temperature as compared to the template switching oligonucleotide. For example, the first amplification product and the barcoded oligonucleotide can have a higher melting temperature as compared to a melting temperature of the first amplification product and the template switching oligonucleotide. In such cases, the second amplification reaction may be performed with an annealing temperature at which the barcoded oligonucleotide is able to hybridize to the first amplification product and initiation primer extension and at which the template switching oligonucleotide is unable to hybridize to the first amplification product and initiate primer extension. In some embodiments, the primer annealing temperature of the second amplification reaction is at least about 0.5° C., 1° C., 2° C., 3° C., 4° C., 5° C., 6° C., 7° C., 8° C., 9° C., 10° C. or greater than a primer annealing temperature of the first amplification reaction. The difference in melting temperatures can result from the presence of modified nucleotides in the template switching oligonucleotide. In some embodiment, the template switching oligonucleotide comprises at least about 10%, 15%, 20%, 25%, 30%, 35%, 40%, 45%, 50%, 55%, 60%, 65%, 70%, 75%, 80%, 85%, 90%, or 95% modified nucleotides. In some embodiments, the template switching oligonucleotide comprises 100% modified oligonucleotides. In some embodiments, the difference in melting temperature can be the result of the presence of modified nucleotides in the barcoded oligonucleotide. In some embodiment, the barcoded oligonucleotide comprises at least 10%, 15%, 20%, 25%, 30%, 35%, 40%, 45%, 50%, 55%, 60%, 65%, 70%, 75%, 80%, 85%, 90%, or 95% modified nucleotides. In some embodiments, the barcoded oligonucleotide comprises 100% modified oligonucleotides. Modified nucleotides include, but are not limited to, 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, and 2' Fluoro bases (e.g., Fluoro C, Fluoro U, Fluoro A, and Fluoro G).

In various embodiments, the first amplification reaction is facilitated using an enzyme comprising polymerase activity. For example, the first amplification reaction can be facilitated by a DNA-dependent polymerase or a reverse-transcriptase (e.g., RNA dependent). In some embodiments, the first amplification reaction comprises polymerase chain reaction. In some embodiments, the first amplification reaction comprises reverse transcription. In various embodiments, the second amplification reaction is facilitated using an enzyme comprising polymerase activity. For example, the second amplification reaction can be facilitated by a DNA-dependent polymerase. In some embodiments, the second amplification reaction comprises polymerase chain reaction.

Following the generation of amplification products, subsequent operations may include purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example first amplification products and/or second amplification products, may be subject to sequencing for sequence analysis.

Although operations with various barcode designs have been discussed individually, individual beads can include barcode oligonucleotides of various designs for simultaneous use.

In addition to characterizing individual cells or cell subpopulations from larger populations, the processes and systems described herein may also be used to characterize individual cells as a way to provide an overall profile of a cellular, or other organismal population. A variety of applications require the evaluation of the presence and quantification of different cell or organism types within a population of cells, including, for example, microbiome analysis and characterization, environmental testing, food safety testing, epidemiological analysis, e.g., in tracing contamination or the like. In particular, the analysis processes described above may be used to individually characterize, sequence and/or identify large numbers of individual cells within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the single cell analysis methods and systems described herein, one can again, characterize, sequence and identify individual cells in an overall population, and identify shifts within that population that may be indicative of diagnostic ally relevant factors. By way of example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is entirely incorporated herein by reference for all purposes. Likewise, identification and diagnosis of infection or potential infection may also benefit from the single cell analyses described herein, e.g., to identify microbial species present in large mixes of other cells or other biological material, cells and/or nucleic acids, including the environments described above, as well as any other diagnostically relevant environments, e.g., cerebrospinal fluid, blood, fecal or intestinal samples, or the like.

The foregoing analyses may also be particularly useful in the characterization of potential drug resistance of different cells or pathogens, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Although described in terms of cells, it will be appreciated that any of a variety of individual biological organisms, or components of organisms are encompassed within this description, including, for example, cells, viruses, organelles, cellular inclusions, vesicles, or the like. Additionally, where referring to cells, it will be appreciated that such reference includes any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms.

Similarly, analysis of different environmental samples to profile the microbial organisms, viruses, or other biological contaminants that are present within such samples, can provide important information about disease epidemiology, and potentially aid in forecasting disease outbreaks, epidemics an pandemics.

As described above, the methods, systems and compositions described herein may also be used for analysis and characterization of other aspects of individual cells or populations of cells.

A method 2000 for characterizing a cell is shown in FIG. 20. The method 2000 may comprise, as shown in operation 2010, providing a partition comprising a cell and at least one labelling agent, all as described herein. The labelling agent may be capable of binding to a cell surface feature of the cell, and may be coupled to a reporter oligonucleotide comprising a nucleic acid barcode sequence that permits identification of the labelling agent. Further, the partition may comprise one or more anchor oligonucleotides (also referred to herein as oligonucleotides and barcoded oligonucleotides) that are capable of interacting with the reporter oligonucleotide barcode, as described in detail herein. Next, in operation 2020, within the partition a nucleic acid molecule comprising at least a portion of the nucleic acid barcode sequence or a complement thereof may be synthesized, as described herein. Next, in operation 2030, the nucleic acid molecule may be sequenced to identify the labelling agent or the cell. In some cases, the labelling agent and/or the reporter oligonucleotide may be delivered into the cell, e.g., by transfection (e.g., using transfectamine), by lipid (e.g., 1,2-Dioleoyl-sn-glycero-3-phosphocholine (DOPC)), or by transporter proteins.

As described herein, a labelling agent may comprise an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, a protein scaffold, and the like, and any combination thereof. As described herein, a cell surface feature may comprise a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction., and the like, and any combination thereof.

In some instances, prior to operation 2010, labelling agents may be subjected to conditions suitable for binding the labelling agents to cell surface features. In some instances, prior to operation 2010, labelling agents may be subjected to conditions suitable for binding the labelling agents to cell surface features when the cell and the labelling agents are free from the partition (e.g., prior to partitioning).

In some instances, prior to operation 2010, the reporter oligonucleotide may be coupled to the labelling agent. In some instances, in operation 2010, at least one labelling agent is bound to the cell surface feature.

In some instances, in operation 2020, the reporter oligonucleotide coupled to the labelling agent may be subjected to a primer extension reaction that generates the nucleic acid molecule. In some instances, in operation 2020, the anchor oligonucleotide may be coupled to a bead also partitioned with the cell and labelling agent(s), as described herein, and the method further comprises releasing the anchor oligonucleotide from the bead prior to synthesizing.

As described herein, the bead may comprise a gel bead. Further, as described herein, the bead may comprise a diverse library of anchor oligonucleotides. In some instances, the bead may comprise at least about 1,000 copies of an anchor oligonucleotide, at least about 10,000 copies of an anchor oligonucleotide, at least about 100,000 copies of an anchor oligonucleotide, at least about 100,000 copies of an anchor oligonucleotide, at least about 1,000,000 copies of an anchor oligonucleotide, at least about 5,000,000 copies of an anchor oligonucleotide, or at least about 10,000,000 copies of an anchor oligonucleotide. In some instances, the bead may comprise at least about 1,000 copies of diverse anchor oligonucleotides, at least about 10,000 copies of diverse anchor oligonucleotides, at least about 100,000 copies of diverse anchor oligonucleotides, at least about 100,000 copies of diverse anchor oligonucleotides, at least about 1,00,000 copies of diverse anchor oligonucleotides, at least about 5,000,000 copies of diverse anchor oligonucleotides, or at least about 10,000,000 copies of diverse anchor oligonucleotides. In some instances, and as described herein, releasing anchor oligonucleotides from the bead may comprise subjecting the bead to a stimulus that degrades the bead. In some instances, as described herein, releasing anchor oligonucleotides from the bead may comprise subjecting the bead to a chemical stimulus that degrades the bead.

A solid support (e.g., a bead) may comprise different types of anchor oligonucleotides for analyzing both intrinsic and extrinsic information of a cell. For example, a solid support may comprise one or more of the following: 1) an anchor oligonucleotide comprising a primer that binds to one or more endogenous nucleic acids in the cell; 2) an anchor oligonucleotide comprising a primer that binds to one or more exogenous nucleic acids in the cell, e.g., nucleic acids from a microorganism (e.g., a virus, a bacterium) that infects the cell, nucleic acids introduced into the cell (e.g., such as plasmids or nucleic acid derived therefrom), nucleic acids for gene editing (e.g., CRISPR-related RNA such as crRNA, guide RNA); 3) an anchor oligonucleotide comprising a primer that binds to a barcode (e.g., a barcode of a nucleic acid, of a protein, or of a cell); and 4) an anchor oligonucleotide comprising a sequence (e.g., a primer) that binds to a protein, e.g., an exogenous protein expressed in the cell, an protein from a microorganism (e.g., a virus, a bacterium) that infects the cell, or an binding partner for a protein of the cell (e.g., an antigen for an immune cell receptor).

Figure 61A:
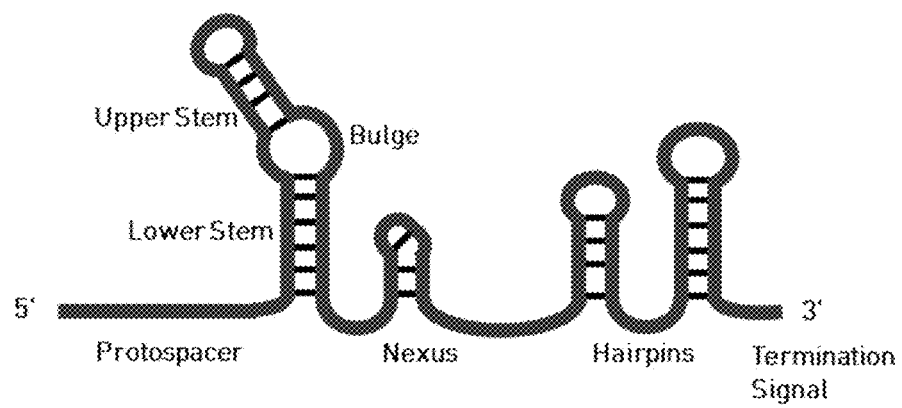
FIGS. 61A-D schematically depict an example barcoding scheme of CRISPR guide RNAs (SEQ ID NOS 59-60, 59-60, 59-60, 59, and 61, respectively, in order of appearance).
Figure 61B:
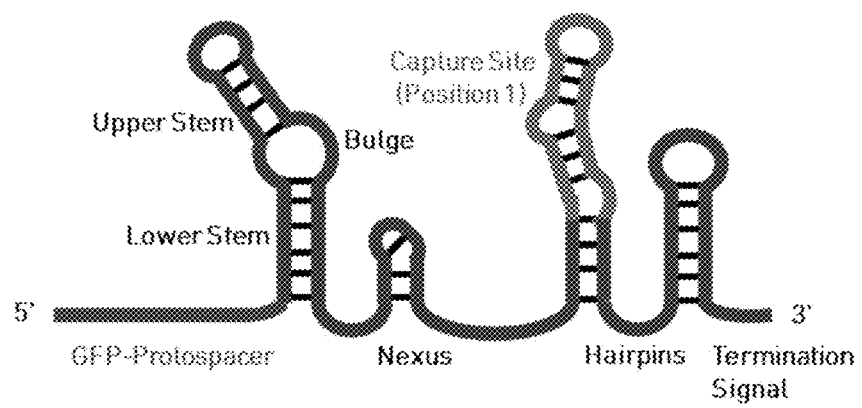
Figure 61C:
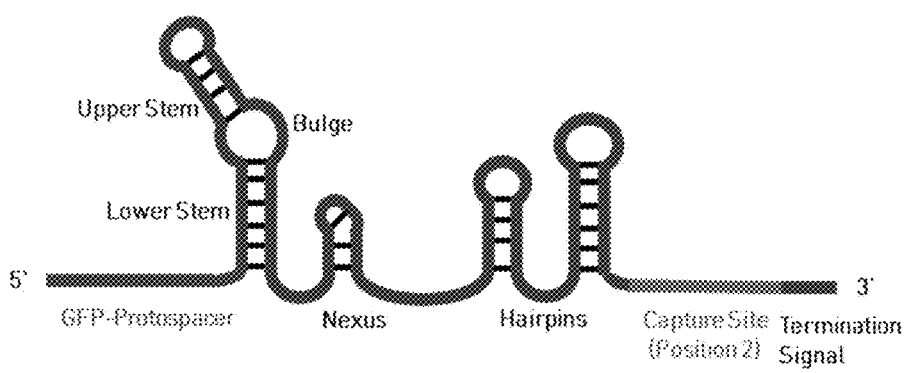
Figure 61D:
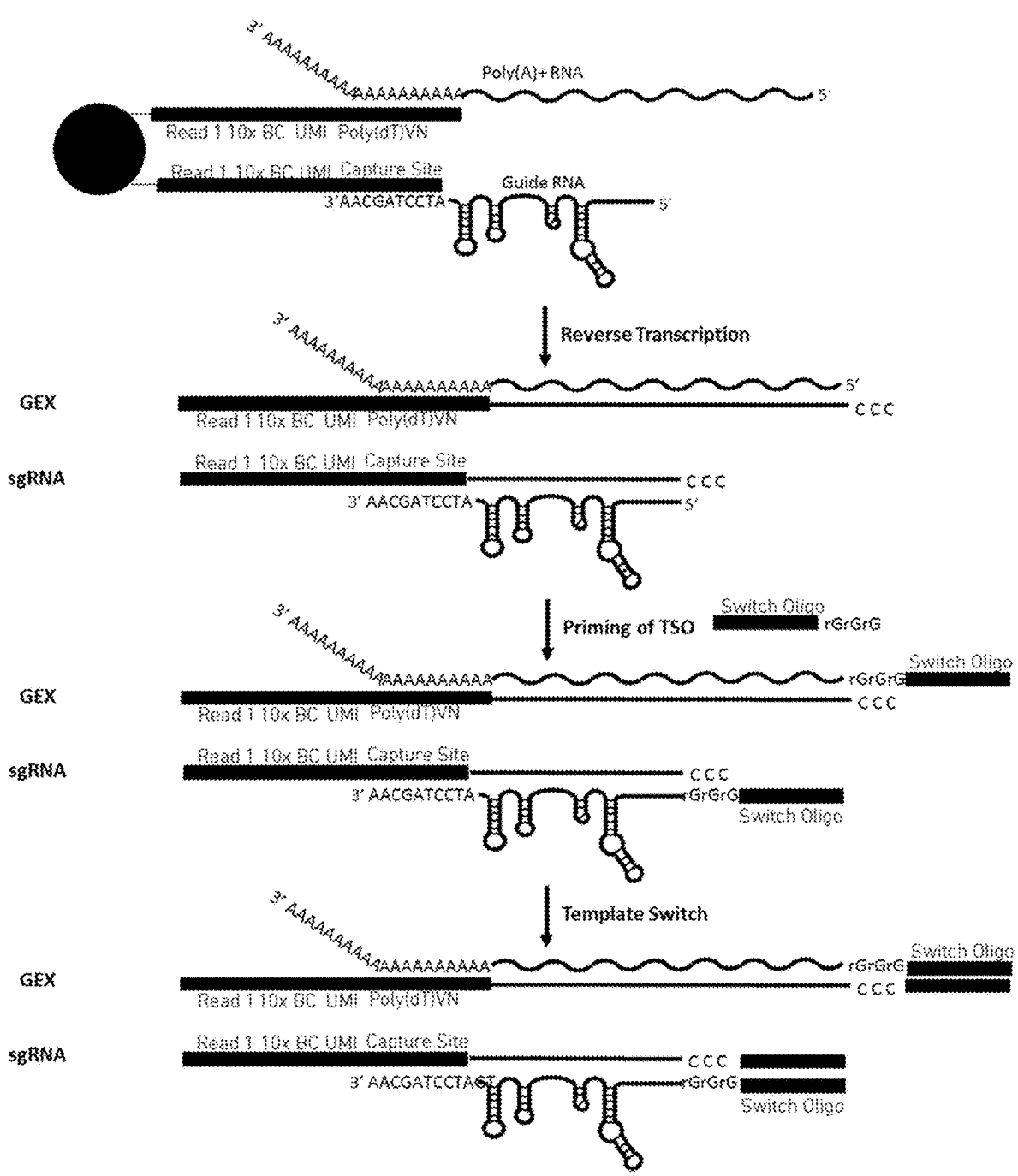

In some cases, the methods may be used to screen cells carrying mutations, e.g., mutations generated by gene editing such as CRISPR technology. For example, a bead comprising a first anchor oligonucleotide with a primer for CRISPR RNA (e.g., crRNA or guide RNA) or its complementary DNA and a second anchor oligonucleotide with a primer endogenous nucleic acid in the cell, e.g., total mRNA or a specific mRNA. The bead may be made into a partition with a cell transfected with CRISPR RNA or a plasmid expressing CRISPR RNA. In some cases, the expressed CRISPR RNA or the plasmid may have a barcode (CRISPR barcode) or a capture sequence. The primers on the bead may be used to amplify and sequence the CRISPR RNA (e.g., using a barcoded adapter oligonucleotide comprising a sequence complementary to the CRISPR capture sequence, see FIGS. 61A-D) and endogenous mRNA (e.g., using a barcoded adapter oligonucleotide comprising an oligo(dT) sequence), thus determining the mutations generated by in the cell (see FIG. 61D). In some cases, the methods may be used to perform single cell RNA sequencing, e.g., as described in Dixit, et al., Perturb-Seq: Dissecting Molecular Circuits with Scalable Single-Cell RNA Profiling of Pooled Genetic Screens. Cell; Dec. 15, 2016; 167(7):1853-1866.e17, which is incorporated herein by reference in its entirety.

An oligonucleotide of an anchor agent or a labelling agent may comprise a backbone. The backbone may comprise one or more of the following elements: a sequencer primer, a barcode, and a UMI. In addition to the backbone, the oligonucleotide may also comprise a primer as described herein, e.g., a poly-T primer, a random N-mer primer, and/or a target-specific primer. Examples of oligonucleotides comprising various backbones and primer sequences are shown in FIGS. 27A-27D.

An example work flow for the methods herein may include inputting fixed reference (e.g., known transcripts from a cell with intrinsic information), reference templates (e.g., design of synthetic barcodes (random or target-specific) with extrinsic information, and sequence reads; and outputting classification of sequence reads as originating from intrinsic or extrinsic sequences, counts of detected copies per transcript/gene per partition, and list and counts of detected barcodes from extrinsic sequences per partition. In some cases, the example workflow may be implemented with software.

In some instances, prior to operation 2030, the method 2000 may comprise releasing the nucleic acid molecule from the partition (e.g., by disruption of the partition). In some instances, operation 2030 may comprise identifying the labelling agent (e.g., the labelling agent bound to a cell surface feature). In some instances, operation 2030 may comprise identifying the cell surface feature from identifying the labelling agent. In some instances, operation 2030 comprises determining an abundance of the given cell surface feature on the cell. In some instances, operation 2030 comprises identifying the cell. In some instances, operation 2030 comprises identifying the labelling agent and the cell.

In method 2000, the reporter oligonucleotide that may be coupled to the labelling agent may comprise a unique molecular identification (UMI) sequence, as described herein. The UMI sequence may permit identification of the cell, the labelling agent, or both. In some instances, operation 2030 of method 2000 may comprise determining a sequence of the UMI sequence and identifying the cell.

In method 2000, the anchor oligonucleotide may comprise a unique molecular identification (UMI) sequence, as described herein. In these instances, the UMI sequence of the anchor oligonucleotide may permit identification of the cell. In some instances, operation 2030 of method 2000 may comprise determining a sequence of the UMI sequence from the reporter oligonucleotide bound to the labelling agent, and a sequence of the UMI sequence from the anchor oligonucleotide, to identify the cell and the cell surface feature.

In method 2000, and as described herein, the partition may comprise a droplet in an emulsion. In some instances, the partition comprises only one cell. In some instances, the cell is bound to at least one labelling agent. In some instances, the labelling agent may comprise at least two of the same labelling agent. In some instances, the labelling agent may comprise at least two different labelling agents. In some instances, the cell may be bound to at least about 5 different labelling agents, at least about 10 different labelling agents, at least about 50 different labelling agents, at least about 100 different labelling agents, at least about 500 different labelling agents, at least about 1,000 different labelling agents, at least about 5,000 different labelling agents, at least about 10,000 different labelling agents, or at least about 50,000 different labelling agents. In some instances, the cell may be bound to between about 2 and 5 different labelling agents, between about 5 and 10 different labelling agents, between about 10 and 100 different labelling agents, between about 100 and 500 different labelling agents, between about 500 and 1,000 different labelling agents, between about 1,000 and 5,000 different labelling agents, between about 5,000 and 10,000 different labelling agents, between about 10,000 and 50,000 different labelling agents, or between about 2 and 50,000 different labelling agents, or any range in-between. In some instances, operation 2030 of method 2000 may comprise determining an identity of at least a subset of the different labelling agents.

In one example process, a sample is provided that contains cells that are to be analyzed and characterized as to their cell surface features. A cell surface feature may include, but is not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. Also provided is at least one labelling agent, such as a library of labelling agents, capable of binding to a cell surface feature of interest. A labelling agent may include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include a reporter oligonucleotide that is indicative of the cell surface feature to which the binding group binds. In particular, a labelling agent that is specific to one type of cell surface feature may have coupled thereto a first reporter oligonucleotide, while a labelling agent that is specific to a different cell surface feature may have a different reporter oligonucleotide coupled thereto. In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies. In some embodiments, the labelling agents may include reporter oligonucleotides attached to them. Thus, a first labelling agent, e.g., an antibody to a first cell surface feature, may have associated with it a reporter oligonucleotide that has a first nucleic acid sequence. Different labelling agents, e.g., antibodies having binding affinity for other, different cell surface features, may have associated therewith reporter oligonucleotides that comprise different nucleic acid sequences, e.g., having a partially or completely different nucleic acid sequence. In some cases, for each type of cell surface feature labelling agent, e.g., antibody or antibody fragment, the reporter oligonucleotide sequence may be known and readily identifiable as being associated with the known cell surface feature labelling agent. These reporter oligonucleotides may be directly coupled to the labelling agent, or they may be attached to a bead, molecular lattice, e.g., a linear, globular, cross-linked, or other polymer, or other framework that is attached or otherwise associated with the labelling agent, which allows attachment of multiple reporter oligonucleotides to a single labelling agent.

In the case of multiple reporter oligonucleotides coupled to a single labelling agent, such reporter oligonucleotides can comprise the same sequence, or a particular labelling agent may include a known set of reporter oligonucleotide sequences. As between different labelling agents, e.g., specific for different cell surface features, the reporter oligonucleotides may be different and attributable to the particular labelling agent.

Attachment (coupling) of the reporter oligonucleotides to the labelling agents may be achieved through any of a variety of direct or indirect, covalent or non-covalent associations or attachments. For example, in the case of oligonucleotide reporter oligonucleotides associated with antibody based labelling agents, such oligonucleotides may be covalently attached to a portion of an antibody or antibody fragment using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. In the case that the labelling agent is a primary antibody, a reporter oligonucleotide may be coupled to the labelling agent through a secondary antibody coupling interaction. Commercially available kits, such as those from Thunderlink and Abcam, and techniques common in the art may be used to couple reporter oligonucleotides to labelling agents as appropriate.

Figure 28:
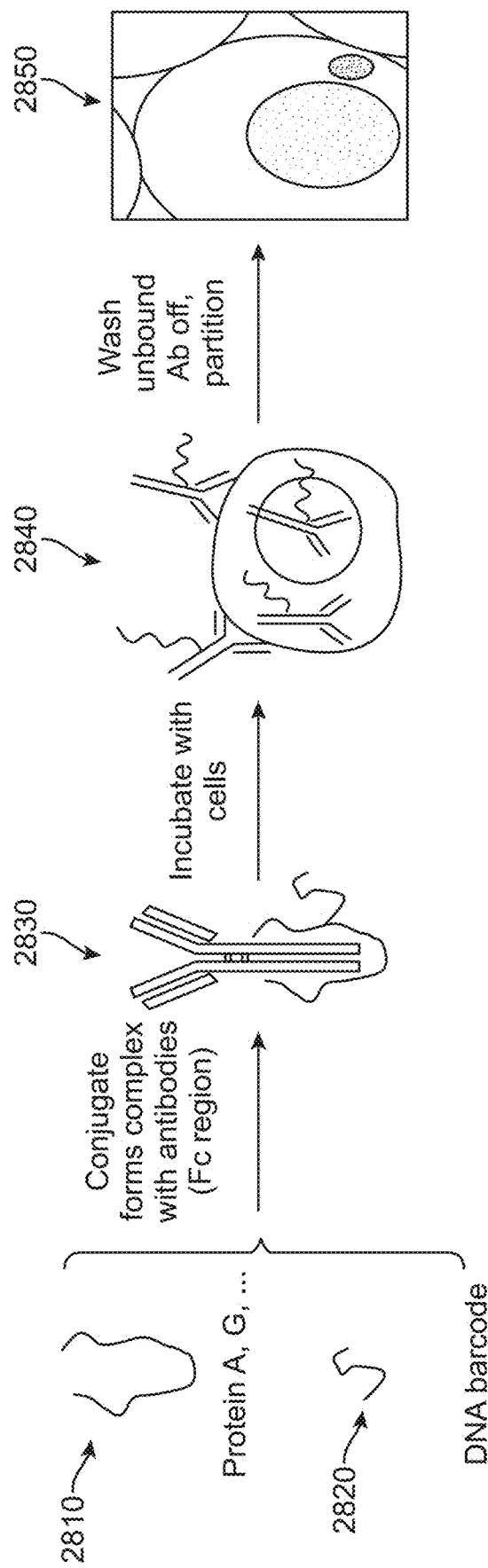
FIG. 28 shows a workflow for conjugating a DNA barcode on an antibody using an antibody-binding protein.

In some cases, a reporter oligonucleotide may be associated (e.g., covalently linked such as conjugated or non-covalently bound through a binding interaction) to an antibody via an antibody-binding protein. For example, a reporter oligonucleotide and an antibody-binding protein may form a complex. The complex may bind to a respective antibody through the antibody-binding protein. FIG. 28 shows an example workflow for associating a nucleic acid (e.g., DNA) barcode on an antibody using an antibody-binding protein. An antibody binding protein 2810, e.g., Protein A or Protein G, and an oligonucleotide comprising a nucleic acid (e.g., DNA) barcode 2820 are conjugated to the Fc region of an antibody, forming a complex 2830 comprising the antibody, the antibody-binding protein 2810, and the DNA barcode 2820. The complex 2830 is incubated with cells and unbound antibody is washed out. When the complex 2830 binds to a cell, the complex and the cell are partitioned into a droplet for further analysis.

An antibody-binding protein may have fast adsorption kinetics, slow desorption kinetics, and/or a low binding equilibrium constant. Any methods for adding chemical functionality to peptides or proteins may be used. Some methods may include attaching a reporter oligonucleotide to specific amino acids or chemical groups (e.g., chemical groups present in multiple types of proteins) on the antibody-binding protein. The conjugation of antibody-binding proteins and oligonucleotides may be performed using methods for forming antibody-nucleic acid conjugation described herein, e.g., using click chemistry. Dissociation of the antibody-binding protein/oligonucleotide complexes may be prevented by crosslinking (e.g., using a crosslinker such as formaldehyde), protein engineering, or adding the protein-binding proteins in excess.

Examples of antibody-binding proteins include proteins that bind to the constant (Fc) region of antibodies, such as Protein A, Protein G, Protein L, or fragments thereof. Other binding proteins (e.g., streptavidin) may be expressed as fusion proteins with antibody-binding proteins, and used to associate oligonucleotides (e.g., by binding of biotinylated oligonucleotides to a streptavidin-Protein A fusion protein). Other antibody-binding proteins or domains may provide additional binding affinity for various antibody classes. In some cases, the antibody-binding protein may be an antibody, e.g., a secondary antibody for the antibody targeting the sample. The secondary antibody may comprise an oligonucleotide described here, e.g., an oligonucleotide with a barcode and a poly-A or poly T terminated sequence.

The antibody-binding proteins may be engineered to introduce additional functionalities. Antibody-binding proteins may be engineered to contain amino acids with functional groups amenable to conjugation with oligonucleotide. For example, the antibody-binding proteins may naturally have or be engineered to have cysteine residues, e.g., for controlling stoichiometry and/or attachment location of the oligonucleotides. The antibody-binding proteins may be engineered to have non-natural amino acid residues, e.g., for targeted crosslinking of binding proteins and antibodies. The antibody-binding proteins may be engineered to have tags, e.g., fluorescent tags (e.g., by fusing with a fluorescent protein such as green fluorescence protein (GFP), red fluorescence protein (RFP), yellow fluorescence protein (YFP)) and/or affinity tags for purification and visualization. The fluorescent tags and/or the affinity tags may be cleavable. In some cases, the antigen-binding protein may be engineered to have one or more (e.g., only one) barcode attachment sites per protein.

Also provided herein are kits comprising antibody-binding proteins conjugated with reporter oligonucleotides, e.g., in well plates. Antibody for an assay may be incubated with the antibody-binding proteins conjugated with reporter oligonucleotides at a specified concentration without interfering with the antibody's binding site and/or without the need for any chemistry to be carried out in the customer's hands to conjugate the reporter oligonucleotide to the antibody.

The reporter oligonucleotides may be provided having any of a range of different lengths, depending upon the diversity of reporter oligonucleotides suitable for a given analysis, the sequence detection scheme employed, and the like. In some cases, these reporter oligonucleotides can be greater than or equal to about 5 nucleotides in length, greater than or equal to about 10 nucleotides in length, greater than or equal to about 5, 10, 20, 30, 40, 50, 60, 70, 80, 90, 100, 120, 150, 200 or 250 nucleotides in length. In some cases, these reporter oligonucleotides may be less than or equal to about 250, 200, 180, 150, 120 100, 90, 80, 70, 60, 50, 40, 30, 20, 10 or 5 nucleotides in length. In some cases, the reporter oligonucleotides may be selected to provide barcoded products that are already sized, and otherwise configured to be analyzed on a sequencing system. For example, these sequences may be provided at a length that ideally creates sequenceable products of a suitable length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample may be incubated with the labelling agents and their associated reporter oligonucleotides, for any of the cell surface features to be analyzed. Following incubation, the cells may be washed to remove unbound labelling agents. Following washing, the cells may be partitioned into separate partitions, e.g., droplets, along with the barcode (also referred to as anchor oligonucleotides) carrying beads described above, where each partition includes a limited number of cells, e.g., a single cell. Upon releasing of the barcodes (or anchor oligonucleotides) from the beads, they may prime the amplification and barcoding of the reporter oligonucleotides coupled to the labelling agents. The barcoded replicates of the reporter oligonucleotides may additionally include functional sequences, such as primer sequences, attachment sequences or the like.

The barcoded reporter oligonucleotides may then subjected to sequence analysis to identify which reporter oligonucleotides were bound to the cells (i.e., cell surface features) within the partitions. Further, by also sequencing the associated barcode sequence, one can identify that a given cell surface feature likely came from the same cell as other, different cell surface features, whose reporter sequences include the same barcode sequence, i.e., they were derived from the same partition.

In some embodiments, anchor oligonucleotides within the partition may interact with the reporter oligonucleotides coupled to labelling agents bound to cell surface features and lead to the synthesizing of a nucleic acid molecule as described herein, where the synthesized nucleic acid molecule may comprise at least a portion of the nucleic acid barcode sequence(s), or complement(s) thereof, that comprise the reporter oligonucleotide, or the anchor oligonucleotide, or both. These synthesized nucleic acid molecules may then be subjected to amplification and sequencing, as described herein.

In some embodiments, more than one labelling agent may be bound to a single cell surface feature, and proximity between the labelling agents may allow the 3' ends of the reporter oligonucleotides coupled thereto to hybridize (wherein this hybridization is discouraged by the melting temperature when unbound in solution). By an extension reaction as described herein, a nucleic acid molecule may be synthesized, amplified, and subjected to sequencing, as described herein.

Based upon the reporter oligonucleotides that emanate from an individual partition based upon the presence of the barcode sequence, one may then create a cell surface feature profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

In some embodiments, the genomic, proteomic, and cell surface information of cells characterized by the methods and systems described herein may be sequenced individually. In some embodiments, the genomic, proteomic, and cell surface information of cells characterized by the methods and systems described herein may be pooled and sequenced together. In some embodiments, the genomic, proteomic, and cell surface information of cells characterized by the methods and systems described herein may be sequenced sequentially (i.e., cell surface information characterized first, then proteomic and genomic information).

Also provided herein are compositions and methods for screening a chemical compound library. The methods may comprise providing a partition comprising at least one chemical compound and an identifier of the partition. The identifier may be an oligonucleotide comprising a nucleic acid barcode sequence as described in the application. The identifier oligonucleotide may be amplified and subject to sequence. The sequence read of the identifier oligonucleotide or a fragment thereof may be used to identify the partition and the at least one chemical compound in the partition. The methods may be used for screening a chemical compound library in a reaction of small volumes, e.g., on the scale of nanoliters. Multiple reactions may be performed in different partitions with the same substrate and/or reagent. The reaction may be multiplexed to decrease the effort and time needed to process the same number of compounds in reactions of larger scale, e.g., on the scale of microliters. The methods and compositions may allow high throughput screening of a chemical compound library with low noise and/or false-positive results. In some cases, a method for screening a chemical compound library may comprise one or more of the following operations: (1) providing a plurality of partitions, wherein a given partition of the plurality of partitions (i) has or is suspected of having at least one chemical compound and (ii) comprises an identifier oligonucleotide comprising a nucleic acid barcode sequence that permits identification of the given partition; (2) subjecting the plurality of partitions to screening under conditions sufficient to select a subset of the plurality of partitions from a remainder of the plurality of partitions, which subset comprises the given partition having or suspected of having the at least one chemical compound; (3) subjecting the subset of the plurality of partitions, including the given partition, to conditions sufficient to generate a nucleic acid molecule comprising at least a portion of the nucleic acid barcode sequence or a complement thereof; and (4) sequencing the nucleic acid molecule to generate sequence reads, which sequence reads permit identification of the at least one chemical compound.

The methods may comprise building combinatorial chemical and identifier oligonucleotide libraries on a solid support, e.g., a monodispersed polymeric bead. The oligonucleotide barcoding may be intrinsically linked to a chemical synthesis path unique for that monodispersed polymer bead. Upon partitioning this polymeric bead, the population of compounds may be released from the substrate to interact with the target molecule unencumbered by the identifier oligonucleotides. Partitions may then be sorted based on positive/negative interactions as indicated by a traditional reporter assay. Positives partitions may then be homogenized and pooled. The identifier oligonucleotides in the positive partitions may be amplified for sequencing. The methods may allow for large quantities of single compounds to be packaged into nanoliter partitions individually and for the subsequent deconvolution of partitions with positive interactions that may be pooled and processed in a multiplexed format.

In some cases, the methods comprise synthesizing a controlled number of chemical compounds on a solid support (e.g., a bead) while simultaneously synthesizing a controlled number of identifier oligonucleotides unique to the compounds on the solid support. The combinatorial libraries of the chemical compounds and identifier oligonucleotides may be made through sequential additions of chemical compound subunits that concord with simultaneous or subsequent sequential additions of identifier oligonucleotides on the solid matrix. The methods may be multiplexed in a single vessel for additions of chemical compounds and identifier oligonucleotides in a massively parallel way. The quantity of the chemical compounds to be screened may be normalized.

The number of chemical compounds and/or identifier oligonucleotides synthesized on a solid support may be controlled by adjusting the number of attachment points. An attachment point may be a location on a solid support where a chemical compound or identifier oligonucleotide may be attached to. Attachment points may include multiple types of chemistries for the cleavage of chemical compounds and/or identifier oligonucleotides. This allows for selective release of chemical compounds and/or identifier oligonucleotides in a controlled fashion. The solid may have a single or multiple attachment points.

The solid support may act as a covalent linker between chemical compounds and identifier oligonucleotides. A single type of solid support or multiple types of solid support may be used in the screening. If multiple types of solid support are used, they may be covalently linked to form a single solid support. In certain cases, if multiple types of solid support are used, they may be commingled (but not covalently linked) and occupy the same physical space. A solid support may have two or more matrices intermingled. In these cases, chemical compounds and the identifier oligonucleotides may be on the same matrix or on separate matrices of the solid support. In the latter case, the chemical compounds and the identifier oligonucleotides are commingled (and not covalently linked) and occupy the same physical space. In some cases, the solid support may be permeable or non-permeable. In certain cases, the solid support may be dissolvable or non-dissolvable.

A chemical compound may be a protein (e.g., an antibody or a fragment thereof, or an antigen or a fragment thereof), a nucleic acid molecule. In some cases, a chemical compound may be a small molecule compound. A small molecule compound may be a low molecular weight (e.g., no greater than 1000 daltons) organic compound that may help regulate a biological process. A small compound may have a size on the order of 1 nm. For example, a small molecule compound may be a small molecule drug.

Screening of a chemical compound library may be performed using methods for screening small molecules for drug discovery. For example, the screening may be performed using high-throughput screening or high-content analysis in drug discovery. A high-throughput screening may be a screening that identifies active compounds, antibodies, or genes that modulate a particular biomolecular pathway. A high-content analysis may be a screening that identifies substances such as small molecules, peptides, or RNAi that alter the phenotype of a cell in certain manner. In some cases, a screening may be an immunoassay, e.g., enzyme-linked immunosorbent assay (ELISA).

Also provided herein are scaffolds for delivery of one or more reagents. In some cases, a reagent is not covalently bound to the solid scaffold. For example, the reagent may be inside the scaffold and hindered (e.g., through steric interaction with the scaffold) from diffusing out of the scaffold. The reagent may be released from the scaffold when the scaffold is dissolved. In some cases, the scaffold may be a microcapsule described herein, such as a gel bead.

The scaffold may be used in a method for characterizing a cell. The method may comprise providing a partition comprising a cell, a scaffold, and an reagent in the scaffold. To characterize the cell in the partition, the scaffold may be dissolved to release the reagent. The reagent then contacts with the cell for determining one or more characteristics of the cell. In some cases, the partition may comprise a plurality of reagents. Any reagent described in the disclosure may be used in this method.

The scaffold may be used to deliver two or more reagents. In some cases, a first reagent be non-covalently bound to the scaffold, and the second reagent may be covalently bound to the scaffold. In other cases, multiple scaffolds may be used to deliver multiple reagents. In these cases, a first reagent may be covalently bound to a first scaffold, and a second reagent may be non-covalently bound to a second scaffold. The first scaffold and the second scaffold may be encapsulated in the same partition with a cell.

The reagent that is non-covalently bound to the scaffold may be released when the scaffold is dissolved. A scaffold is dissolved when at least 0.01%, 0.1, 1%, 5%, 10%, 20%, 30%, 40%, 50%, 60%, 70%, 80%, 90%, 95%, 99%, or 100% of the volume of the scaffold is dissolved in the solution around it.

The scaffold may comprise one or more pores and the reagent non-covalently bound to the scaffold may be in the one or more pores. The diameter of the one or more pores may be up to 0.01 nm, 0.1 nm, 1 nm, 5 nm, 10 nm, 50 nm, 100 nm, 200 nm, 400 nm, 600 nm, 800 nm, 1μm, or 10 μm.

Figure 29:
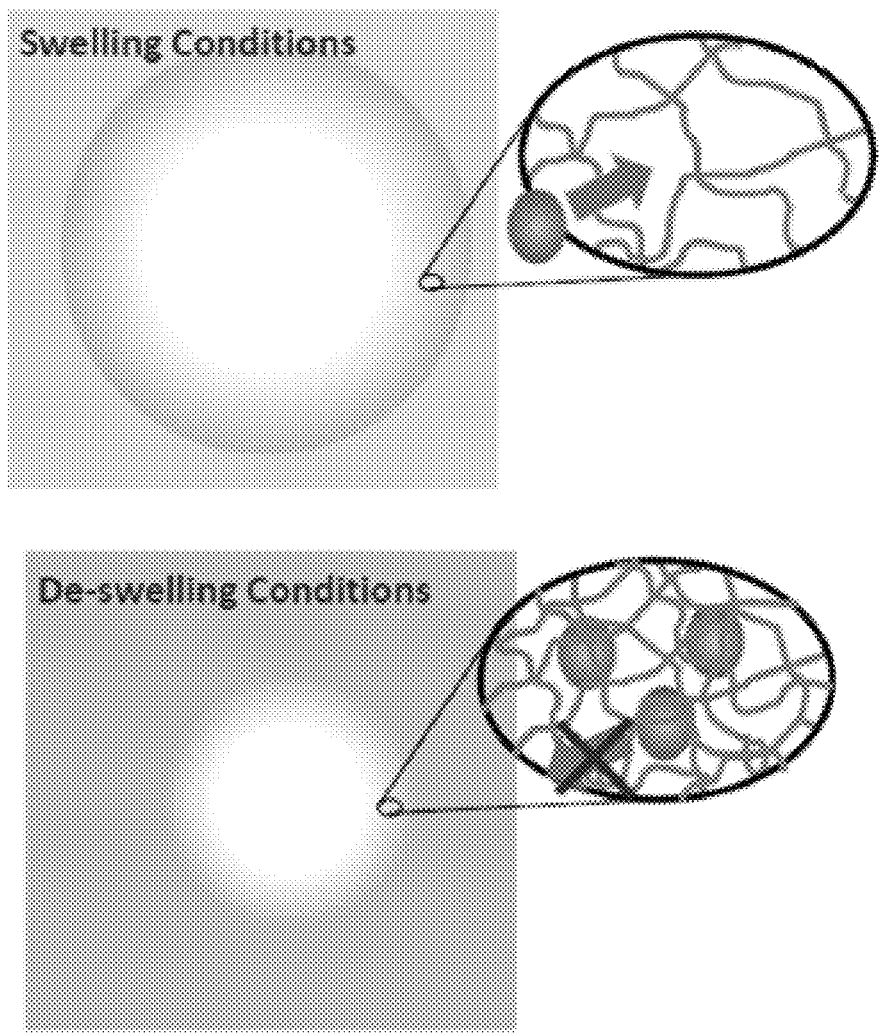
FIG. 29 demonstrates swelling conditions and de-swelling conditions in the process of making gel beads with magnetic particles.

A scaffold loaded with a non-covalently bound reagent may be made using any method of incorporating an agent in a solid substance. In some cases, the scaffold loaded with a non-covalently bound reagent may be made using the one or more of following operations: 1) Placing the scaffold (e.g., gel bead) and the reagent under a condition that causes the scaffold to swell and the pores defined by the polymer scaffold to enlarge. Such condition may include: in a thermodynamically-favorable solvent, at higher or lower temperatures (e.g., for temperature-responsive hydrogel materials), in a solvent with higher or lower ion concentration and/or in the presence or absence of an electric field for electric charge-/field-responsive hydrogel materials; 2) Allowing sufficient time for the reagent to diffuse into the interior of the scaffold; 3) Transferring the scaffold into a condition that causes the pores to shrink. The reagent molecules within the scaffold are then hindered from diffusing out of the scaffold by steric interactions with the polymer scaffold. The transfer in operation 3) may be achieved microfluidically, e.g., by moving the scaffold from one co-flowing solvent stream to another. FIG. 29 demonstrates examples of swelling conditions and de-swelling conditions in the process. The swellability and pore sizes of the scaffold may be adjusted by changing the polymer composition.

In a partition comprising a scaffold loaded with non-covalently bound reagent, the composition of the partition may be adjusted by including a scaffold of a certain volume. For example, when a partition has a fixed volume, the concentration of the reagent in the partition may be upregulated by including a reagent-loaded scaffold of a larger volume. In some cases, the adjustment may be performed without changing the initial concentration of the components in the partition. In certain cases, the adjustment may be performed without changing the total volume of the partition. Such methods are useful for delivering a reagent that interferes with the partition generation, e.g., a cell lysis agent.

Figure 30:
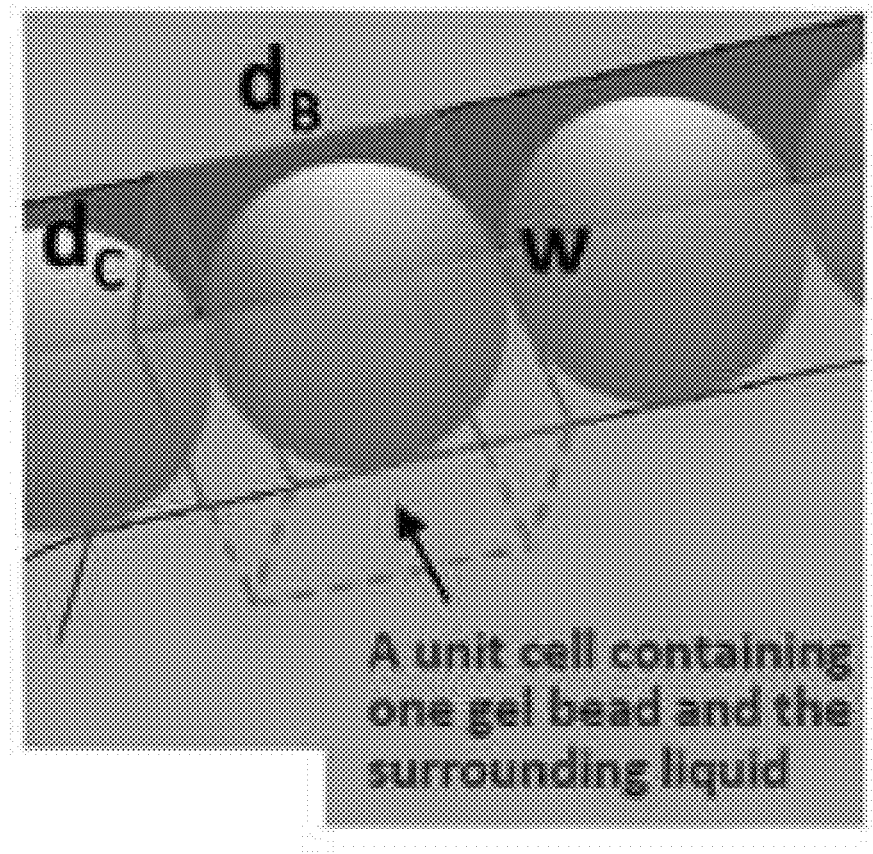
FIG. 30 shows a unit cell comprising a scaffold and liquid immediately surrounding the scaffold.

A partition with the scaffold may be generated using methods described in the disclosure. In certain cases, during the partition generation, both the scaffold and the liquid immediately surrounding the scaffold are encapsulated in a single partition as shown in FIG. 30. The volume of the scaffold and the surrounding liquid comprise a "unit cell". Unit cells may be defined by the geometry of the microchannel in which scaffolds flow and by the pressure applied. For example, higher pressures may compress the scaffold, which are deformable, thereby reducing the volume of the unit cell.

The composition of a partition may be determined by the volume of scaffold suspension (Z1) and the volume of the sample (Z2) encapsulated in that partition. The characteristic of the composition may be described by the ratio of these two volumes (Z1/Z2). The maximum Z1 possible for single-scaffold encapsulations is equal to the volume of the unit cell. Thus, to increase the concentration of a reagent delivered by the scaffold in a partition of a fixed volume without increasing the concentration of the reagent in the scaffold suspension, the dimensions of the scaffold may be increased. Thus, the encapsulated unit cell may occupy a greater volume of the partition (at higher Z1/Z2 ratio). In a microchannel for making the partitions, the dimension of the microchannel may or may not have to be increased to accommodate the larger partitions, depending on the mechanical properties of the scaffolds. When higher pressures are applied, the scaffold may compress, the volume of the unit cell may decrease, and a lower Z1/Z2 ratio may be achieved.

Also provided herein are methods and compositions for sequencing DNA (e.g., genomic DNA) molecules and RNA (e.g., mRNA) molecules from a cell in parallel and/or simultaneously. In some cases, the methods and compositions may be used for sequencing the genome and transcriptome from a single cell in parallel. The methods may be useful to dissect the functional consequences of genetic variations.

A microcapsule (e.g., a bead) entrapping one or more magnetic particles may be used in the methods. The magnetic particles may not diffuse out of the microcapsule until the microcapsule is dissolved. The microcapsule may comprise an oligonucleotide comprising a DNA primer. For example, the DNA primer may be a genomic DNA primer. The DNA primer may bind to DNA molecules from a cell. The DNA primer may be used to amplify and/or sequence DNA molecules from a cell. DNA primers may be entrapped and/or bound to the microcapsule and released when the microcapsule is dissolved.

Figure 31:
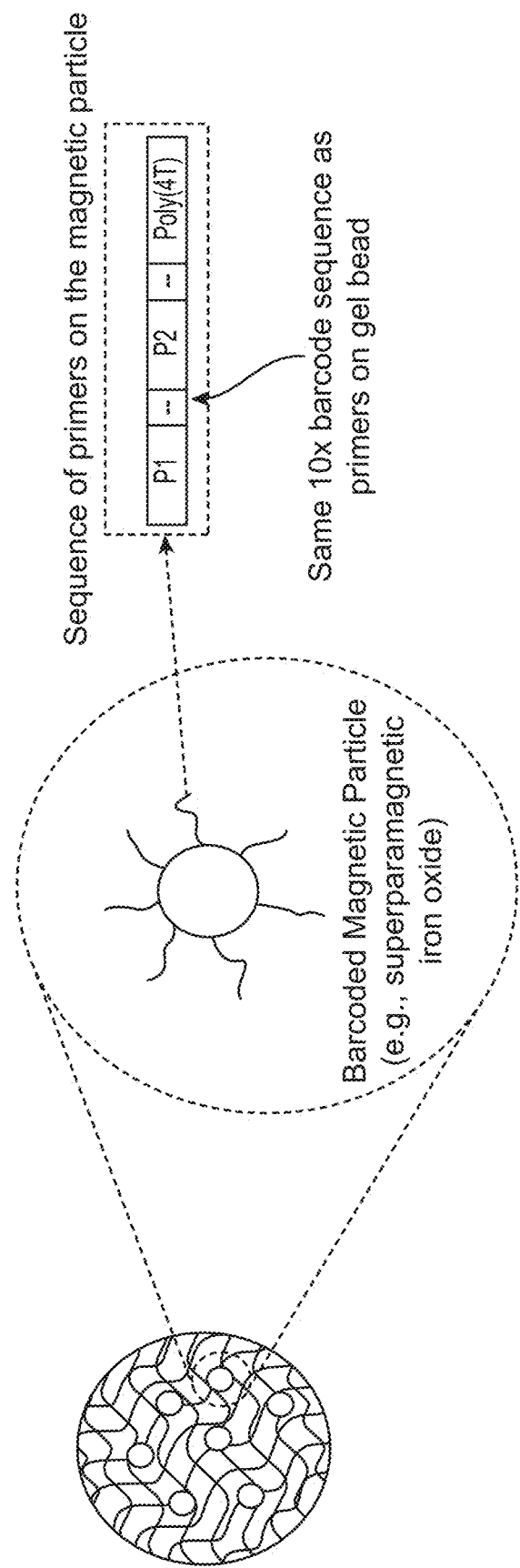
FIG. 31 shows a microcapsule with a barcoded magnetic particle entrapped.

The magnetic particles entrapped within the microcapsule may comprise an oligonucleotide comprising an RNA primer. The RNA primer may bind to RNA molecules from a cell. In some cases, the RNA primer is an mRNA primer that binds to the mRNA molecules from the cell. For example, the mRNA primer may comprise a poly-T sequence that binds to the poly-A sequence of the mRNA molecules from the cell. FIG. 31 shows a microcapsule with a barcoded magnetic particle entrapped.

The magnetic particles may be made from materials such as iron oxide (e.g., superparamagnetic iron oxide), ferromagnetic, ferrimagnetic, or paramagnetic materials. Ferromagnetic materials may be strongly susceptible to magnetic fields and capable of retaining magnetic properties when the field can be removed. Ferromagnetic materials include, but are not limited to, iron, cobalt, nickel, alloys thereof, and combinations thereof. Other ferromagnetic rare earth metals or alloys thereof can also be used to make the magnetic particles.

The oligonucleotides on both the microcapsule and the magnetic particle may comprise the same barcode sequence. The barcode sequence may allow matching the information (e.g., sequence reads) of DNA and RNA from the same cell.

In some cases, the barcode sequence may comprise a unique identifier of the cell. For example, the unique identifier may distinguish a cell from other cells in a sample. Thus, the unique identifier may allow parallel analysis of DNA molecules and RNA molecules in a plurality of cells, e.g., at least 10, 50, 100, 200, 300, 400, 500, 600, 800, or 1000 cells. For example, the unique identifier may allow parallel analysis of DNA molecules and RNA molecules in a plurality of cells, e.g., at least 200, or 500 cells.

In some cases, the microcapsule may also contain one or more reagents for analyzing cells. For example, the microcapsule may contain a lysis agent. When the microcapsule is dissolved, the lysis agent may be released and lyse the cell in the same partition with the microcapsule.

In some cases, the microcapsule may be a gel bead. An example method for making a gel bead with one or more magnetic particles may comprise one or more of the following operations: 1) Magnetic particles are added to the aqueous phase of the material for making the gel beads, e.g., the gel beads monomer mixture; 2) The gel beads are made using a microfluidic approach, e.g., by forming droplets that polymerize to form the gel beads. When the droplets polymerize, the magnetic particles are entrapped within; 3) The same barcode sequence is added to the gel bead and the magnetic particles entrapped within, e.g., using dual ligation strategy.

Once a partition is generated to include a cell, a microcapsule, and a magnetic particle entrapped in the microcapsule, the partition may be incubated with one or more reagents (e.g., a lysis agent) to lyse the cell and dissolve the microcapsule. The incubation may be performed on a microfluidic chip device, e.g., with a delay line device as described in Frenz et al., Reliable microfluidic on-chip incubation of droplets in delay-lines. Lab Chip. 2009 May 21; 9(10):1344-8, which is incorporated herein by reference in its entirety. After the incubation, the partition may be collected and placed in a container e.g., a strip tube or plate.

The incubation may be performed for a period that allows sufficient time for the cell to lyse and the magnetic particles to be released from the microcapsule. The incubation time may also allow sufficient binding of the RNA primers on the magnetic particles with the RNA molecules from the cell. In some cases, the incubation time may be from 1 minute to 100 minutes, from 5 minutes to 50 minutes, from 10 minutes to 30 minutes, or from 10 minutes to 20 minutes.

One or more RNA molecules bound to the RNA primers on the magnetic particles may be separated from other components in the partition. The separation may be performed by concentrating the magnetic particles. The magnetic particles may be concentrated by a magnetic field. The separation may be performed on a microfluidic device, e.g., a device as described in Gao et al., Wash-free magnetic immunoassay of the PSA cancer marker using SERS and droplet microfluidics, Lab Chip, 2016, 16, 1022-1029; Brouzes et al., Rapid and continuous magnetic separation in droplet microfluidic devices. Lab Chip. 2015 Feb. 7; 15(3): 908-19; or Lombardi et al., Droplet microfluidics with magnetic beads: a new tool to investigate drug-protein interactions. Anal Bioanal Chem. 2011 January; 399(1):347-52, which are incorporated herein by reference in their entireties. In some cases, the one or more RNA molecules may be separated from DNA molecules. The separated RNA molecules and DNA molecules from a single cell may be analyzed using approaches described herein, e.g., sequencing, to determine a characteristic of the cell.

Figure 32:
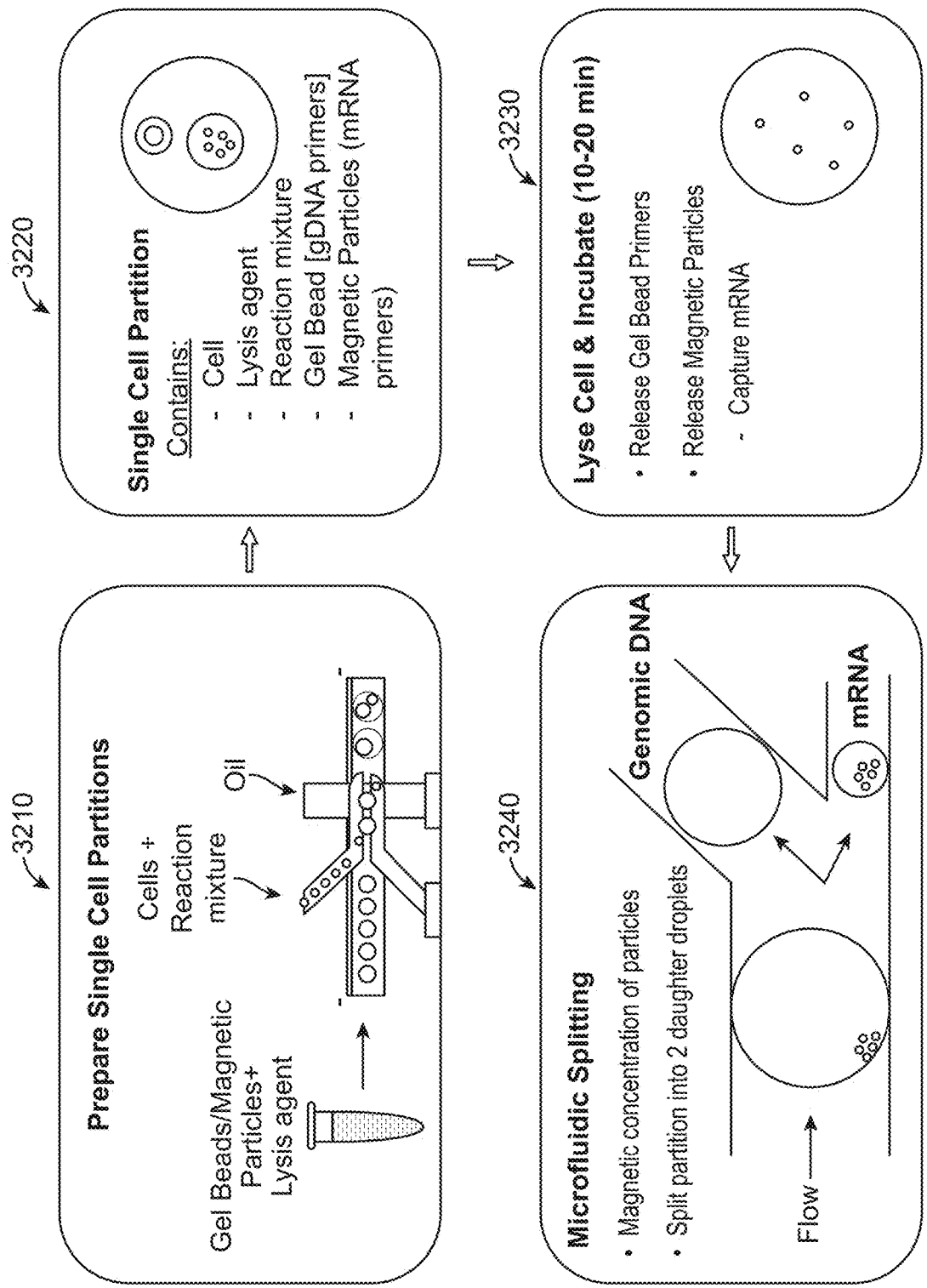
FIG. 32 shows a method for parallel sequencing DNA molecules and RNA molecules in a cell.

FIG. 32 shows a method for parallel sequencing DNA (e.g., genomic DNA) and RNA (e.g., mRNA) in a cell. In operation 3210, single cell partitions are prepared by mixing gel beads with magnetic particles, cells and reaction reagents, e.g., a lysis agent. Droplets are generated from the mixture. A single droplet 3220 contains one cell, a gel bead with magnetic particles, and reaction reagents. The gel bead has genomic DNA primers and the magnetic particles have mRNA primers. The gel bead and the magnetic particles in the partition have the same barcode sequence. In 3230, the gel bead is dissolved to release the magnetic particles and genomic DNA primers. The cell is also lysed to release the genomic DNA molecules and mRNA molecules. The mRNA molecules are captured on the magnetic particles by binding with the mRNA primers. In operation 3240, on a microfluidic device, the partition split into two daughter droplets. The magnetic particles with the captured mRNA molecules are collected in only one of the daughter droplets, thus being separated from other components, e.g., genomic DNA in the other daughter droplet. Thus, the genomic DNA molecules and mRNA molecules from a single cell are separated and may be used for further analysis.

Also provided herein are methods and compositions for analyzing one or more proteins and one or more nucleic acids from a sample (e.g., a single cell). For example, the methods and compositions may be used for analyzing the proteome, the genome and/or the transcriptome in a single cell. The methods may comprise generating a partition that contains the sample, a labelling agent for proteins and a labelling agent for nucleic acids. In some cases, the labelling agent for proteins may interact with one or more proteins in the sample. For example, the labelling agent for proteins may comprise an antibody. In other cases, the labelling agent for proteins may be coupled with a protein probe that interacts with one or more proteins in the sample. For example, the labelling agent for proteins may be coupled with an antibody. The labelling agent for nucleic acids may interact with one or more nucleic acids in the sample. The labelling agent for nucleic acids may comprise a primer, e.g., a primer that bind to a DNA molecule and/or RNA molecule. The labelling agent for proteins and the labelling agent for nucleic acids may comprise the same reporter oligonucleotide. The reporter oligonucleotide may comprise a barcode and/or a UMI. The barcode and/or the UMI may allow for matching proteins with nucleic acids from the same sample. When bound to the labelling agent for nucleic acids, the nucleic acids from a sample may be sequenced. The reporter oligonucleotide or a portion thereof may also be sequenced. In some cases, the methods may comprise one or more of the following operations: a) providing a partition comprising a biological sample comprising a protein and a first nucleic acid molecule, a labelling agent that is (i) capable of binding to the protein and (ii) is coupled to a reporter oligonucleotide comprising a nucleic acid barcode sequence that permits identification of the labelling agent, a first anchor oligonucleotide coupled to a support, which first anchor oligonucleotide is capable of interacting with the reporter oligonucleotide; and a second anchor oligonucleotide coupled to the support, which second anchor oligonucleotide is capable of interacting with the first nucleic acid molecule; (b) in the partition, synthesizing a second nucleic acid molecule comprising at least a portion of the nucleic acid barcode sequence or a complement thereof; and (c) subjecting the first nucleic acid molecule and the second nucleic acid molecule to sequencing. When the labelling agent for proteins and a protein probe is separate molecules, the protein probe may be incubated with the sample before making the partition in operation (a).

Two anchor agents may be used in the methods described herein. The first anchor agent may interact with one or more nucleic acids from a sample. Additionally or alternatively, the first anchor agent may be coupled with a labelling agent for nucleic acids. For example, the first anchor agent may comprise an oligonucleotide that bind to a labelling agent for nuclei acid. The second anchor agent may interact with one or more proteins from a sample. Additionally or alternatively, the second anchor agent may interact be coupled with a labelling agent for proteins. For example, the second anchor agent may comprise an element that interacts with the labelling agent for proteins. In some cases, the second anchor agent may comprise a nucleic acid sequence that interacts with an oligonucleotide sequence coupled to a labelling agent for proteins.

The labelling agent for proteins may comprise one or more elements. The labelling agent may comprise an element (e.g., an oligonucleotide sequence) that interacts with an anchor agent. The labelling agent may comprise a reporter oligonucleotide, e.g., an oligonucleotide comprising a barcode that allows for identifying the protein targeted by the labelling agent. For example, in the cases where the labelling agent for proteins comprises an antibody, the reporter oligonucleotide may allow for identifying the antibody, thereby identifying the protein bound by the antibody.

Figure 33:
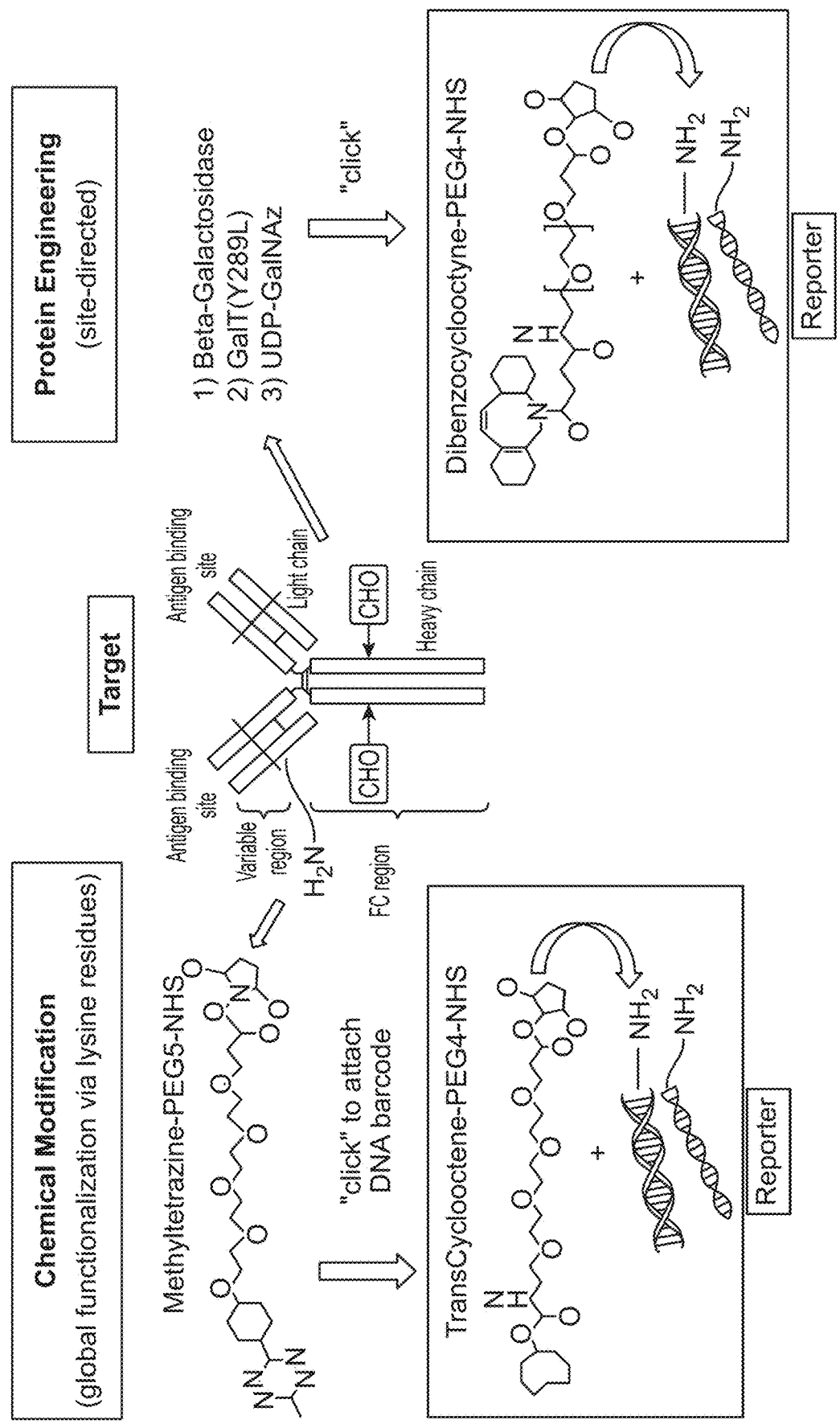
FIG. 33 shows various approaches for making antibody-reporter oligonucleotide conjugates.

The labelling agent for proteins may comprise a reactive moiety that allows the labelling agent to be coupled with a protein probe, e.g., antibody. The labelling agent may be coupled with a protein probe by any chemistry descried herein for attaching a reporter oligonucleotide to a labelling agent. In some cases, the reactive moiety may include a click chemistry linker, such as Methyltetrazine-PEG5-NHS Ester or TCO-PEG4-NHS Ester. The reactive moiety on the labelling agent may also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., $NH_2$). The reactive moiety on the protein probe may be a chemical compound or group that binds to the reactive moiety on the labelling agent. Example strategies to conjugate the protein probe to the labelling agent include using of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the protein probe is an antibody, the antibody may be modified for conjugating the reporter oligonucleotide. For example, the antibody may be glycosylated with a substrate-permissive mutant of β-1, 4-galactosyltransferase, GalT (Y289L) and azide-bearing uridine diphosphate-N-acetylgalactosamine analog uridine diphosphate-GalNAz. The modified antibody may be conjugated with a reporter oligonucleotide with a dibenzocyclooctyne-PEG4-NHS group. FIG. 33 shows example strategies for antibody-reporter oligonucleotide conjugation. In some cases, some strategy (e.g., COOH activation (e.g., EDC) and homobifunctional cross linkers) may be avoided to prevent the protein probes from conjugating to themselves.

The two anchor agents may be coupled to a solid support, e.g., a microcapsule. For example, the microcapsule may be a bead, e.g., a gel bead. In some cases, the two anchor agents are coupled to the same solid support. In other cases, the two anchor agents are coupled to different solid supports. The two anchor agent may comprise the same reporter oligonucleotide.

Figure 34:
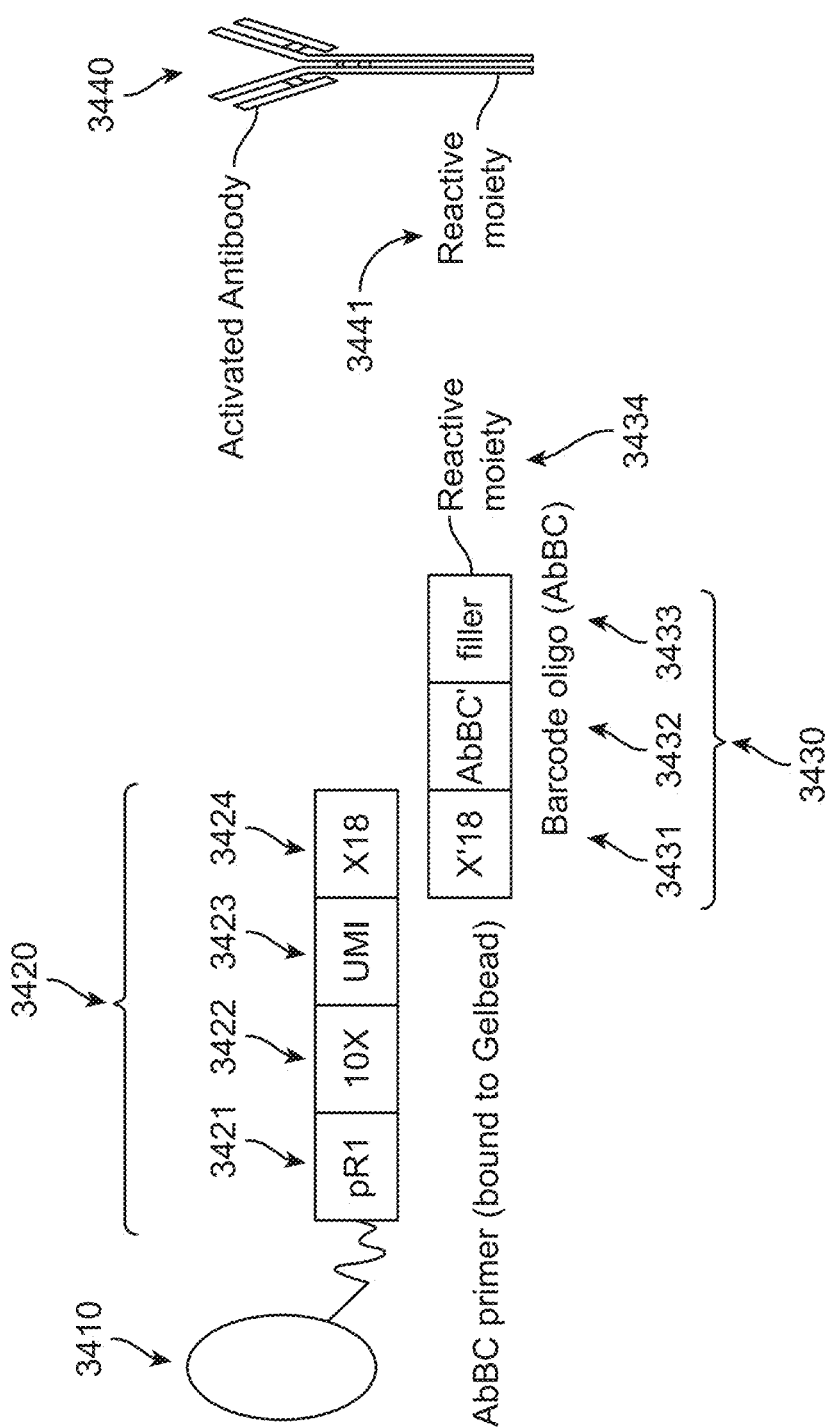
FIG. 34 shows an antibody-reporter oligonucleotide conjugation.

FIG. 34 shows example reagents used in the methods. An anchor agent 3420 is coupled to a bead 3410. The anchor agent comprises a barcode sequence 3422 and a UMI 3423. The anchor agent also comprises an oligonucleotide sequence 3424 that allows binding to the labelling agent 3430. The labelling agent 3430 comprises an oligonucleotide 3431 for binding to the anchor agent. The labelling agent 3430 also comprises a barcode 3432 that allows identifying the antibody it is coupled to. The labelling agent 3430 further comprises a reactive moiety 3434 that allows the labelling agent to couple with an antibody 3440.

An additional example of reagents and schemes suitable for analysis of barcoded labelling agents is shown in panels I and II of FIG. 52B. As shown in FIG. 52B (panel I), a labelling agent (e.g., antibody, an MHC moiety) 5201 is directly (e.g., covalently bound, bound via a protein-protein interaction, such as with Protein G) coupled to an oligonucleotide 5202 comprising a barcode sequence 5203 that identifies the label agent 5201. Oligonucleotide 5202 also includes additional sequences (sequence 5204 comprising a reverse complement of a template switch oligo and sequence 5205 comprising a PCR handle) suitable for downstream reactions. FIG. 52B (panel I) also shows an additional oligonucleotide 5206 (e.g., which may have been released from a bead as described elsewhere herein) comprising a barcode sequence 5208, a UMI sequence 5209 and additional sequences (sequence 5207 comprising a sequencing read primer binding site 'pR1' and sequence 5210 comprising a template switch oligo) suitable for downstream reactions. During analysis, the labelling agent is bound to its target cell surface feature and the rGrGrG sequence of sequence 5210 hybridizes with sequence 5204 and both oligonucleotides 5202 and 5206 are extended via the action of a polymerizing enzyme (e.g., a reverse transcriptase, a polymerase), where oligonucleotide 5206 then comprises complement sequences to oligonucleotide 5202 at its 3' end. These constructs can then be optionally processed as described elsewhere herein and subject to sequencing to, for example, identify the target cell surface feature (via the complementary barcode sequence generated from oligonucleotide 5202) and associate it with the cell, identified by the barcode sequence of oligonucleotide 5206.

In another example, shown in FIG. 52B (panel II), a labelling agent (e.g., antibody) 5221 is indirectly (e.g., via hybridization) coupled to an oligonucleotide 5222 comprising a barcode sequence 5223 that identifies the label agent

5221. Labelling agent 5221 is directly (e.g., covalently bound, bound via a protein-protein interaction, such as with Protein G) coupled to a hybridization oligonucleotide 5232 that hybridizes with sequence 5231 of oligonucleotide 5222. Hybridization of oligonucleotide 5232 to oligonucleotide 5231 couples label agent 5221 to oligonucleotide 5222. Oligonucleotide 5222 also includes additional sequences (sequence 5224 comprising a reverse complement of a template switch oligo and sequence 5225 comprising a PCR handle) suitable for downstream reactions. FIG. 52B (panel II) also shows an additional oligonucleotide 5226 (e.g., which may have been released from a bead as described elsewhere herein) comprising a barcode sequence 5228, a UMI sequence 5229 and additional sequences (sequence 5227 comprising a sequencing read primer binding site 'pR1' and sequence 5220 comprising a template switch oligo) suitable for downstream reactions. During analysis, the labelling agent is bound to its target cell surface feature and the rGrGrG sequence of sequence 5220 hybridizes with sequence 5224 and both oligonucleotides 5222 and 5226 are extended via the action of a polymerizing enzyme (e.g., a reverse transcriptase, a polymerase), where oligonucleotide 5226 then comprises complement sequences to oligonucleotide 5222 at its 3' end. These constructs can then be optionally processed as described elsewhere herein and subject to sequencing to, for example, identify the target cell surface feature (via the complementary barcode sequence generated from oligonucleotide 5222) and associate it with the cell, identified by the barcode sequence of oligonucleotide 5226.

Figure 35A:
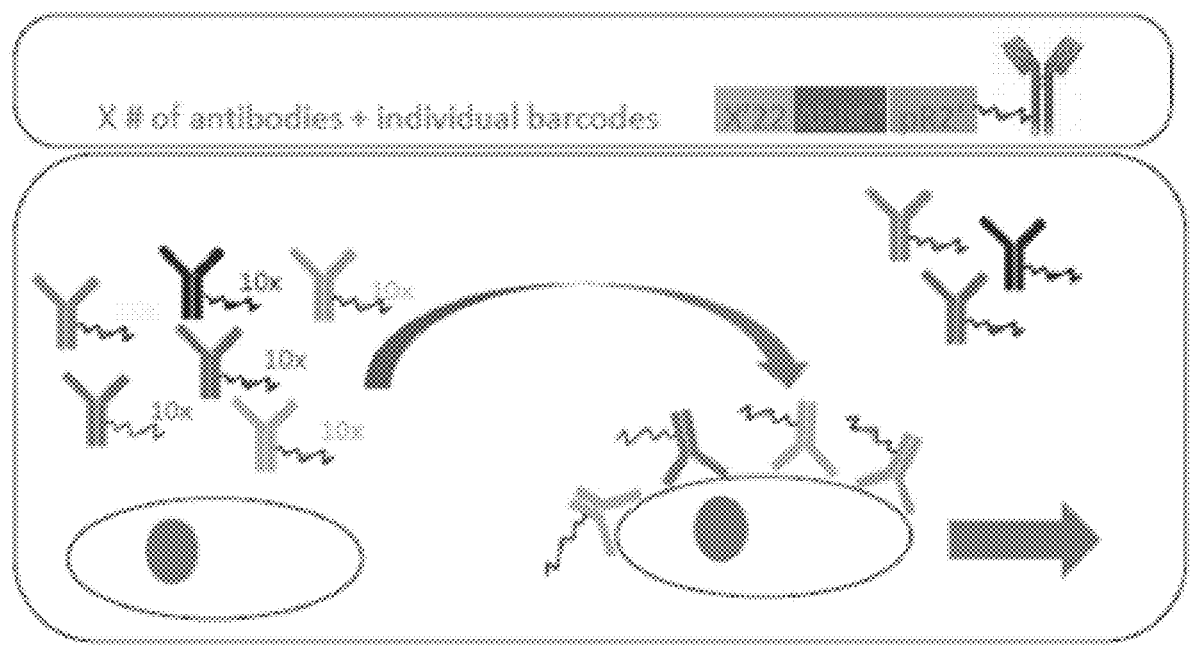
FIGS. 35A-35C show a method for analyzing mRNA molecules and proteins from a single cell ("AAAAAAAAAAAAAAAAAAAAAA" disclosed as SEQ ID NO: 23)
Figure 35B:
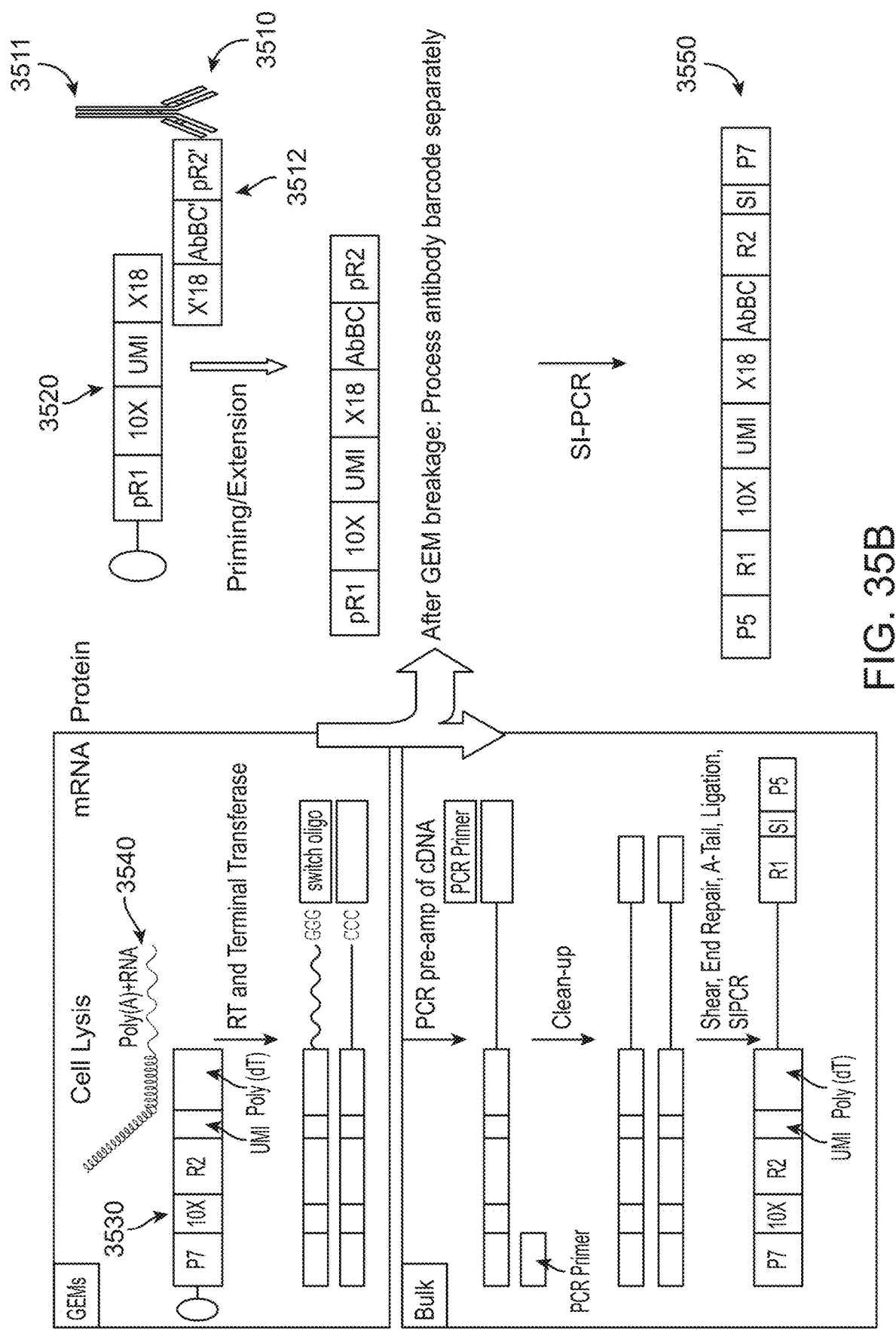
Figure 35C:
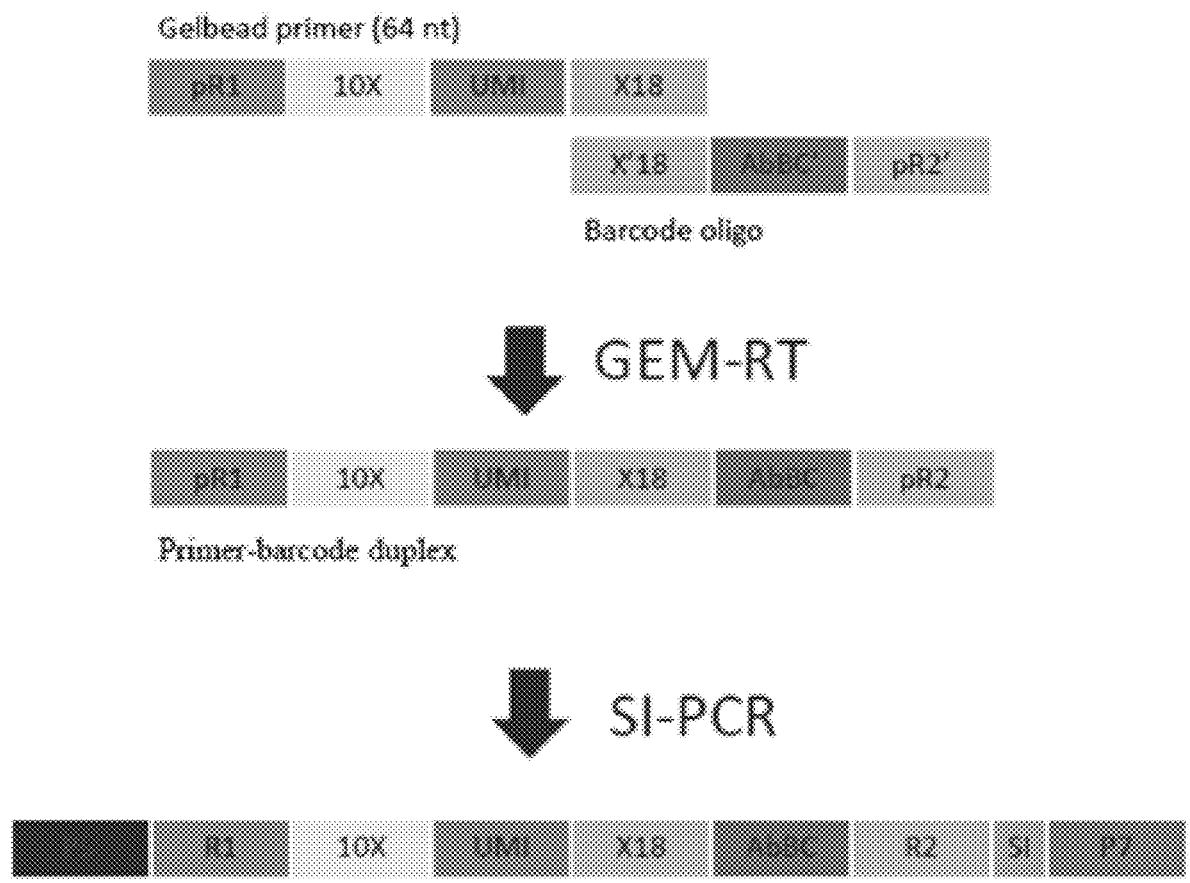

An example of the methods for analyzing mRNA molecules and proteins from a single cell is shown in FIGS. 35A and 35B. The method uses a barcoded antibody 3510 containing an antibody 3511 conjugated with an oligonucleotide 3512. The oligonucleotide 3512 can bind to a first anchor oligonucleotide 3520 coupled to a bead. The barcoded antibody 3510 is incubated with cells such that the antibody binds to an antigen on the cell, and form antibody-cell complexes (FIG. 35A). Unbound antibodies are washed out. The antibody-cell complexes are made into emulsion partitions. Each partition contains an antibody-cell complex, the first anchor oligonucleotide 3520, and a second anchor oligonucleotide 3530 that binds to mRNA molecules from the cell. The cell is lysed and the mRNA molecules are released from the cell. As shown in FIG. 35B, the mRNA molecules are reverse transcribed to cDNA and amplified with the help of the second anchor oligonucleotide. The amplified cDNA molecules have the barcode and UMI that are the same as the barcode and UMI on the first anchor oligonucleotide 3520. Primer extension is performed on the complex of the first anchor oligonucleotide 3520 and the oligonucleotide 3512, thus generating a reporter oligonucleotide 3550 comprising the barcode and UMI the same as those on the second anchor oligonucleotide. The reporter oligonucleotide 3550 also comprises an antibody identifier (antibody barcode (AbBC)) that identifies the antibody and the antigen bound by the antibody. When the cDNA molecules are sequenced, the sequence reads are correlated to the antigen in the same cell using the barcode and UMI. FIG. 35C shows the primer extension of the first anchor oligonucleotide and oligonucleotide 3512 conjugated with the antibody. The resulting oligonucleotides may be separated from cDNA synthesized from mRNA from the cell (e.g., by size-based selection). The first anchor oligonucleotide and the complex of the second anchor oligonucleotide with oligonucleotide 3512 may be processed and/or sequenced separately or jointly. In some cases, the anchor agents 3520 and 3530 may be coupled to the same bead.

Also provided herein are the microfluidic devices used for partitioning the cells as described above. Such microfluidic devices can comprise channel networks for carrying out the partitioning process like those set forth in FIGS. 1 and 2. Briefly, these microfluidic devices can comprise channel networks, such as those described herein, for partitioning cells into separate partitions, and co-partitioning such cells with oligonucleotide barcode library members, e.g., disposed on beads. These channel networks can be disposed within a solid body, e.g., a glass, semiconductor or polymer body structure in which the channels are defined, where those channels communicate at their termini with reservoirs for receiving the various input fluids, and for the ultimate deposition of the partitioned cells, etc., from the output of the channel networks. By way of example, and with reference to FIG. 2, a reservoir fluidly coupled to channel 202 may be provided with an aqueous suspension of cells 214, while a reservoir coupled to channel 204 may be provided with an aqueous suspension of beads 216 carrying the oligonucleotides. Channel segments 206 and 208 may be provided with a non-aqueous solution, e.g., oil, into which the aqueous fluids are partitioned as droplets at the channel junction 212. An outlet reservoir may be fluidly coupled to channel 210 into which the partitioned cells and beads can be delivered and from which they may be harvested. As will be appreciated, while described as reservoirs, it will be appreciated that the channel segments may be coupled to any of a variety of different fluid sources or receiving components, including tubing, manifolds, or fluidic components of other systems.

Also provided are systems that control flow of these fluids through the channel networks e.g., through applied pressure differentials, centrifugal force, electrokinetic pumping, capillary or gravity flow, or the like.

Also provided herein are kits for analyzing individual cells or small populations of cells. The kits may include one, two, three, four, five or more, up to all of partitioning fluids, including both aqueous buffers and non-aqueous partitioning fluids or oils, nucleic acid barcode libraries that are releasably associated with beads, as described herein, labelling agents, as described herein, anchor oligonucleotides, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

Another aspect of the disclosure provides a composition for characterizing a plurality of analytes, comprising a partition comprising a plurality of barcode molecules and the plurality of analytes. The plurality of barcode molecules can also include at least 1,000 barcode molecules. Moreover, (i) a first individual barcode molecule of the plurality of barcode molecules can comprise a first nucleic acid barcode sequence that is capable of coupling to a first analyte of the plurality of analytes; and (ii) a second individual barcode molecule of the plurality of barcoded molecules can comprise a second nucleic acid barcode sequence that is capable of coupling to a second analyte of the plurality of analytes, where the first analyte and the second analyte are different types of analytes (e.g., DNA and RNA, DNA and protein, RNA and protein, or DNA, RNA and protein). In some cases, the composition comprises a plurality of partitions comprising the partition.

An additional aspect of the disclosure provides a method for analyte characterization. The method comprises: (a)

providing a plurality of partitions, where a given partition of the plurality of partitions comprises a plurality of barcode molecules and a plurality of analytes. The plurality of barcode molecules can comprise at least 1,000 barcode molecules. Moreover, (i) a first individual barcode molecule of the plurality of barcode molecules can comprise a first nucleic acid barcode sequence that is capable of coupling to a first analyte of the plurality of analytes; and (ii) a second individual barcode molecule of the plurality of barcoded molecules can comprise a second nucleic acid barcode sequence that is capable of coupling to a second analyte of the plurality of analytes; where the first analyte and the second analyte are different types of analytes. The method also includes (b) in said given partition (i) synthesizing a first nucleic acid molecule comprising at least a portion of the first nucleic acid barcode sequence or complement thereof; and (ii) synthesizing a second nucleic acid molecule comprising at least a portion of the second nucleic acid barcode sequence or complement thereof; and (c) removing said first nucleic acid molecule and said second molecule from said given partition. In some cases, the method further comprises subjecting the first nucleic acid molecule and the second nucleic acid molecule, or a derivative of the first nucleic acid molecule and/or second nucleic acid molecule, to sequencing to characterize the first and/or the second analyte.

Characterizing the first analyte and/or the second analyte generally provides information regarding the first analyte and/or second analyte. This information can be used to select first and/or second analytes for one or more additional cycles of (a)-(c). Accordingly, the method may further comprise repeating (a)-(c) based on a characterization of the first analyte or the second analyte from sequencing. In some cases, the method further comprises selecting the first analyte and/or the second analyte based on a characterization of the first analyte or the second analyte obtained from the sequencing a subsequent sequencing upon repeating (a)-(c).

Moreover, in some cases, (b) further comprises: (1) synthesizing the first nucleic acid molecule comprising at least a portion of the first nucleic acid barcode sequence or complement thereof, and (2) synthesizing the second nucleic acid molecule comprising at least a portion of the second nucleic acid barcode sequence or complement thereof. For example, the first nucleic acid molecule and/or the second nucleic acid molecules may be synthesized with the aid of one or more primer extension reactions that make use of a primer that hybridizes with a first or second analyte. Such a primer may comprise a barcode sequence and/or a UMI sequence as described elsewhere herein. In some cases, the first nucleic acid molecule and/or the second nucleic acid molecule may be synthesized with the aid of ligation between two nucleic acid molecules.

In some cases, the method further comprises performing one or more reactions subsequent to removing the first nucleic acid molecule and the second nucleic acid molecule from the given partition. Such reactions can include the addition of additional nucleic acid sequences (e.g., sample index sequences, a sequence for function in a particular sequencing platform) via additional primer extension reactions, nucleic acid amplification schemes (e.g., PCR) or ligation. In some cases, portions of the first and/or second nucleic acid molecules may be removed (e.g., via restriction enzymes, via shearing) prior to or after the addition of additional nucleic acid sequences. Moreover, these reactions can be performed in bulk, such that processing of the first and second nucleic acid molecules and first and second nucleic acid molecules from other partitions are processed simultaneously in bulk. Such processing can be completed in a single pot reaction. Examples of such one or more other reactions are provided in U.S. Patent Publication No. 2015/0376609, which is entirely incorporated herein by reference.

An additional aspect of the disclosure provides a system for characterizing a plurality of analytes. The system comprises a partitioning unit for providing a partition comprising a plurality of barcode molecules and the plurality of analytes, where: (i) a first individual barcode molecule of the plurality of barcode molecules comprises a first nucleic acid barcode sequence and is capable of coupling to a first analyte of the plurality of analytes; and (ii) a second individual barcode molecule of the plurality of barcode molecules comprises a second nucleic acid barcode sequence and is capable of coupling to a second analyte of the plurality of analytes, where the first analyte and the second analyte are different types of analytes. The system also can include a controller coupled to the partitioning unit, where the controller is programmed to: (i) direct the partitioning unit to provide the partition; subject the partition to conditions that are sufficient to: (1) synthesize a first nucleic acid molecule comprising at least a portion of the first nucleic acid barcode sequence or complement thereof; and (2) synthesize a second nucleic acid molecule comprising at least a portion of the second nucleic acid barcode sequence or complement thereof. Sequencing of the first nucleic acid molecule and the second nucleic acid molecule, or derivatives thereof, can characterize the first analyte or the second analyte. In some cases, the partitioning unit can provides a plurality of partitions comprising the partition.

In some cases, the partitioning unit comprises a multi-well plate. In some cases, the partitioning unit comprises a plurality of channels, which may be microfluidic channels. The plurality of channels may come together to form at least one channel junction that provides the partition. In some cases, a partitioning unit may comprise a first (i) a first channel fluidically connected to the at least one channel junction and configured to provide a first fluid to the at least one channel junction; (ii) and a second channel fluidically connected to the at least one channel junction and configured to provide a second fluid, immiscible with the first fluid, to the at least one channel junction. In an example, then first channel may be configured to provide an aqueous phase comprising aqueous phase reagents (e.g., nucleic acids, including barcoded nucleic acids, labelling agents, beads, an agent that can degrade beads, amplification/primer extension reagents, sample nucleic acids, cells, cell lysis reagents, etc.) and the second channel may be configured to provide an oil phase comprising an oil (e.g., an oil comprising a fluoro-surfactant) that is immiscible with the aqueous phase. Upon contact of the aqueous phase with the oil phases, aqueous phase droplets comprising aqueous phase reagents are generated.

In various aspects, the partition or the given partition may comprise at least 1,000 barcode molecules, at least 2,500 barcode molecules at least 5,000 barcode molecules, at least 7,500 barcode molecules, at least 10,000 barcode molecules, at least 20,000 barcode molecules, at least 30,000 barcode molecules, at least 50,000 barcode molecules, at least 60,000 barcode molecules, at least 70,000 barcode molecules, at least 80,000 barcode molecules, at least 90,000 barcode molecules, at least 100,000 barcode molecules, at least 200,000 barcode molecules, at least 300,000 barcode molecules, at least 400,000 barcode molecules, at least 500,000 barcode molecules, at least 600,000 barcode molecules, at least 700,000 barcode molecules, at least 800,000 barcode molecules, at least 900,000 barcode molecules, at least 1,000,000 barcode molecules, at least 2,500,000 barcode molecules, at least 5,000,000 barcode molecules, at least 7,500,000 barcode molecules at least 10,000,000 barcode molecules, at least 50,000,000 barcode molecules, at least 100,000,000 barcode molecules or more.

In various aspects, at least one of the first individual barcode molecule and the second individual barcode molecule may be coupled (e.g., via a covalent bond, via non-covalent interactions, via a labile bond, etc.) to a bead. In some cases, the bead comprises a gel bead and/or is degradable as described elsewhere herein. In methods described herein, the first or second barcode molecule can be released from the bead after a partition or partitions are provided. In some cases, release of a barcode molecule may occur prior to, simultaneous to, or following its use in barcoding a respective nucleic acid molecule. Where release happens after barcoding, barcoded constructs are initially coupled to the bead. Moreover, a partition may comprise an agent capable of degrading the bead. In some cases, such a reagent is a reducing agent that can reduce disulfide bonds of the bead and/or any disulfide linkages between species coupled to the bead and the bead itself. Moreover, in various aspects, the partition or a given partition can be any suitable partition such as a droplet among a plurality of droplets (e.g., droplets in an emulsion) or a well among a plurality of wells. Furthermore, in various aspects, the first nucleic acid barcode sequence and the second nucleic acid barcode sequence are identical.

In various aspects, the first analyte or the second analyte can be a nucleic acid molecule, including any type of nucleic acid molecule described elsewhere herein. For example, the nucleic acid molecule may be genomic deoxyribonucleic acid (gDNA). In another example, the nucleic acid molecule is messenger ribonucleic acid (mRNA).

Moreover, in various aspects, the first analyte or the second analyte is a labelling agent capable of coupling to a cell surface feature of a cell. The partition or the given partition can comprise the cell or one or more components of the cell (e.g., such as free cellular surface features remaining after cell lysis). In some cases, the partition or given partition comprises a single cell. The labelling agent can be any labelling agent, including a type of labelling agent described elsewhere herein including an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, a protein scaffold, an antigen, an antigen presenting particle and a major histocompatibility complex (MHC). Examples of cell surface features include a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, a T-cell receptor, a B-cell receptor, a chimeric antigen receptor, a gap junction, an adherens junction and any other cell surface feature described elsewhere herein.

In some cases, cells are incubated in bulk with one or more labelling agents prior to partitioning of cells. The one or more labelling agents can be chosen such that they are directed to particular cell surface features of interest in a given assay. Upon binding of the one or more labeling agents to respective cell surface features, where present, the cells can then be washed to remove unbound labelling agents and the resulting cells then subject to partitioning.

Moreover, in some cases, the first individual barcode molecule or the second individual barcode molecule may be capable of coupling to the labelling agent via a third nucleic acid molecule coupled to the labelling agent. The third nucleic acid molecule can be coupled to the labelling agent and comprise a third nucleic acid barcode sequence that identifies the coupled labelling agent (and, thus, a cell surface feature to which the labelling agent is bound). In a primer extension reaction, the first individual barcode molecule or the second individual barcode molecule can be extended such that a complement of the third barcode sequence is added to the first or second individual barcode molecule. During sequencing, the first or second barcode sequence of these molecules can identify the partition from which the molecules were synthesized and, where a partition comprises a single cell, the third barcode sequence can associate a particular cell surface feature with that single cell.

In various aspects, the first analyte and second analyte can be different types of nucleic acid molecules. For example, the first analyte may be a deoxyribonucleic acid molecule (e.g., gDNA) and the second analyte may be ribonucleic acid molecule (e.g., mRNA), such as, for example, a transcript. Where implemented, a cell's genomic DNA and also the cell's transcriptome can be analyzed and characterized.

Moreover, where the first and second analytes are nucleic acid molecules, the first individual barcode molecule and/or the second individual barcode molecule may comprise a priming sequence capable of hybridizing to the first analyte and/or second analyte respectively. In addition to the first nucleic acid barcode molecule or the second nucleic acid barcode molecule, may also include a UMI sequence, that can be useful for identifying (and even quantifying) particular molecules that are barcoded within a given partition, as is described elsewhere herein.

Figure 46A:
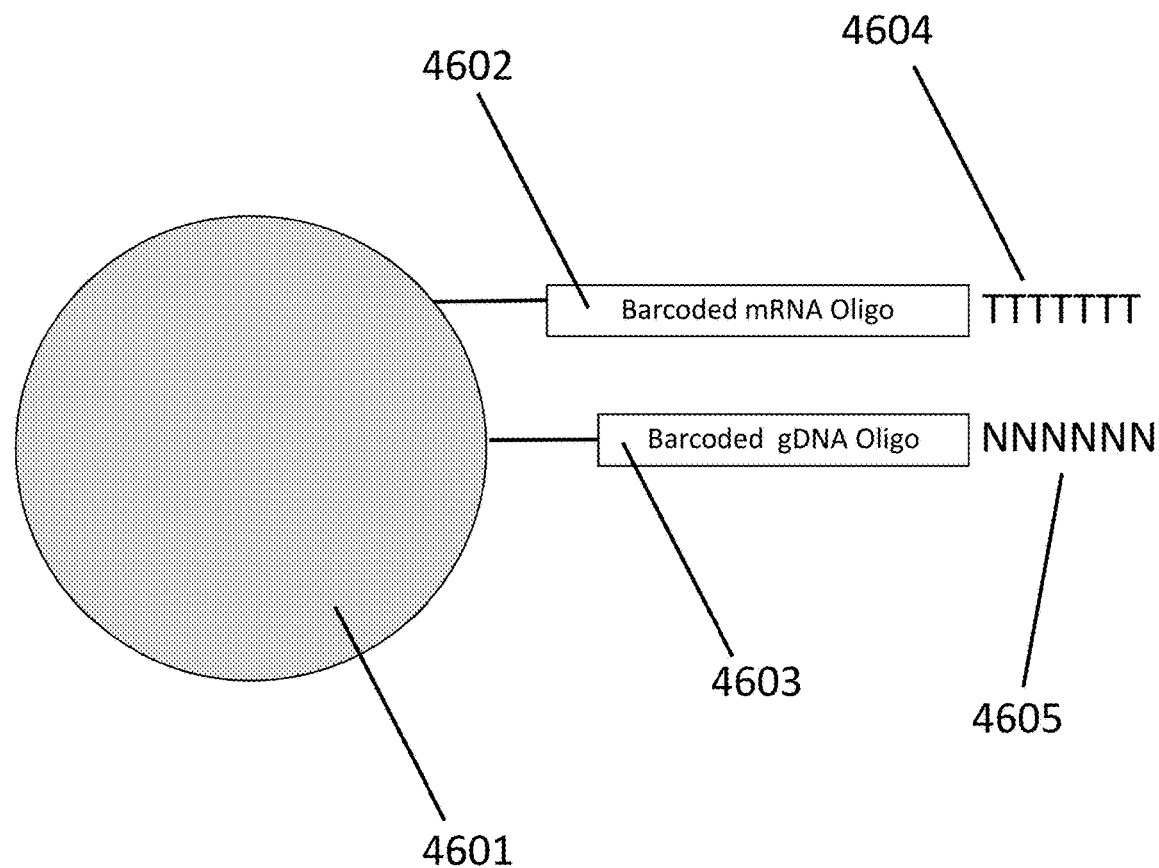
FIGS. 46A-46E schematically depict components of example multi-assay schemes described herein.

In an example, schematically depicted in FIG. 46A, a partition (e.g., a droplet, a well or any other type of partition described herein) comprises a bead 4601, which is coupled (e.g., reversibly coupled) to barcoded oligonucleotides 4602 and 4603. The bead 4601 and barcoded oligonucleotides 4602 and 4603 are schematically depicted in FIG. 46A. Barcoded oligonucleotide 4602 comprises a first nucleic acid barcode sequence and a poly-T priming sequence 4604 that can hybridize with the poly-A tail of an mRNA transcript. Barcoded oligonucleotide 4602 may also comprise a UMI sequence that can uniquely identify a given transcript. Barcoded oligonucleotide 4603 comprises a second nucleic acid barcode sequence and a random N-mer priming sequence 4605 that is capable of randomly hybridizing with gDNA. In this configuration, barcoded oligonucleotides 4602 and 4603 comprise the same nucleic acid barcode sequence, which permits association of downstream sequencing reads with the partition. In some cases, though, the first nucleic acid barcode sequence and the second nucleic acid barcode sequence are different.

The partition also comprises a cell (not shown) and lysis agents that aid in releasing nucleic acids from the cell and can also include an agent (e.g., a reducing agent) that can degrade the bead and/or break a covalent linkage between the barcoded oligonucleotides 4602 and 4603 and bead 4601, releasing them into the partition. The released barcoded oligonucleotide 4602 can hybridize with mRNA released from the cell and the released barcoded oligonucleotide 4603 can hybridize with gDNA released from the cell. Barcoded constructs A and B can then be generated for each of the mRNA and barcoded oligonucleotide 4623 as described elsewhere herein, such as via the action of a polymerase (and/or reverse transcriptase) and/or primer extension. Barcoded construct A can comprises a sequence corresponding to the original barcode sequence from the bead and a sequence corresponding to a transcript from the cell. Barcoded construct B can comprise a sequence corresponding to the original barcode sequence from the bead and a sequence corresponding to genomic DNA from the cell. The barcoded constructs can then be released/removed from the partition and, in some cases, further processed to add any additional sequences. The resulting constructs are then sequenced, sequencing data processed, and the results used to characterize the mRNA and the gDNA from the cell. Analysis can be completed, for example, as described elsewhere herein. The information received from the characterization can then be used in a subsequent analysis of another cell in a partition. Moreover, barcoded oligonucleotides 4602 and 4603 can be designed to prime any particular type of nucleic acid, including those that are not derived from a cell. Moreover, the priming sequences shown in FIG. 46A are for example purposes only and are not meant to be limiting.

In various aspects, the first analyte may be a nucleic acid molecule (e.g., deoxyribonucleic acid (e.g., gDNA), ribonucleic acid (e.g., mRNA), a transcript) and the second analyte a labelling agent capable of coupling to a cell surface feature. In such a case, the first individual barcode molecule may comprise a priming sequence capable of hybridizing to the nucleic acid molecule and may also include a UMI sequence. Moreover, the second individual barcode molecule may comprise a priming sequence capable of hybridizing with a third nucleic acid molecule coupled to the labelling agent. As noted elsewhere herein, this third nucleic acid molecule can include a barcode sequence that identifies the labelling agent. It may also include a UMI sequence. The labelling agent can be any suitable labelling agent, including a type of example labelling agents described elsewhere herein, and may be targeted to any suitable cell surface feature to which it can selectively bind. Non-limiting examples of such cell surface features are provided elsewhere herein. Furthermore, in some cases, the partition comprises a cell having the cell surface feature and, in some cases, may comprise only one cell.

Figure 46B:
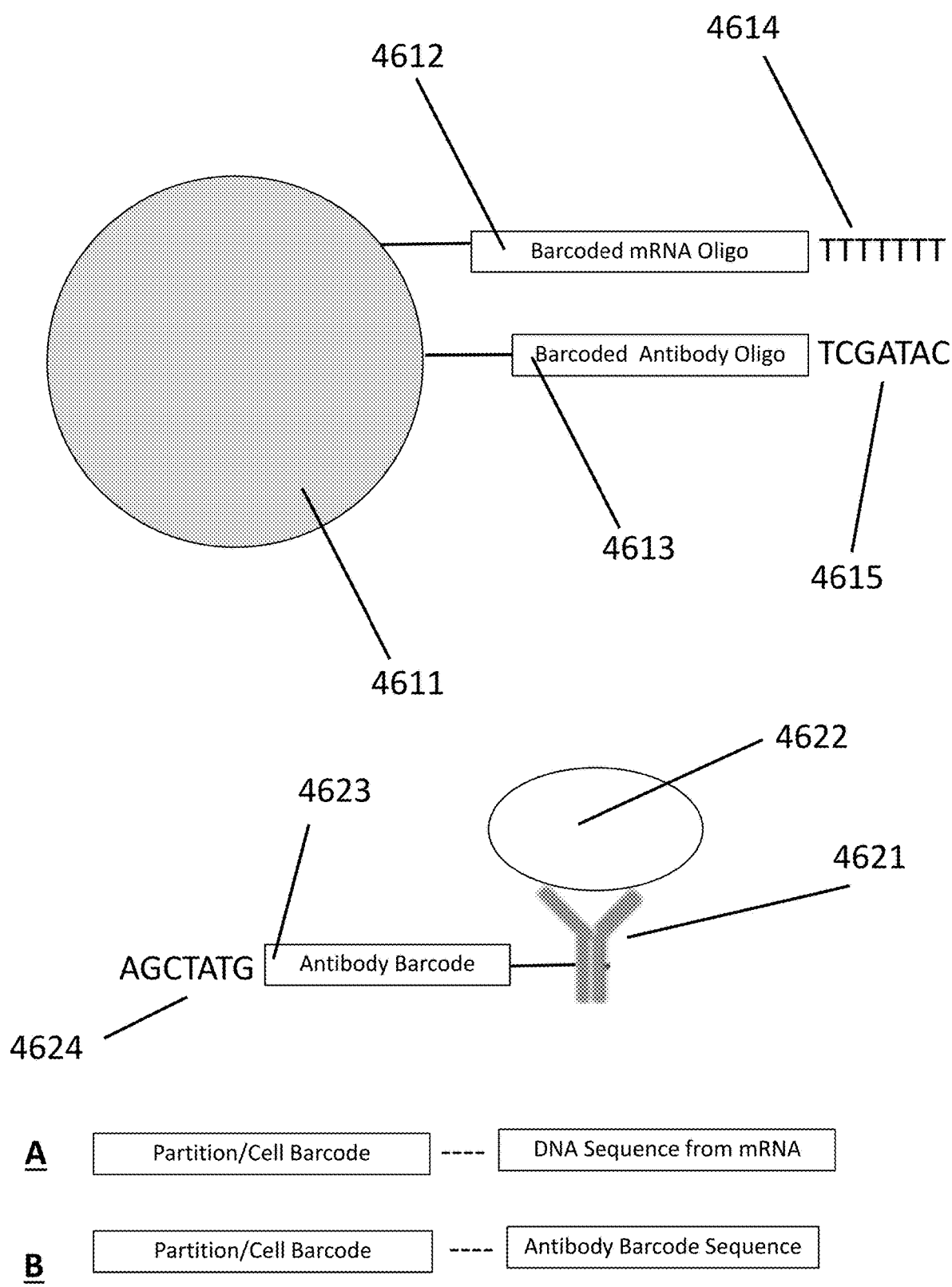

In an example, schematically depicted in FIG. 46B, a partition (e.g., a droplet, a well, a microcapsule, or any other type of partition described herein) comprises a bead 4611, which is coupled (e.g., reversibly coupled) to barcoded oligonucleotides 4612 and 4613. The bead 4611 and barcoded oligonucleotides 4612 and 4613 are schematically depicted in FIG. 46B. Barcoded oligonucleotide 4612 comprises a first nucleic acid barcode sequence and a poly-T priming sequence 4614 that can hybridize with the poly-A tail of an mRNA transcript. Barcoded oligonucleotide 4612 may also comprise a UMI sequence that can uniquely identify a given transcript. Barcoded oligonucleotide 4613 comprises a second nucleic acid barcode sequence and a targeted priming sequence that is capable of specifically hybridizing with a barcoded oligonucleotide 4623 (via a complementary portion 4624 of barcoded oligonucleotide 4623 coupled to an antibody 4621 that is bound to the surface of a cell 4622. Barcoded oligonucleotide 4623 comprises a barcode sequence that uniquely identifies the antibody 4621 (and thus, the particular cell surface feature to which it is bound). In this configuration, barcoded oligonucleotides 4612 and 4613 comprise the same nucleic acid barcode sequence, which permit downstream association of barcoded nucleic acids with the partition. In some cases, though, the first nucleic acid barcode sequence and the second nucleic acid barcode sequence are different. Furthermore, barcoded labelling agents, including antibodies, may be produced by any suitable route, including via example coupling schemes described elsewhere herein.

As shown in FIG. 46B, the partition also comprises cell 4622, lysis agents that aid in releasing nucleic acids from the cell 4622 and can also include an agent (e.g., a reducing agent) that can degrade the bead and/or break a covalent linkage between the barcoded oligonucleotides 4612 and 4613 and bead 4611, releasing them into the partition. The released barcoded oligonucleotide 4612 can hybridize with mRNA released from the cell and the released barcoded oligonucleotide 4613 can hybridize with barcoded oligonucleotide 4623. Barcoded constructs A and B can then be generated for each of the mRNA and barcoded oligonucleotide 4623 as described elsewhere herein, such as via the action of a polymerase (and/or reverse transcriptase) and/or primer extension. Barcoded construct A may comprise a sequence corresponding to the original barcode sequence from the bead and a sequence corresponding to a transcript from the cell. Barcoded construct B may comprise a sequence corresponding to the original barcode sequence from the bead and an additional sequence corresponding to the barcode sequence coupled to the labelling agent. The barcoded constructs can then be released/removed from the partition and, in some cases, further processed to add any additional sequences. The resulting constructs are then sequenced, sequencing data processed, and the results used to characterize the mRNA and cell surface feature of the cell. Analysis, for example, can be completed as described elsewhere herein. The information received from the characterization can then be used in a subsequent analysis of another cell in a partition. Moreover, the priming sequences shown in FIG. 46B are for example purposes only and are not meant to be limiting. In addition, the scheme shown in FIG. 46B may also be used for concurrent analysis of genomic DNA and cell surface features. In some cases, the partition comprises only one cell.

Furthermore, in various aspects, the first analyte may comprise a nucleic acid molecule with a nucleic acid sequence (mRNA, complementary DNA derived from reverse transcription of mRNA) encoding at least a portion of a V(D)J sequence of an immune cell receptor. Accordingly, a first barcode molecule may comprise a priming sequence that can prime such a nucleic acid sequence, as is described elsewhere herein. In some cases, the nucleic acid molecule with a nucleic acid sequence encoding at least a portion of a V(D)J sequence of an immune cell receptor is cDNA first generated from reverse transcription of the corresponding mRNA, using a poly-T containing primer. The cDNA that is generated can then be barcoded using a primer, comprising a barcode sequence (and optionally, a UMI sequence) that hybridizes with at least a portion of the cDNA that is generated. In some cases, a template switching oligonucleotide in conjunction a terminal transferase or a reverse transcriptase having terminal transferase activity may be employed to generate a priming region on the cDNA to which a barcoded primer can hybridize during cDNA generation. Terminal transferase activity can, for example, add a poly-C tail to a 3' end of the cDNA such that the template switching oligonucleotide can bind via a poly-G priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in U.S. Provisional Patent Application Ser. No. 62/410,326, filed Oct. 19, 2016 and U.S. Provisional Patent Application Ser. No. 62/490,546, filed Apr. 26, 2017, both of which applications are herein incorporated by reference in their entireties. In one example, the scheme described elsewhere herein and schematically depicted in FIG. 19 may be used for V(D)J analysis.

V(D)J analysis may also be completed with the use of one or more labelling agents that bind to particular surface features of immune cells and are associated with barcode sequences as described elsewhere herein. In some cases, the one or more labelling agents comprise an MHC.

In some cases, different types of analytes do not include labelling agents directed to separate cell surface features of a cell.

Moreover, in various aspects, the first analyte may comprise a nucleic acid capable of functioning as a component of a gene editing reaction, such as, for example, clustered regularly interspaced short palindromic repeats (CRISPR)-based gene editing. Accordingly, the first barcode molecule may comprise a priming sequence that can prime such a nucleic acid sequence, as is described elsewhere herein.

While the examples described with respect to FIGS. 46A and 46B involve the analysis of two different types of analytes, these examples are not meant to be limiting. Any suitable number of analytes may be evaluated. Accordingly, in various aspects, there may be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100 or more different analytes present in a partition, that can be subject to barcoded sequencing analysis. Higher number, multi-assay analysis can be completed by including primer species (one or more of which may be barcoded) that are capable of generating barcoded constructs and capable of specifically hybridizing with a particular analyte or oligonucleotide coupled to a labelling agent that is itself coupled to a particular analyte in the partition and subjecting the partition to suitable conditions for barcoding.

Figure 46C:
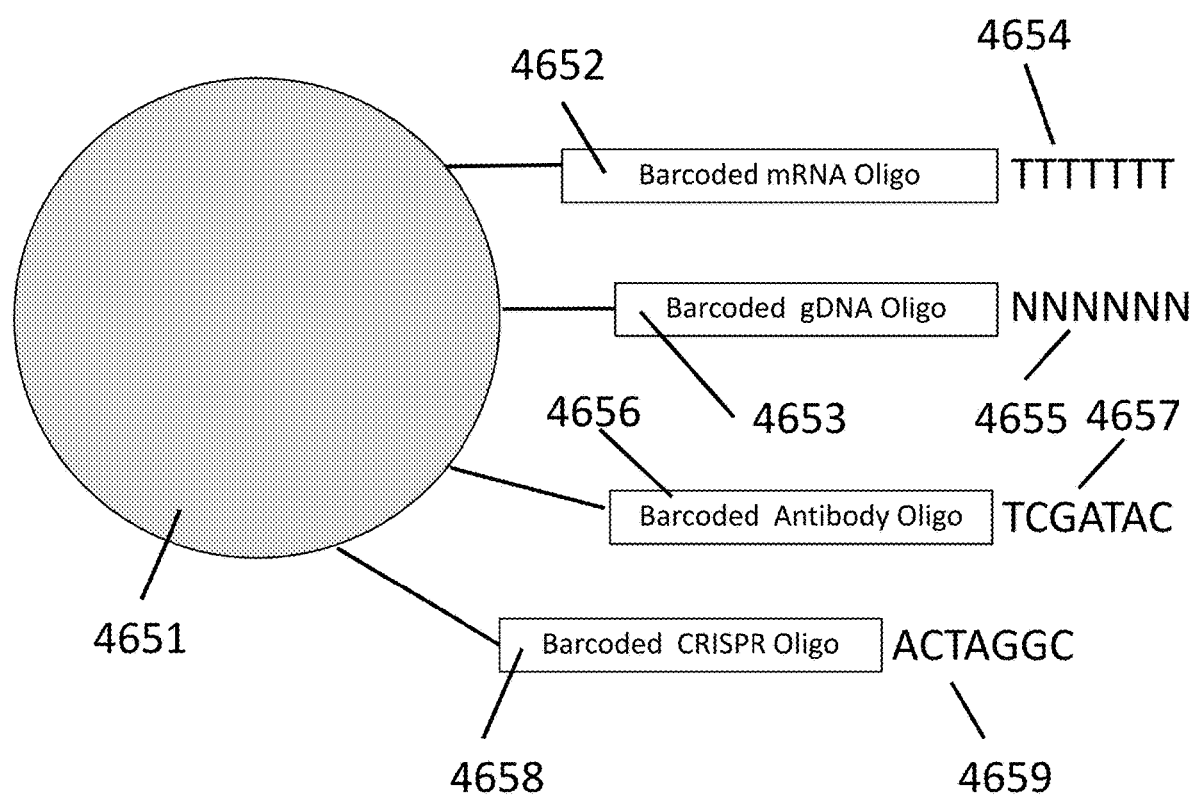

An example reagent for multi-assay analysis is schematically depicted in FIG. 46C. As shown in FIG. 46C, a partition can include a bead 4651 that is coupled to barcoded primers that can each participate in an assay of a different analyte. The bead 4651 is coupled (e.g., reversibly coupled) to a barcoded oligonucleotide 4652 that comprises a poly-T priming sequence 4654 for mRNA analysis and is also coupled (e.g., reversibly coupled) to barcoded oligonucleotide 4653 that comprises a random N-mer priming sequence 4655 for gDNA analysis. Moreover, bead 4651 is also coupled (e.g., reversibly coupled) to a barcoded oligonucleotide 4656 that can specifically bind an oligonucleotide coupled to a labelling agent (e.g., an antibody), via its targeted priming sequence 4657. Bead 4651 is also coupled to a barcoded oligonucleotide 4658 that can specifically bind a nucleic acid molecule that can function in a CRISPR assay (e.g., CRISPR/Cas9), via its targeted priming sequence 4659. In this example, each of the various barcoded primers comprises the same barcode sequence. Each barcoded oligonucleotide can be released from the bead 4651 within the partition and subject to conditions suitable for analysis of its respective analyte. In some cases, one or more of the analytes is associated with or derived from a cell, which itself, may be in the partition. In some cases, the partition comprises only one cell. Barcoded constructs A, B, C and D can be generated as described elsewhere herein and analyzed. Barcoded construct A may comprise a sequence corresponding to the barcode sequence from the bead and a DNA sequence corresponding to a target mRNA. Barcoded construct B may comprise a sequence corresponding to the barcode sequence from the bead and a sequence corresponding to genomic DNA. Barcoded construct C comprises a sequence corresponding to the barcode sequence from the bead and a sequence corresponding to barcode sequence associated with an antibody labelling agent. Barcoded construct D comprises a sequence corresponding to the barcode sequence from the bead and a sequence corresponding to a CRISPR nucleic acid (which, in some embodiments, also comprises a barcode sequence). Each construct can be analyzed via sequencing and the results associated with the given cell from which the various analytes originated. While only four different barcoded constructs are shown in FIG. 46C, barcoded (or even non-barcoded) constructs can be tailored for analyses of any given analyte associated with a nucleic acid and capable of binding with such a construct.

For example, a partition can include a bead (e.g., a gel bead) that is coupled (e.g., reversibly coupled) to barcoded oligonucleotides that can participate in an assay of at least two different analytes. See FIG. 46A for an exemplary bead coupled to a barcoded oligonucleotide 4602 that comprises a poly-T priming sequence 4604 for mRNA analysis and a barcoded oligonucleotide 4603 that comprises a random N-mer priming sequence 4605 for gDNA analysis. See FIG. 46B for an exemplary bead coupled to a barcoded oligonucleotide 4612 that comprise a poly-T priming sequence 4614 for mRNA analysis and a barcoded oligonucleotide 4613 that comprises a capture sequence 4615 that can specifically bind an oligonucleotide coupled to a labelling agent (e.g., an antibody), via its targeted priming sequence 4624.

Additional exemplary assays for measuring at least two different analytes include a bead coupled to a barcoded oligonucleotide (e.g., 4602) that comprises a poly-T priming sequence (e.g., 4604) for mRNA analysis and a barcoded oligonucleotide (e.g., 4658) that comprises a capture sequence 4659 that can specifically bind a nucleic acid molecule that can function in a CRISPR assay (e.g., CRISPR/Cas9), via its targeted priming sequence (see, e.g., FIGS. 61A-D). Further exemplary assays for measuring at least two different analytes include a bead coupled to a barcoded oligonucleotide (e.g., 4613) that comprises a capture sequence (e.g., 4615) that can specifically bind an oligonucleotide coupled to a labelling agent (e.g., an antibody), via its targeted priming sequence (e.g., 4624) and a barcoded oligonucleotide (e.g., 4603) that comprises a random N-mer priming sequence (e.g., 4605) for gDNA analysis. Additional exemplary assays for measuring at least two different analytes include a bead coupled a barcoded oligonucleotide (e.g., 4613) that comprises a capture sequence (e.g., 4615) that can specifically bind an oligonucleotide coupled to a labelling agent (e.g., an antibody), via its targeted priming sequence (e.g., 4624) and a barcoded oligonucleotide (e.g., 4658) that comprises a capture sequence (e.g., 4659) that can specifically bind a nucleic acid molecule that can function in a CRISPR assay (e.g., CRISPR/Cas9), via its targeted priming sequence (see, e.g., FIGS. 61A-D). Further exemplary assays for measuring at least two different analytes include a bead coupled a barcoded oligonucleotide (e.g., 4603) that comprises a random N-mer priming sequence (e.g., 4605) for gDNA analysis and a barcoded oligonucleotide (e.g., 4658) that comprises a capture sequence (e.g., 4659) that can specifically bind a nucleic acid molecule that can function in a CRISPR assay (e.g., CRISPR/Cas9), via its targeted priming sequence (see, e.g., FIGS. 61A-D).

Figure 46D:
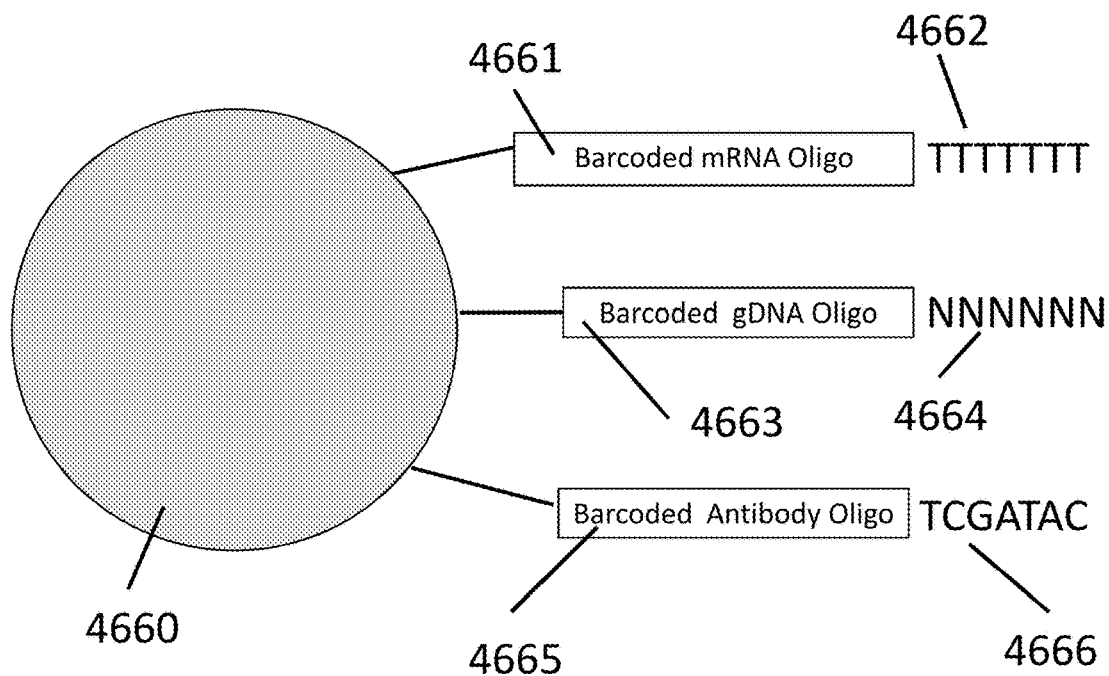
Figure 46E:
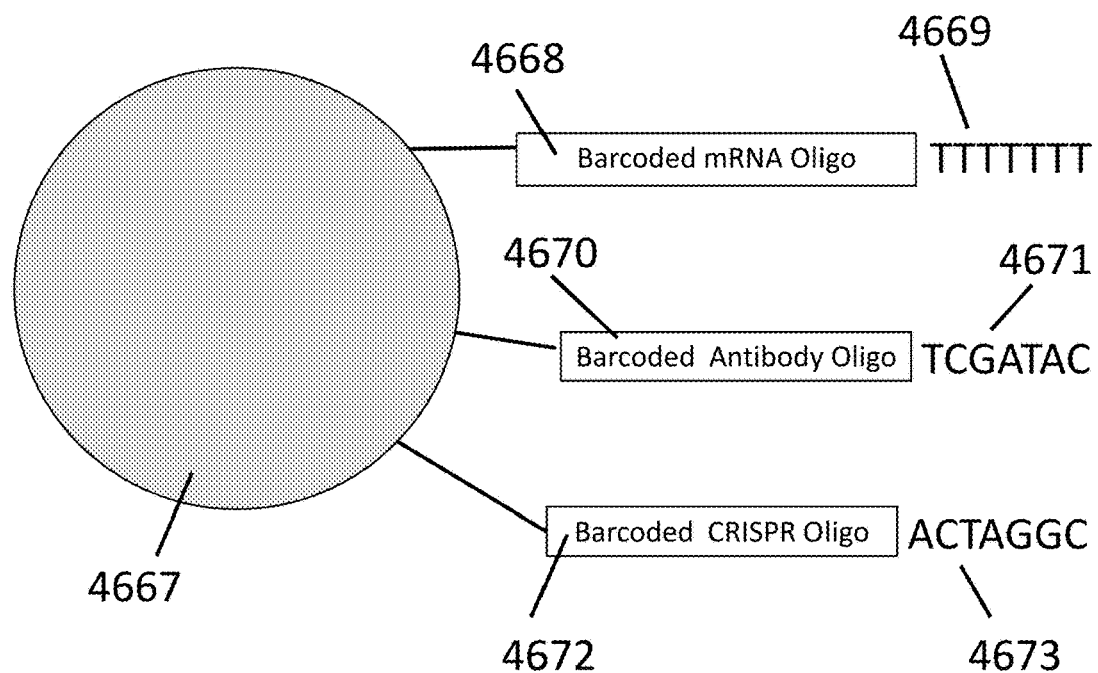

For example, a partition can include a bead (e.g., a gel bead) that is coupled (e.g., reversibly coupled) to barcoded oligonucleotides that can participate in an assay of at least three different analytes. See FIG. 46D for an exemplary bead 4660 coupled to a barcoded oligonucleotide 4661 that comprises a poly-T priming sequence 4662 for mRNA analysis; a barcoded oligonucleotide 4663 that comprises a random N-mer priming sequence 4664 for gDNA analysis; and a barcoded oligonucleotide 4665 that comprises a capture sequence 4666 that can specifically bind an oligonucleotide coupled to a labelling agent (e.g., an antibody), via its targeted priming sequence (e.g., 4624). See FIG. 46E for an exemplary bead 4667 coupled to a barcoded oligonucleotide 4661 that comprises a poly-T priming sequence 4662 for mRNA analysis; a barcoded oligonucleotide 4665 that comprises a capture sequence 4666 that can specifically bind an oligonucleotide coupled to a labelling agent (e.g., an antibody), via its targeted priming sequence (e.g., 4624); and a barcoded oligonucleotide 4672 that comprises a capture sequence 4673 that can specifically bind a nucleic acid molecule that can function in a CRISPR assay (e.g., CRISPR/Cas9), via its targeted priming sequence (see, e.g., FIGS. 61A-D).

Additional exemplary assays for measuring at least three different analytes include a bead coupled to a barcoded oligonucleotide (e.g., 4661) that comprises a poly-T priming sequence (e.g., 4662) for mRNA analysis; a barcoded oligonucleotide (e.g., 4663) that comprises a random N-mer priming sequence (e.g., 4664) for gDNA analysis; and a barcoded oligonucleotide (e.g., 4672) that comprises a capture sequence (e.g., 4673) that can specifically bind a nucleic acid molecule that can function in a CRISPR assay (e.g., CRISPR/Cas9), via its targeted priming sequence (see, e.g., FIGS. 61A-D).

Figure 17:
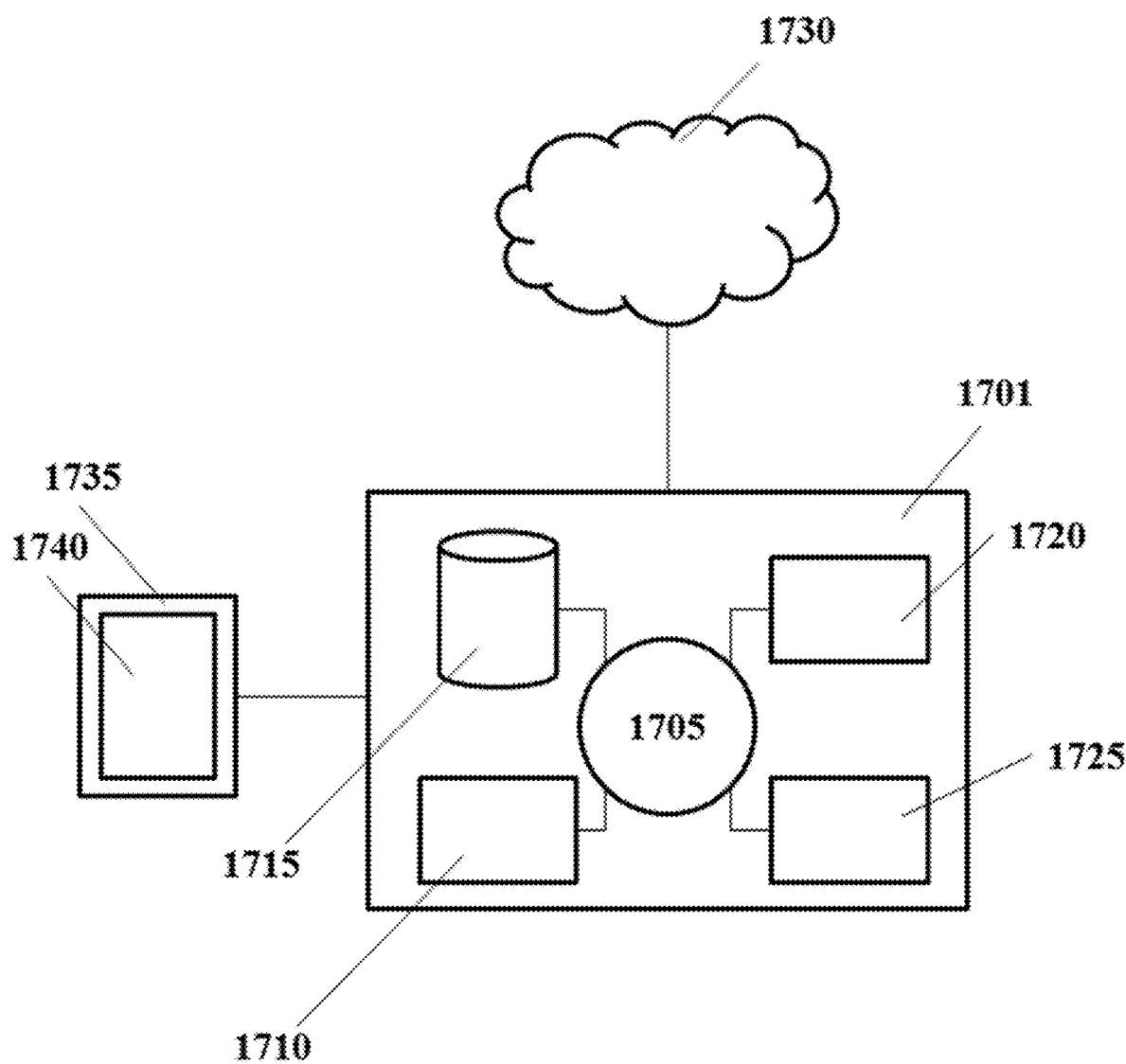
FIG. 17 shows an example computer control system that is programmed or otherwise configured to implement methods provided herein.

The present disclosure provides computer control systems that are programmed to implement methods of the disclosure, i.e., protocols of the disclosure. For example, the present disclosure provides computer control systems programmed to implement method 2000 of the present disclosure. FIG. 17 shows a computer system 1701 that is programmed or otherwise configured to implement methods of the disclosure including nucleic acid sequencing methods, cell surface feature identification methods, interpretation of nucleic acid sequencing data and analysis of cellular nucleic acids, such as RNA (e.g., mRNA), interpretation of nucleic acid sequencing data and analysis of nucleic acids derived from the characterization of cell surface features, and characterization of cells from sequencing data. The computer system 1701 can be an electronic device of a user or a computer system that is remotely located with respect to the electronic device. The electronic device can be a mobile electronic device.

The computer system 1701 includes a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise conFIG. the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are external to the computer system 1701, such as located on a remote server that is in communication with the computer system 1701 through an intranet or the Internet.

The computer system 1701 can communicate with one or more remote computer systems through the network 1730. For instance, the computer system 1701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display screen 1735 that comprises a user interface (UI) 1740 for providing, for example, results of nucleic acid sequencing, analysis of nucleic acid sequencing data, characterization of nucleic acid sequencing samples, cell characterizations, etc. Examples of UI's include, without limitation, a graphical user interface (GUI) and web-based user interface. The system 1701 may comprise an electronic display screen 1735 comprising a user interface 1740 that displays a graphical element that is accessible by a user to execute a protocol per the methods described herein, (e.g. to characterize cells), and a computer processor coupled to the electronic display screen and programmed to execute the protocol upon selection of the graphical element by the user.

Methods and systems of the present disclosure can be implemented by way of one or more algorithms. An algorithm can be implemented by way of software upon execution by the central processing unit 1705. The algorithm can, for example, initiate nucleic acid sequencing, process nucleic acid sequencing data, interpret nucleic acid sequencing results, characterize nucleic acid samples, characterize cells, etc.

Barcoded oligonucleotides as described elsewhere herein may be generated in any suitable manner and comprise one or more sequences in addition to a barcode sequence. As noted elsewhere herein, one such sequence can be a priming sequence that can aid in barcoding analytes. Moreover, a barcoded oligonucleotide may also comprise one or more additional functional sequences that may, for example, aid in rendering the barcoded oligonucleotide compatible with a given sequencing platform (e.g., functional sequences may be flow cell adaptor immobilization sequences (such as, for example, P7 and P5 from an Illumina platform), sequencing primer binding site sequences (such as, for example, R1 from an Illumina platform), and other priming sites for downstream amplification, such as, for example, a Nextera functional sequence or a TruSeq functional sequence.

Figure 50A:
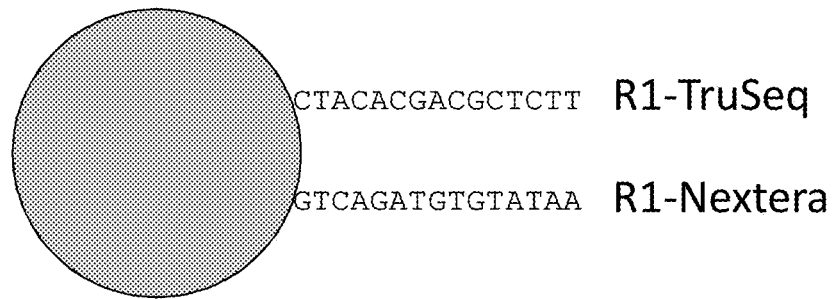
FIG. 50A schematically depicts an example bead comprising oligonucleotides having two different functional sequences (SEQ ID NOS 24 and 32, respectively, in order of appearance)

In some cases, barcoded oligonucleotides are coupled to beads and beads may comprise oligonucleotides having a first type functional sequence at a given position and oligonucleotides having a second, different type of functional sequence at the given position. An example is depicted in FIG. 50A. As shown in FIG. 50A, a bead may be coupled to oligonucleotides comprising a TruSeq functional sequence and also to oligonucleotides comprising a Nextera functional sequence. Onto each of these sequences additional sequences can be added to generate a full oligonucleotide also comprising a nucleic acid barcode sequence, an optional UMI sequence and a priming sequence. Attachment of these sequences can be via ligation (including via splint ligation as is described in U.S. Patent Publication No. 20140378345, which is herein incorporated by reference in its entirety) or any other suitable route. Sequences of example barcoded oligonucleotides comprising a TruSeq functional group are shown in FIG. 50B and sequences of example barcoded oligonucleotides comprising a Nextera functional group are shown in FIG. 50C. Each of the example barcoded oligonucleotides shown in FIG. 50B and FIG. 50B (top sequence for each construct) are shown hybridized with splint sequences (bottom sequence for each construct) that can be helpful in constructing complete barcoded oligonucleotides.

In some aspects, methods provided herein may also be used to prepare polynucleotide contained within cells in a manner that enables cell-specific information to be obtained. The methods enable detection of genetic variations (e.g., SNPs, mutations, indels, copy number variations, transversions, translocations, inversions, etc.) from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method comprises partitioning a cellular sample (or crude cell extract) such that at most one cell (or extract of one cell) is present per partition, lysing the cells, fragmenting the polynucleotides contained within the cells by any of the methods described herein, attaching the fragmented polynucleotides to barcodes, pooling, and sequencing.

The barcodes and other reagents may be contained within a microcapsule. These microcapsules may be loaded into a partition (e.g., a microwell, a droplet) before, after, or concurrently with the loading of the cell, such that each cell is contacted with a different microcapsule. This technique may be used to attach a unique barcode to polynucleotides obtained from each cell. The resulting tagged polynucleotides may then be pooled and sequenced, and the barcodes may be used to trace the origin of the polynucleotides. For example, polynucleotides with identical barcodes may be determined to originate from the same cell, while polynucleotides with different barcodes may be determined to originate from different cells.

The methods described herein may be used to detect the distribution of oncogenic mutations across a population of cancerous tumor cells. For example, some tumor cells may have a mutation, or amplification, of an oncogene (e.g., HER2, BRAF, EGFR, KRAS) in both alleles (homozygous), others may have a mutation in one allele (heterozygous), and still others may have no mutation (wild-type). The methods described herein may be used to detect these differences, and also to quantify the relative numbers of homozygous, heterozygous, and wild-type cells. Such information may be used, for example, to stage a particular cancer and/or to monitor the progression of the cancer and its treatment over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

EXAMPLES

Example I: Cellular RNA Analysis Using Emulsions

In an example, reverse transcription with template switching and cDNA amplification (via PCR) is performed in emulsion droplets with operations as shown in FIG. 9A. The reaction mixture that is partitioned for reverse transcription and cDNA amplification (via PCR) includes 1,000 cells or 10,000 cells or 10 ng of RNA, beads bearing barcoded oligonucleotides/0.2% Tx-100/5× Kapa buffer, 2× Kapa HS HiFi Ready Mix, 4 µM switch oligo, and Smartscribe. Where cells are present, the mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are purified with Dynabeads and 0.6×SPRI as in operation 956.

Figure 13A:
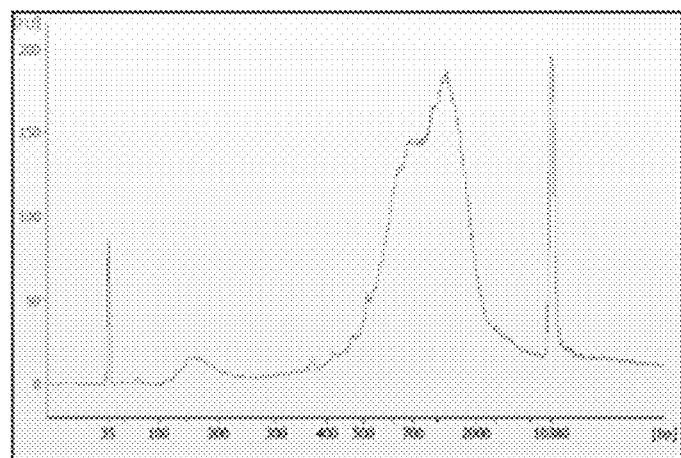
FIGS. 13A-13C provide illustrations of example yields from template switch reverse transcription and PCR in partitions.
Figure 13B:
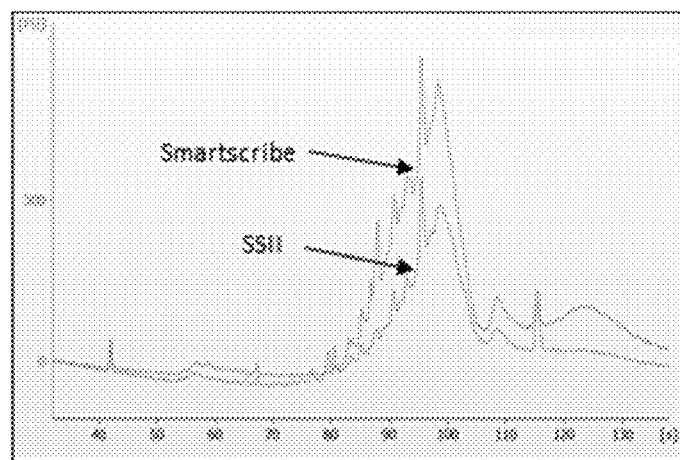
Figure 13C:
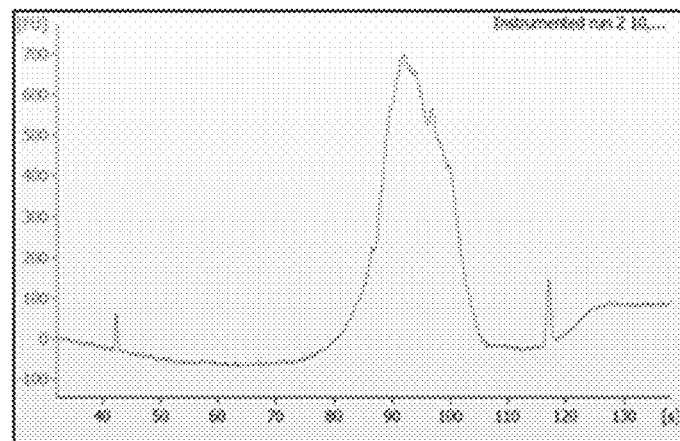

The yield from template switch reverse transcription and PCR in emulsions is shown for 1,000 cells in FIG. 13A and 10,000 cells in FIG. 13C and 10 ng of RNA in FIG. 13B (Smartscribe line). The cDNAs from RT and PCR performed in emulsions for 10 ng RNA is sheared and ligated to functional sequences, cleaned up with 0.8×SPRI, and is further amplified by PCR as in operation 958. The amplification product is cleaned up with 0.8×SPRI. The yield from this processing is shown in FIG. 13B (SSII line).

Example II: Cellular RNA Analysis Using Emulsions

Figure 14A:
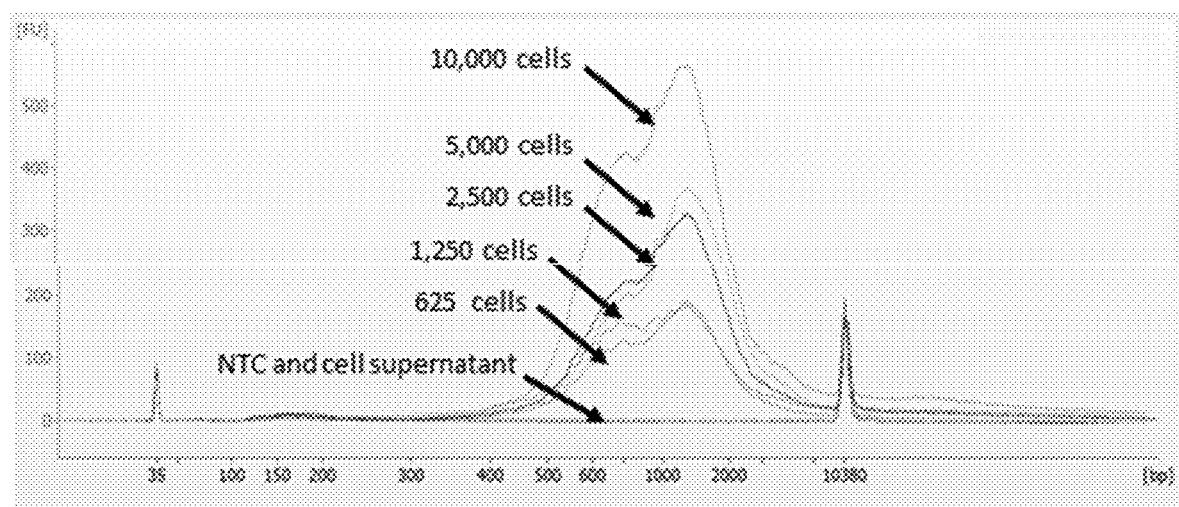
FIGS. 14A-14B provide illustrations of example yields from reverse transcription and cDNA amplification in partitions with various cell numbers.
Figure 14B:
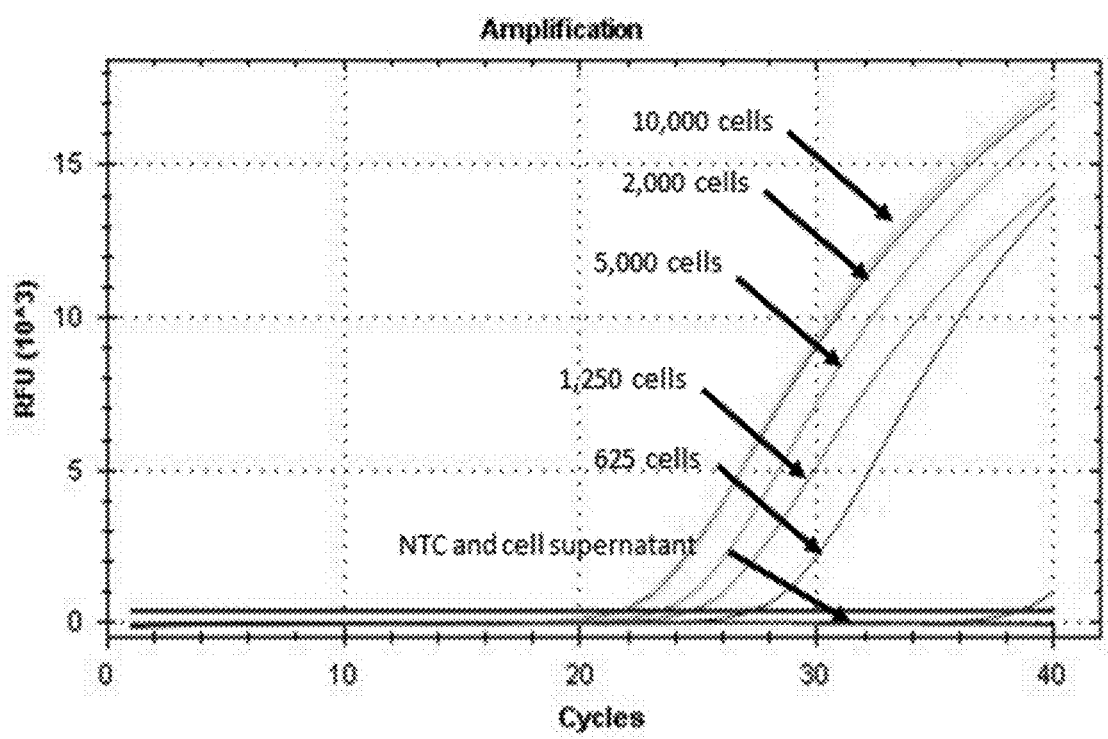

In another example, reverse transcription with template switching and cDNA amplification (via PCR) is performed in emulsion droplets with operations as shown in FIG. 9A. The reaction mixture that is partitioned for reverse transcription and cDNA amplification (via PCR) includes Jurkat cells, beads bearing barcoded oligonucleotides/0.2% TritonX-100/5× Kapa buffer, 2× Kapa HS HiFi Ready Mix, 4 µM switch oligo, and Smartscribe. The mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are cleaned-up with Dynabeads and 0.6×SPRI as in operation 956. The yield from reactions with various cell numbers (625 cells, 1,250 cells, 2,500 cells, 5,000 cells, and 10,000 cells) is shown in FIG. 14A. These yields are confirmed with GADPH qPCR assay results shown in FIG. 14B.

Example III: RNA Analysis Using Emulsions

Figure 15:
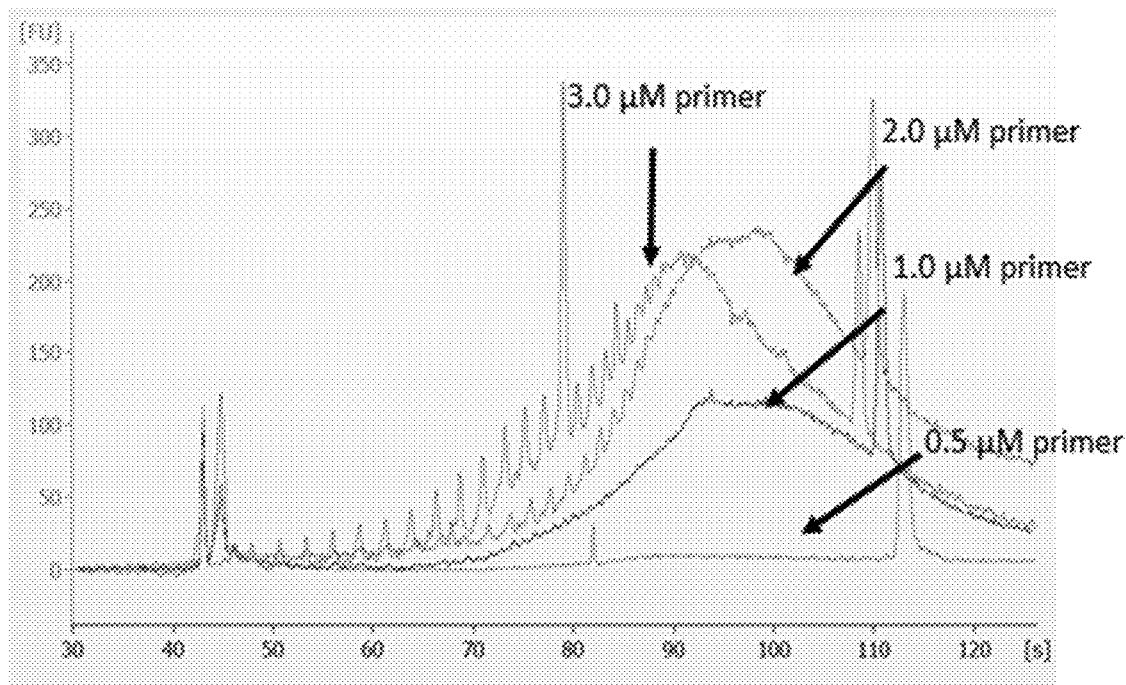
FIG. 15 provides an illustration of example yields from cDNA synthesis and real-time quantitative PCR at various input cell concentrations and also the effect of varying primer concentration on yield at a fixed cell input concentration.

In another example, reverse transcription is performed in emulsion droplets and cDNA amplification is performed in bulk in a manner similar to that as shown in FIG. 9C. The reaction mixture that is partitioned for reverse transcription includes beads bearing barcoded oligonucleotides, 10 ng Jurkat RNA (e.g., Jurkat mRNA), 5× First-Strand buffer, and Smartscribe. The barcoded oligonucleotides are released from the bead, and the poly-T segment of the barcoded oligonucleotide hybridizes to the poly-A tail of the RNA as in operation 961. The poly-T segment is extended in a reverse transcription reaction as in operation 963. The thermal cycling conditions for reverse transcription are one cycle at 42° C. for 2 hours and one cycle at 70° C. for 10 min. Following thermal cycling, the emulsion is broken and RNA and cDNAs are denatured as in operation 962. A second strand is then synthesized by primer extension with a primer having a biotin tag as in operation 964. The reaction conditions for this primer extension include cDNA as the first strand and biotinylated extension primer ranging in concentration from 0.5-3.0 µM. The thermal cycling conditions are one cycle at 98° C. for 3 min and one cycle of 98° C. for 15 sec, 60° C. for 20 sec, and 72° C. for 30 min. Following primer extension, the second strand is pulled down with Dynabeads MyOne Streptavidin C1 and T1, and cleaned-up with Agilent SureSelect XT buffers. The second strand is pre-amplified via PCR as in operation 965 with the following cycling conditions—one cycle at 98° C. for 3 min and one cycle of 98° C. for 15 sec, 60° C. for 20 sec, and 72° C. for 30 min. The yield for various concentrations of biotinylated primer (0.5 µM, 1.0 µM, 2.0 µM, and 3.0 µM) is shown in FIG. 15.

Example IV: RNA Analysis Using Emulsions

Figure 16:
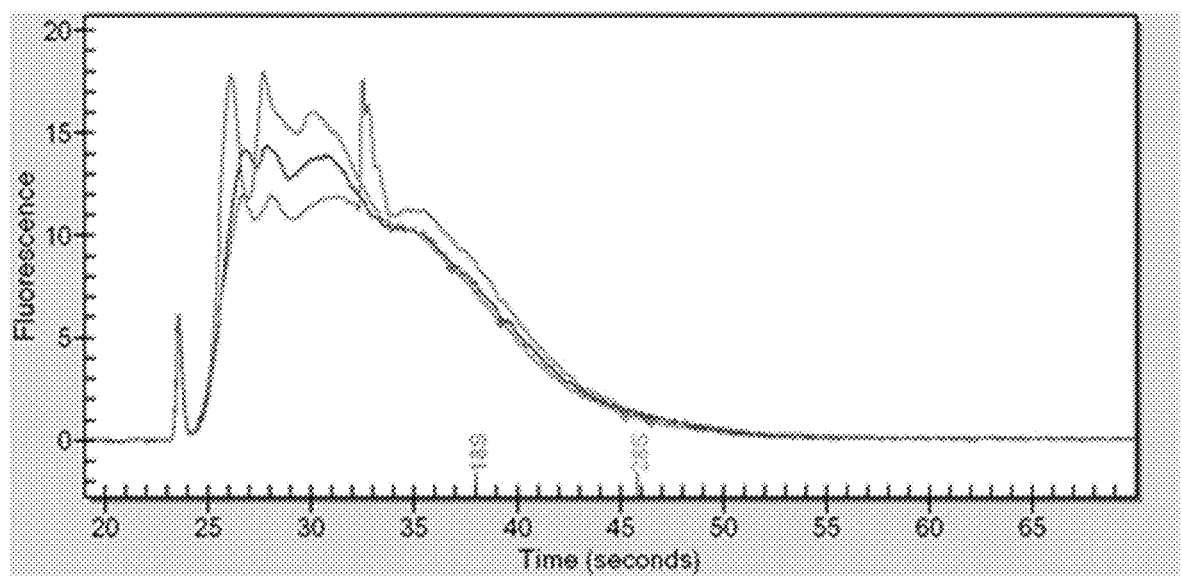
FIG. 16 provides an illustration of example yields from in vitro transcription.

In another example, in vitro transcription by T7 polymerase is used to produce RNA transcripts as shown in FIG. 10. The mixture that is partitioned for reverse transcription includes beads bearing barcoded oligonucleotides which also include a T7 RNA polymerase promoter sequence, 10 ng human RNA (e.g., human mRNA), 5× First-Strand buffer, and Smartscribe. The mixture is partitioned such that a majority or all of the droplets comprise a single bead. The barcoded oligonucleotides are released from the bead, and the poly-T segment of the barcoded oligonucleotide hybridizes to the poly-A tail of the RNA as in operation 1050. The poly-T segment is extended in a reverse transcription reaction as in operation 1052. The thermal cycling conditions are one cycle at 42° C. for 2 hours and one cycle at 70° C. for 10 min. Following thermal cycling, the emulsion is broken and the remaining operations are performed in bulk. A second strand is then synthesized by primer extension as in operation 1054. The reaction conditions for this primer extension include cDNA as template and extension primer. The thermal cycling conditions are one cycle at 98° C. for 3 min and one cycle of 98° C. for 15 sec, 60° C. for 20 sec, and 72° C. for 30 min. Following this primer extension, the second strand is purified with 0.6×SPRI. As in operation 1056, in vitro transcription is then performed to produce RNA transcripts. In vitro transcription is performed overnight, and the transcripts are purified with 0.6×SPRI. The RNA yields from in vitro transcription are shown in FIG. 16.

Example V: Delivering Lysis Agent to a Partition Using Gel Beads

A lysis agent is introduced into the partition (GEM) via the gel bead suspension (GBS). The lysis agent is a surfactant that causes wetting failures (uncontrolled droplet formation) to occur when its concentration in the GBS exceeds a threshold.

Figure 36A:
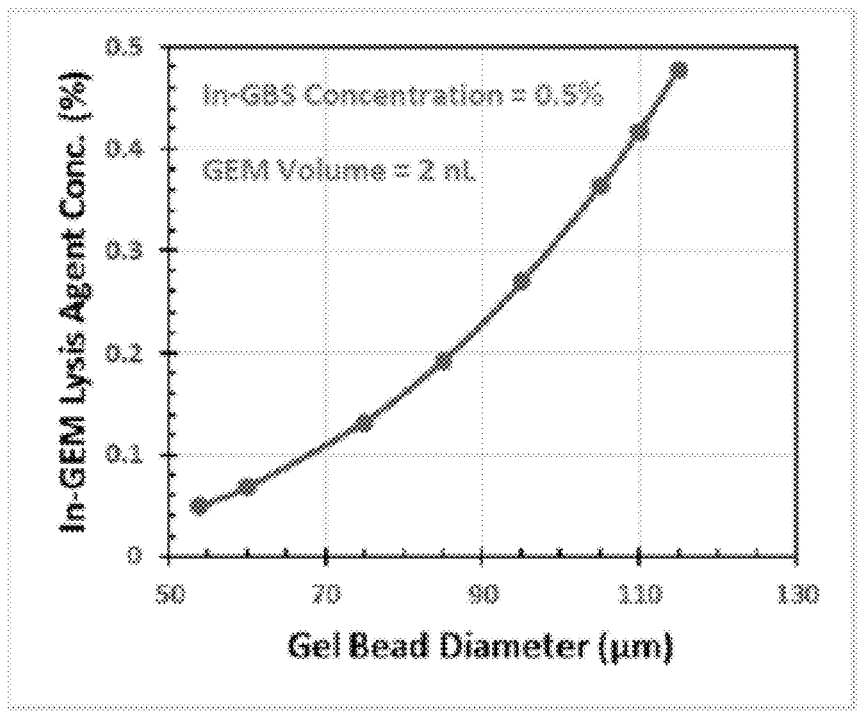
FIG. 36A shows a relationship between a diameter of a gel bead and a regent inside the gel bead.

A larger gel bead can be used to increase the in-partition concentration of the lysis agent, without increasing the in-GBS concentration (to avoid wetting failures) and without decreasing the total volume of the partition (which may not be reduced without decreasing the sensitivity of the assay) (FIG. 36A). Alternatively, a larger gel bead can be used to increase the volume of the partition (which increases the sensitivity of the assay) and preserve the existing in-partition lysis agent concentration without increasing the in-GBS concentration.

Figure 36B:
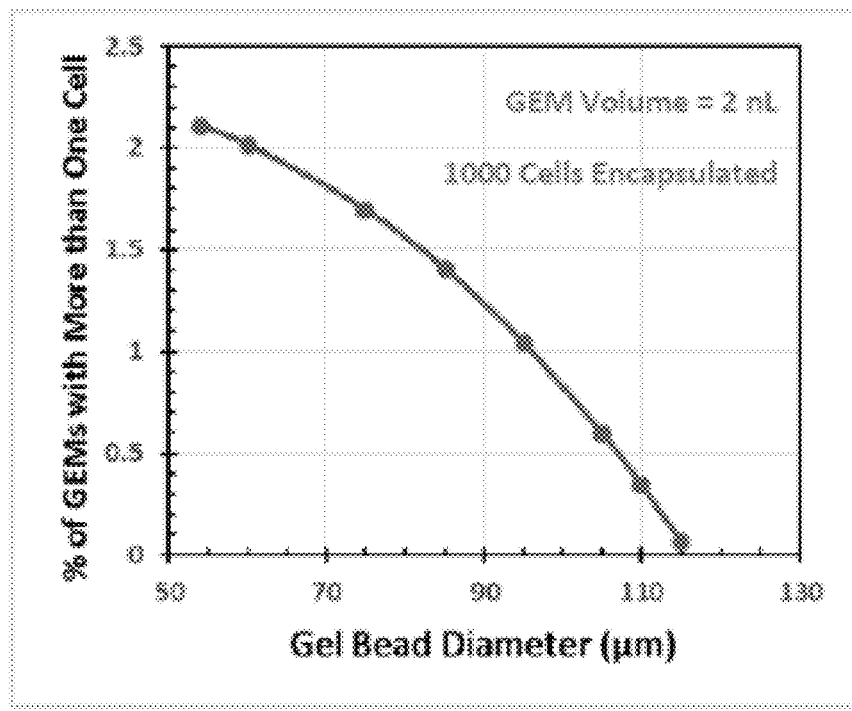
FIG. 36B shows the relationship between the diameter of a gel bead and the number of droplets with more than one cell.

The size of the gel bead can also affect how cells are partitioned. By replacing a portion of the sample volume (Z2) with the gel bead suspension volume (Z1), larger gel beads decrease the in-partition concentration of cells, which, according to Poisson statistics, results in a lower probability of the unfavorable encapsulation of more than one cell per partition (FIG. 36B).

Example VI: Producing CD3 Protein Conjugated with Short ssDNA Molecules

The CD3 protein and the ssDNA molecule are first activated for click chemistry reaction. The CD3 protein is activated with 5-(methacrylamido)tetrazole (MTet) and the ssDNA molecule is activated with trans-cyclooctene (TCO). The ssDNA molecule comprises a biotin group. The activated CD3 protein and ssDNA molecule are mixed for conjugation by click chemistry reactions. The ssDNA molecule concentration is 5 times excess over the CD3 protein concentration to avoid multiple barcode copies conjugating on the same protein molecule. In some cases, the ssDNA concentration is 10 times excess over the CD3 protein to maximize barcode attachment. A biotin group may also be incorporated in the activated CD3-ssDNA conjugate for purification. The CD3 protein and ssDNA conjugate is purified and tested as shown in FIG. 37.

Example VII: Labelling Jurkat Cells with Human CD3 and Mouse CD3

Figure 38:
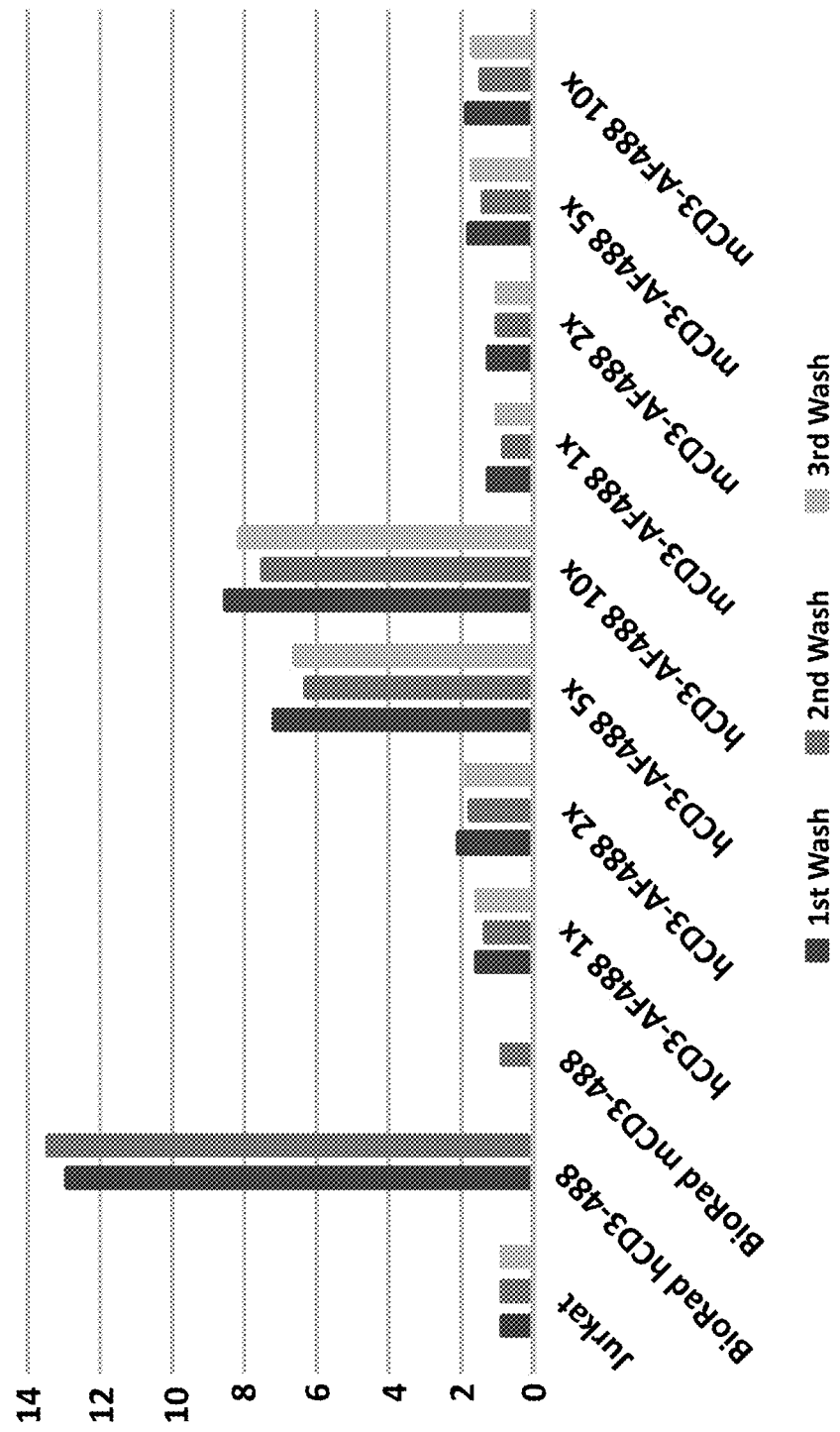
FIG. 38 shows the fluorescence signals from the cells bound by labeled antibodies.

The impact of DNA conjugation on the binding of CD3 on Jurkat cells is tested. Human CD3 (hCD3, MCA463) and mouse CD3 (mCD3, MCA500) are incubated with AF488-NHS, where the concentration of AF499-NHS is 1×, 2×, 5×, and 10× excess over the CD3 protein, in order to generate labeled CD3, where the AF999 is coupled to an amine of the CD3. The conjugated hCD3 and mCD3 are incubated with Jurkat cells. Unbound CD3 proteins are washed away. The fluorescence signals from the labeled cells are determined (FIG. 38). The fluorescent signals are normalized by comparing to commercial Jurkat cells control. The data show that Jurkat cells specifically bind to hCD3 over mCD3, indicating that the conjugation of dye/DNA does not affect the binding of CD3 proteins with Jurkat cells. Blocking reagents (e.g., FBS, 5% BSA) may be added to improve specificity.

Example VIII: Conjugating a DNA Barcode to IgG of an Antibody

Figure 39A:
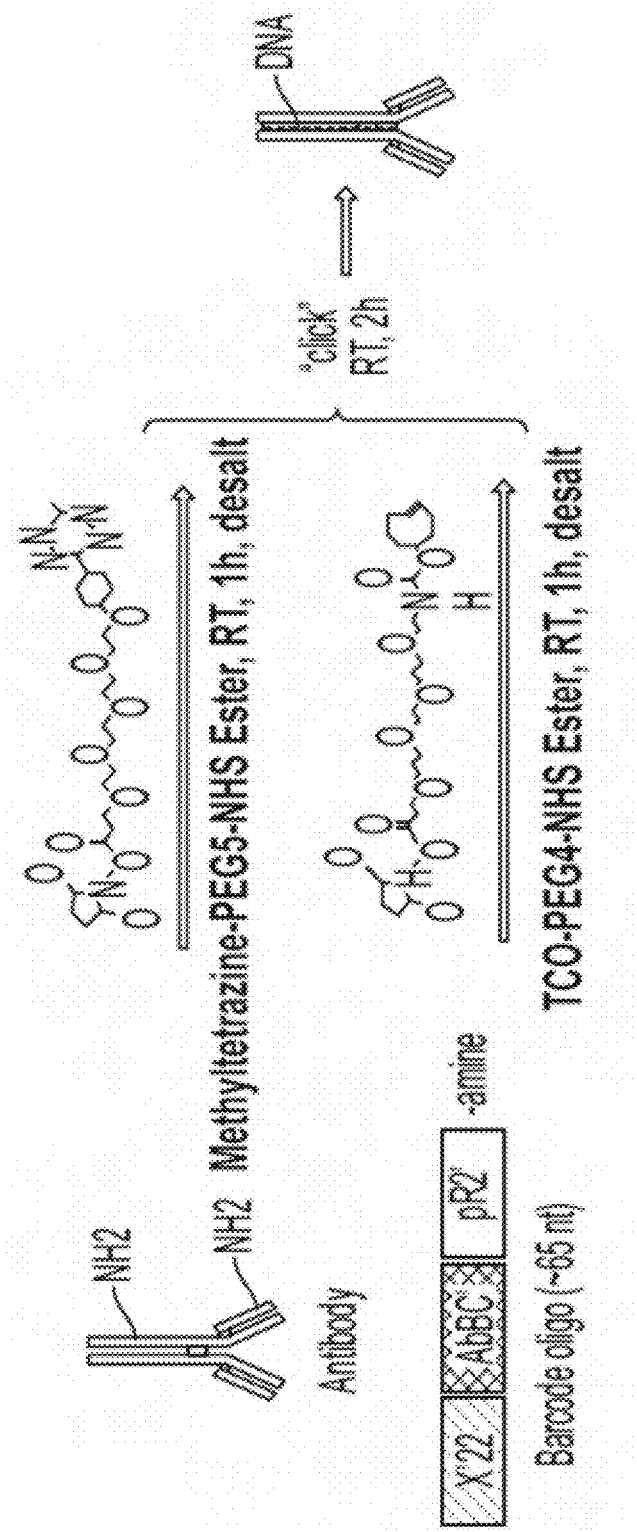
FIG. 39A shows an approach for conjugating an oligonucleotide with an antibody.
Figure 39B:
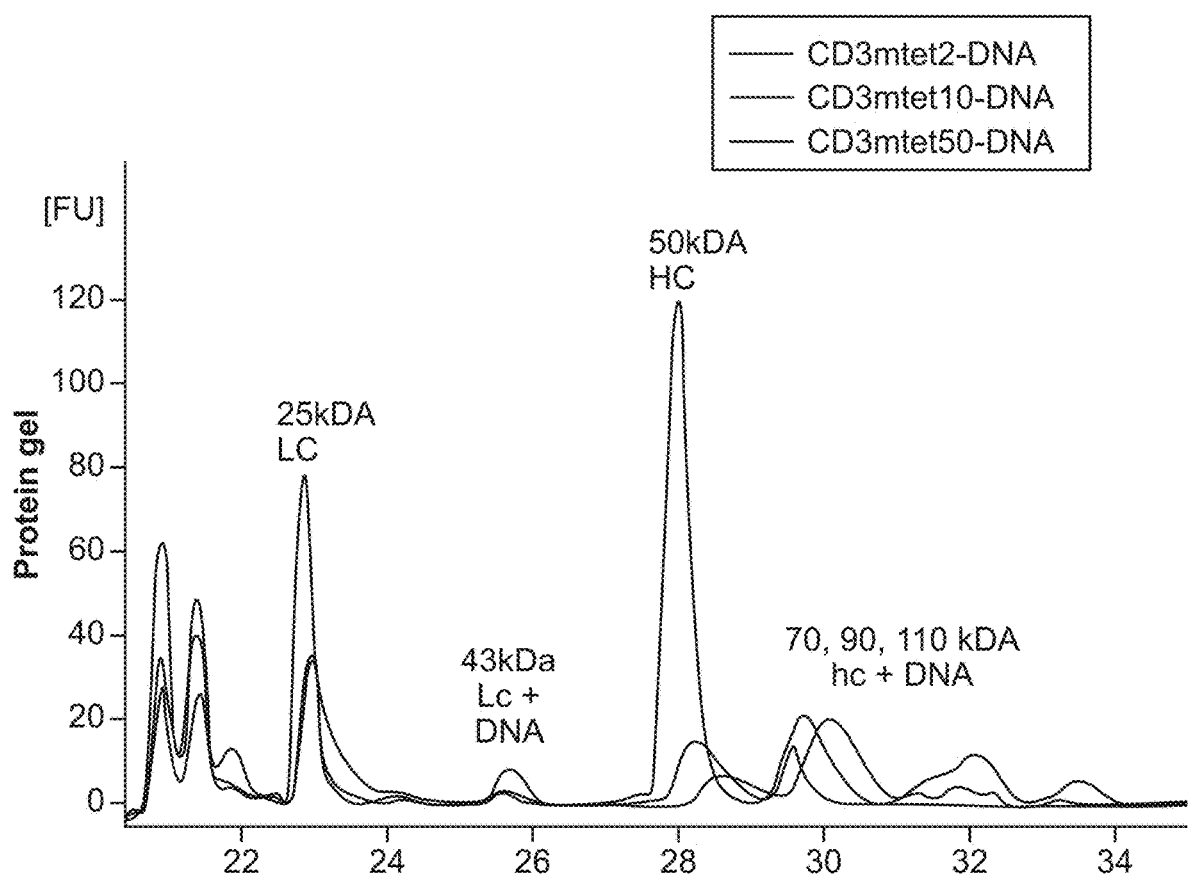
FIG. 39B shows analysis results of barcoded antibodies.

An antibody is incubated with Methyltetrazine-PEG5-NHS Ester at room temperature for 1 hour and desalted. A DNA barcode of about 65 nt long is incubated with TCO-PEG4-NHS Ester at room temperature for an hour and desalted. The resulting antibody and DNA barcode are incubated at room temperature for 2 hours for conjugation. FIG. 39A shows the conjugation strategy. The conjugated antibody-DNA complex is subject to protein gel analysis. As shown in FIG. 39B, protein gel shifts of about 20 kDa indicates successful conjugation of the DNA barcode to IgG of the antibody. Multiple viable chemistries for primary antibody barcoding are validated (e.g., mTet, dibenzocyclooctyne (DBCO), SiteClick). The conjugated antibody-DNA complex is incubated with cells for labelling.

Figure 40:
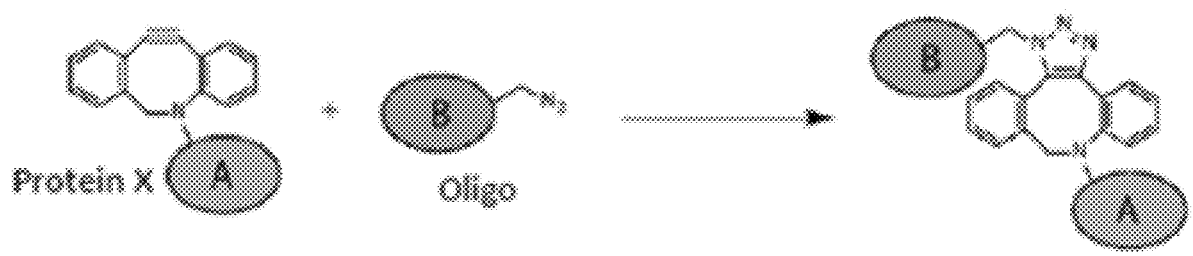
FIG. 40 shows a conjugate of a functionalized antibody-binding protein and a functionalized oligonucleotide.
Figure 41:
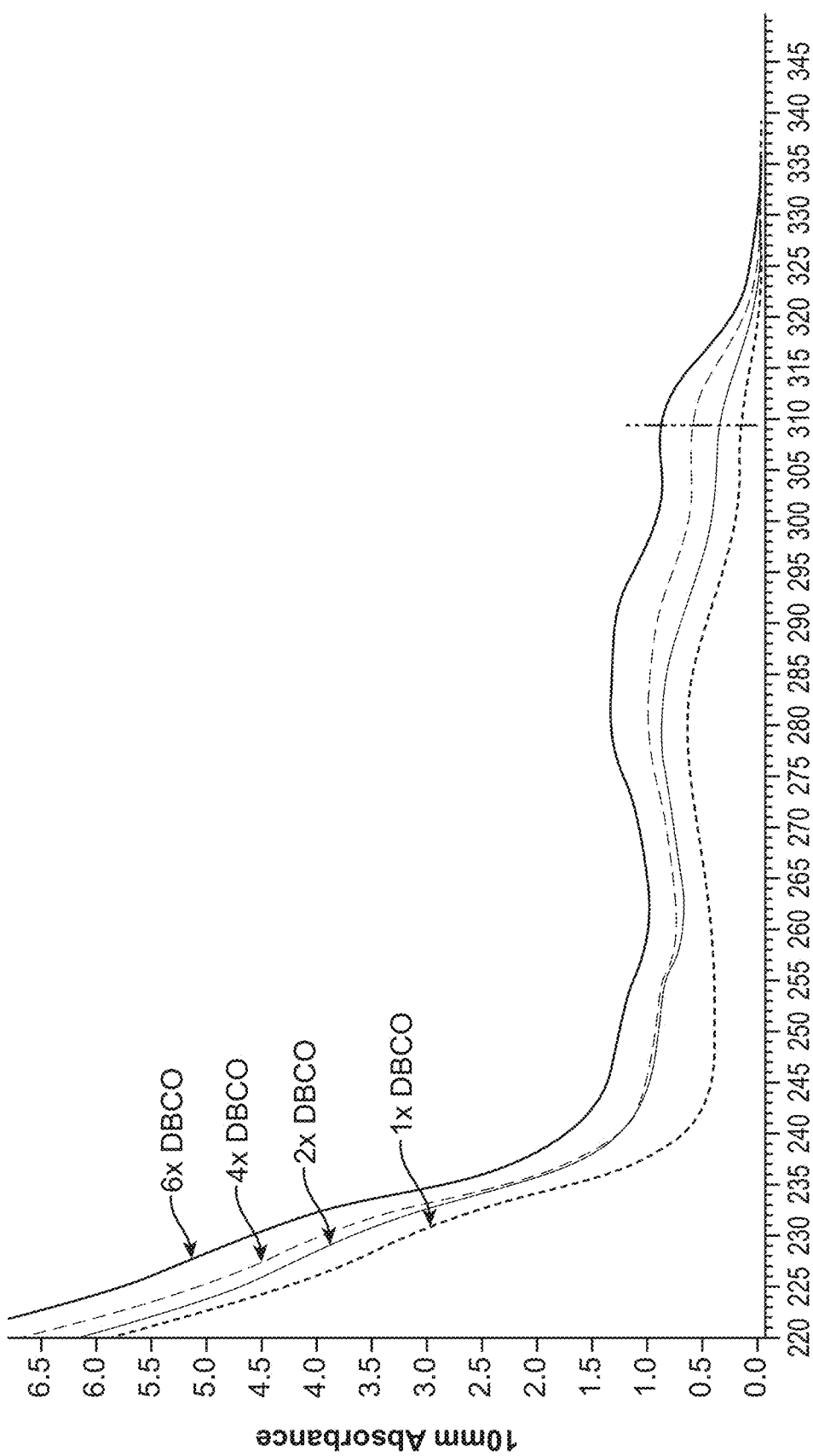
FIG. 41 shows a relationship between a degree of dibenzocyclooctyne (DBCO) incorporation and input dibenzocyclooctyne-N-hydroxysuccinimidyl ester (DBCO-NHS) concentrations.

Example IX: Conjugating Oligonucleotides to Antibodies Using Antibody-Binding Proteins Antibody-binding proteins Protein X (Protein A or Protein G) are functionalized with dibenzocyclooctyne-N-hydroxysuccinimidyl ester (DBCO-NHS). Fluorescein amidite (FAM)-labeled oligoX22-azide (3 eq) is used as the oligonucleotides to be conjugated with the antibody-binding proteins. The functionalized antibody-binding proteins and the oligonucleotides are conjugated as shown in FIG. 40. The degree of conjugation between the dibenzocyclooctyne (DBCO) and Protein G may be controlled based on Gong et al., Simple Method To Prepare Oligonucleotide-Conjugated Antibodies and Its Application in Multiplex Protein Detection in Single Cells. Bioconjugate Chem., 2016, which is incorporated herein by reference in its entirety. Degree of DBCO incorporation may be controlled by adjusting input DBCO-NHS concentration as shown in FIG. 41.

Figure 42:
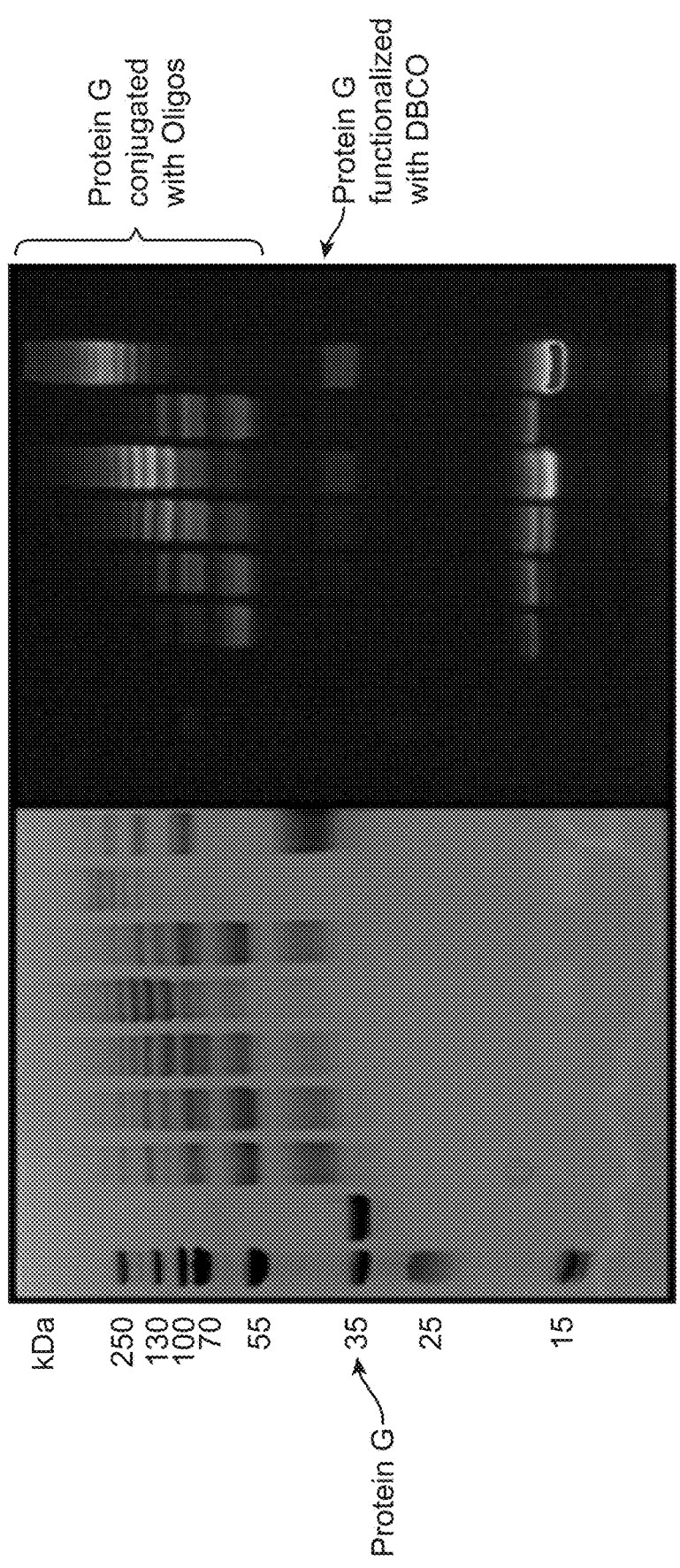
FIG. 42 shows an example relationship between the degree of conjugation and oligonucleotide equivalence.

Moreover, the degree of conjugation may be controlled through oligonucleotide equivalence as shown in FIG. 42. A crude protein-oligonucleotide conjugation reaction was analyzed by gel electrophoresis (SDS-PAGE) to determine conjugation efficiency and the number of oligonucleotides conjugated. Increase of oligonucleotide equivalence with respect to the protein leads to a higher degree of conjugation as shown in FIG. 42. Because the oligonucleotide contains a fluorescent molecule, the unused oligonucleotide can easily be visualized with in-gel fluorescence imaging (black panel in FIG. 42).

Figure 43:
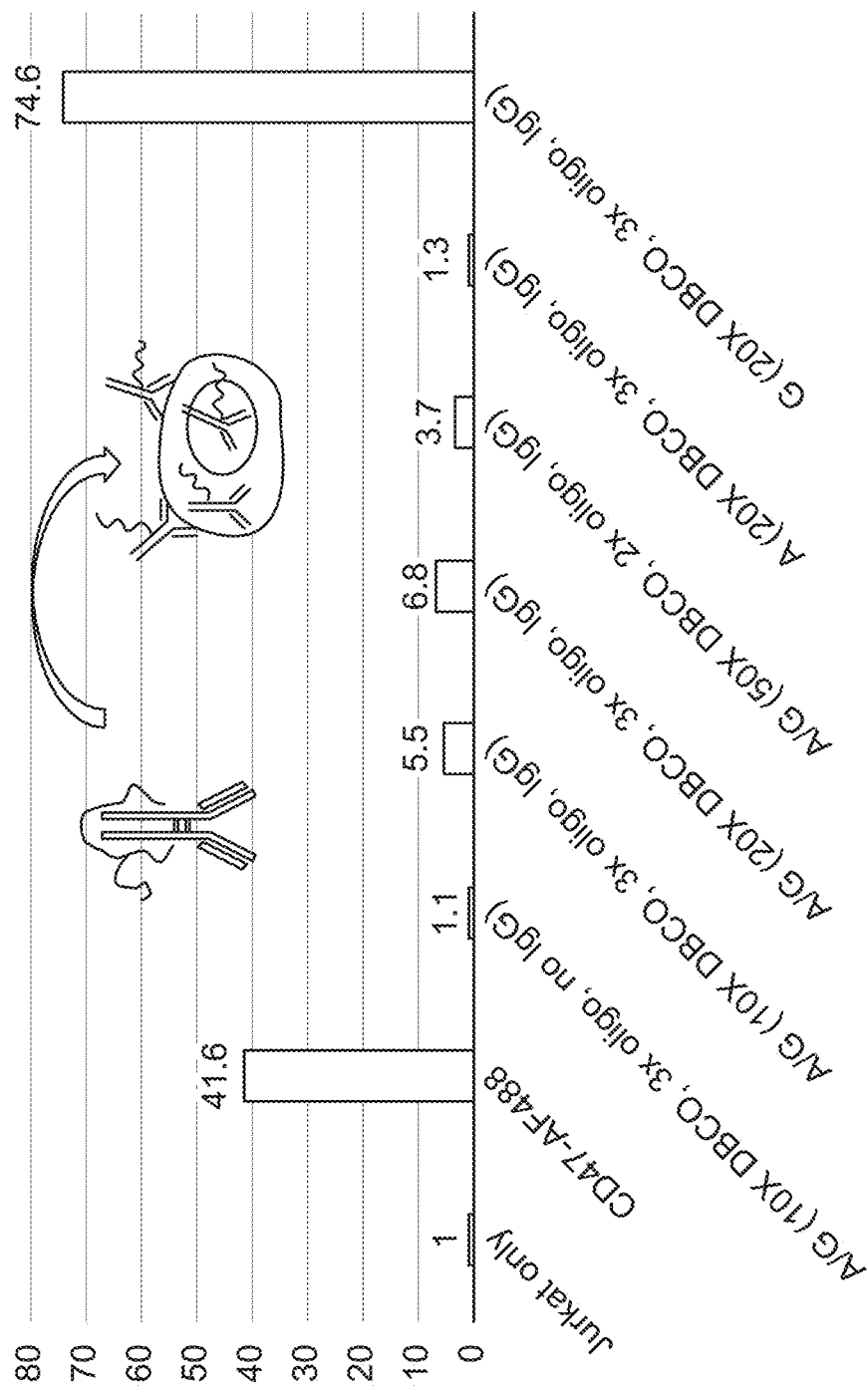
FIG. 43 shows fluorescence signals of labeled cells measured by flow cytometry.

The oligonucleotide-Protein X conjugates are incubated with CD47 antibodies to form labeled antibodies. The labeled antibodies are incubated with Jurkat cells and washed twice to make labeled cells. The labelling of cells is measured by fluorescence signals using flow cytometry (FIG. 43).

Figure 44:
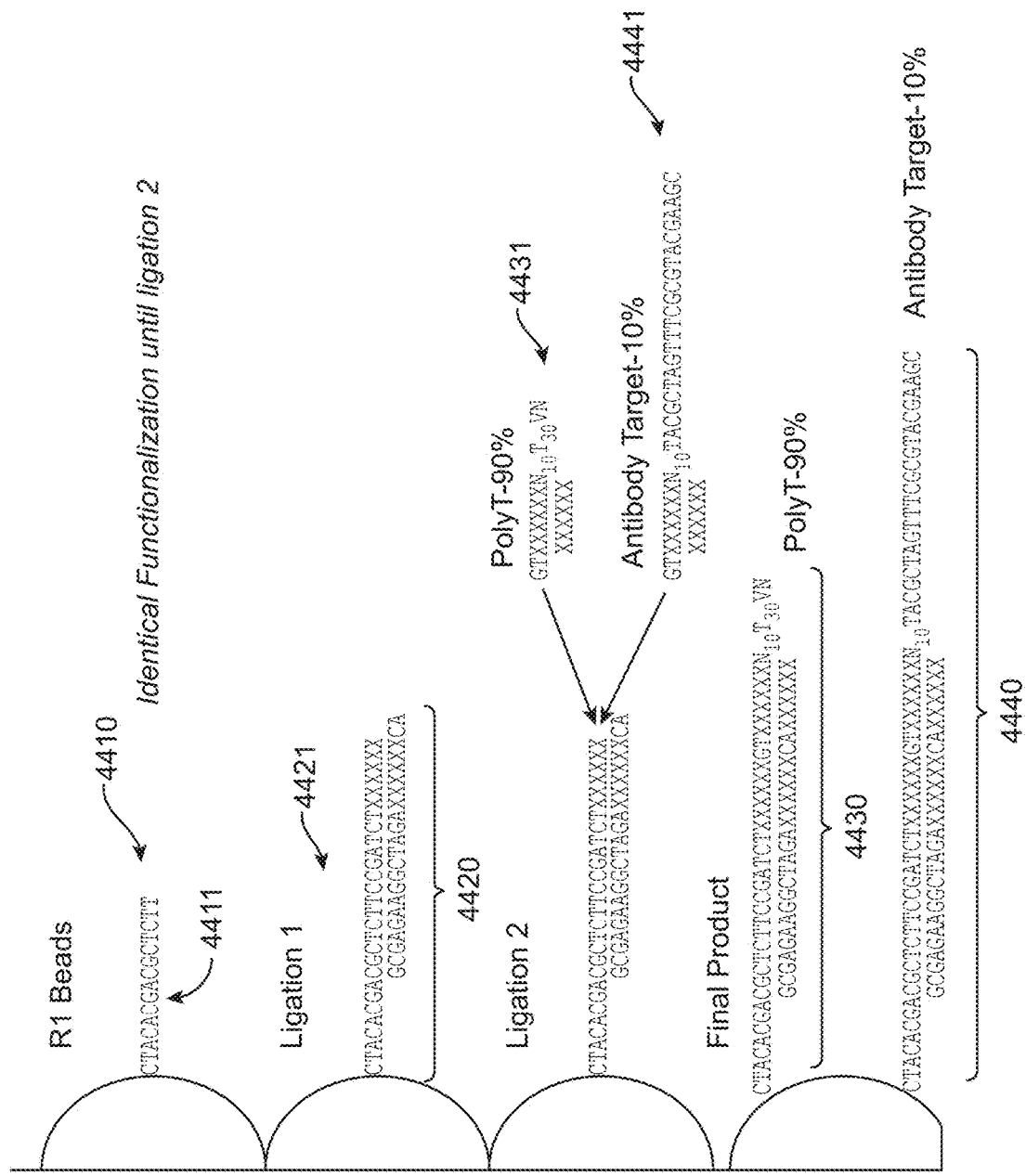
FIG. 44 shows a method for producing a bead coupled with oligonucleotides with different primer sequences (SEQ ID NOS 24-26, 25-28, 15, 45, 29, and 45, respectively, in order of appearance)
Figures 45A, 45B:
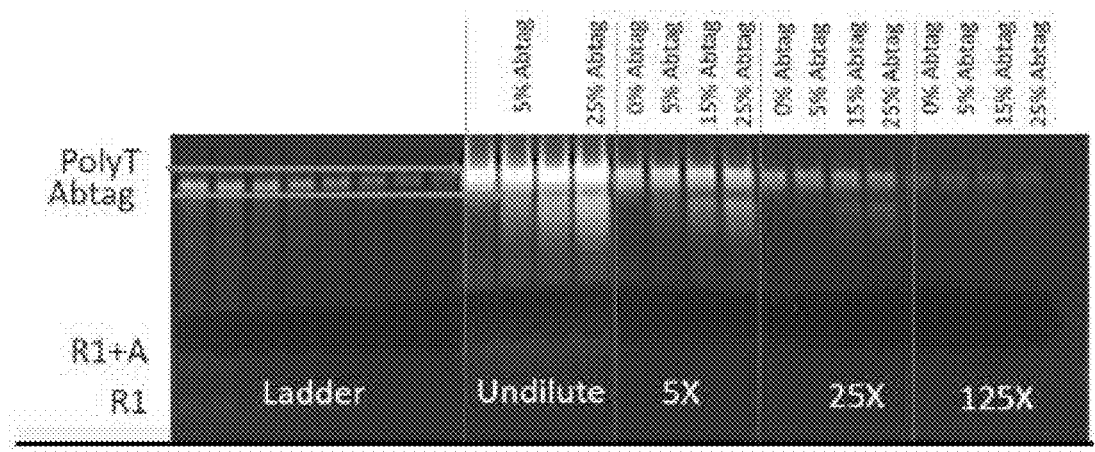
FIG. 45A shows a bead coupled with a plurality of oligonucleotides (SEQ ID NOS 30, 30, 30-31, 30, 30, 30, 30, 30, 30, 30-31, 30, and 30, respectively, in order of appearance).
FIG. 45B shows results from gel electrophoresis analysis of beads. On the beads, 0%, 5%, 15%, or 25% of coupled oligonucleotides contain antibody target primers.

Example X: Producing a Bead Coupled with Oligonucleotides with Different Primer Sequences This example shows a method for producing a bead coupled with oligonucleotides with different primer sequences. The work flow is shown in FIG. 44. A barcode sequence 4421 is ligated to a sequence primer R1 4411 coupled to a bead. The R1 primer 4411 and barcode sequence 4421 form the backbone 4420 of the oligonucleotides on the bead. A plurality of backbone oligonucleotides 4420 are coupled to the same bead. Different primers sequences are then ligated to the backbone oligonucleotides 4420. The primers include a poly-T primer 4431 that targets the poly-A of mRNA molecules. The primers also include a target specific primer, e.g., an antibody target primer that binds to a barcode on an antibody. After the second ligation, the bead comprises oligonucleotides with poly-T primers (4430) and oligonucleotides with antibody target primers (4440). The resulting product from the method is a bead coupled with a plurality of oligonucleotides (FIG. 45A). All of the oligonucleotides comprise the same backbone. Some of the oligonucleotide comprises poly-T primers and some comprises the antibody target primers. Beads with 0%, 5%, 15%, and 25% of coupled oligonucleotides containing antibody target primers are analyzed by gel electrophoresis (FIG. 45B)

Figure 47A:
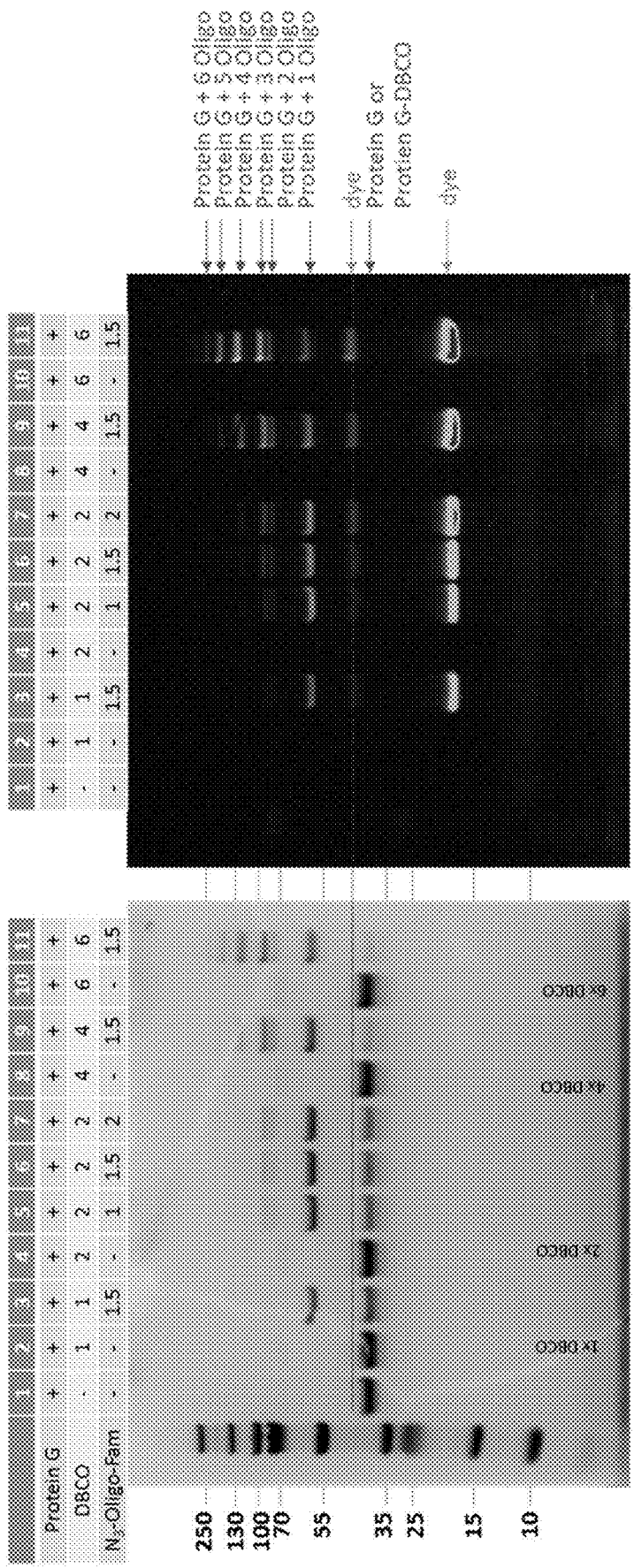

Example XI: Barcoding Antibody Labelling Agents and Cell Surface Feature Analysis In a first set of experiments, a barcoded oligonucleotide comprising an azide functional group and a FAM dye was conjugated to a Protein G labelling agent using a click chemistry reaction scheme. The barcoded oligonucleotide included a barcode sequence that may be used to identify Protein G and also a sequence that may be used as a priming site. Protein G was mixed with increasingly higher molar equivalents of DBCO-NHS (0×, 1×, 2×, 4× and 6×) in a series of mixtures. The DBCO-NHS was used to activate amine groups to become reactive to azide. Also included were varying equivalents of azide oligonucleotide to DBCO (0×, 1×, 1.5× and 2×) in the mixtures. Reactions were then allowed to proceed for 4 hours and the reaction mixtures evaluated with gel electrophoresis on a 4-12% bis-Tris gel. The results of the analysis are graphically depicted in FIGS. 47A-B. Protein G having up to 6 oligonucleotides linked were observed.

The various labeled Protein G moieties were then mixed with CD47 antibody to bind the labeled Protein G moieties to CD47 antibodies. The resulting Protein G-CD47 complexes were then incubated with 293T cells such that the complexes may bind CD47 on the surface of cells. Cells were washed to remove unbound complex and then subject to flow cytometry to observe binding of antibodies via the oligo-bound FAM dye. Results of flow cytometry are graphically depicted in FIG. 48.

Next, labeled cells were mixed with a bead coupled to an oligonucleotide comprising a nucleic acid barcode sequence, a UMI and a poly-T sequence capable of binding the poly-A sequence of mRNA transcripts in a cell. Also included was a barcoded primer having a priming sequence capable of specifically hybridizing the barcoded oligonucleotide coupled to CD47 antibodies via the barcoded oligonucleotide's priming site. The mixture was then partitioned into a droplets in an emulsion. The emulsion was then subject to conditions suitable for priming sequences to hybridize with their respective targets (mRNA or barcoded antibody oligonucleotide) and for extension of primers via the action of a polymerase or reverse transcriptase. Extension generated barcoded constructs. Following reactions, the emulsion was broken. Barcoded transcript constructs still attached to beads were removed by removing beads and the supernatant subject to 2× SPRI separation to recover the ~110 bp antibody barcode. The recovered products were then analyzed, with results shown in FIGS. 49A-D.

Example XII: Coupling of Barcodes

In a bulk experiment, two oligonucleotides shown in FIG. 51A, 5101 and 5102, were linked together via extension reactions. Oligonucleotide 5101 represented an oligonucleotide comprising a barcode sequence that may be used to identify a partition comprising the oligonucleotide 5101 and oligonucleotide 5102 represented an oligonucleotide comprising a barcode sequence that may be used to identify a labelling agent, such as an antibody coupled to oligonucleotide 5102. Oligonucleotide 5102 also included a FAM dye and a 3' reverse complement of a template switch oligonucleotide spacer-rGrGrG region included on oligonucleotide 5101. In the experiment, 50 nM AbBC of oligonucleotide 5102 was mixed with oligonucleotide 5101 in two separate mixtures. Included in the mixture were reagents for conducting a primer extension reaction, including one of two reverse transcriptases capable of facilitating a primer extension reaction and dNTPs. Extension products were then analyzed via capillary electrophoresis.

Figure 51B:
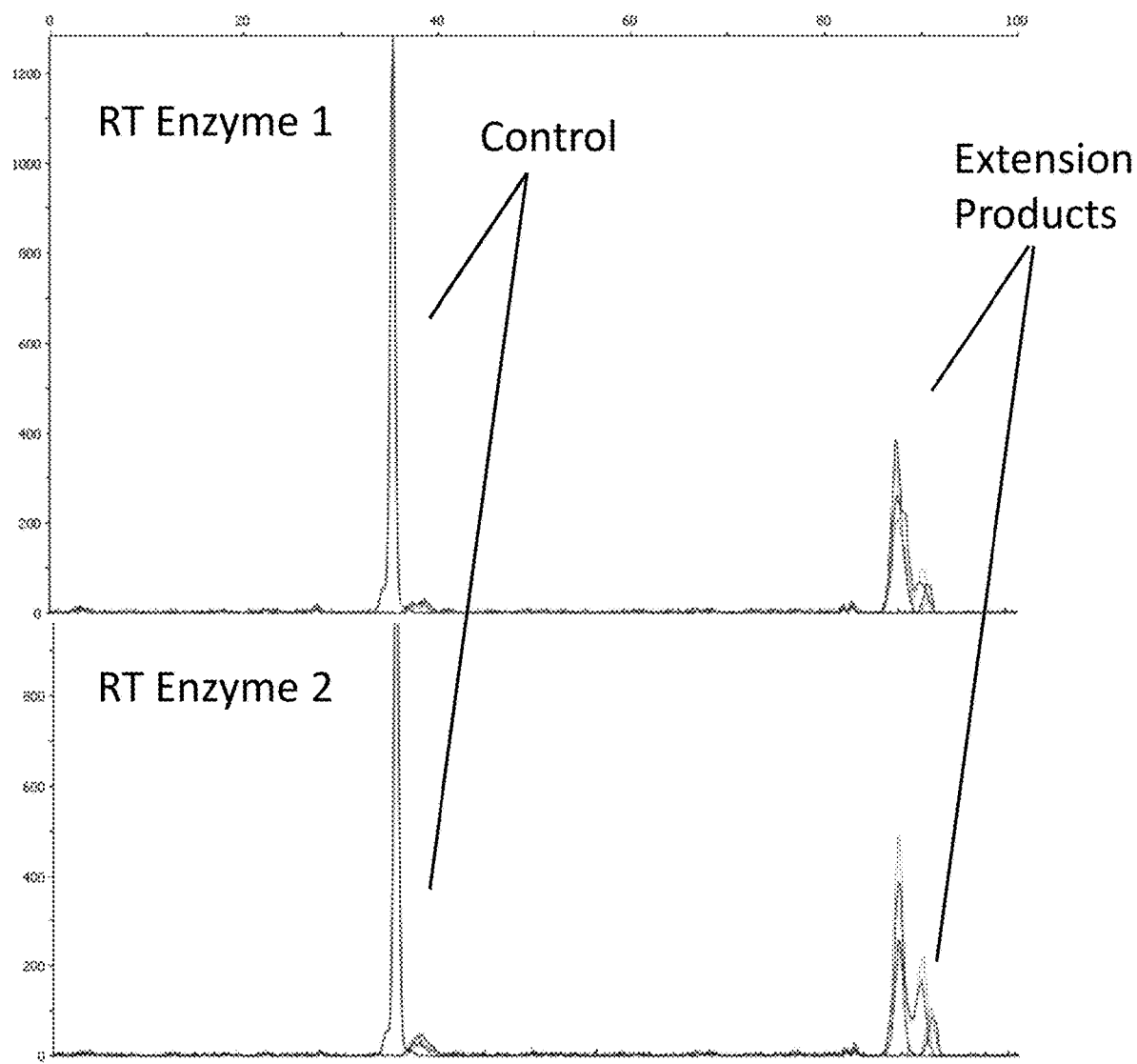
FIG. 51B graphically depicts data from an example experiment described in Example XII.

The results of the experiment are graphically shown in FIG. 51B. As shown, expected extension products having both a sequence corresponding to the barcode sequence of oligonucleotide 5101 (or a complement of the barcode sequence) and a sequence corresponding to the barcode sequence of oligonucleotide 5102 (or a complement of the barcode sequence) were detected. These results confirm that the reverse transcriptases tested may be used to generate extension products having sequences corresponding to both barcode sequences of oligonucleotides 5101 and 5102.

Example XIII: Single-Cell Barcode Behavior

Figure 52A:
FIG. 52A depicts data obtained from an example experiment described in Example XIII.

Anti-CD47 and Anti-CD99 antibodies were obtained and both types were coupled to an oligonucleotide comprising a barcode sequence that was suitable for identifying its respective antibody and also comprising a unique molecular identification (UMI) sequence and a template switch oligonucleotide reverse complement sequence (e.g., C C C). The antibody-oligonucleotide constructs were generated by linking the oligonucleotides to protein G and then binding the protein G-oligonucleotide constructs to the antibodies. The oligonucleotides were linked to protein G by modifying protein G with a single cysteine residue and linking it to oligonucleotides via the cysteine residue. Protein G also included a His×6 tag (SEQ ID NO: 40) which may be used to separate unconjugated oligonucleotides from those coupled to Protein G. Sample data from gel electrophoresis analysis of generated constructs is shown in FIG. 52A. The lanes in FIG. 52A show expression of a cysteine-containing protein G antibody binding protein. The culture lane depicts a homogenized cell culture, the flow through lane depicts is all proteins that did not bind to a nickel-NTA column, and the two elution lanes are eluted purified protein G.

Jurkat cells were then incubated with antibody-oligonucleotide constructions to bind antibodies to the surface of cells via their respective cell surface feature targets. The cells were then partitioned into aqueous droplets in an emulsion, along with beads linked to oligonucleotides comprising a barcode sequence, a UMI sequence, a priming sequences capable of hybridizing with antibody-bound oligonucleotides (e.g., primer sequence include a template switch sequence, such as rGrGrG). A reducing agent, capable of disrupting disulfide linkages of beads and linkages between beads and its oligonucleotides was also included in the partitions. The reducing agent released the bead's oligonucleotides and the droplets were then subjected to conditions suitable for hybridizing the previously bead-bound oligonucleotides to cell-bound antibody oligonucleotides via an interaction of sequences of the two oligonucleotides, including via an rGrGrG/CCC interaction. While a particular sequence is shown, hybridization may be achieved via any constant sequence at the ends of the two oligonucleotides.

The two hybridized oligonucleotides were then extended in primer extension reactions to generate constructs comprising sequences corresponding to both bead oligonucleotide and antibody barcode sequences, similar to the example scheme shown in FIG. 52B (panel I). The emulsion was then broken, the extended products further processed and then subject to sequencing. Sequencing results for Jurkat+CD47 and Jurkat+CD47/CD99 runs are graphically depicted in panels I and II, respectively, of FIG. 53A and tabulated in FIG. 53B. The data shown in FIG. 53A and FIG. 53B indicate that the antibody-oligonucleotide constructions comprising barcode sequences were able to show single cell behavior, as evidenced, for example, by an approximately 2-log enrichment of antibody-oligonucleotide UMIs in bead-originating barcode constructs corresponding to cells.

Example XIV: Antibody Barcode Staining Parameters

Various parameters associated with methods described herein were evaluated in the context of their effects on antibody-barcode construct binding, including a reverse transcription deactivation process and the concentration of reducing agent in partitions (e.g., reducing agent used to degrade barcoded beads as described elsewhere herein).

Reverse transcription can be deactivated by elevating the temperature of reverse transcription reaction mixtures to relatively high temperatures (a "heat kill"). However, such high temperatures may result in antibody-barcode constructs precipitating out of reaction mixtures, resulting in an inability to bind to cells. Various anti-CD3 barcode construct samples were tested against cells, with some samples subject to heat kill and others not subjected to heat kill. Sequencing data for the experiments is tabulated in FIGS. 54A and 54B. As shown in FIGS. 54A and 54B, a number of sequencing metrics are improved when no heat kill is used, including reads mapped confidently and complexity.

Figure 55:
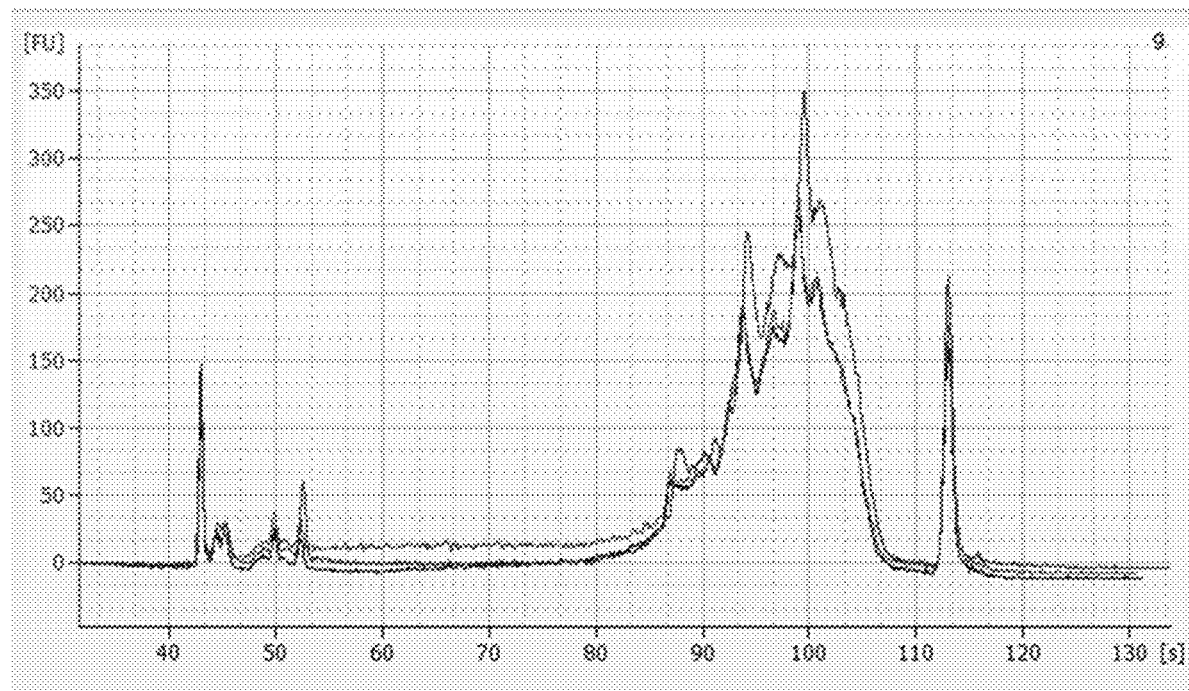

Moreover, high concentrations of reducing agents can also degrade antibodies used to label cell-surface features. Accordingly, the effect of lower reducing agent (e.g., DTT) concentration by 10-fold was tested on overall efficiency of reverse transcription in partitions. As show in FIG. 55, traces are similar for all samples tested (22 mM DTT vs. 2.2 mM DTT), suggesting that reverse transcription, as described elsewhere herein, can effectively proceed at substantially reduced DTT concentrations. In another experiment, 0.15 mM DTT was also shown to be effective.

Example XV: Linking T-Cell Receptor Sequence to Antigen Binding Phenotype Using Barcoded MHC-Antigen Multimers Many TCRs can bind a particular antigen (with varying affinity) and identifying individual clonotypes specific to a particular antigen is difficult. While flow cytometry and bead-based enrichment schemes allow physical sorting of antigen-binding cells, when cells are rare or samples are limited, cell losses associated with traditional methodologies can be unacceptable. Moreover, traditional approaches based on fluorescent detection have important limitations with regard to multiplexing (the ability to simultaneously assay the binding properties of multiple independent antigens/ligands in single experiment) due to the small number of spectrally distinguishable fluorescent labels that can be effectively used in combination. Furthermore, multiple antigen-binding clonotypes may be present in a heterogeneous sample, which makes identifying specific antigen-binding TCR complexes difficult, even when the cells expressing antigen-binding clonotypes are physically sorted.

The compositions, methods, and systems described herein allow functionalization of MHC-peptide multimers with an oligonucleotide (DNA or RNA) that includes a unique peptide barcode sequence specific to the MHC-peptide identity (e.g., Barcode 1 associated with peptide EGALIYWPN (SEQ ID NO: 62), Barcode 2 associated with peptide AHMRDSQQ (SEQ ID NO: 63), etc). A single peptide-MHC complex or peptide-MHC library can be exposed to a cell population (e.g., T-cells) to produce cells "tagged" with barcoded MHC multimers. These cells can then be partitioned and processed as described herein to assemble TCR sequences and quantify the number of MHC-peptide barcodes associated with each cell. Clonotypes with low levels of MHC-peptide derived UMIs have a low affinity for the MHC-peptide while clonotypes with high levels of the MHC-peptide UMIs have a high affinity for the antigen.

Barcoded, peptide-bound MHC tetramers bound to a streptavidin core were generated generally as depicted in FIG. 56A and as described below. Although Class I MHC-tetramers were utilized in the following series of experiments, there are many possible configurations of Class I and/or Class II MHC-antigen multimers that can be utilized with the compositions, methods, and systems disclosed herein, e.g., MHC pentamers (MHC assembled via a coiled-coil domain, e.g., Pro5® MHC Class I Pentamers, (ProImmune, Ltd.), MHC decorated dextran molecules (e.g., MHC Dextramer® (Immudex)), etc.

Figure 57A:
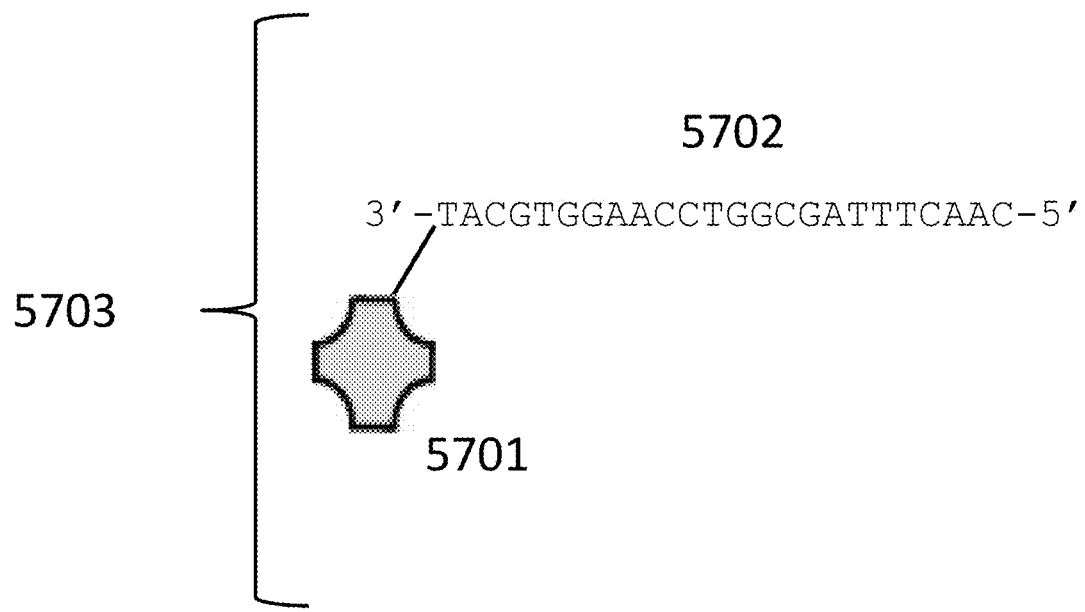
FIGS. 57A-B graphically depicts an exemplary barcoded streptavidin complex (SEQ ID NOS 57-58 and 57, respectively, in order of appearance).
Figure 57B:
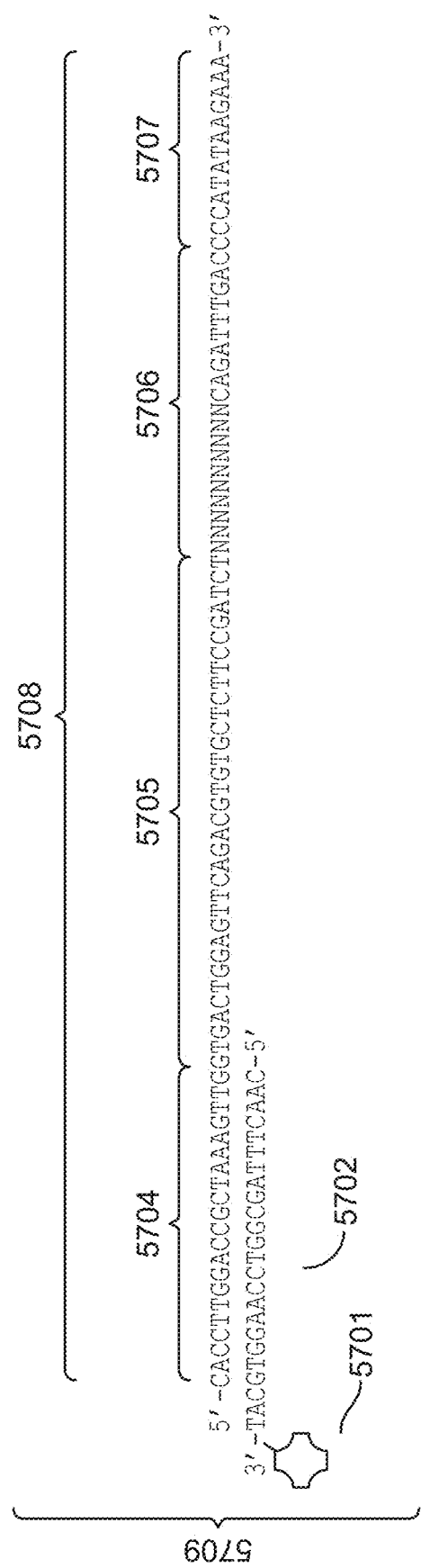
Figure 58A:
FIGS. 58A-B illustrates an exemplary analysis of barcoded streptavidin complexes.

Streptavidin molecules (5701) were conjugated to a hybridization oligonucleotide (5702) using general lysine chemistry (streptavidin modified via lysine residues with NHS-DBCO; subsequently an azide-modified oligonucleotide was attached via the DBCO functional group) to produce streptavidin-conjugated oligonucleotides (5703) as depicted in FIG. 57A. Streptavidin-conjugated oligonucleotides (5703) were then analyzed on a TBE-urea denaturing agarose gel. As shown in FIG. 58A, 0.6 µM, 1.2 µM, 1.8 µM, 2.4 µM, and 3 µM of unmodified oligonucleotide were all observed to have bands of a similar size while streptavidin-conjugated oligonucleotides exhibited a clear shift in molecular weight indicating successful streptavidin conjugation. The multiple bands observed in the streptavidin-conjugated oligonucleotide lane correspond to conjugated streptavidin molecules with increasing numbers of oligonucleotides attached (e.g., 1 oligo, 2 oligos, 3 oligos, etc.). As seen in FIG. 58A, streptavidin-conjugated oligonucleotides are produced with minimal excess non-conjugated oligonucleotide.

Figure 58B:
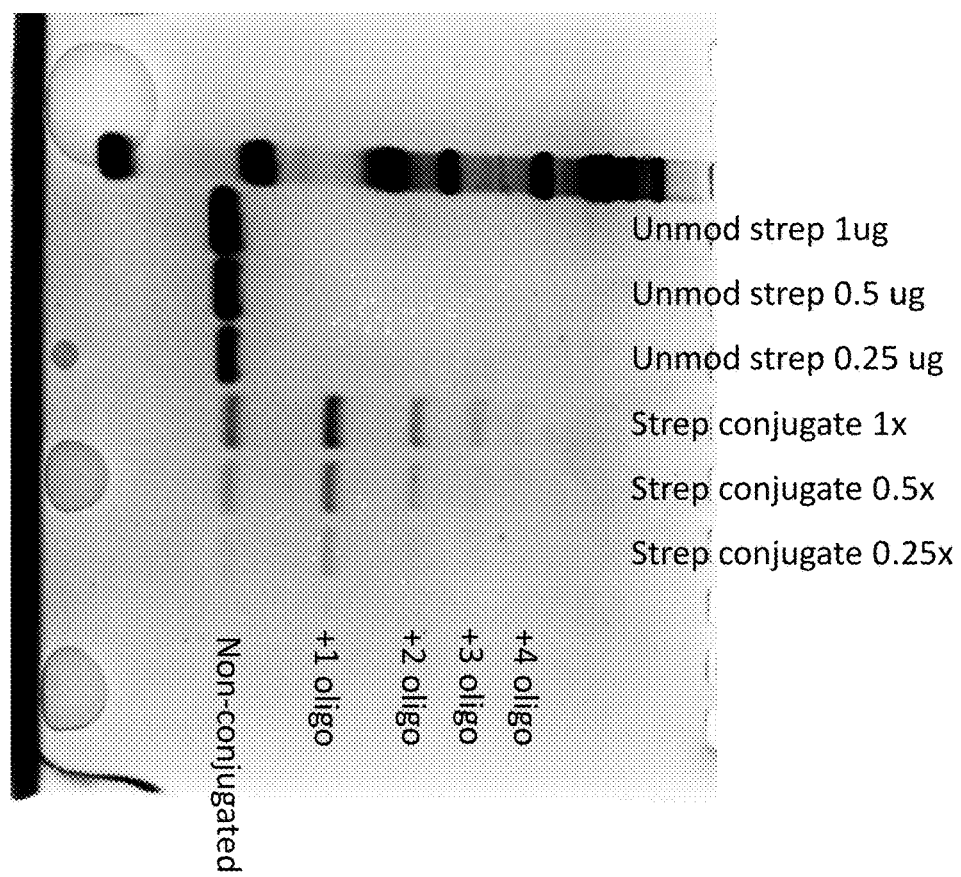

Streptavidin-conjugated oligonucleotides (5703) were also analyzed on an SDS-PAGE protein gel. As shown in FIG. 58B, 0.25 µg, 0.5 µg, and 1.0 µg of unmodified streptavidin exhibit a similar molecular weight while streptavidin-conjugated oligonucleotides exhibit a molecular weight shift indicative of streptavidin conjugated with 0, 1, 2, 3, 4 (or more) oligonucleotides. Quantification of the conjugated oligonucleotide can be estimated by comparing the density of the conjugated oligonucleotide bands with the density of the 0.25 µg, 0.5 µg, and 1.0 µg unmodified streptavidin bands. From this comparison, the overall degree of conjugation is approximately 1 oligonucleotide per each streptavidin subunit (resulting in approximately 4 oligonucleotides per each MHC tetramer).

Following quantification of the degree of conjugation, barcode oligonucleotides (5708) are hybridized to the streptavidin-conjugated oligonucleotides (5703) via the reverse complement (5704) of the hybridization oligo sequence (5702) at a stoichiometry of between 0.25:1 to 1:1 of barcode oligonucleotides (5708) to streptavidin-conjugated oligonucleotides (5703). Here, the barcode oligonucleotides (5708) comprise a sequence that is the reverse complement (5704) of the hybridization oligo sequence (5702), a TruSeq R2 sequencing primer sequence (5705), a unique molecular identification (UMI) (series of any "N" nucleotides) and a barcode sequence (5706), and an adapter sequence (5707) that is complementary to a sequence on a gel bead. Alternatively, the barcode oligonucleotide can be directly conjugated to the streptavidin.

After hybridization, the barcoded streptavidin (5709) is added to a pool of biotinylated HLA-A-02:01 MHC monomers (see, e.g., 5606) displaying an Epstein-Barr Virus (EBV) peptide antigen (GLCTLVAML (SEQ ID NO: 64)) to produce barcoded MHC tetramers (see, e.g., 5608). The barcoded streptavidin (5709) is added until a 1:1 ratio of biotinylated EBV WIC monomers to biotin binding sites is achieved (4 biotinylated MHC monomers/streptavidin complex).

Barcoded MHC tetramers (0.4 µg or 4.0 µg) are then incubated for 30 minutes with ~200,000 (100 µL) EBV antigen-expanded T-cells (Astarte Biologics) and/or ~200,000 (100 µL) of naïve T cells. Cells were washed three times with PBS/1% FBS to remove unbound multimers. The cells were then resuspended in PBS+0.04% BSA and partitioned into droplets comprising a barcoded MHC bound T-cell and a barcoded gel bead (see, e.g., FIG. 11). Barcoded MHC tetramers are then generally processed as described herein (see, e.g., FIG. 56C and accompanying text). T-cells are then lysed and released mRNA molecules are generally processed as described herein (see, e.g., FIG. 11 and accompanying text). The droplet emulsion was then broken and bulk PCR-amplification used to enrich for barcoded, full-length V(D)J segments from TCR cDNA. A second library was prepared to quantify the number of MHC-EBV peptide UMIs associated with each cell. The fully constructed sequencing libraries were then sequenced using an Illumina sequencer. T-cell receptor clonotypes were assembled bioinformatically and the number of UMI counts from barcoded WIC tetramers were quantified per cell and per clonotype.

Figure 59:
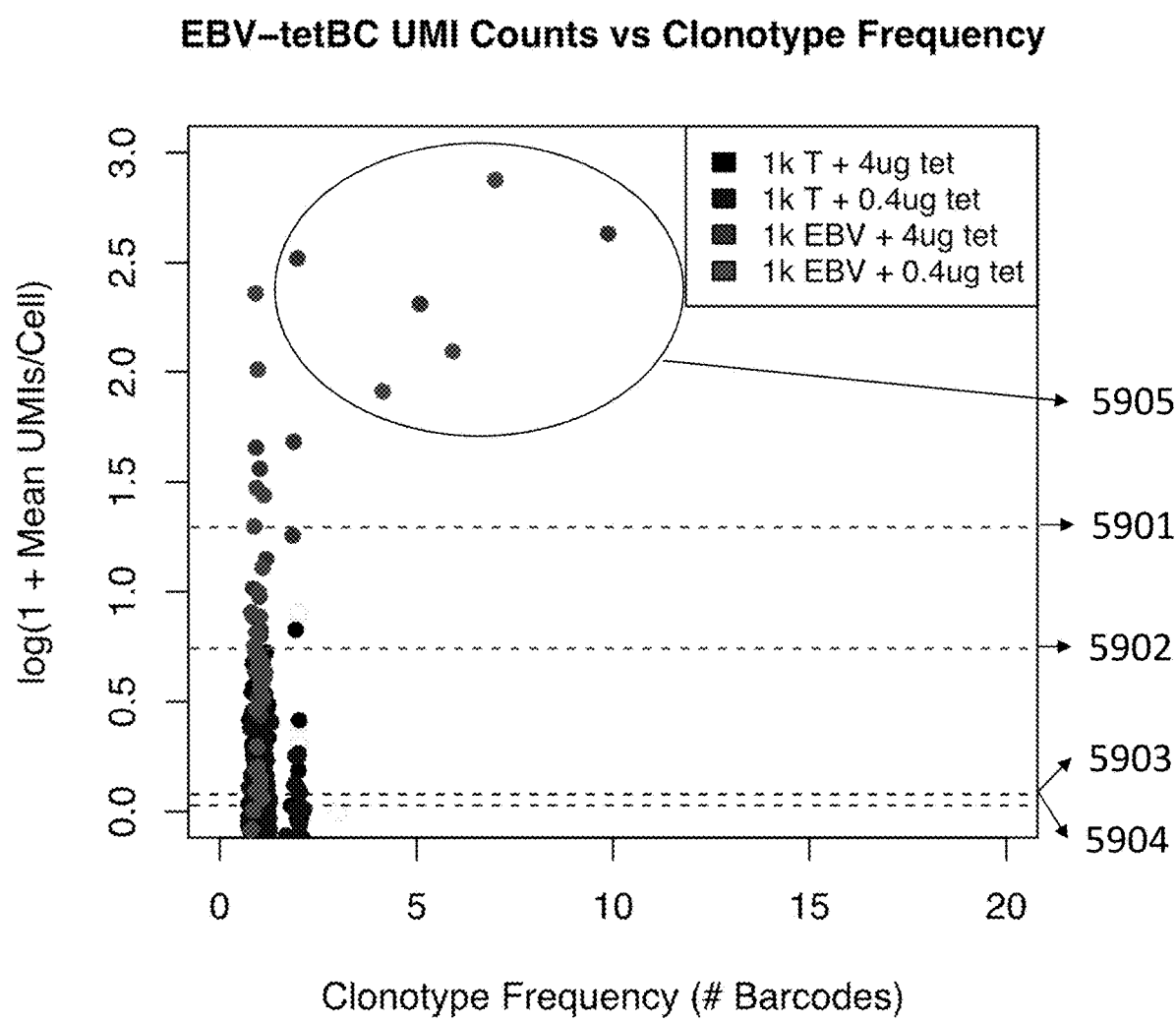
FIG. 59 shows results of data obtained from an example barcoded MHC tetramer T-cell experiment as described in Example XV.

FIG. 59 shows the number of UMI counts from barcoded MHC tetramers vs. the clonotype frequency as measured by the number of barcodes. For each clonotype detected, the average number of WIC multimer-derived UMI counts per cell-barcode was computed for all cell-associated cell-barcodes corresponding to that clonotype, and the log 10 of one plus its mean UMI counts per cell value is plotted on the y-axis. The number of cell-associated cell-barcodes detected with each clonotype is plotted on the x-axis. For visualization purposes, a random amount of Gaussian noise was added to each point's x and y coordinate values to avoid overplotting. Feature 5901 shows the mean y-axis value of log 10 (1+UMI counts per cell) averaged across all clonotypes from EBV-expanded T-cells incubated with 4 µg MHC multimer ("lk EBC+4 ug tet"); feature 5902 shows the mean y-axis value of log 10 (1+UMI counts per cell) averaged across all clonotypes from EBV-expanded T-cells incubated with 0.4 µg MHC multimer ("lk EBC+0.4 ug tet"); feature 5903 shows the mean y-axis value of log 10 (1+UMI counts per cell) averaged across all clonotypes from naïve T-cells incubated with 4 µg WIC multimer ("lk T+4 ug tet"); and feature 5904 shows the mean y-axis value of log 10 (1+UMI counts per cell) averaged across all clonotypes from naïve T-cells incubated with 0.4 µg MHC multimer ("lk T+0.4 ug tet"). As seen in FIG. 59, the EBV-expanded cell types have the most UMI counts associated with the tetramer (Features 5901 and 5902) as compared to the values obtained for the naïve T cell populations (Features 5903 and 5904). Moreover, clonotypes from the EBV-expanded cells that occur at high frequency within the EBV-expanded cell population (bounded circle, feature 5905) exhibited even greater values of MHC-tetramer UMIs, indicating their enriched frequency in the EBV-expanded population is associated with preferential MHC-tetramer binding. Conversely, naïve T-cells are not expected to preferentially bind the antigen and all have low background levels of tetramer-associated UMIs.

Figure 60:
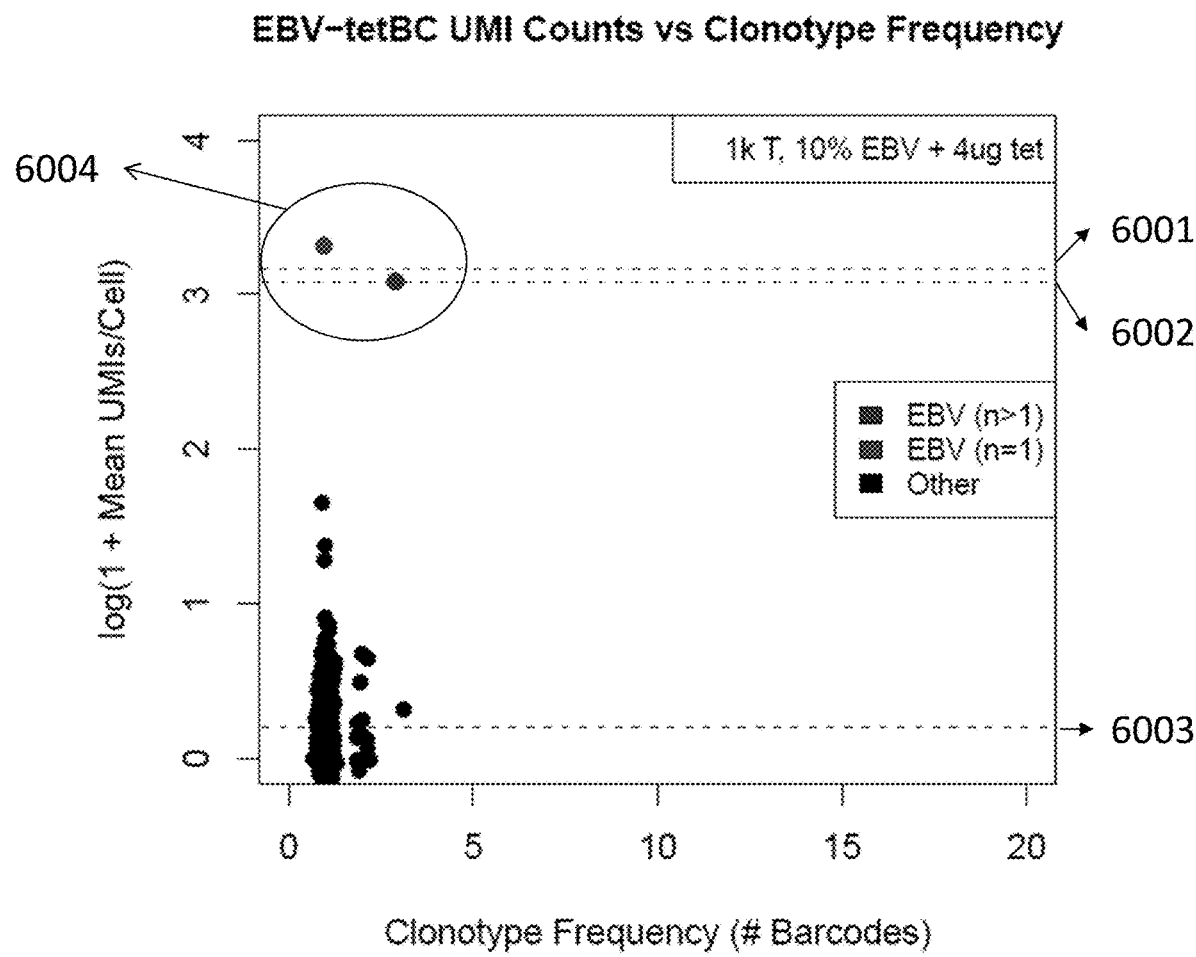
FIG. 60 shows results of data obtained from example EBV-expanded T-cell spike-in experiment as described in Example XV.

In another experiment, EBV-expanded T-cells were spiked-into a naïve T cell background prior to incubation with the barcoded MHC tetramer described above. Cells were then processed, sequenced, and analyzed as previously described. FIG. 60 shows the number of UMI counts from barcoded MHC tetramers vs. the clonotype frequency from the mixed T-cell population (following the axes and plotting conventions used in FIG. 59). Feature 6001 shows the mean y-axis value of log 10 (1+UMI counts per cell) averaged across all clonotypes from cells containing clonotypes which were previously observed to occur in at least one sample of independently processed EBV-expanded cells ("EBV (n=1)"); feature 6002 shows the mean y-axis value of log 10 (1+UMI counts per cell) averaged across all clonotypes from cells containing clonotypes which were previously observed to occur in more than one sample of independently processed EBV-expanded cells ("EBV (n>1)"); while feature 6003 shows the mean y-axis value of log 10 (1+UMI counts per cell) averaged across all clonotypes from all cells detected in the experiment ("Other"). As seen in FIG. 60, while the precise number of cells originating from the EBV spike-in is unknown (due to differences in cell recovery during washing between naïve T cells and EBV-expanded cells), two clonotypes representing a total of four cells (bounded circle, feature 6004) were detected in this mixed sample that exhibited very high tetramer-associated UMI counts (~1000× greater than background). These four cells were determined to correspond to the clonotype of the most frequently detected cell in the EBV-expanded sample and corresponded to the EBV spike-in cells. Thus, particular clonotypes of interest can be distinguished from a mixed population of cells containing a complex distribution of clonotypes.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of immune receptor analysis, comprising:
   (a) contacting a plurality of cells with a plurality of antigens to provide a cell bound to an antigen, wherein said antigen comprises a deoxyribonucleic acid (DNA) reporter molecule comprising (i) a reporter sequence that identifies said antigen and (ii) a capture sequence;
   (b) partitioning cells of said plurality of cells and a plurality of beads into a plurality of partitions to provide a partition comprising:
      (i) said cell bound to said antigen, wherein said cell comprises a messenger ribonucleic acid (mRNA) molecule encoding for an immune receptor;
      (ii) a bead of said plurality of beads, wherein said bead comprises a plurality of nucleic acid barcode molecules attached thereto comprising, from 5' to 3', a common barcode sequence, an adapter sequence complementary to said capture sequence, and a template switching oligonucleotide (TSO) sequence configured to facilitate a template switching reaction; and
      (iii) a primer comprising a sequence complementary to said mRNA molecule;
   (c) hybridizing said DNA reporter molecule to said adapter sequence and performing a nucleic acid extension reaction to generate a first barcoded nucleic acid product comprising (i) said common barcode sequence or a reverse complement thereof and (ii) said reporter sequence or a reverse complement thereof; and
   (d) hybridizing said primer to said mRNA molecule and performing a reverse transcription reaction using said mRNA molecule as a template to generate a complementary deoxyribonucleic acid (cDNA) molecule, performing a template switching reaction onto a nucleic acid barcode molecule of said plurality of nucleic acid barcode molecules, and extending a 3' end of said cDNA molecule using said nucleic acid barcode molecule as a template to generate a barcoded cDNA molecule comprising a reverse complement of said common barcode sequence.

2. The method of claim 1, wherein said DNA reporter molecule is covalently bound to said antigen.

3. The method of claim 1, wherein said DNA reporter molecule is indirectly coupled to said antigen.

4. The method of claim 1, wherein a sequence of said mRNA molecule comprises a VDJ region or VJ region.

5. The method of claim 1, further comprising (e) sequencing (i) said first barcoded nucleic acid product or a derivative generated therefrom and (ii) said barcoded cDNA molecule or a derivative generated therefrom, thereby generating sequencing information corresponding to said first barcoded nucleic acid product and said barcoded cDNA molecule.

6. The method of claim 5, further comprising using said sequencing information to associate said antigen and said immune receptor with said cell.

7. The method of claim 1, wherein said cell is a B-cell, wherein said immune receptor is a B-cell receptor, and wherein said antigen binds said B-cell receptor.

8. The method of claim 1, wherein said immune receptor is an immunoglobulin (Ig) heavy chain, wherein said cell comprises an additional mRNA molecule encoding for an Ig light chain, and wherein the method further comprises hybridizing an additional primer to said additional mRNA molecule and performing a reverse transcription reaction to generate an additional cDNA molecule, performing a template switching reaction onto an additional nucleic acid barcode molecule of said plurality of nucleic acid barcode molecules, and extending said additional cDNA molecule to generate an additional barcoded cDNA molecule comprising a reverse complement of said common barcode sequence.

9. The method of claim 8, further comprising (e) sequencing (i) said first barcoded nucleic acid product or a derivative generated therefrom, (ii) said barcoded cDNA molecule or a derivative generated therefrom, and (iii) said additional barcoded cDNA molecule or a derivative generated therefrom, thereby generating sequencing information corresponding to said first barcoded nucleic acid product, said barcoded cDNA molecule, and said additional barcoded cDNA molecule.

10. The method of claim 9, further comprising using said sequencing information to associate said antigen, said Ig heavy chain, and said Ig light chain with said cell.

11. The method of claim 8, wherein said barcoded cDNA molecule comprises a complementarity determining region (CDR) sequence of said Ig heavy chain and wherein said additional barcoded cDNA molecule comprises a CDR sequence of said Ig light chain.

12. The method of claim 11, further comprising using said sequencing information to associate said antigen, said CDR sequence of said Ig heavy chain, and said CDR sequence of said Ig light chain with said cell.

13. The method of claim 1, wherein said bead is a gel bead.

14. The method of claim 13, wherein said gel bead is degradable upon application of a stimulus.

15. The method of claim 1, wherein said plurality of nucleic acid barcode molecules is releasable from said bead upon application of a stimulus.

16. The method of claim 1, wherein said common barcode sequence of said plurality of nucleic acid barcode molecules attached to said bead is distinct from common barcode sequences of other barcode molecules attached to other beads of said plurality of beads.

17. The method of claim 1, wherein said plurality of partitions is a plurality of droplets in an emulsion.

18. The method of claim 1, wherein said plurality of partitions is a plurality of microwells in a microwell array, wherein said microwell array comprises at least 1,000 microwells.

19. The method of claim 1, wherein said antigen is an antigen presenting particle.

20. The method of claim 1, wherein said sequence complementary to said mRNA molecule comprises a poly-thymine (poly-T) sequence.

21. The method of claim 1, wherein said sequence complementary to said mRNA molecule is complementary to a sequence encoding a constant region of said immune receptor.

22. The method of claim 1, wherein said reverse transcription reaction comprises use of an enzyme with terminal transferase activity that appends a polynucleotide sequence to a 3' end of said cDNA molecule and wherein said TSO sequence is complementary to said polynucleotide sequence.

23. The method of claim 22, wherein said polynucleotide sequence comprises a polycytosine (polyC) sequence and wherein said TSO sequence comprises a polyguanine (polyG) sequence.

24. The method of claim 23, wherein said polyG sequence comprises a ribonucleotide.

25. The method of claim 1, wherein said reporter molecule comprises, from 5' to 3', an additional adapter sequence, said reporter sequence, and said capture sequence and wherein said first barcoded nucleic acid product comprises said additional adapter sequence or a reverse complement thereof.

26. The method of claim 25, wherein said reporter molecule is less than 250 nucleotides in length.

27. The method of claim 1, wherein said primer further comprised an additional adapter sequence that is not complementary to said mRNA molecule and wherein said barcoded cDNA molecule comprises said additional adapter sequence.

28. The method of claim 1, wherein said plurality of nucleic acid barcode molecules further comprises one or more functional sequences.

29. The method of claim 28, wherein said one or more functional sequences comprise one or more sequences selected from the group consisting of a primer sequence, a primer binding sequence, a sequence that attaches to a flow cell of a sequencer, and a unique molecular index (UMI).

* * * * *

UNITED STATES PATENT AND TRADEMARK OFFICE
CERTIFICATE OF CORRECTION

PATENT NO. : 10,954,562 B2  
APPLICATION NO. : 16/773750  
DATED : March 23, 2021  
INVENTOR(S) : Phillip Belgrader et al.

Page 1 of 1

It is certified that error appears in the above-identified patent and that said Letters Patent is hereby corrected as shown below:

In the Claims

In Column 147, Lines 20 and 21, please change "further comprised" to -- further comprises --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 64

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aaaaaa                                                    16

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaaa a                                                         11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttttttt t                                                         11

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g
<220> FEATURE:
<221> NAME/KEY: modified_base
<222> LOCATION: (78)..(78)
<223> OTHER INFORMATION: a, c, t, or g

<400> SEQUENCE: 4
ctacacgacg ctcttccgat ctnnnnnntc nnnnnnnnnn nnnnnntttt tttttttttt      60
tttttttttt tttttttvn                                                   78

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g

<400> SEQUENCE: 5
ctacacgacg ctcttccgat ctnnnnnntc nnnnnnnnnn nnnnnn                     46

<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, or g
<220> FEATURE:
<221> NAME/KEY: modified_base
<222> LOCATION: (41)..(52)
<223> OTHER INFORMATION: a, c, t, or g

<400> SEQUENCE: 6
ctacacgacg ctcttccgat ctnnnnnnnn nnnnnnnntc nnnnnnnnnn nn              52

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(36)
<223> OTHER INFORMATION: a, c, t, or g
<220> FEATURE:
<221> NAME/KEY: modified_base
<222> LOCATION: (39)..(44)
<223> OTHER INFORMATION: a, c, t, or g

<400> SEQUENCE: 7
```
ctacacgacg ctcttccgat ctnnnnnnnn nnnnnntcnn nnnn         44

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(21)
<223> OTHER INFORMATION: a, c, t, or g
<220> FEATURE:
<221> NAME/KEY: modified_base
<222> LOCATION: (53)..(53)
<223> OTHER INFORMATION: a, c, t, or g

<400> SEQUENCE: 8
nnnnnnnnnn nnnnnnnnnn ntttttttttt tttttttttt tttttttttt tvn         53

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(20)
<223> OTHER INFORMATION: a, c, t, or g
<220> FEATURE:
<221> NAME/KEY: modified_base
<222> LOCATION: (52)..(52)
<223> OTHER INFORMATION: a, c, t, or g

<400> SEQUENCE: 9
nnnnnnnnnn nnnnnnnnnn tttttttttt tttttttttt tttttttttt vn         52

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(32)
<223> OTHER INFORMATION: a, c, t, or g

<400> SEQUENCE: 10
tttttttttt tttttttttt tttttttttt vn         32

<210> SEQ ID NO 11
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, or g
<220> FEATURE:
<221> NAME/KEY: modified_base
<222> LOCATION: (33)..(38)
<223> OTHER INFORMATION: a, c, t, or g
<220> FEATURE:

-continued

```
<221> NAME/KEY: modified_base
<222> LOCATION: (73)..(82)
<223> OTHER INFORMATION: a, c, t, or g
<220> FEATURE:
<221> NAME/KEY: modified_base
<222> LOCATION: (114)..(114)
<223> OTHER INFORMATION: a, c, t, or g

<400> SEQUENCE: 11
caagcagaag acggcatacg agatnnnnnn gtnnnnnngt gactggagtt cagacgtgtg    60
ctcttccgat ctnnnnnnnn nnttttttttt tttttttttt tttttttttt ttvn         114

<210> SEQ ID NO 12
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, or g
<220> FEATURE:
<221> NAME/KEY: modified_base
<222> LOCATION: (33)..(38)
<223> OTHER INFORMATION: a, c, t, or g
<220> FEATURE:
<221> NAME/KEY: modified_base
<222> LOCATION: (73)..(82)
<223> OTHER INFORMATION: a, c, t, or g
<220> FEATURE:
<221> NAME/KEY: modified_base
<222> LOCATION: (114)..(114)
<223> OTHER INFORMATION: a, c, t, or g

<400> SEQUENCE: 12
caagcagaag acggcatacg agatnnnnnn cannnnnngt gactggagtt cagacgtgtg    60
ctcttccgat ctnnnnnnnn nnttttttttt tttttttttt tttttttttt ttvn         114

<210> SEQ ID NO 13
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, or g
<220> FEATURE:
<221> NAME/KEY: modified_base
<222> LOCATION: (33)..(38)
<223> OTHER INFORMATION: a, c, t, or g
<220> FEATURE:
<221> NAME/KEY: modified_base
<222> LOCATION: (73)..(82)
<223> OTHER INFORMATION: a, c, t, or g
<220> FEATURE:
<221> NAME/KEY: modified_base
<222> LOCATION: (114)..(114)
<223> OTHER INFORMATION: a, c, t, or g

<400> SEQUENCE: 13
caagcagaag acggcatacg agatnnnnnn agnnnnnngt gactggagtt cagacgtgtg    60
ctcttccgat ctnnnnnnnn nnttttttttt tttttttttt tttttttttt ttvn         114

<210> SEQ ID NO 14
<211> LENGTH: 114
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, or g
<220> FEATURE:
<221> NAME/KEY: modified_base
<222> LOCATION: (33)..(38)
<223> OTHER INFORMATION: a, c, t, or g
<220> FEATURE:
<221> NAME/KEY: modified_base
<222> LOCATION: (73)..(82)
<223> OTHER INFORMATION: a, c, t, or g
<220> FEATURE:
<221> NAME/KEY: modified_base
<222> LOCATION: (114)..(114)
<223> OTHER INFORMATION: a, c, t, or g

<400> SEQUENCE: 14
caagcagaag acggcatacg agatnnnnnn tcnnnnnngt gactggagtt cagacgtgtg    60
ctcttccgat ctnnnnnnnn nnttttttt tttttttttt ttttttttt ttvn          114

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g
<220> FEATURE:
<221> NAME/KEY: modified_base
<222> LOCATION: (78)..(78)
<223> OTHER INFORMATION: a, c, t, or g

<400> SEQUENCE: 15
ctacacgacg ctcttccgat ctnnnnnngt nnnnnnnnnn nnnnnntttt tttttttttt    60
tttttttttt tttttvn                                                   78

<210> SEQ ID NO 16
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g
<220> FEATURE:
<221> NAME/KEY: modified_base
<222> LOCATION: (78)..(78)
<223> OTHER INFORMATION: a, c, t, or g

<400> SEQUENCE: 16
ctacacgacg ctcttccgat ctnnnnnnca nnnnnnnnnn nnnnnntttt tttttttttt    60
```
tttttttttt tttttvn                                                          78

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g
<220> FEATURE:
<221> NAME/KEY: modified_base
<222> LOCATION: (78)..(78)
<223> OTHER INFORMATION: a, c, t, or g

<400> SEQUENCE: 17
ctacacgacg ctcttccgat ctnnnnnnag nnnnnnnnnn nnnnnntttt tttttttttt     60
tttttttttt tttttvn                                                          78

<210> SEQ ID NO 18
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(35)
<223> OTHER INFORMATION: a, c, t, or g
<220> FEATURE:
<221> NAME/KEY: modified_base
<222> LOCATION: (38)..(43)
<223> OTHER INFORMATION: a, c, t, or g
<220> FEATURE:
<221> NAME/KEY: modified_base
<222> LOCATION: (77)..(86)
<223> OTHER INFORMATION: a, c, t, or g
<220> FEATURE:
<221> NAME/KEY: modified_base
<222> LOCATION: (118)..(118)
<223> OTHER INFORMATION: a, c, t, or g

<400> SEQUENCE: 18
aatgatacgg cgaccaccga gatctacacn nnnnngtnnn nnnacactct ttccctacac     60
gacgctcttc cgatctnnnn nnnnnntttt tttttttttt tttttttttt tttttvn       118

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g
<220> FEATURE:
<221> NAME/KEY: modified_base
<222> LOCATION: (78)..(78)
<223> OTHER INFORMATION: a, c, t, or g

<400> SEQUENCE: 19
cagacgtgtg ctcttccgat ctnnnnnngt nnnnnnnnnn nnnnnntttt tttttttttt    60
tttttttttt tttttttvn                                                 78

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, or g
<220> FEATURE:
<221> NAME/KEY: modified_base
<222> LOCATION: (41)..(52)
<223> OTHER INFORMATION: a, c, t, or g

<400> SEQUENCE: 20
ctacacgacg ctcttccgat ctnnnnnnnn nnnnnnnngt nnnnnnnnnn nn             52

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, or g
<220> FEATURE:
<221> NAME/KEY: modified_base
<222> LOCATION: (41)..(52)
<223> OTHER INFORMATION: a, c, t, or g

<400> SEQUENCE: 21
ctacacgacg ctcttccgat ctnnnnnnnn nnnnnnnnca nnnnnnnnnn nn             52

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, or g
<220> FEATURE:
<221> NAME/KEY: modified_base
<222> LOCATION: (41)..(52)
<223> OTHER INFORMATION: a, c, t, or g

<400> SEQUENCE: 22
ctacacgacg ctcttccgat ctnnnnnnnn nnnnnnnnag nnnnnnnnnn nn             52

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
aaaaaaaaaa aaaaaaaaaa a                                               21

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctacacgacg ctctt                                                      15

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g

<400> SEQUENCE: 25
ctacacgacg ctcttccgat ctnnnnnn                                        28

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, or g

<400> SEQUENCE: 26
acnnnnnnag atcggaagag cg                                              22

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(18)
<223> OTHER INFORMATION: a, c, t, or g
<220> FEATURE:
<221> NAME/KEY: modified_base
<222> LOCATION: (50)..(50)
<223> OTHER INFORMATION: a, c, t, or g

<400> SEQUENCE: 27
gtnnnnnnnn nnnnnnnntt tttttttttt tttttttttt ttttttttvn                50

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(18)
<223> OTHER INFORMATION: a, c, t, or g

<400> SEQUENCE: 28
gtnnnnnnnn nnnnnnnnta cgctagtttc gcgtacgaag c                      41

<210> SEQ ID NO 29
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, or g
<220> FEATURE:
<221> NAME/KEY: modified_base
<222> LOCATION: (31)..(46)
<223> OTHER INFORMATION: a, c, t, or g

<400> SEQUENCE: 29
ctacacgacg ctcttccgat ctnnnnnngt nnnnnnnnnn nnnnnntacg ctagtttcgc   60
gtacgaagc                                                          69

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(48)
<223> OTHER INFORMATION: a, c, t, or g
<220> FEATURE:
<221> NAME/KEY: modified_base
<222> LOCATION: (80)..(80)
<223> OTHER INFORMATION: a, c, t, or g

<400> SEQUENCE: 30
ctacacgacg ctcttccgat ctnnnnnnnn nnnnnnnnnn nnnnnnnntt tttttttttt   60
tttttttttt ttttttttvn                                              80

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(48)
<223> OTHER INFORMATION: a, c, t, or g

<400> SEQUENCE: 31
ctacacgacg ctcttccgat ctnnnnnnnn nnnnnnnnnn nnnnnnnnac gctagtttcg   60
cgtacgaagc                                                         70

<210> SEQ ID NO 32

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcagatgtg tataa                                                        15

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, or g
<220> FEATURE:
<221> NAME/KEY: modified_base
<222> LOCATION: (32)..(48)
<223> OTHER INFORMATION: a, c, t, or g
<220> FEATURE:
<221> NAME/KEY: modified_base
<222> LOCATION: (80)..(80)
<223> OTHER INFORMATION: a, c, t, or g

<400> SEQUENCE: 33
ctacacgacg ctcttccgat ctnnnnnng tnnnnnnnnn nnnnnnnntt tttttttttt         60
tttttttttt tttttttvn                                                    80

<210> SEQ ID NO 34
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, or g
<220> FEATURE:
<221> NAME/KEY: modified_base
<222> LOCATION: (32)..(48)
<223> OTHER INFORMATION: a, c, t, or g
<220> FEATURE:
<221> NAME/KEY: modified_base
<222> LOCATION: (80)..(80)
<223> OTHER INFORMATION: a, c, t, or g

<400> SEQUENCE: 34
ctacacgacg ctcttccgat ctnnnnnnnc annnnnnnnn nnnnnnnntt tttttttttt         60
tttttttttt tttttttvn                                                    80

<210> SEQ ID NO 35
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, or g
<220> FEATURE:
<221> NAME/KEY: modified_base
```

<222> LOCATION: (32)..(48)
<223> OTHER INFORMATION: a, c, t, or g
<220> FEATURE:
<221> NAME/KEY: modified_base
<222> LOCATION: (80)..(80)
<223> OTHER INFORMATION: a, c, t, or g

<400> SEQUENCE: 35
ctacacgacg ctcttccgat ctnnnnnnna gnnnnnnnnn nnnnnnnntt tttttttttt    60
tttttttttt tttttttttvn                                              80

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, or g
<220> FEATURE:
<221> NAME/KEY: modified_base
<222> LOCATION: (32)..(48)
<223> OTHER INFORMATION: a, c, t, or g
<220> FEATURE:
<221> NAME/KEY: modified_base
<222> LOCATION: (80)..(80)
<223> OTHER INFORMATION: a, c, t, or g

<400> SEQUENCE: 36
ctacacgacg ctcttccgat ctnnnnnnnt cnnnnnnnnn nnnnnnnntt tttttttttt    60
tttttttttt tttttttttvn                                              80

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, or g
<220> FEATURE:
<221> NAME/KEY: modified_base
<222> LOCATION: (32)..(48)
<223> OTHER INFORMATION: a, c, t, or g

<400> SEQUENCE: 37
gtcagatgtg tataagagac agnnnnnnng tnnnnnnnnn nnnnnnnngc ttcgtacgcg    60
aaactagcgt                                                          70

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(47)
<223> OTHER INFORMATION: a, c, t, or g

<400> SEQUENCE: 38
ctacacgacg ctcttccgat ctnnnnnnnn nnnnnnnnnn nnnnnnnttt cttatatggg        60

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caactttagc ggtccaaggt gcagtcagat cccatataag aaa                         43

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
1               5

<210> SEQ ID NO 41
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, or g
<220> FEATURE:
<221> NAME/KEY: modified_base
<222> LOCATION: (43)..(48)
<223> OTHER INFORMATION: a, c, t, or g

<400> SEQUENCE: 41
agatcggaag agcacacgtc tgaactccag tcacnnnnnn acnnnnnnat ctcgtatgcc        60
g                                                                        61

<210> SEQ ID NO 42
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, or g
<220> FEATURE:
<221> NAME/KEY: modified_base
<222> LOCATION: (43)..(48)
<223> OTHER INFORMATION: a, c, t, or g

<400> SEQUENCE: 42
agatcggaag agcacacgtc tgaactccag tcacnnnnnn tgnnnnnnat ctcgtatgcc        60
g                                                                        61

<210> SEQ ID NO 43

```
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, or g
<220> FEATURE:
<221> NAME/KEY: modified_base
<222> LOCATION: (43)..(48)
<223> OTHER INFORMATION: a, c, t, or g

<400> SEQUENCE: 43
agatcggaag agcacacgtc tgaactccag tcacnnnnnn ctnnnnnnat ctcgtatgcc     60
g                                                                    61

<210> SEQ ID NO 44
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, or g
<220> FEATURE:
<221> NAME/KEY: modified_base
<222> LOCATION: (43)..(48)
<223> OTHER INFORMATION: a, c, t, or g

<400> SEQUENCE: 44
agatcggaag agcacacgtc tgaactccag tcacnnnnnn gannnnnnat ctcgtatgcc     60
g                                                                    61

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, or g
<220> FEATURE:
<221> NAME/KEY: modified_base
<222> LOCATION: (9)..(14)
<223> OTHER INFORMATION: a, c, t, or g

<400> SEQUENCE: 45
nnnnnnacnn nnnnagatcg gaagagcg                                       28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, or g
<220> FEATURE:
<221> NAME/KEY: modified_base
```

```
<222> LOCATION: (9)..(14)
<223> OTHER INFORMATION: a, c, t, or g

<400> SEQUENCE: 46
nnnnnntgnn nnnnagatcg gaagagcg                                        28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, or g
<220> FEATURE:
<221> NAME/KEY: modified_base
<222> LOCATION: (9)..(14)
<223> OTHER INFORMATION: a, c, t, or g

<400> SEQUENCE: 47
nnnnnnctnn nnnnagatcg gaagagcg                                        28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, or g
<220> FEATURE:
<221> NAME/KEY: modified_base
<222> LOCATION: (9)..(14)
<223> OTHER INFORMATION: a, c, t, or g

<400> SEQUENCE: 48
nnnnnngann nnnnagatcg gaagagcg                                        28

<210> SEQ ID NO 49
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, or g
<220> FEATURE:
<221> NAME/KEY: modified_base
<222> LOCATION: (42)..(47)
<223> OTHER INFORMATION: a, c, t, or g

<400> SEQUENCE: 49
agatcggaag agcgtcgtgt agggaaagag tgtnnnnnna cnnnnnngtg tagatctcgg      60
tg                                                                    62

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
```

```
                                  oligonucleotide
<220> FEATURE:
<221> NAME/KEY: modified_base
<222> LOCATION: (1)..(6)
<223> OTHER INFORMATION: a, c, t, or g
<220> FEATURE:
<221> NAME/KEY: modified_base
<222> LOCATION: (9)..(14)
<223> OTHER INFORMATION: a, c, t, or g

<400> SEQUENCE: 50
nnnnnnacnn nnnnagatcg gaagagc                                           27

<210> SEQ ID NO 51
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agatcggaag agcg                                                         14

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, or g
<220> FEATURE:
<221> NAME/KEY: modified_base
<222> LOCATION: (10)..(16)
<223> OTHER INFORMATION: a, c, t, or g

<400> SEQUENCE: 52
nnnnnnnacn nnnnnnagat cggaagagcg                                        30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, or g
<220> FEATURE:
<221> NAME/KEY: modified_base
<222> LOCATION: (10)..(16)
<223> OTHER INFORMATION: a, c, t, or g

<400> SEQUENCE: 53
nnnnnnntgn nnnnnnagat cggaagagcg                                        30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(7)
<223> OTHER INFORMATION: a, c, t, or g
<220> FEATURE:
<221> NAME/KEY: modified_base
<222> LOCATION: (10)..(16)
<223> OTHER INFORMATION: a, c, t, or g

<400> SEQUENCE: 54
nnnnnnnctn nnnnnnagat cggaagagcg                              30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, or g
<220> FEATURE:
<221> NAME/KEY: modified_base
<222> LOCATION: (10)..(16)
<223> OTHER INFORMATION: a, c, t, or g

<400> SEQUENCE: 55
nnnnnnngan nnnnnnagat cggaagagcg                              30

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, or g
<220> FEATURE:
<221> NAME/KEY: modified_base
<222> LOCATION: (10)..(16)
<223> OTHER INFORMATION: a, c, t, or g

<400> SEQUENCE: 56
nnnnnnnacn nnnnnnctgt ctcttataca c                            31

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caactttagc ggtccaaggt gcat                                    24

<210> SEQ ID NO 58
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (56)..(65)
<223> OTHER INFORMATION: a, c, t, or g
```

-continued

<400> SEQUENCE: 58
caccttggac cgctaaagtt ggtgactgga gttcagacgt gtgctcttcc gatctnnnnn    60
nnnnncagat ttgaccccat ataagaaa                                        88

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aaaaaaaaaa aaaaaaaaaa                                                20

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atcctagcaa                                                           10

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgatcctagc aa                                                        12

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Gly Ala Leu Ile Tyr Trp Pro Asn
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala His Met Arg Asp Ser Gln Gln
1               5

<210> SEQ ID NO 64
<211> LENGTH: 9
<212> TYPE: PRT
<213> ORGANISM: Epstein-Barr virus

```
<400> SEQUENCE: 64

Gly Leu Cys Thr Leu Val Ala Met Leu
1               5
```